United States Patent
Vianello et al.

(10) Patent No.: US 10,961,255 B2
(45) Date of Patent: *Mar. 30, 2021

(54) IMIDAZOLES AS HISTONE DEMETHYLASE INHIBITORS

(71) Applicant: Istituto Europeo di Oncologia S.r.l., Milan (IT)

(72) Inventors: Paola Vianello, Milan (IT); Alessia Romussi, Genoa (IT); Anna Cappa, Visso (IT); Paolo Trifiro', Como (IT); Mario Varasi, Milan (IT); Luca Sartori, Brunate (IT); Ciro Mercurio, Legnano (IT)

(73) Assignee: Istituto Europeo di Oncologia S.r.l., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/722,554

(22) Filed: Dec. 20, 2019

(65) Prior Publication Data

US 2020/0299303 A1    Sep. 24, 2020

Related U.S. Application Data

(63) Continuation of application No. 16/301,875, filed as application No. PCT/EP2017/062009 on May 18, 2017, now Pat. No. 10,562,914.

(30) Foreign Application Priority Data

May 18, 2016   (EP) .................................. 16170238

(51) Int. Cl.
   - *A61K 31/4178* (2006.01)
   - *C07D 495/04* (2006.01)
   - *A61P 3/04* (2006.01)
   - *A61P 35/00* (2006.01)

(52) U.S. Cl.
   CPC .............. *C07D 495/04* (2013.01); *A61P 3/04* (2018.01); *A61P 35/00* (2018.01)

(58) Field of Classification Search
   None
   See application file for complete search history.

(56) References Cited

U.S. PATENT DOCUMENTS

| | | |
|---|---|---|
| 5,204,018 A | 4/1993 | Kelly |
| 9,133,166 B2 | 9/2015 | Kanouni et al. |
| 9,278,931 B2 | 3/2016 | Tomita et al. |
| 9,982,237 B2 | 5/2018 | Deng et al. |
| 10,005,769 B2 | 6/2018 | Leban et al. |
| 10,183,952 B2 | 1/2019 | Vianello et al. |
| 10,562,914 B2 | 2/2020 | Vianello et al. |
| 2010/0324147 A1 | 12/2010 | McCafferty et al. |

FOREIGN PATENT DOCUMENTS

| | | |
|---|---|---|
| EP | 2740474 | 6/2014 |
| EP | 2 993 175 A1 | 3/2016 |
| WO | WO 2006/077412 | 7/2006 |
| WO | WO 2011/131576 A1 | 10/2011 |
| WO | WO 2012/045883 A1 | 4/2012 |
| WO | WO 2012/049277 A1 | 4/2012 |
| WO | WO 2012/099952 A2 | 7/2012 |
| WO | WO 2013/025805 A1 | 2/2013 |
| WO | WO 2014/164867 A1 | 10/2014 |
| WO | WO 2016/007731 A1 | 1/2016 |
| WO | WO 2016/034946 A2 | 3/2016 |

OTHER PUBLICATIONS

Anand, R. et al. "Structure and Mechanism of Lysine-specific Demethylase Enzymes", Journal of Biologocal Chemistry, 2007, vol. 282, No. 49, p. 35425-35429.
Benelkebir et al. "Enantioselective synthesis of tranylcypromine analogues as lysine demethylase (LSD1) inhibitors", Bioorganic & Medicinal Chemistry, 2011, vol. 19, p. 3709-3716.
Bennani-Baiti I. M. et al. "Lysine-specific demethylase 1 (LSD1/KDM1A/AOF2/ BHC110) is expressed and is an epigenetic drug target in chondrosarcoma, Ewing's sarcoma, osteosarcoma, and rhabdomyosarcoma", Human Pathology, 2012, vol. 43, p. 1300-1307.
Binda et al. "Biochemical, Structural, and Biological Evaluation of Tranylcypromine Derivatives as Inhibitors of Histone Demethylases LSD1 and LSD2", J. Am. Chem. Soc., 2011, vol. 132, p. 6827-6833.
Binda C. et al. "Insights into the mode of inhibition of human mitochondrial monoamine oxidase B from high-resolution crystal structures", Proc. Natl. Acad. Sci. USA, 2003, p. 9750-9755.
CAS 1204944-60-4, Feb. 9, 2010.
CAS 1204935-35-2, Feb. 9, 2010.
CAS 1205349-51-4, Feb. 10, 2010.
CAS 1205627-53-7, Feb. 10, 2010.
CAS 1205797-86-9, Feb. 11, 2010.
CAS 1206030-07-0, Feb. 11, 2010.
CAS 1204934-97-3, Feb. 9, 2010.
CAS 1205463-37-1, Feb. 10, 2010.
CAS 1206029-55-1, Feb. 11, 2010.
CAS 1374527-29-3, May 25, 2012.
CAS 1374629-24-9, May 27, 2012.
Centers for Disease Control. "Strategies to Prevent Obesity." © 2017. Available from: https://www.cdc.gov/obesity/strategies/ >.

(Continued)

*Primary Examiner* — Samantha L Shterengarts
(74) *Attorney, Agent, or Firm* — Cooley LLP

(57) ABSTRACT

The present invention relates to imidazole derivatives, wherein A, R, $R^1$, and $R^2$ are as defined in the specification, pharmaceutical compositions containing such compounds and to their use in therapy.

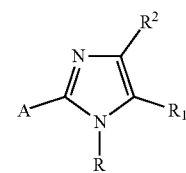

(I)

26 Claims, No Drawings

(56) References Cited

OTHER PUBLICATIONS

Cho, H. S. et al. "Demethylation of RB Regulator MYPT1 by Histone Demethylase LSD1 Promotes Cell Cycle Progression in Cancer Cells", Cancer Research, 2011, vol. 71, p. 655-660.
Choi, J. et al. "Histone demethylase LSD1 is required to induce skeletal muscle differentiation by regulating myogenic factors", Biochem. Biophys. Res. Commun. 2010, vol. 401, p. 327-332.
Ciccone, D. N. et al. "KDM1B is a histone H3K4 demethylase required to establish maternal genomic imprints", Nature, 2009, vol. 461, p. 415-418.
Culhane, J.C. et al. "LSD1 and the chemistry of histone demethylation", Curr. Opin. Chem. Biol. 2007, vol. 11, p. 561-568.
Duteil et al. "LSD1 promotes oxidative metabolism of white adipose tissue", Nature Communications, 2014, 14 pages.
Emedicinehealth "Leukemia." © 2017. Available from: https://www.emedicinehealth.com/leukemia-health/page7.htm >.
Fang R. et al. "Human LSD2/KDM1b/AOF1 Regulates Gene Transcription by Modulating Intragenic H3K4me2 Methylation", Molecular Cell, 2010, vol. 39, p. 222-233.
Florida Hospital "Glioma." © 2017. Available from: https://www.floridahospital.com/glioma/prevention-glioma >.
Forneris, F. et al. "LSD1: oxidative chemistry for multifaceted functions in chromatin regulation", Trends Biochem, Sci, 2008, vol. 33, p. 181-189.
Forneris, F. et al. "Structural Basis of LSD1-CoREST Selectivity in Histone H3 Recognition", Journal of Biological Chemistry, 2007, vol. 282, p. 20070-20074.
Gooden et al. "Facile synthesis of substituted trans-2-arylcyclopropylamine inhibitors of the human histone demethylase LSD1 and monoamine oxidases A", Science Direct, Bioorganic & Medicinal Chemistry Letters, 2008, vol. 18, p. 3047-3051.
Goswami, R. et al. "Structure-guided discovery of 1,3,5 trisubstituted benzenes as potent and selective matriptase inhibitors exhibiting in vivo antitumor efficacy", Bioorganic & Medicinal Chemistry, 2014, vol. 22, p. 3187-3203.
Gu, H. J. et al. "Engagement of the Lysine-Specific Demethylase/HDAC1/CoREST/REST Complex by Herpes Simplex Virus 1", Viral. 2009, vol. 83, p. 4376-4385.
Harris et al. "The Histone Demethylase KDM1A Sustains the Oncogenic Potential of MLL-AF9 Leukemia Stem Cells", Cancer Cell, 2012, vol. 21, p. 473-487.
Hayami, S. et al. "Overexpression of LSD1 contributes to human carcinogenesis through chromatin regulation in various cancers", International Journal of Cancer, 2011, vol. 128, p. 574-586.
Hino S. et al. "FAD-dependent lysine-specific demethylase-1 regulates cellular energy expenditure", Nature Communications, 2012, 12 pages.
Hitchin J. et al. "Development and evaluation of selective, reversible LSD1 inhibitors derived from fragments", Med. Chem. Commun. 2013, vol. 4, p. 1513-1522.
Hu, X. et al. "LSD1-mediated epigenetic modification is required for TAL1 function and hematopoiesis", Proc. Natl. Acad. Sci. USA 2009, vol. 106, No. 25, p. 10141-10146.
Huang, Y. et al. "Inhibition of lysine-specific demethylase 1 by polyamine analogues results in reexpression of aberrantly silenced genes", Proc. Natl. Acad. Sci. U S A. 2007, vol. 104, p. 8023-8028.
Huang, Y. et al. "Novel Oligoamine Analogues Inhibit Lysine-Specific Demethylase 1 and Induce Reexpression of Epigenetically Silenced Genes", Clin. Cancer Res. 2009, vol. 15, p. 7217-7228.
Ismail, M.A. et al. "Synthesis and Antiprotozoal Activity of Aza-Analogues of Furamidine", J. Med. Chem. 2003, vol. 46, p. 4761-4769.
Jnaneshwara, G. K. et al. "Palladium-catalysed Transfer Hydrogenation of Azobenzenes and Oximes using Ammonium Formate", J. Chem. Research, 1998, p. 160-161.
Kahl, P. et al. "Androgen Receptor Coactivators Lysine-Specific Histone Demethylase 1 and Four and a Half LIM Domain Protein 2 Predict Risk of Prostate Cancer Recurrence", Cancer Research, 2006, vol. 66, p. 11341-11347.

Karytinos, A. et al. "A Novel Mammalian Flavin-dependent Histone Demethylase", Journal of Biological Chemistry, 2009, vol. 284, p. 17775-17782.
Lange, U. E. W et al."D-Phe-Pro-Arg Type Thrombin Inhibitors: Unexpected Selectivity by Modification of the P1 Moiety", Bioorganic & Medicinal Chemistry Letters, 2003, vol. 13, p. 2029-2033.
Lee, M. G. et al. "Histone H3 Lysine 4 Demethylation Is a Target of Nonselective Antidepressive Medications", Chemistry & Biology, 2006, vol. 13, p. 563-567.
Li, B. et al. "An Optimized Process for Formation of 2,4-Disubstituted Imidazoles from Condensation of Amidines and a.-Haloketones", Organic Process Research & Development, 2002, vol. 6, p. 682-683.
Li, Y. et al. "Dynamic interaction between TAL1 oncoprotein and LSD1 regulates TAL1 function in hematopoiesis and leukemogenesis", Oncogene, 2012, vol. 31, p. 5007-5018.
Lim, S. et al. "Lysine-specific demethylase 1 (LSD1) is highly expressed in ER-negative breast cancers and a biomarker predicting aggressive biology", Carcinogenesis 2010, vol. 31, p. 512-520.
Lin, T. et al. "Requirement of the histone demethylase LSD1 in Snail-mediated transcriptional repression during epithelial-mesenchymal transition", Oncogene, 2010, vol. 29, p. 4896-4904.
Lv, S. et al. "LSD1 is required for chromosome segregation during mitosis", European Journal of Cell Biology, 2010, vol. 89, p. 557-563.
Mahajan, U. S. et al. "Prepaparation of Amidines from Amidoximes via Transfer Hydrogenation", Synthetic Communications 2011, vol. 41, p. 2195-2199.
Mayo Clinic "Lung cancer." © 2017. Available from: https://www.mayoclinic.org/diseases-conditions/lung-cancer/symptoms-causes/syc-2037 4620?p= 1 >.
Mayo Clinic "Liver cancer." © 2017. Available from: https://www.mayoclinic.org/diseases-conditions/liver-cancer/symptoms-causes/syc-20353659?p=1 >.
Metzger, E. et al. "The expanding world of histone lysine demethylases", Natural Structural & Molecular Biology, 2007, vol. 14, p. 252-254.
Murphy, W. et al. "Intramolecular Alkylation of Phenols. Part 5.1 A Regiospecific Anionic Ring Closure of Phenols via Ouinone Methides", J. Chem. Soc., 1980, vol. 7, p. 1567-1577.
Musri, M. M. et al. "Histone Demethylase LSD1 Regulates Adipogenesis", Journal of Biological Chemistry, 2010, vol. 285, p. 30034-30041.
Nadrah, K. et al. "Preparation of Amidines by Amidoxime Reduction with Potassium Formate", Synlett, 2007, p. 1257-1258.
Portela, A. et al. "Epigenetic modifications and human disease", Nature Biotechnology, 2010, vol. 28, p. 1057-1068.
Roizman, B. "The Checkpoints of Viral Gene Expression in Productive and Latent Infection: the Role of the HDAC/CoREST/LSD1/REST Repressor Complex", Journal of Virology, 2011, vol. 85, No. 15, p. 7474-7482.
Sakane, N. et al. "Activation of HIV Transcription by the Viral Tat Protein Requires a Demethylation Step Mediated by Lysinespecific Demethylase 1 (LSD1/KDM1)", PloS Pathogens, 2011, vol. 7, Issue 8, e1002184, 12 pages.
Sanger A.R. "Reactions of Benzonitrile with Lithium Amides", Inorg. Nucl. Chem. Lett. 1973, vol. 9, p. 351-354.
Schenk T. et al. "Inhibition of the LSD1 (KDM1A) demethylase reactivates the all-trans-retinoic acid differentiation pathway in acute myeloid leukemia", Nature Medicine, 2012, vol. 18, p. 605-611.
Schildhaus, H. U. et al. "Lysine-specific demethylase 1 is highly expressed in solitary fibrous tumors, synovial sarcomas, rhabdomyosarcomas, desmoplastic small round cell tumors, and malignant peripheral nerve sheath tumors", Human Pathology, 2011, vol. 42, p. 1667-1675.
Schmidt, D. M. Z. et al. "trans-2-Phenylcyclopropylamine Is a Mechanism-Based Inactivator of the Histone Demethylase LSD1", Biochemistry 2007, vol. 46, p. 4408-4416.
Schulte, J. H. et al. "Lysine-Specific Demethylase 1 Is Strongly Expressed in Poorly Differentiated Neuroblastoma: Implications for Therapy", Cancer Res. 2009, vol. 69, p. 2065-2071.

(56) References Cited

OTHER PUBLICATIONS

Scoumanne, A. et al. "The Lysine-specific Demethylase 1 Is Required for Cell Proliferation in Both p53-dependent and -independent Manners" Journal of Biological Chemistry, 2007, vol. 282, No. 21, p. 15471-15475.

Sorna et al. "High-Throughput Virtual Screening Identifies Novel N'-(1- Phenylethylidene)-benzohydrazides as Potent, Specific, and Reversible LSD1 Inhibitors", Journal of Medicinal Chemistry, 2013, vol. 56, p. 9496-9508.

Sun, G. et al. "Histone Demethylase LSD1 Regulates Neural Stem Cell Proliferation", Molecular and Cellular Biology, 2010, vol. 30, p. 1997-2005.

Suva al. "Reconstructing and Reprogramming the Tumor-Propagating Potential of Glioblastoma Stem-like Cells", Cell, 2014, vol. 157, p. 580-594.

Varier R. et al. "Histone lysine methylation and demethylation pathways in cancer", BBA—Reviews on Cancer, vol. 1815, No. 1, 2011, pp. 75-89.

Wang, J. et al. "The lysine demethylase LSD1 (KDM1) is required for maintenance of global DNA methylation", Nature Genetics, 2009, vol. 41, No. 1, p. 125-129.

Wang, J. et al. "Novel Histone Demethylase LSD1 Inhibitors Selectively Target Cancer Cells with Pluripotent Stem Cell Properties", Cancer Research, 2011, vol. 71, p. 7238-7249.

Yee Y. K. et al. "$N^2$-Aroylanthranilamide inhibitors of human factor Xa", J. Med. Chem. vol. 43, No. 5, 2000, p. 873-882.

Zibetti C. et al. "Alternative Splicing of the Histone Demethylase LSD1/KDM1 Contributes to the Modulation of Neurite Morphogenesis in the Mammalian Nervous System", Journal of Neuroscience, 2010, vol. 30, p. 2521-2532.

IMIDAZOLES AS HISTONE DEMETHYLASE INHIBITORS

RELATED APPLICATIONS

This application is a continuation of U.S. application Ser. No. 16/301,875, now U.S. Pat. No. 10,562,914, filed on Nov. 15, 2018, which is a U.S. National Phase application, filed under 35 U.S.C. § 371(c), of International Application No. PCT/EP2017/062009, filed May 18, 2017, which claims priority to and the benefit of European Application No. 16170238.6, filed May 18, 2016, each of which is incorporated by reference herein in its entirety for all purposes.

FIELD OF THE INVENTION

The present invention relates to imidazole derivatives, pharmaceutical compositions containing such compounds and to their use in therapy.

BACKGROUND OF THE INVENTION

Alterations in the structural and functional states of chromatin, mainly determined by post-translational modifications of histone components, are involved in the pathogenesis of a variety of diseases. The enzymatic processes, which govern these post-translational modifications on the nucleosomes, have become potential targets for the so-called epigenetic therapies (Portela, A. et al. Nat. Biotechnol. 2010, 28, 1057-1068).

The discovery of an increasing number of histone lysine demethylases has highlighted the dynamic nature of the regulation of histone methylation, a key chromatin modification that is involved in eukaryotic genome and gene regulation. Histone lysine demethylases represent attractive targets for epigenetic drugs, since their expression and/or activities are often misregulated in cancer (Varier, R. A. et al. Biochim. Biophys. Acta. 2011, 1815, 75-89). A lysine can be mono-, di-, and tri-methylated and each modification, even on the same amino acid, can have different biological effects.

Histone lysine demethylases exert their activity through two different type of mechanism (Anand, R. et al. J. Biol. Chem. 2007, 282, 35425-35429; Metzger, E. et al. Nat. Struct. Mol. Biol. 2007, 14, 252-254). While the Jumonji domain-containing histone demethylases, which are iron and 2-oxoglutarate dependent oxygenases, act on mono-, di- and trimethylated lysines, the flavin-dependent (FAD) histone demethylases catalyse the cleavage of mono and dimethylated lysine residues. Currently, two FAD dependent demethylases have been identified: LSD1, also known as KDM1A, and LSD2, also known as KDM1B. (Culhane, J. C. et al. Curr. Opin. Chem. Biol. 2007, 11, 561-568, Ciccone, D. N. et al. Nature 2009, 461, 415-418).

KDM1A is a constituent in several chromatin-remodeling complexes and is often associated with the co-repressor protein CoREST. KDM1A specifically removes the methyl groups from mono- and di-methyl Lys4 of histone H3, which is a well-characterized gene activation mark. KDM1A represents an interesting target for epigenetic drugs due to its over-expression in solid and hematological tumors (Schulte, J. H. et al. Cancer Res. 2009, 69, 2065-2071; Lim, S. et al. Carcinogenesis 2010, 31, 512-520; Hayami, S. et al. Int. J. Cancer 2011, 128, 574-586; Schildhaus, H. U. et al. Hum. Pathol. 2011, 42, 1667-1675; Bennani-Baiti, I. M. et al. Hum. Pathol. 2012, 43, 1300-1307). Its over-expression correlates to tumor recurrence in prostate cancer (Kahl, P. et al. Cancer Res. 2006, 66, 11341-11347), and KDM1A has a role in various differentiation processes, such as adipogenesis (Musri, M. M. et al. J. Biol. Chem. 2010, 285, 30034-30041), muscle skeletal differentiation (Choi, J. et al. Biochem. Biophys. Res. Commun. 2010, 401, 327-332), and hematopoiesis (Hu, X. et al. Proc. Natl. Acad. Sci. USA 2009, 106, 10141-10146; Li, Y. et al. Oncogene. 2012, 31, 5007-5018). KDM1A is further involved in the regulation of cellular energy expenditure (Hino S. Et al. Nat Commun. 2012, doi: 10.1038/ncomms1755), in the regulation of thermogenesis and oxidative metabolism in adipose tissue (Duteil et al. Nat Commun. 2014 Jun. 10; 5:4093. doi: 10.1038/ncomms5093.), in the control of checkpoints of viral gene expression in productive and latent infections (Roizman, B. J. Virol. 2011, 85, 7474-7482), and more specifically in the control of herpes virus infection (Gu, H. J. Virol. 2009, 83, 4376-4385) and HIV transcription (Sakane, N. et al. PLoS Pathog. 2011, 7(8):e1002184). The role of KDM1A in the regulation of neural stem cell proliferation (Sun, G. et al. Mol. Cell Biol. 2010, 30, 1997-2005) and in the control of neuritis morphogenesis (Zibetti, C. et al. J. Neurosci. 2010, 30, 2521-2532) suggests its possible involvement in neurodegenerative diseases.

Furthermore, KDM1A has been found to be relevant in the control of other important cellular processes, such as DNA methylation (Wang, J. et al. Nat. Genet. 2009, 41(1): 125-129), cell proliferation (Scoumanne, A. et al. J. Biol. Chem. 2007, 282, 15471-15475; Cho, H. S. et al. Cancer Res. 2011, 71, 655-660), epithelial mesenchimal transition (Lin, T. et al. Oncogene. 2010, 29, 4896-4904) and chromosome segregation (Lv, S. et al. Eur. J. Cell Biol. 2010, 89, 557-563). Moreover, KDM1A inhibitors were able to reactivate silenced tumor suppressor genes (Huang, Y. et al. Proc. Natl. Acad. Sci. USA. 2007, 104, 8023-8028; Huang, Y. et al. Clin. Cancer Res. 2009, 15, 7217-7228), to target selectively cancer cells with pluripotent stem cell properties (Wang, J. et al. Cancer Res. 2011, 71, 7238-7249), as well as to reactivate the all-trans-retinoic acid differentiation pathway in acute myeloid leukemia (Schenk, T. et al. Nat Med. 2012, 18, 605-611). Moreover, KDM1A has a clear role in sustaining the oncogenic potential of MLL-AF9 translocation in leukaemia stem cells (Harris et al. Cancer Cell, 21 (2012), 473-487), as well as in the stem-like tumor propagating cells of human glioblastoma (Suva et al. Cell 2014, 157, 580-594).

The more recently discovered demethylase KDM1B (LSD2) displays similarly to KDM1A specificity for mono- and di-methylated Lys4 of histone H3. KDM1B, differently from KDM1A, does not bind CoREST and it has not been found up to now in any of KDM1A-containing protein complexes (Karytinos, A. et al. J. Biol. Chem. 2009, 284, 17775-17782). On the contrary, KDM1B forms active complexes with euchromatic histone methyltransferases G9a and NSD3 as well as with cellular factors involved in transcription elongation. KDM1B has been reported to have a role as regulator of transcription elongation rather than that of a transcriptional repressor as proposed for KDM1A (Fang, R. et al. Mol. Cell 2010, 39, 222-233).

KDM1A and KDM1B are both flavo amino oxidase dependent proteins sharing a FAD coenzyme-binding motif, a SWIRM domain and an amine oxidase domain, all of which are integral to the enzymatic activity of KDM1 family members. Moreover, both KDM1A and KDM1B show a structural similarity with the monoamine oxidases MAO-A and MAO-B. Indeed, tranylcypromine, a MAO inhibitor used as antidepressant agent, was found to be also able to inhibit KDM1A. The compound acts as an irreversible inhibitor forming a covalent adduct with the FAD cofactor.

(Lee, M. G. et al. Chem. Biol. 2006, 13, 563; Schmidt, D. M. Z. et al. Biochemistry 2007, 46, 4408). Tranylcypromine analogs and their KDM1A inhibitory activity have been described in Bioorg. Med. Chem. Lett. 2008, 18, 3047-3051, in Bioorg. Med. Chem. 2011, 19, 3709-3716, and in J. Am. Chem. Soc 2011, 132, 6827-6833. Further arylcyclopropylamine and heteroarylcyclopropylamine derivatives as KDM1A, MAO-A and/or MAO-B enzyme inhibitors are disclosed in US2010/324147, in WO2012/045883, in WO2013/022047 and in WO2011/131576.

Reversible KDM1A inhibitors are not so common and no clinical data for them are so far available. Examples of reversible inhibitors are aminothiazoles as described in Med. Chem. Commun. 2013, 4, 1513-1522, a N-(1-phenylethylidene)-benzohydrazide series (J. Med. Chem. 2013, 56, 9496-9508, WO2013025805), or thienopyrrole derivatives (WO2016/034946). Thus, there is still a need for further reversible inhibitors having useful antitumor properties, adequate selectivity and stability of action, and possibly showing a higher activity with respect to specific subclasses thereof.

DESCRIPTION OF THE INVENTION

The present invention relates to substituted imidazole derivatives having highly potent inhibitory activities of the KDM1A enzyme and selective over monoamine oxidases (MAOs), useful in the prevention or therapy of diseases and conditions associated with the activity of the histone demethylases.

According to the present invention there are provided compounds of general formula (I):

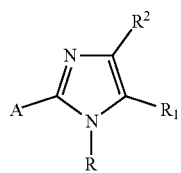

(I)

wherein
A is

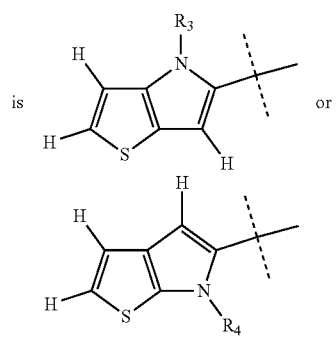

R is hydrogen or $L^1$-$R^5$;
$R^1$, $R^2$ are independently, hydrogen, $C_1$-$C_4$-alkyl, $C_3$-$C_7$ cycloalkyl, aryl, heteroaryl, —$(CH_2)_z CF_3$, or $R^1$ and $R^2$, taken together with the carbon atoms they are bound to, form with the imidazole a fused heterocycle or a fused heteroaryl;

z is an integer from zero to 6
$R^3$, $R^4$ are hydrogen or $C_1$-$C_4$-alkyl;
$L^1$ is —$(CH_2)_j$—Y—, or —$CH_2$—
j is an integer from 2 to 6;
Y is a bond, oxygen, or $CH_2$;
$R^5$ is $C_1$-$C_4$-alkyl or aryl, wherein the aryl is optionally substituted by halogen, $C_1$-$C_6$-alkyl or $L^2$-$R^6$;
$L^2$ is —$(CH_2)_m$—; —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6;
W is oxygen, sulphur, NH, or $CH_2$;
or stereoisomers or pharmaceutically acceptable salts thereof.

In one embodiment, $R^1$ and $R^2$ are independently hydrogen, $C_1$-$C_4$-alkyl, $C_3$-$C_7$ cycloalkyl, aryl, heteroaryl, or $R^1$ and $R^2$, taken together with the carbon atoms they are bound to, form with the imidazole a fused heterocycle or a fused heteroaryl.

Preferably, $R^3$ or $R^4$ are methyl or ethyl.
In a more preferred embodiment:
R is hydrogen or $L^1$-$R^5$;
$R^1$, $R^2$ are independently, hydrogen, $C_1$-$C_4$-alkyl, cyclopropyl, cyclobutyl, phenyl, pyridyl, or $R^1$ and $R^2$, taken together with the carbon atoms they are bound to, form with the imidazole a fused heterocycle or a fused heteroaryl;
$R^3$, $R^4$ are methyl or ethyl;
$L^1$ is —$(CH_2)_2$—Y— or —$CH_2$—;
Y is a bond, oxygen, or $CH_2$;
$R^5$ is methyl or phenyl optionally substituted by $L^2$-$R^6$;
$L^2$ is —W—$(CH_2)_p$—;
$R^6$ is heterocyclyl, wherein the heterocyclyl is optionally substituted by $C_1$-$C_6$-alkyl;
p is zero or an integer from 1 to 6;
W is oxygen;
or stereoisomers or pharmaceutically acceptable salts thereof.

Particularly preferred compounds of general formula (I) include:
4-methyl-5-(4-phenyl-1H-imidazol-2-yl)thieno[3,2-b]pyrrole;
5-(4-ethyl-1H-imidazol-2-yl)-4-methyl-thieno[3,2-b]pyrrole;
4-methyl-5-(4-methyl-1H-imidazol-2-yl)thieno[3,2-b]pyrrole;
5-(4-isopropyl-1H-imidazol-2-yl)-4-methyl-thieno[3,2-b]pyrrole;
5-(4-cyclopropyl-1H-imidazol-2-yl)-4-methyl-thieno[3,2-b]pyrrole;
4-methyl-5-(4-propyl-1H-imidazol-2-yl)thieno[3,2-b]pyrrole;
5-(4-cyclobutyl-1H-imidazol-2-yl)-4-methyl-thieno[3,2-b]pyrrole;
4-methyl-5-(5-methyl-4-phenyl-1H-imidazol-2-yl)thieno[3,2-b]pyrrole;
5-(5-ethyl-4-phenyl-1H-imidazol-2-yl)-4-methyl-thieno[3,2-b]pyrrole;
5-(5-isopropyl-4-phenyl-1H-imidazol-2-yl)-4-methyl-thieno[3,2-b]pyrrole;
4-ethyl-5-(4-ethyl-1H-imidazol-2-yl)thieno[3,2-b]pyrrole;
5-(4-cyclobutyl-1H-imidazol-2-yl)-4-ethyl-thieno[3,2-b]pyrrole;
4-methyl-5-(4-phenyl-5-propyl-1H-imidazol-2-yl)thieno[3,2-b]pyrrole;
5-(4-ethyl-1H-imidazol-2-yl)-6-methyl-thieno[2,3-b]pyrrole;

5-(5-ethyl-4-phenyl-1H-imidazol-2-yl)-6-methyl-thieno[2,3-b]pyrrole;
4-methyl-5-(4,5,6,7-tetrahydro-1H-benzimidazol-2-yl)thieno[3,2-b]pyrrole;
5-[4-ethyl-1-[2-[3-(4-piperidyloxy)phenoxy]ethyl]imidazol-2-yl]-4-methyl-thieno[3,2-b]pyrrole;
5-[5-ethyl-1-[2-[3-(4-piperidyloxy)phenoxy]ethyl]imidazol-2-yl]-4-methyl-thieno[3,2-b]pyrrole;
5-[4-ethyl-1-[2-[4-(4-piperidyloxy)phenoxy]ethyl]imidazol-2-yl]-4-methyl-thieno[3,2-b]pyrrole;
5-[5-ethyl-1-[2-[4-(4-piperidyloxy)phenoxy]ethyl]imidazol-2-yl]-4-methyl-thieno[3,2-b]pyrrole;
5-[4-ethyl-1-[2-[4-(pyrrolidin-3-ylmethoxy)phenoxy]ethyl]imidazol-2-yl]-4-methyl-thieno[3,2-b]pyrrole;
5-[4-ethyl-1-[2-[4-(4-piperidylmethoxy)phenoxy]ethyl]-imidazol-2-yl]-4-methyl-thieno[3,2-b]pyrrole;
5-[5-ethyl-1-[2-[4-(4-piperidylmethoxy)phenoxy]ethyl]-imidazol-2-yl]-4-methyl-thieno[3,2-b]pyrrole;
5-[1-[2-[4-(azepan-4-yloxy)phenoxy]ethyl]-4-ethyl-imidazol-2-yl]-4-methyl-thieno[3,2-b]pyrrole;
5-[1-[2-[4-(azepan-4-yloxy)phenoxy]ethyl]-5-ethyl-imidazol-2-yl]-4-methyl-thieno[3,2-b]pyrrole;
5-[4-ethyl-1-[3-[4-(4-piperidyloxy)phenyl]propyl]imidazol-2-yl]-4-methyl-thieno[3,2-b]pyrrole;
5-[5-ethyl-1-[3-[4-(4-piperidyloxy)phenyl]propyl]imidazol-2-yl]-4-methyl-thieno[3,2-b]pyrrole;
5-[4-cyclobutyl-1-[2-[4-(4-piperidyloxy)phenoxy]ethyl]imidazol-2-yl]-4-methyl-thieno[3,2-b]pyrrole;
5-[5-cyclobutyl-1-[2-[4-(4-piperidyloxy)phenoxy]ethyl]imidazol-2-yl]-4-methyl-thieno[3,2-b]pyrrole;
5-[5-ethyl-4-phenyl-1-[2-[4-(4-piperidyloxy)phenoxy]ethyl]imidazol-2-yl]-4-methyl-thieno[3,2-b]pyrrole;
5-[5-ethyl-4-phenyl-1-[2-[3-(4-piperidyloxy)phenoxy]ethyl]imidazol-2-yl]-4-methyl-thieno[3,2-b]pyrrole;
5-[4-ethyl-5-phenyl-1-[2-[3-(4-piperidyloxy)phenoxy]ethyl]imidazol-2-yl]-4-methyl-thieno[3,2-b]pyrrole;
5-[1-[2-[3-(azepan-4-yloxy)phenoxy]ethyl]-4-ethyl-imidazol-2-yl]-4-methyl-thieno[3,2-b]pyrrole;
5-[1-[2-[3-(azepan-4-yloxy)phenoxy]ethyl]-5-ethyl-imidazol-2-yl]-4-methyl-thieno[3,2-b]pyrrole;
5-[1-[2-[4-(azepan-4-yloxy)phenoxy]ethyl]-4-cyclobutyl-imidazol-2-yl]-4-methyl-thieno[3,2-b]pyrrole;
5-[1-[2-[4-(azepan-4-yloxy)phenoxy]ethyl]-5-cyclobutyl-imidazol-2-yl]-4-methyl-thieno[3,2-b]pyrrole;
5-[4-ethyl-1-[3-[4-(pyrrolidin-3-ylmethoxy)phenyl]propyl]imidazol-2-yl]-4-methyl-thieno[3,2-b]pyrrole;
5-[4-ethyl-1-[2-[4-(4-piperidyloxy)phenoxy]ethyl]imidazol-2-yl]-6-methyl-thieno[2,3-b]pyrrole;
4-methyl-5-[5-phenyl-1-[2-[4-(4-piperidyloxy)phenoxy]ethyl]-4-propyl-imidazol-2-yl]thieno[3,2-b]pyrrole;
4-methyl-5-[4-phenyl-1-[2-[4-(4-piperidyloxy)phenoxy]ethyl]-5-propyl-imidazol-2-yl]thieno[3,2-b]pyrrole;
5-[4-ethyl-1-[3-[4-(4-piperidylmethoxy)phenyl]propyl]imidazol-2-yl]-4-methyl-thieno[3,2-b]pyrrole;
5-[5-ethyl-1-[3-[4-(4-piperidylmethoxy)phenyl]propyl]imidazol-2-yl]-4-methyl-thieno[3,2-b]pyrrole;
5-[1-[3-[4-(azepan-4-yloxy)phenyl]propyl]-4-ethyl-imidazol-2-yl]-4-methyl-thieno[3,2-b]pyrrole;
5-[1-[3-[4-(azepan-4-yloxy)phenyl]propyl]-5-ethyl-imidazol-2-yl]-4-methyl-thieno[3,2-b]pyrrole;
5-[5-ethyl-4-phenyl-1-[3-[4-(4-piperidyloxy)phenyl]propyl]imidazol-2-yl]-4-methyl-thieno[3,2-b]pyrrole;
5-[4-ethyl-5-phenyl-1-[3-[4-(4-piperidyloxy)phenyl]propyl]imidazol-2-yl]-4-methyl-thieno[3,2-b]pyrrole;
5-[4-isopropyl-5-phenyl-1-[2-[4-(4-piperidyloxy)phenoxy]ethyl]imidazol-2-yl]-4-methyl-thieno[3,2-b]pyrrole;
5-[4-cyclobutyl-1-[3-[4-(4-piperidyloxy)phenyl]propyl]imidazol-2-yl]-4-methyl-thieno[3,2-b]pyrrole;
5-[5-cyclobutyl-1-[3-[4-(4-piperidyloxy)phenyl]propyl]imidazol-2-yl]-4-methyl-thieno[3,2-b]pyrrole;
4-methyl-5-[4-phenyl-1-[3-[4-(4-piperidyloxy)phenyl]propyl]imidazol-2-yl]thieno[3,2-b]pyrrole;
5-[1-[3-[3,4-bis(4-piperidylmethoxy)phenyl]propyl]-4-ethyl-imidazol-2-yl]-4-methyl-thieno[3,2-b]pyrrole;
4-methyl-5-[1-[2-[4-(4-piperidyloxy)phenoxy]ethyl]-4-propyl-imidazol-2-yl]thieno[3,2-b]pyrrole;
4-methyl-5-[1-[2-[4-(4-piperidyloxy)phenoxy]ethyl]-5-propyl-imidazol-2-yl]thieno[3,2-b]pyrrole;
5-[1-[3-[4-(azepan-4-yloxy)phenyl]propyl]-4-propyl-imidazol-2-yl]-4-methyl-thieno[3,2-b]pyrrole;
5-[1-[3-[4-(azepan-4-yloxy)phenyl]propyl]-5-propyl-imidazol-2-yl]-4-methyl-thieno[3,2-b]pyrrole;
5-[1-[3-[3,4-bis(4-piperidylmethoxy)phenyl]propyl]-5-ethyl-imidazol-2-yl]-4-methyl-thieno[3,2-b]pyrrole;
5-[4-ethyl-1-[2-[4-(4-piperidyloxy)phenyl]ethyl]imidazol-2-yl]-4-methyl-thieno[3,2-b]pyrrole;
5-[4-cyclobutyl-1-[3-[4-(pyrrolidin-3-ylmethoxy)phenyl]propyl]imidazol-2-yl]-4-methyl-thieno[3,2-b]pyrrole;
5-[5-cyclobutyl-1-[3-[4-(pyrrolidin-3-ylmethoxy)phenyl]propyl]imidazol-2-yl]-4-methyl-thieno[3,2-b]pyrrole;
5-[1-[3-[4-(azepan-4-yloxy)phenyl]propyl]-4-cyclobutyl-imidazol-2-yl]-4-methyl-thieno[3,2-b]pyrrole;
5-[1-[3-[4-(azepan-4-yloxy)phenyl]propyl]-5-cyclobutyl-imidazol-2-yl]-4-methyl-thieno[3,2-b]pyrrole;
4-methyl-5-[1-[3-[4-(4-piperidyloxy)phenyl]propyl]-4-propyl-imidazol-2-yl]thieno[3,2-b]pyrrole;
4-methyl-5-[1-[3-[4-(4-piperidyloxy)phenyl]propyl]-5-propyl-imidazol-2-yl]thieno[3,2-b]pyrrole;
5-[4-cyclobutyl-1-[3-[4-(4-piperidylmethoxy)phenyl]propyl]imidazol-2-yl]-4-methyl-thieno[3,2-b]pyrrole;
5-[5-cyclobutyl-1-[3-[4-(4-piperidylmethoxy)phenyl]propyl]imidazol-2-yl]-4-methyl-thieno[3,2-b]pyrrole;
4-methyl-5-[4-propyl-1-[3-[4-(pyrrolidin-3-ylmethoxy)phenyl]propyl]imidazol-2-yl]thieno[3,2-b]pyrrole;
4-methyl-5-[5-propyl-1-[3-[4-(pyrrolidin-3-ylmethoxy)phenyl]propyl]imidazol-2-yl]thieno[3,2-b]pyrrole;
5-[4-cyclobutyl-1-[2-[4-(4-piperidyloxy)phenyl]ethyl]imidazol-2-yl]-4-methyl-thieno[3,2-b]pyrrole;
5-[4-ethyl-1-[3-[3-(4-piperidyloxy)phenyl]propyl]imidazol-2-yl]-4-methyl-thieno[3,2-b]pyrrole;
5-[5-ethyl-1-[3-[3-(4-piperidyloxy)phenyl]propyl]imidazol-2-yl]-4-methyl-thieno[3,2-b]pyrrole;
4-methyl-5-[1-[2-[4-(4-piperidyloxy)phenyl]ethyl]-4-propyl-imidazol-2-yl]thieno[3,2-b]pyrrole;
4-methyl-5-[1-[2-[4-(4-piperidyloxy)phenyl]ethyl]-5-propyl-imidazol-2-yl]thieno[3,2-b]pyrrole;
4-methyl-5-[1-[3-[4-(4-piperidyloxymethyl)phenyl]propyl]-4-propyl-imidazol-2-yl]thieno[3,2-b]pyrrole;
4-methyl-5-[1-[3-[4-(4-piperidyloxymethyl)phenyl]propyl]-5-propyl-imidazol-2-yl]thieno[3,2-b]pyrrole;
5-[1-[2-[4-(azepan-4-yloxy)phenoxy]ethyl]-4-propyl-imidazol-2-yl]-4-methyl-thieno[3,2-b]pyrrole;
5-[1-[2-[4-(azepan-4-yloxy)phenoxy]ethyl]-5-propyl-imidazol-2-yl]-4-methyl-thieno[3,2-b]pyrrole;
5-[5-ethyl-1-(2-methoxyethyl)imidazol-2-yl]-4-methyl-thieno[3,2-b]pyrrole;
5-[4-ethyl-1-(2-methoxyethyl)imidazol-2-yl]-4-methyl-thieno[3,2-b]pyrrole;
5-[5-ethyl-1-(2-phenoxyethyl)imidazol-2-yl]-4-methyl-thieno[3,2-b]pyrrole;
5-[4-ethyl-1-(2-phenoxyethyl)imidazol-2-yl]-4-methyl-thieno[3,2-b]pyrrole;

5-(1-benzyl-5-ethyl-imidazol-2-yl)-4-methyl-thieno[3,2-b]pyrrole;
4-methyl-5-[4-(4-pyridyl)-1H-imidazol-2-yl]thieno[3,2-b]pyrrole;
5-(1H-benzimidazol-2-yl)-4-methyl-thieno[3,2-b]pyrrole;
4-methyl-5-[1-[3-[4-(4-piperidyloxy)phenyl]propyl]benzimidazol-2-yl]thieno[3,2-b]pyrrole;
5-[4-cyclobutyl-1-[3-[4-(4-piperidyloxy)phenyl]propyl]imidazol-2-yl]-6-methyl-thieno[2,3-b]pyrrole
5-[5-cyclobutyl-1-[3-[4-(4-piperidyloxy)phenyl]propyl]imidazol-2-yl]-6-methyl-thieno[2,3-b]pyrrole
5-[4-cyclobutyl-1-[3-[4-[[(3R)-pyrrolidin-3-yl]methoxy]phenyl]propyl]imidazol-2-yl]-4-methyl-thieno[3,2-b]pyrrole
5-[5-cyclobutyl-1-[3-[4-[[(3R)-pyrrolidin-3-yl]methoxy]phenyl]propyl]imidazol-2-yl]-4-methyl-thieno[3,2-b]pyrrole
5-[4-cyclobutyl-1-[3-[4-[[(3 S)-pyrrolidin-3-yl]methoxy]phenyl]propyl]imidazol-2-yl]-4-methyl-thieno[3,2-b]pyrrole
5-[5-cyclobutyl-1-[3-[4-[[(3 S)-pyrrolidin-3-yl]methoxy]phenyl]propyl]imidazol-2-yl]-4-methyl-thieno[3,2-b]pyrrole
5-[4-cyclobutyl-1-[2-[4-(4-piperidylmethoxy)phenoxy]ethyl]imidazol-2-yl]-4-methyl-thieno[3,2-b]pyrrole
5-[4-cyclobutyl-1-[3-[3-(4-piperidyloxy)phenyl]propyl]imidazol-2-yl]-4-methyl-thieno[3,2-b]pyrrole
5-[5-cyclobutyl-1-[3-[3-(4-piperidyloxy)phenyl]propyl]imidazol-2-yl]-4-methyl-thieno[3,2-b]pyrrole
5-[4-cyclobutyl-1-[2-[3-(4-piperidyloxy)phenoxy]ethyl]imidazol-2-yl]-4-methyl-thieno[3,2-b]pyrrole
5-[5-cyclobutyl-1-[2-[3-(4-piperidyloxy)phenoxy]ethyl]imidazol-2-yl]-4-methyl-thieno[3,2-b]pyrrole
4-methyl-5-[4-methyl-1-[3-[4-(4-piperidyloxy)phenyl]propyl]imidazol-2-yl]thieno[3,2-b]pyrrole
4-methyl-5-[5-methyl-1-[3-[4-(4-piperidyloxy)phenyl]propyl]imidazol-2-yl]thieno[3,2-b]pyrrole
5-[4-cyclobutyl-1-[2-[4-(4-piperidylmethoxy)phenyl]ethyl]imidazol-2-yl]-4-methyl-thieno[3,2-b]pyrrole
4-methyl-5-[1-[3-[3-(4-piperidyloxy)phenyl]propyl]-4-propyl-imidazol-2-yl]thieno[3,2-b]pyrrole
4-methyl-5-[1-[3-[3-(4-piperidyloxy)phenyl]propyl]-5-propyl-imidazol-2-yl]thieno[3,2-b]pyrrole
4-methyl-5-[1-[2-[3-(4-piperidyloxy)phenoxy]ethyl]-4-propyl-imidazol-2-yl]thieno[3,2-b]pyrrole
4-methyl-5-[1-[2-[3-(4-piperidyloxy)phenoxy]ethyl]-5-propyl-imidazol-2-yl]thieno[3,2-b]pyrrole
4-methyl-5-[1-[3-[4-(4-piperidylmethoxy)phenyl]propyl]-4-propyl-imidazol-2-yl]thieno[3,2-b]pyrrole
4-methyl-5-[1-[3-[4-(4-piperidylmethoxy)phenyl]propyl]-5-propyl-imidazol-2-yl]thieno[3,2-b]pyrrole
5-[1-[2-[4-(azepan-4-yloxy)phenoxy]ethyl]-4-propyl-imidazol-2-yl]-4-methyl-thieno[3,2-b]pyrrole
5-[1-[2-[4-(azepan-4-yloxy)phenoxy]ethyl]-5-propyl-imidazol-2-yl]-4-methyl-thieno[3,2-b]pyrrole
4-methyl-5-[4-(3,3,3-trifluoropropyl)-1H-imidazol-2-yl]thieno[3,2-b]pyrrole
4-methyl-5-[1-[3-[4-(4-piperidyloxy)phenyl]propyl]-4-(3,3,3-trifluoropropyl)imidazol-2-yl]thieno[3,2-b]pyrrole or stereoisomers or pharmaceutically acceptable salts thereof.

In one embodiment, the compound of general formula (I) is a reversible KDM1A (LSD1) inhibitor.

In another embodiment, the invention provides the compounds of general formula (I) for use as medicament.

In another embodiment, the invention provides the compounds of general formula (I) for the use in the treatment and/or prevention of cancer, infectious diseases or a disease characterized by aberration of cellular energy metabolism, such as obesity. Preferably, the compounds of general formula (I) are for the use in the treatment and/or prevention of leukemia, non-small cell lung cancer, hepatocellular carcinoma, or glioblastomas. Still preferably the glioblastomas are giant cell glioblastoma or gliosarcoma.

In another embodiment, the invention provides a method for treating or preventing cancer, such as leukemia, non-small cell lung cancer, hepatocellular carcinoma, or glioblastomas, infectious diseases or a disease characterized by aberration of cellular energy metabolism, such as obesity, wherein the method comprises the step of administering a compound of general formula (I) to a subject in an effective amount.

In a further embodiment, the invention provides the use of a compound of general formula (I) for the manufacture of a medicament for treating or preventing cancer, such as leukemia, non-small cell lung cancer, hepatocellular carcinoma, or glioblastomas, infectious diseases or a disease characterized by aberration of cellular energy metabolism, such as obesity.

A further embodiment of the invention is a pharmaceutical composition comprising a compound of general formula (I), together with a pharmaceutically acceptable excipient and/or diluent. The pharmaceutical composition may further comprise at least one further therapeutic agent, preferably selected from the group consisting of histone deacetylase inhibitors, retinoid receptor modulators, anti-proliferative/antineoplastic agents, cytostatic agents, agents which inhibit cancer cell invasion, inhibitors of growth factor function, anti-angiogenic agents, cell cycle inhibitors, proteasome inhibitors, HSP90 inhibitors, selective COX-2 inhibitors or a chemotherapeutic agent. In the present invention, "aryl" represents a mono or bicyclic aromatic ring system of, respectively, 6, 9 or 10 atoms, examples of such an aryl are phenyl, indenyl, indanyl and naphthyl and tetrahydronaphthalenyl. Substituted aryl means that the hydrogen atoms on independently each carbon atom may be independently replaced by a substituent as defined herein above.

"Heteroaryl" represents a mono or bicyclic heteroaromatic ring system of, respectively, 5 to 10 members, which contains one, two, three or four heteroatoms selected from nitrogen, oxygen or sulphur and one to nine carbon atoms. Examples of said heteroaryls include, but are not limited to: pyrrolyl, furyl, thienyl, pyrazolyl, imidazolyl, oxazolyl, thiazolyl, 1,2,3-oxadiazolyl, 1,3,4-thiadiazolyl, tetrazolyl, pyridyl, pyridazinyl, pyrimidinyl, pyrazinyl, indolyl, isoindolyl, benzo[b]furanyl, benzo[b]thienyl, benzopyranyl, indazolyl, benzimidazolyl, purinyl, quinolyl, isoquinolyl, quinazolinyl, and quinoxalinyl.

"Heterocyclyl" represents a mono, bicyclic or a spirocyclic saturated or partially saturated non-aromatic ring system of, respectively, 4 to 12 members, which contains one, two, or three heteroatoms selected from nitrogen, oxygen, and sulphur and three to eleven carbon atoms. Examples of such heterocycles include, but are not limited to: pyrrolidyl, pyrrolidinyl, piperidyl, piperidinyl, piperazinyl, tetrahydrofuranyl, tetrahydropyranyl, morpholinyl, thiomorpholinyl, tetrahydroquinolinyl, tetrahydroisoquinolinyl, tetrahydroquinoxalinyl, benzodioxolyl, 2,3-dihydro-benzodioxinyl, benzoxazolyl, azetidyl, azepinyl, and diazapinyl. Examples of bicyclic ring systems include, but are not limited to, 2-aza-bicyclo[2.2.1]heptanyl, 2,5-diaza-bicyclo[2.2.1]hept-2-yl or 8-azabicyclo[3.2.1]octanyl. Examples of spirocyclic ring systems include, but are not limited to, 3,8-diazaspiro[4.5]decane. Substituted heterocyclyl means that one or two hydrogen atoms on independently each carbon atom or heteroatom may be independently replaced by a substituent as defined herein above.

"Fused heterocycle" represents a bicyclic partially saturated non-aromatic ring system of, respectively, 8 to 12 members. Examples of such heterocycles include, but are not limited to: tetrahydrocyclopenta[d]imidazole, tetrahydrobenzimidazol or hexahydrocyclohepta[d]imidazole.

"Fused heteroaryl" represents a bicyclic aromatic ring system. In accordance with the invention, one ring of the fused heteroaryl is formed from the imidazole ring of the compound of formula I. An example of such heteroaryl includes but is not limited to benzimidazol.

The term "$C_1$-$C_6$ alkyl" refers to a straight or branched hydrocarbon chain radical, consisting solely of carbon and hydrogen atoms, having from one to six carbon atoms. The "$C_1$-$C_6$ alkyl" group is preferably a linear or branched $C_1$-$C_4$ alkyl group, more preferably a $C_1$-$C_2$ alkyl group. Suitable examples of $C_1$-$C_6$ alkyl include methyl, ethyl, n-propyl, isopropyl, butyl, tert-butyl, pentyl, and hexyl. The term "$C_1$-$C_4$ alkyl" refers to a straight or branched hydrocarbon chain radical, consisting solely of carbon and hydrogen atoms, having from one to four carbon atoms.

The term "$C_{3-7}$ cycloalkyl" refers to a saturated monocyclic hydrocarbon ring system having three to seven carbon atoms. Suitable examples of $C_{3-6}$-cycloalkyl groups include cyclopropyl, cyclobutyl, cyclopentyl, and cyclohexyl.

The term "halogen" refers to fluoro, chloro, bromo, or iodo. "Halogens" are preferably fluorine, chlorine or bromine, being in particular fluorine or chlorine.

"Leaving group" refers to halogen, preferably to chloride, bromide or iodide.

"Reversible inhibitor" is an inhibiting molecular entity that interacts with an enzyme by non-covalent interactions and is able to associate/dissociate to the enzyme.

Pharmaceutically acceptable salts comprise conventional non-toxic salts obtained by salification of a compound of formula (I) with inorganic acids (e.g. hydrochloric, hydrobromic, sulphuric, or phosphoric acids), or with organic acids (e.g. acetic, propionic, succinic, benzoic, sulfanilic, 2-acetoxy-benzoic, cinnamic, mandelic, salicylic, glycolic, lactic, oxalic, malic, maleic, malonic, fumaric, tartaric, citric, p-toluenesulfonic, methanesulfonic, ethanesulfonic, or naphthalensulfonic acids). For reviews on suitable pharmaceutical salts see Berge S. M. et al., J. Pharm. Sci. 1977, 66, 1-19; Gould P. L. Int. J. Pharm 1986, 33, 201-217; and Bighley et al. Encyclopedia of Pharmaceutical Technology, Marcel Dekker Inc, New York 1996, Volume 13, page 453-497. Other salts, which are not pharmaceutically acceptable, for example the trifluoroacetate salt, may be useful in the preparation of compounds of this invention and these form a further aspect of the invention. The invention includes within its scope all possible stoichiometric and non-stoichiometric forms of the salts of the compounds of formula (I).

In addition, the compounds of formula (I) may exist in unsolvated as well as in solvated forms with pharmaceutically acceptable solvents such as water, EtOH and the like.

Certain compounds of formula (I) may exist in stereoisomeric forms (e.g. they may contain one or more asymmetric carbon atoms). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted.

The invention also includes all suitable isotopic variations of a compound of the invention. Examples of isotopes that can be incorporated into compounds of the invention include isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the invention, for example, those in which a radioactive isotope such as $^3H$ or $^{14}C$ is incorporated, are useful in drug and/or substrate tissue distribution studies. Further, substitution with isotopes such as deuterium $^2H$, may afford certain therapeutic advantages resulting from greater metabolic stability. Isotopic variations of the compounds of the invention can generally be prepared by conventional procedures such as by the illustrative methods or by the preparations described in the examples hereafter using appropriate isotopic variations of suitable reagents.

Imidazoles of formula (I), wherein R is hydrogen, can be synthesized from amidine of formula A1 by condensation with α-halogeno ketones of formula A2, which are commercially available or can be prepared according conventional methods well known to a person skilled in art or following the procedures described in WO 2012/049277, and where X is chlorine, bromine or iodine (Li, B. et al. Org. Process Res. Dev. 2002, 6, 682-683) in a suitable solvent, for instance THF or a THF/water mixture, at temperatures ranging from room temperature to reflux, as represented in Scheme A-I below.

Scheme A-I

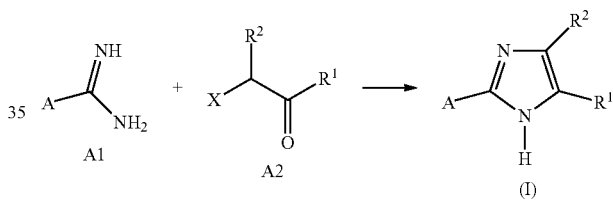

wherein A, $R^1$, and $R^2$ are as defined above and X is a chlorine, bromine or iodine.

Imidazoles of formula (I), wherein R is $L^1$-$R^5$ and $L^1$ and $R^5$ are as defined above, can obtained by reaction of compounds of formula (I), wherein R is hydrogen, with derivatives of formula A3, wherein LG is a leaving group, for example bromine, in a suitable solvent, for instance dimethylacetamide, and in presence of a base as represented in Scheme A2 below:

Scheme A-II

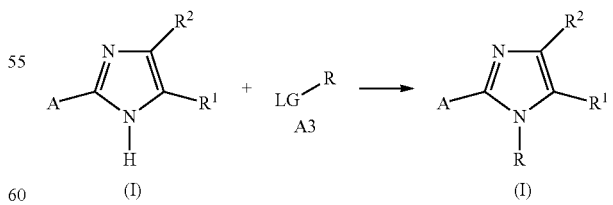

wherein A, $R^1$, and $R^2$ are as defined above, R is $L^1$-$R^5$ (with $L^1$ and $R^5$ as defined above) and LG is a leaving group.

Amidines of formula A1 can be prepared starting from compounds of formula B1 and B2 as described in Scheme B below:

Scheme B

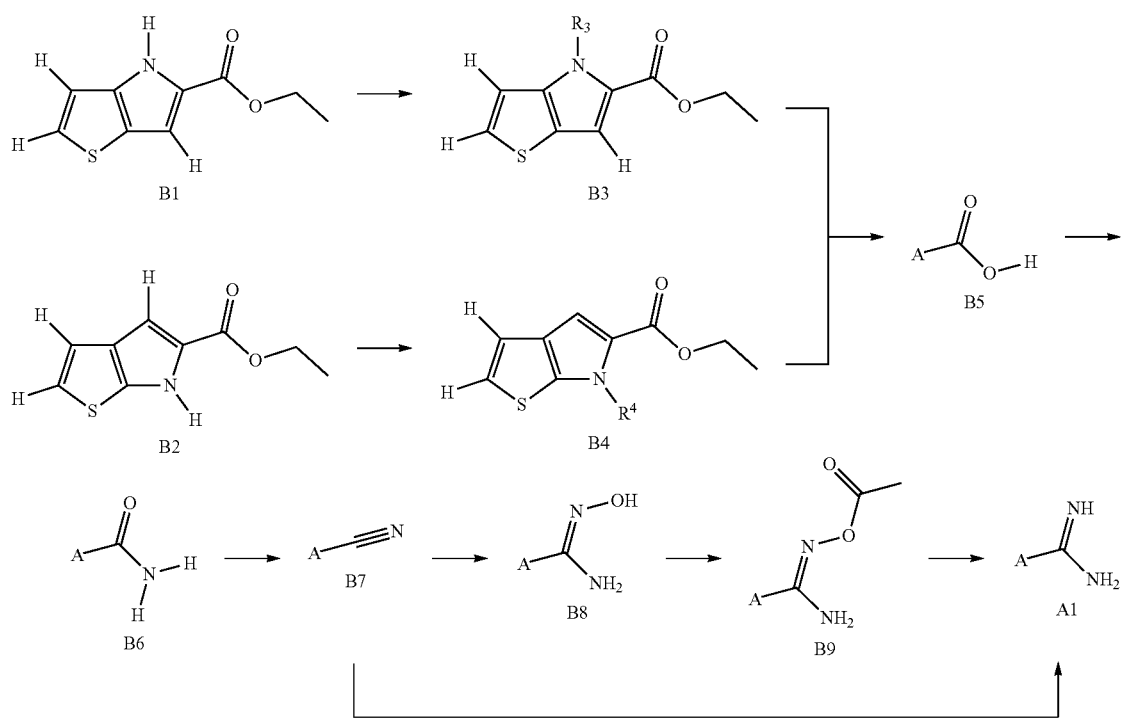

wherein R³, R⁴ and A are as defined above.

Ethyl 4H-thieno[3,2-b]pyrrole-5-carboxylate (compound B1, Fluorochem, Cat No. 067104) and ethyl 6H-thieno[2,3-b]pyrrole-5-carboxylate (compound B2, Sigma Aldrich, Cat. No. PH011284) are commercially available. Compound B1 or B2 can be alkylated with a suitable alkyl halide $R^3$-$LG^1$ or $R^4$-$LG^1$, where $R^3$ and $R^4$ are as defined above and $LG^1$ is a leaving group, for example bromide or iodide, in presence of a suitable base, such as NaH, in a suitable solvent, such as DMF, at a temperature ranging from about 0° C. to about 50° C.

The ethyl ester group of a compound of formula B3 or B4 can be hydrolysed into a carboxylic acid of formula B5 according to known methods, e.g. by treatment with a base, such as LiOH or NaOH, in a suitable solvent, for example in ethanol, in THF or in a ethanol/water mixture. The hydrolysis of the ethyl ester can be carried out at a temperature ranging from 0° C. to the boiling point of the solvent.

The carboxylic acid of formula B5 is converted into the primary amide of formula B6 according to conventional methods well known to a person skilled in art. For example, the carboxylic acid of formula B5 is converted into a suitable acylating agent, such as an acyl chloride, which is then treated with $NH_3$ in a suitable solvent such as water at 0° C.

Compound of formula B6 can be transformed into nitrile of formula B7 with dehydrating agents such as phosphorus pentoxide, $SOCl_2$, DBU/ethyl dichlorophosphate in a suitable solvent, for example $CH_2Cl_2$, toluene, acetonitrile at a temperature ranging from about 0° C. to reflux.

Amidine of formula A1 can be prepared from a compound of formula B7 by amidation of imidates (Pinner reaction), hydrolysis of N-silylated arylamidines (A. R. Sanger, Inorg. Nucl. Chem. Lett. 1973, 9, 351), addition of aluminium amide to nitrile (Tetrahedron Letters 1995, 48, 8761-8764), or by reduction of acylated amidoxime of formula B9, that can be obtained by reaction of nitrile of formula B7 with hydroxyl amine, followed by reaction with acetic anhydride. Reduction of a compound of formula B9 can be carried out for instance by catalytic hydrogenation with palladium on charcoal using reducing agents such as $H_2$ (Ismail, M. A. et al. J. Med. Chem. 2003, 46, 4761-4769, Lange, U. E. W et al. Bioorg. Med. Chem. Lett. 2003, 13, 2029-2033), potassium or ammonium formiate (Nadrah, K. et al. Synlett, 2007, 1257-125, Jnaneshwara, G. K. et al. J. Chem. Research 1998, 160-161), triethyl silane (Mahajan, U. S. et al. Synthetic Communications 2011, 41, 2195-2199) or with Zn in acetic acid (Goswami, R. et al. Bioorg. Med. Chem. 2014, 22, 3187-3203).

Compounds of formula A3 can be prepared by known methods. For instance a compound of formula C5, where LG and $R^6$ are as defined above, Y and $L^2$ are oxygen can be obtained by the reaction of a diol derivative of formula C1 with an alcohol of formula C2, that is carried out under the standard conditions of the Mitsunobu reaction, for instance by reaction with triphenylphosphine and diethylazodicarboxylate, at a temperature ranging from about 0° C. to 80° C., in a suitable solvent, such as tetrahydrofuran or toluene, for a time varying from about 30 min up to 72 h, to give a compound of formula C3. Reaction of a compound of formula C3 with an alcohol of formula C4 under the standard condition of the Mitsunobu reaction provides the intermediate C5 as represented in Scheme C below:

Scheme C

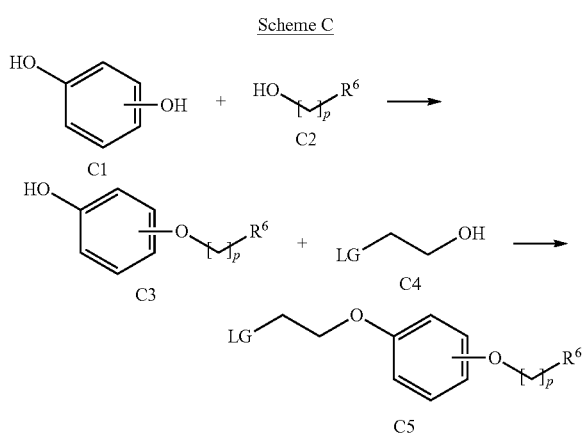

wherein p, R⁶ and LG are as defined above.

Compounds of formula C1, C2, and C4 are known compounds or can be prepared by known methods.

Alternatively, reaction of a compound of formula D1 with an alcohol of formula D2 under the standard condition of the Mitsunobu reaction provides the intermediate D3 as represented in Scheme D below:

Scheme D

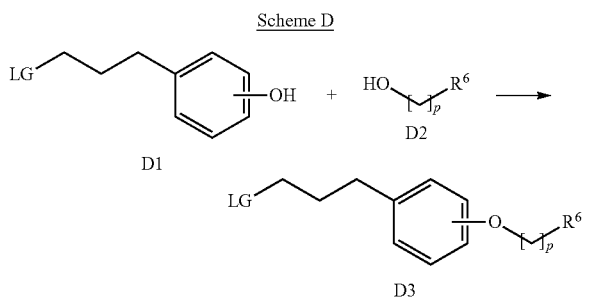

wherein p, R⁶ and LG are as defined above.

Compounds of formula D1 and D2 are known compounds or can be prepared by known methods. In the case it is necessary to protect a chemical group of a compound of the present invention and/or an intermediate thereof, before carrying out one of the before described reactions, said chemical group can be protected and deprotected according to known methods. A thorough discussion for protection/deprotection steps is provided for example in Greene and Wuts (Greene, T. W.; Wuts, P. G. M. "Protective Groups in Organic Synthesis", John Wiley & Sons Inc., 2006) or in Kocienski (Kocienski, P. J. "Protecting Groups", George Thieme Verlag, 2005).

Salification of the compounds of formula (I), and preparation of compounds of formula (I), free of their salts, can be carried out by known conventional methods.

In view of the above described mechanisms of action, the compounds of the present invention are useful in the prevention or treatment of tumor type diseases, including but not limited to: acute and chronic myeloid leukaemia, acute and chronic lymphoblastic leukaemia, myelodysplastic syndromes, multiple myeloma, Hodgkin's disease, non-Hodgkin's lymphomas, cutaneous and peripheral T-cell lymphoma, adult T-cell leukemia, large B-cell lymphoma; mammary tumors; pulmonary tumors and pleural mesotheliomas, adenocarcinoma, non-small lung cancer, small-cell lung cancer; skin tumors including basal cell carcinomas (basaliomas), melanomas, squamous cell carcinoma, Kaposi's sarcoma, keratocanthomas, osteosarcomas, fibrosarcomas, rhabdomyosarcomas, neuroblastomas, glioblastomas, cerebral tumors, head and neck cancer, testicular and ovarian tumors, cervical carcinoma, endometrial and prostate tumors (for example advanced prostate cancer), thyroid carcinomas (for example tyroid follicular cancer), colon cancers (for example colon adenocarcinoma, colon adenoma), gastric tumors and gastrointestinal adenocarcinomas, hepatocellular carcinomas, pancreatic carcinomas (for example exocrine pancreatic carcinoma), renal tumors, teratocarcinomas and embryonic carcinomas.

The compounds of the invention are also useful in the prevention or treatment of infections, including, but not limited to, infections caused by protozoa, fungi, phytotoxic agents, viruses and parasites, for example HIV or herpes virus infections.

Furthermore, the compounds of the invention are also useful in the prevention or treatment of obesity.

The compounds of formula (I), can also be used in combination with additional agents, in particular anti-tumor and differentiating agents, either by separate administrations, or by including the two active principles in the same pharmaceutical formulation. Non-exhaustive examples of suitable additional agents include:

a) histone deacetylase inhibitors (for example, but not limited to SAHA, PXD101, JNJ-26481585, SB939, ITF-2357, LBH589, PCI-24781, valproic acid, butyric acid, MS-275, MGCD0103 and FK-228);

b) retinoid receptor modulators such as 13-cis-retinoic acid, 9-cis-retinoic acid, bexarotene, alitretinoin, or tretinoin; vitamin D;

c) antiproliferative/antineoplastic drugs and combinations thereof, as used in medical oncology, such as alkylating agents (for example platin derivatives like cis-platin, carboplatin, oxaliplatin, lobaplatin, satraplatin, nedaplatin, heptaplatin; nitrogen mustard such as chlorambucil, melphalan, chlormethine, cyclophosphamide, ifosfamide, trofosfamide, uramustine, bendamustine, estramustine; busulphan, temozolomide or nitrosoureas); antimetabolites (for example antifolates such as aminopterin, methotrexate, pemetrexed, raltitrexed); purines such as cladribine, clofarabine, fludarabine, mercaptopurine, pentostatin, thioguanine; pyrimidines like capecitabine, cytarabine, fluorouracil, floxuridine, gemcitabine; azacitidine, decitabine; cytosine arabinoside or hydroxyurea; antitumour antibiotics (for example anthracyclines like aclarubicin, amrubicin, daunomycin, doxorubicin, epirubicin, idarabicin, valrubicin, zorubicine; mitoxantrone; or antibiotics from streptomyces like actinomycin, bleomycin, mitomycin, or plicamycin); antimitotic agents (for example vinca alkaloids like vincristine, vinblastine, vindesine or vinorelbine; taxoids like docetaxel, paclitaxel or tesetaxel; epothilones like ixabepilone) and topoisomerase inhibitors (for example epipodophyllotoxins like etoposide and teniposide; amsacrine, camptothecin, irinotecan, rubitecan, and topotecan);

d) cytostatic agents such as antioestrogens (for example but not limited to tamoxifen, toremifene, raloxifene, droloxifene and idoxifene), oestrogen receptor down regulators (for example but not limited to fulvestrant), antiandrogens (for example but not limited to bicalutamide, flutamide, nilutamide, liarozole or cyproterone acetate), LHRH antagonists or LHRH agonists (for example but not limited to goserelin, leuprorelin or buserelin), progestogens (for example but not limited to megestrol acetate), aromatase inhibitors (for example but not limited to anastrozole, letrozole, vorazole and exemestane) and inhibitors of 5-alpha-reductase such as finasteride;

e) agents which inhibit cancer cell invasion (for example metalloproteinase inhibitors and inhibitors of urokinase plasminogen activator receptor function);

f) inhibitors of growth factor function, for example growth factor antibodies, growth factor receptor antibodies (for example but not limited to the anti-erbb2 antibody trastuzumab, the anti-erbb1 antibody cetuximab and panitumumab, the anti IGF1R antibody figitumumab), farnesyl transferase inhibitors, MEK inhibitors, tyrosine kinase inhibitors and serine/threonine kinase inhibitors, for example enzastaurin, dasatinib, erlotinib, gefitinib, imatinib, lapatinib, nilotinib, sorafenib, sunitinib, everolimus, sirolimus or temsirolimus;

g) antiangiogenic agents such as those which inhibit the effects of vascular endothelial growth factor, for example the anti-vascular endothelial cell growth factor antibody bevacizumab, lenalidomide or thalidomide;

h) cell cycle inhibitors including for example CDK inhibitors (for example but not limited to flavopiridol, roscovitine) and other inhibitors of cell cycle checkpoints; inhibitors of aurora kinase and other kinases involved in mitosis and cytokinesis regulation;

i) proteasome inhibitors (for example but not limited to lactacystin, bortezomib, epoxomicin);

j) HSP90 inhibitors (for example but not limited to AT-13387, KOS-953, KOS-1022, CNF-1010, CNF-2024, SNX 5422, STA-9090, NVP-HSP990, NVP-AUY922, PU-H17 and XL-888)

k) Selective COX-2 inhibitors (for example but not limited to celecoxib), or non selective NSAIDs (for example but not limited to diclofenac, flurbiprofen, ibuprofen, ketoprofen, or naproxen).

In another aspect, a compound of general formula (I) can be used in combination with radiation therapy. In yet another aspect, a compound of general formula (I) may be administered in combination with standard chemotherapy combinations such as, but not restricted to, CMF (cyclophosphamide, methotrexate and 5-fluorouracil), CAF (cyclophosphamide, doxorubicin and 5-fluorouracil), AC (doxorubicin and cyclophosphamide), FEC (5-fluorouracil, epirubicin, and cyclophosphamide), ACT or ATC (doxorubicin, cyclophosphamide, and paclitaxel), or CMFP (cyclophosphamide, methotrexate, 5-fluorouracil and prednisone).

The invention also provides pharmaceutical compositions comprising one or more compounds of formula (I), and one or more pharmaceutically acceptable excipient and/or diluent. The pharmaceutical compositions can be chosen on the basis of the treatment requirements. Such compositions are prepared by blending and are suitably adapted to oral or parenteral administration, and as such can be administered in the form of tablets, capsules, oral preparations, powders, granules, pills, injectable or infusible liquid, solutions, suspensions, emulsions, suppositories, ointments, creams, lotions, gels, pastes, transdermal delivery devices.

Tablets and capsules for oral administration are normally presented in unit dose form and contain conventional excipients such as binders, fillers (including cellulose, mannitol, lactose), diluents, tableting agents, lubricants (including magnesium stearate), detergents, disintegrants (e.g. polyvinylpyrrolidone and starch derivatives such as sodium glycolate starch), coloring agents, flavoring agents, and wetting agents (for example sodium lauryl sulfate).

The oral solid compositions can be prepared by conventional methods of blending, filling or tableting. The blending operation can be repeated to distribute the active principle throughout compositions containing large quantities of fillers. Such operations are conventional.

Oral liquid preparations can be in the form of, for example, aqueous or oily suspensions, solutions, emulsions, syrups or elixirs, or can be presented as a dry product for reconstitution with water or with a suitable vehicle before use. Such liquid preparations can contain conventional additives such as suspending agents, for example sorbitol, syrup, methyl cellulose, gelatin, hydroxyethyl cellulose, carboxymethyl cellulose, aluminium stearate gel, or hydrogenated edible fats; emulsifying agents, such as lecithin, sorbitan monooleate, or acacia; non-aqueous vehicles (which can include edible oils), such as almond oil, fractionated coconut oil, oily esters such as esters of glycerine, propylene glycol, or ethyl alcohol; preservatives, such as methyl or propyl p-hydroxybenzoate or sorbic acid, and if desired, conventional flavoring or coloring agents. Oral formulations also include conventional slow-release formulations such as enterically coated tablets or granules.

Pharmaceutical preparation for administration by inhalation can be delivered from an insufflator or a nebulizer pressurized pack.

For parenteral administration fluid unit dosages can be prepared, containing the compound and a sterile vehicle. The compound can be either suspended or dissolved, depending on the vehicle and concentration. The parenteral solutions are normally prepared by dissolving the compound in a vehicle, sterilising by filtration, filling suitable vials and sealing. Advantageously, adjuvants such as local anaesthetics, preservatives and buffering agents can also be dissolved in the vehicle. To increase the stability, the composition can be frozen after having filled the vials and removed the water under vacuum. Parenteral suspensions are prepared in substantially the same manner, except that the compound can be suspended in the vehicle instead of being dissolved, and sterilized by exposure to ethylene oxide before suspending in the sterile vehicle. Advantageously, a surfactant or wetting agent can be included in the composition to facilitate uniform distribution of the compound of the invention.

For buccal or sublingual administration the compositions may be tablets, lozenges, pastilles, or gel.

The compounds can be pharmaceutically formulated as suppositories or retention enemas, e.g. containing conventional suppositories bases such as cocoa butter, polyethylene glycol, or other glycerides, for a rectal administration.

Another means of administering the compounds of the invention regards topical treatment. Topical formulations can contain for example ointments, creams, lotions, gels, solutions, pastes and/or can contain liposomes, micelles and/or microspheres. Examples of ointments include oleaginous ointments such as vegetable oils, animal fats, semisolid hydrocarbons, emulsifiable ointments such as hydroxystearin sulfate, anhydrous lanolin, hydrophilic petrolatum, cetyl alcohol, glycerol monostearate, stearic acid, water soluble ointments containing polyethylene glycols of various molecular weights. Creams, as known to formulation experts, are viscous liquids or semisolid emulsions, and contain an oil phase, an emulsifier and an aqueous phase. The oil phase generally contains petrolatum and an alcohol such as cetyl or stearic alcohol. Formulations suitable for topical administration to the eye also include eye drops, wherein the active ingredient is dissolved or suspended in a suitable carrier, especially an aqueous solvent for the active ingredient.

A further method of administering the compounds of the invention regards transdermal delivery. Typical transdermal formulations comprise conventional aqueous and non-aqueous vectors, such as creams, oils, lotions or pastes or can be in the form of membranes or medicated patches.

A reference for the formulations is the book by Remington ("Remington: The Science and Practice of Pharmacy", Lippincott Williams & Wilkins, 2000).

The compounds of the present invention may be employed alone as a sole therapy or in combination with other therapeutic agents for the treatment of the above-mentioned conditions. The combination can be administered as separate compositions (simultaneous, sequential) of the individual components of the treatment or as a single dosage form containing both agents. When the compounds of this invention are in combination with others active ingredients, the active ingredients may be separately formulated into single-ingredient preparations of one of the above-described forms and then provided as combined preparations, which are given at the same time or different times, or may be formulated together into a two- or more-ingredient preparation.

Compounds of general formula (I) may be administered to a patient in a total daily dose of, for example, from 0.001 to 1000 mg/kg body weight daily. Dosage unit compositions may contain such amounts of submultiples thereof to make up the daily dose. The determination of optimum dosages for a particular patient is well known to one skilled in the art.

As is common practice, the compositions are normally accompanied by written or printed instructions for use in the treatment in question.

The following examples and biological data are presented in order to further illustrate the invention.

1. Chemical Synthesis

Unless otherwise indicated, commercially available reagents and solvents (HPLC grade) were used without further purification. Specifically, the following abbreviations may have been used in the descriptions of the experimental methods:

| | |
|---|---|
| NMR (Nuclear Magnetic Resonance) | $^1$H (proton) |
| MHz (Megahertz) | Hz (Hertz) |
| HPLC (High Performance Liquid Chromatography) | LC-MS (Liquid Chromatography Mass Spectrum) |
| s (seconds) | min (minutes) |
| h (hours) | mg (milligrams) |
| g (grams) | μL (microlitres) |
| mL (millilitres) | mmol (millimoles) |
| nm (nanometers) | μM (micromolar) |
| M (molarity) | RT (room temperature) |
| AcOH (acetic acid) | |
| BOC or boc (tert-butyloxycarbonyl) | (BOC)$_2$O (di-tert-butyl dicarbonate) |
| CBr$_4$ (carbon tetrabromide) | CDCl$_3$ (euterated chloroform) |
| CH$_2$Cl$_2$ (dichloromethane) | DBU (1,8-diazabicyclo[5.4.0]undec-7-ene) |
| CH$_3$CN (acetonitrile) | DIAD (diisopropyl azodicarboxylate) |
| DIPEA (N,N-diisopropylethylamine) | |
| DMA (dimethylacetamide) | DMAP (dimethylaminopyridine) |
| DMF (dimethylformamide) | DMSO (dimethyl sulfoxide) |
| DMSO-d$_6$ (deuterated dimethyl sulfoxide) | DTT (dithiothreitol) |
| Et$_2$O (diethyl ether) | EtOAc (ethyl acetate) |
| EtOH (ethanol) | HCl (hydrochloric acid) |
| LiHMDS ([bis(trimethylsilyl)amino]lithium) | LiOH (lithium hydroxide) |
| K$_2$CO$_3$ (potassium carbonate) | MAO A (monoamine oxidase A) |
| MAO B (monoamine oxidase B) | MeOH (methanol) |
| MeOH-d$_4$ (deuterated methanol) | NaBH$_4$ (sodium borohydride) |
| NaBH(OAc)$_3$ (sodium triacetoxyborohydride) | NaH (sodium hydride) |
| NaCl (sodium chloride) | NaHCO$_3$ (sodium bicarbonate) |
| Na$_2$SO$_4$ (sodium sulphate) | NBS (1-bromopyrrolidine-2,5-dione) |
| NH$_3$ (ammonia) | NH$_4$Cl (ammonium chloride) |
| PPh$_3$ (triphenylphosphine) | SOCl$_2$ (thionyl chloride) |
| TEA (triethylamine) | THF (tetrahydrofuran) |
| Tris (tris(hydroxymethyl)aminomethane) | Pd(dba)$_2$ (bis(dibenzylideneacetone)palladium(0)) |

Except where indicated otherwise, all temperatures are expressed in ° C. (degrees centigrade) or K (Kelvin).

The $^1$H-NMR spectra were acquired with a Varian 500 MHz instrument. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were carried out on a Waters Acquity UPLC or Waters Acquity UPLC H-Class linked to with a SQD Single quadrupole (Waters) using an Acquity UPLC BEH C18 (50×2.1 mm, 1.7 m) or Acquity UPLC HSS T3 (50×2.1 mm, 1.8 m) column. Phase A was composed by either Milli-Q water/CH$_3$CN 95/5+0.07% formic acid or Milli-Q water+0.07% formic acid; Phase B by CH$_3$CN+ 0.05% formic acid; flow rate: 0.6 mL/min; UV detection (DIODE array) from 210 to 400 nm; ESI+ detection in the 100-2000 m/z range. The yields were calculated assuming that products were 100% pure if not stated otherwise.

Intermediate 1: 4-Methylthieno[3,2-b]pyrrole-5-carboxylic acid

4-Methylthieno[3,2-b]pyrrole-5-carboxylate was prepared as described in EP application 14183755.9.

Intermediate 2: 4-Ethylthieno[3,2-b]pyrrole-5-carboxylic acid

4-Ethylthieno[3,2-b]pyrrole-5-carboxylate was prepared as described in EP application 14183755.9.

Intermediate 3: 4-Methylthieno[3,2-b]pyrrole-5-carboxamide

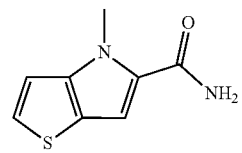

1.7 g (14 mmol, 1 mL) of SOCl$_2$ and 3 drops of dry DMF were added at RT to a solution of 2.12 g (11.7 mmol) of 4-methylthieno[3,2-b]pyrrole-5-carboxylic acid (Intermediate 1) dissolved in 15 mL of dry CH$_2$Cl$_2$/THF (3:1, v:v). The mixture was stirred for 2 h at reflux, then cooled down to RT and added dropwise to 8.2 mL (58.5 mmol) of a 28% solution in water of ammonium hydroxide at 0° C. After 5 min the reaction mixture was diluted with water and extracted with EtOAc. The organic phases were dried over Na₂SO₄, filtered and evaporated to dryness to give 2.1 g of 4-methylthieno[3,2-b]pyrrole-5-carboxamide (99%) as brown solid. ¹H NMR (DMSO) δ (ppm): 7.70-7.65 (bs, 1H), 7.44 (d, J=5.4 Hz, 1H), 7.18 (d, J=5.4 Hz, 1H), 6.87-6.84 (bs, 1H), 7.09 (s, 1H), 3.97 (s, 3H); MS (ESI): m/z: 181 [M+H]⁺.

Intermediate 4: 4-Ethylthieno[3,2-b]pyrrole-5-carboxamide

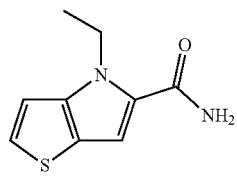

4-Ethylthieno[3,2-b]pyrrole-5-carboxamide was prepared according to the procedure for Intermediate 3, starting from 4-ethylthieno[3,2-b]pyrrole-5-carboxylic acid (Intermediate 2), providing 4-ethylthieno[3,2-b]pyrrole-5-carboxamide (99%) as a brown solid. ¹H NMR (CDCl₃) δ (ppm): 7.31 (d, J 5.4 Hz, 1H), 6.98 (d, J 5.4 Hz, 1H), 6.85 (s, 1H), 5.57 (bs, 2H), 4.59 (q, J=6.8 Hz, 2H), 1.44 (t, J=6.8 Hz, 3H); MS (ESI): m/z: 195 [M+H]⁺.

Intermediate 5: 4-Methylthieno[3,2-b]pyrrole-5-carbonitrile

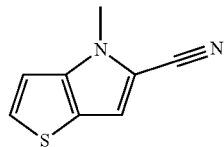

0.62 g (3.84 mmol, 0.39 mL) of ethyl dichlorophosphate and 0.93 g (5.76 mmol, 0.58 mL) of DBU were added to a solution of 0.35 g (1.92 mmol) of 4-ethylthieno[3,2-b]pyrrole-5-carboxamide (Intermediate 3) in dry CH₂Cl₂ (10 mL) at 0° C. After stirring at RT for 12 h further 0.62 g (3.84 mmol) of ethyl dichlorophosphate and 0.93 g (5.76 mmol, 0.58 mL) of DBU were added and the reaction was carried out for additional 2 h. The mixture was then diluted with water and brought to acidic pH with 2 M HCl; the aqueous phase was extracted with CH₂Cl₂ and the combined organic layers were dried over Na₂SO₄, filtered and evaporated to dryness. The crude product was purified by flash chromatography on silica gel (hexane/EtOAc, 1% of EtOAc to 10% of EtOAc) to give 0.234 g of 4-methylthieno[3,2-b]pyrrole-5-carbonitrile (75%) as pale yellow solid. ¹H NMR (CDCl₃) δ (ppm): 7.41 (d, J=5.4 Hz, 1H), 7.02 (s, 1H), 6.97 (d, J 5.4 Hz, 1H), 3.90 (s, 3H).

Intermediate 6: 4-Ethylthieno[3,2-b]pyrrole-5-carbonitrile

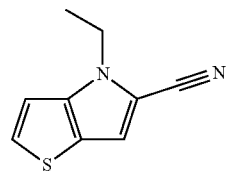

4-Ethylthieno[3,2-b]pyrrole-5-carbonitrile was prepared according to the procedure for Intermediate 5, starting from 4-ethylthieno[3,2-b]pyrrole-5-carboxamide (Intermediate 4), providing 4-ethylthieno[3,2-b]pyrrole-5-carbonitrile intermediate (73%) as a pale yellow solid. ¹H NMR (CDCl₃) δ (ppm): 7.43 (d, J 5.4 Hz, 1H), 7.01 (s, 1H), 6.95 (d, J=5.4 Hz, 1H), 4.28 (q, J=7.3 Hz, 2H), 1.51 (t, J=7.3 Hz, 3H).

Intermediate 7: N'-Hydroxy-4-methyl-thieno[3,2-b]pyrrole-5-carboxamidine

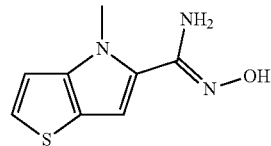

0.58 g (8.3 mmol) of hydroxylamine hydrochloride and 1.07 g (8.34 mmol, 1.45 mL) of DIPEA were added to a solution of 1.23 g (7.58 mmol) of 4-methylthieno[3,2-b]pyrrole-5-carbonitrile (Intermediate 5) in 16 mL of dry EtOH. The mixture was heated at 55° C. for 2 h, then further 0.2 g (2 mmol) of hydroxylamine hydrochloride and 0.3 g (2 mmol, 0.4 mL) of DIPEA were added and the mixture was stirred for additional 2 h. The solution was concentrated and the residue was portioned between CH₂C12/water. The aqueous layer was extracted with CH₂Cl₂ and the combined organic layers were dried over Na₂SO₄, filtered and evaporated to dryness to give 1.47 g of N'-hydroxy-4-methyl-thieno[3,2-b]pyrrole-5-carboxamidine (99%) as pale yellow solid. ¹H NMR (DMSO-d₆) δ (ppm): 9.62 (s, 1H), 7.28 (d, J 5.4 Hz, 1H), 7.13 (d, J 5.4 Hz, 1H), 6.71 (s, 1H), 5.72 (bs, 2H), 3.86 (s, 3H); MS (ESI): m/z: 196 [M+H]⁺.

Intermediate 8: 4-Ethyl-N'-hydroxy-thieno[3,2-b]pyrrole-5-carboxamidine

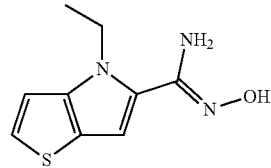

4-Ethyl-N'-hydroxy-thieno[3,2-b]pyrrole-5-carboxamidine was prepared according to the procedure for Intermediate 7 starting from 4-ethylthieno[3,2-b]pyrrole-5-carbonitrile Intermediate 6) providing 4-ethyl-N'-hydroxy-thieno[3, 2-b]pyrrole-5-carboxamidine (99%) as a pale yellow solid. ¹H NMR (CDCl₃) δ (ppm): 7.19 (d, J=5.4 Hz, 1H), 6.95 (d, J=45.4 Hz, 1H), 6.65 (s, 1H), 4.86 (bs, 2H), 4.39 (q, J=7.3 Hz, 2H), 1.38 (t, J=7.3 Hz, 3H); MS (ESI): m/z: 210 [M+H]+.

Intermediate 9: Amino-(4-methylthieno[3,2-b]pyrrol-5-yl)methylene]amino]acetate

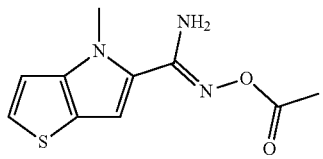 [SMILES: CC(=O)O/N=C(\N)c1cc2sccc2n1C]

0.95 g (9.3 mmol, 0.88 mL) of acetic anhydride were added to a solution of 1.52 g (7.79 mmol) of N'-hydroxy-4-methyl-thieno[3,2-b]pyrrole-5-carboxamidine (Intermediate 7) in 20 mL of AcOH at RT and the mixture was stirred at RT for 15 min. Then the mixture was diluted with water/CH₂Cl₂ and neutralized with a saturated solution of NaHCO₃. The aqueous phase was extracted with CH₂Cl₂ and the organic layers were dried over Na₂SO₄, filtered and evaporated to dryness. The obtained dark solid was purified by column chromatography on silica gel (EtOAc/hexane 1:10, v:v to 8; 2, v:v) to provide 1.57 g of amino-(4-methylthieno[3,2-b]pyrrol-5-yl)methylene]amino]acetate (85%) as a dark solid. ¹H NMR (DMSO-d₆) δ (ppm): 7.39 (d, J 5.4 Hz, 1H), 7.17 (d, J 5.4 Hz, 1H), 6.89 (s, 1H), 6.70 (s, 2H), 3.92 (s, 3H), 2.15 (s, 3H); MS (ESI): m/z: 497 [2M+Na]⁺.

Intermediate 10: Amino-(4-ethylthieno[3,2-b]pyrrol-5-yl)methylene]amino]acetate

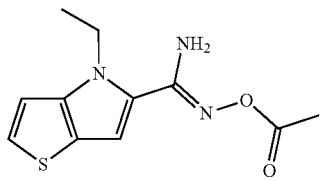 [SMILES: CCn1c(/C(N)=N/OC(C)=O)cc2sccc21]

Amino-(4-ethylthieno[3,2-b]pyrrol-5-yl)methylene] amino]acetate was obtained as a dark solid following the procedure for Intermediate 9 starting from 4-ethyl-N'-hydroxy-thieno[3,2-b]pyrrole-5-carboxamidine (Intermediate 8) (80%). ¹H NMR (CDCl₃) δ (ppm): 7.23 (d, J=5.4 Hz, 1H), 6.96 (d, J=5.4 Hz, 1H), 6.75 (s, 1H), 5.00 (bs, 2H), 4.50 (q, J=7.2 Hz, 2H), 2.28 (s, 3H), 1.42 (t, J=7.2 Hz, 3H); MS (ESI): m/z: 274 [M+Na]⁺.

Intermediate 11: 4-Methylthieno[3,2-b]pyrrole-5-carboxamidine acetate

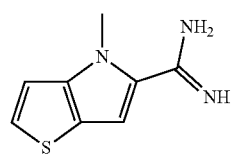

1.56 g (6.57 mmol) of amino-(4-methylthieno[3,2-b]pyrrol-5-yl)methylene]amino]acetate (Intermediate 9) were dissolved in 250 mL of EtOH and 3 mL of AcOH were added. The mixture was hydrogenated in an H-cube apparatus using a 10% Pd/C cartridge at 35° C. and at atmospheric pressure with a flow of 0.5 mL/min. Then the solution was concentrated and the residue was precipitated with Et₂O. The solid was filtered off and dried to afford 1.07 g of 4-methylthieno[3,2-b]pyrrole-5-carboxamidine acetate (70%) as a grey powder. ¹H NMR (DMSO-d₆) δ (ppm): 10.99-8.34 (bs, 4H), 7.52 (d, J=5.4 Hz, 1H), 7.24 (d, J=5.4 Hz, 1H), 7.00 (s, 1H), 3.91 (s, 3H), 1.74 (s, 3H); MS (ESI): m/z: 180 [M+H]⁺.

Alternatively intermediate 11 can be obtained directly from 4-methylthieno[3,2-b]pyrrole-5-carbonitrile intermediate 5. 2.09 g (12.88 mmol) of intermediate 5 was dissolved in dry THF (7 mL) and added to a 1M solution of lithium bis(trimethylsilyl)amide (14.17 mmol, 14.17 mL). After stirring at rt for 4.5 h the reaction mixture was quenched at 0° C. with a 2N solution of HCl in ether (57.96 mmol, 30 mL) and stirred at 0° C. for 15 minutes.

After overnight standing in the fridge the mixture was filtered and the solid was washed with ether and dried to give 4-methylthieno[3,2-b]pyrrole-5-carboxamidine hydrochloride intermediate 11 (96%) as beige powder.

Intermediate 12: 4-Ethylthieno[3,2-b]pyrrole-5-carboxamidine acetate

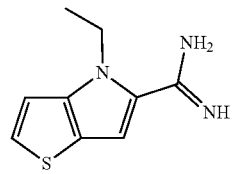

0.097 g (0.83 mmol, 0.13 mL) of triethylsilane were added dropwise at 0° C. 0.06 g (0.06 mmol) to a suspension of 10% Pd/C and of 0.07 g (0.28 mmol) of amino-(4-ethylthieno[3,2-b]pyrrol-5-yl)methylene]amino]acetate (Intermediate 10) in 0.5 mL of dry MeOH. The mixture was allowed to reach RT within 1 h and was stirred at RT for further 30 min. The mixture was filtered on a celite bed, concentrated and the residue was triturated with CH₂Cl₂/Et₂O to afford 49 mg of 4-ethylthieno[3,2-b]pyrrole-5-carboxamidine acetate (69%) as a grey powder. ¹H NMR (DMSO-d₆) δ (ppm): 10.60-8.43 (bs, 4H), 7.48 (d, J 5.4 Hz, 1H), 7.25 (d, J 45.4 Hz, 1H), 6.96 (s, 1H), 4.45 (q, J=7.1 Hz, 2H), 1.74 (s, 3H), 1.22 (t, J=7.1 Hz, 3H); MS (ESI): m/z: 194 [M+H]⁺.

Intermediate 13: 6-methylthieno[2,3-b]pyrrole-5-carboxamidine hydrochloride

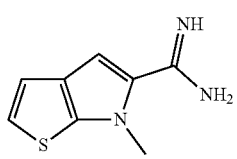

6-Methylthieno[2,3-b]pyrrole-5-carboxylic acid 6-methylthieno[2,3-b]pyrrole-5-carboxylic acid was prepared as described in EP application 14183755.9.

6-methylthieno[2,3-b]pyrrole-5-carboxamide 6-methylthieno[2,3-b]pyrrole-5-carboxamide was prepared according to the procedure for Intermediate 3, starting from 6-methylthieno[2,3-b]pyrrole-5-carboxylic acid providing 6-methylthieno[2,3-b]pyrrole-5-carboxamide (99%) as a pale yellow solid. $^1$H NMR (DMSO-d$_6$) δ (ppm): 7.65 (bs, 1H), 7.11 (d, J=4.9 Hz, 1H), 7.06 (s, 1H), 7.05-7.02 (m, 2H), 7.05 (3.94 (s, 3H). MS (ESI): m/z: 181 [M+H]$^+$.

6-methylthieno[2,3-b]pyrrole-5-carbonitrile 6-methylthieno[2,3-b]pyrrole-5-carbonitrile was prepared according to the procedure for Intermediate 5, starting from 6-methylthieno[2,3-b]pyrrole-5-carboxamide providing 6-methylthieno[2,3-b]pyrrole-5-carbonitrile (64%) as a pale yellow solid. $^1$H NMR (CDCl$_3$) δ (ppm): 7.03-7.02 (d, J=5.4 Hz, 1H), 7.00 (s, 1H), 6.99 (d, J=5.4 Hz, 1H), 3.87 (s, 3H).

6-methylthieno[2,3-b]pyrrole-5-carboxamidine hydrochloride 0.391 g (2.41 mmol) of 6-methylthieno[2,3-b]pyrrole-5-carbonitrile was dissolved in 2.5 mL of dry THF and was added at RT dropwise to 3.1 mL (3.1 mmol) of a 1 M solution of lithium hexamethyldisilazide in THF. The mixture was stirred at RT overnight. Then further 0.2 mL (0.2 mmol) of a 1 M solution of lithium hexamethyldisilazide were added. After stirring at RT for further 3 h, 1.2 mL (2.4 mmol) of a 2 M solution of HCl in Et$_2$O were added dropwise at 0° C. and the mixture was allowed to reach RT in 15 min. Some precipitate was observed and the mixture was diluted with Et$_2$O, filtered and the residue was washed with Et$_2$O providing 0.444 g of 6-methylthieno[2,3-b]pyrrole-5-carboxamidine hydrochloride (86%) as a beige powder. $^1$H NMR (DMSO-d$_6$) δ (ppm): 8.61 (bs, 4H), 7.23 (d, J 4.9 Hz, 1H), 7.10 (d, J 4.9 Hz, 1H), 7.04 (s, 1H), 3.88 (s, 3H). MS (ESI): m/z: 180 [M+H]$^+$.

Example 1: 4-Methyl-5-(4-phenyl-1H-imidazol-2-yl)thieno[3,2-b]pyrrole

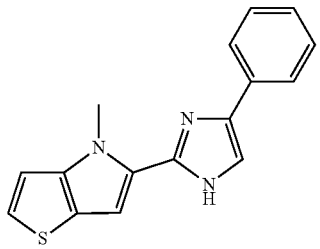 [SMILES: Cn1c(-c2nc(-c3ccccc3)c[nH]2)cc2sccc21]

A solution of 0.018 g (0.092 mmol) of 2-bromo-1-phenylethanone (Sigma-Aldrich, Cat. No. 115835) in THF (0.05 mL) was added dropwise to 0.016 g (0.092 mmol) of 4-methylthieno[3,2-b]pyrrole-5-carboxamidine acetate (Intermediate 11) suspended in 0.55 mL THF/water (4:1, v:v).

The mixture was heated to reflux for 30 min. Then the solution was concentrated and the residue was diluted with water and extracted with EtOAc. The combined organic layers were dried over Na$_2$SO$_4$, filtered and concentrated. The obtained crude product was purified by flash chromatography on silica gel (hexane/EtOAc, 97:3, v:v to 7:3, v:v) and then triturated with Et$_2$O to give 0.013 g of N'-hydroxy-4-methyl-thieno[3,2-b]pyrrole-5-carboxamidine (51%) as a white powder. $^1$H NMR (CDCl$_3$) δ (ppm): 7.83-7.73 (m, 2H), 7.46-7.38 (m, 2H), 7.34 (s, 1H), 7.32-7.28 (m, 1H), 7.17 (d, J=5.4 Hz, 1H), 6.96 (d, J=5.4 Hz, 1H), 6.73 (s, 1H), 4.18 (s, 3H); MS (ESI): m/z: 280 [M+H]$^+$.

The following compounds (see Table 1) were prepared starting from 4-methylthieno[3,2-b]pyrrole-5-carboxamidine acetate (Intermediate 11: Examples 2-10, 13 and 16-17) 4-ethylthieno[3,2-b]pyrrole-5-carboxamidine acetate (Intermediate 12: Examples 11-12) or 6-methylthieno[2,3-b]pyrrole-5-carboxamidine hydrochloride (Intermediate 13: Examples 14-15) and the appropriate α-bromo ketone or α-chloro ketone according to the procedure described for Example 1.

TABLE 1

| Ex. | Name | α-halogeno ketone | Structure | Analytical Data |
|---|---|---|---|---|
| 2 | 5-(4-ethyl-1H-imidazol-2-yl)-4-methyl-thieno[3,2-b]pyrrole | (Sigma-Aldrich, Cat. No. 243299) | 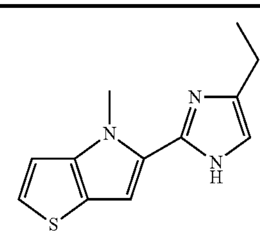 | $^1$H NMR (DMSO-d$_6$) δ (ppm): 12.19-11.77 (bs, 1 H), 7.26 (d, J = 5.4 Hz, 1 H), 7.15 (d, J = 5.4 Hz, 1 H), 6.82 (bs, 1 H), 6.77 (s, 1 H), 4.08 (s, 3 H), 2.63-2.52 (m, 2 H), 1.21 (t, J = 7.6 Hz, 3 H); MS (ESI): m/z: 232 [M + H]$^+$. |
| 3 | 4-methyl-5-(4-methyl-1H-imidazol-2-yl)thieno[3,2-b]pyrrole | (Sigma-Aldrich, Cat. No. 167479)http://www.sigmaaldrich.com/catalog/product/aldrich/167479?lang=it&region=IT | 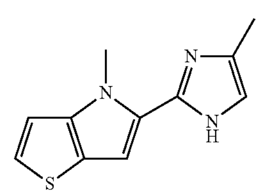 | $^1$H NMR (DMSO-d$_6$) δ (ppm): 12.30 (bs, 1 H), 7.28 (d, J = 5.4 Hz, 1 H), 7.16 (d, J = 4.9 Hz, 1 H), 6.84 (bs, 1 H), 6.78 (s, 1 H), 4.06 (s, 3 H), 2.20 (s, 3 H); MS (ESI): m/z: 218 [M + H]$^+$. |

TABLE 1-continued

| Ex. | Name | α-halogeno ketone | Structure | Analytical Data |
|---|---|---|---|---|
| 4 | 5-(4-isopropyl-1H-imidazol-2-yl)-4-methyl-thieno[3,2-b]pyrrole | 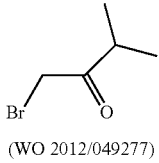<br>(WO 2012/049277) | 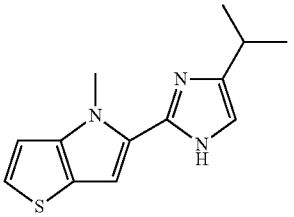 [SMILES: CC(C)c1c[nH]c(-c2cc3sccc3n2C)n1] | $^1$H NMR (CDCl$_3$) δ (ppm): 7.14 (d, J = 5.4 Hz, 1 H), 6.92 (d, J = 5.4 Hz, 1 H), 6.81 (s, 1 H), 6.64 (s, 1 H), 4.06 (s, 3 H), 3.05-2.94 (m, 1 H), 1.35-1.29 (m, 6 H); MS (ESI): m/z: 246 [M + H]$^+$. |
| 5 | 5-(4-cyclopropyl-1H-imidazol-2-yl)-4-methyl-thieno[3,2-b]pyrrole | 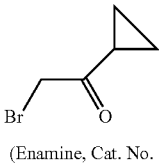<br>(Enamine, Cat. No. EN300-57214) | 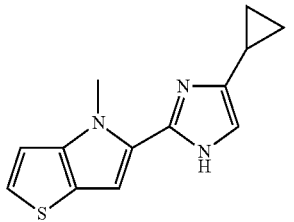 [SMILES: Cn1c(-c2nc(C3CC3)c[nH]2)cc2sccc21] | $^1$H NMR (CDCl$_3$) δ (ppm): 7.16-7.14 (d, J = 5.4 Hz, 1 H), 6.95 (d, J = 5.4 Hz, 1 H), 6.78 (s, 1 H), 6.59 (s, 1 H), 4.08 (s, 3 H), 1.92-1.82 (m, 1 H), 0.96-0.70 (m, 4 H); MS (ESI): m/z: 244 [M + H]$^+$. |
| 6 | 4-methyl-5-(4-propyl-1H-imidazol-2-yl)thieno[3,2-b]pyrrole | 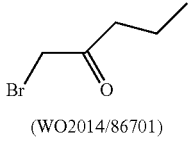<br>(WO2014/86701) | 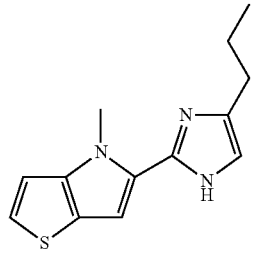 [SMILES: CCCc1c[nH]c(-c2cc3sccc3n2C)n1] | $^1$H NMR (CDCl$_3$) δ (ppm): 7.14 (d, J = 5.4 Hz, 1 H), 6.92 (d, J = 5.4 Hz, 1 H), 6.82 (s, 1 H), 6.65 (s, 1 H), 4.07 (s, 3 H), 2.63 (t, J = 7.4 Hz, 2 H), 1.70 (qd, J = 7.4, 15.0 Hz, 2 H), 1.00 (t, J = 7.4 Hz, 3 H); MS (ESI): m/z: 246 [M + H]$^+$. |
| 7 | 5-(4-cyclobutyl-1H-imidazol-2-yl)-4-methyl-thieno[3,2-b]pyrrole | 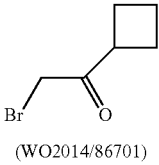<br>(WO2014/86701) | 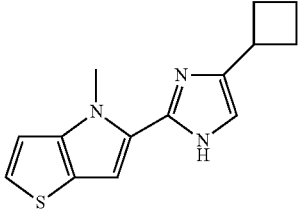 [SMILES: Cn1c(-c2nc(C3CCC3)c[nH]2)cc2sccc21] | $^1$H NMR (CDCl$_3$) δ (ppm): 7.14 (d, J = 5.4 Hz, 1 H), 6.91 (d, J = 5.4 Hz, 1 H), 6.86 (s, 1 H), 6.66 (s, 1 H), 4.06 (s, 3 H), 3.61-3.51 (m, 1 H), 2.43-2.33 (m, 2 H), 2.25-2.14 (m, 2 H), 2.10-1.88 (m, 2 H); MS (ESI): m/z: 258 [M + H]$^+$. |
| 8 | 4-methyl-5-(5-methyl-4-phenyl-1H-imidazol-2-yl)thieno[3,2-b]pyrrole | 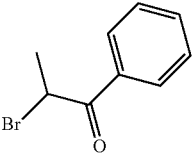<br>(Sigma-Aldrich, Cat. No. 471607) | 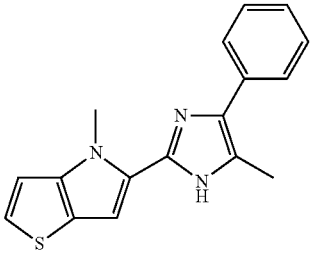 [SMILES: Cc1[nH]c(-c2cc3sccc3n2C)nc1-c1ccccc1] | $^1$H NMR (CDCl$_3$) δ (ppm): 7.67-7.60 (m, 2 H), 7.46-7.39 (m, 2 H), 7.33-7.28 (m, 1 H), 7.15 (d, J = 5.4 Hz, 1 H), 6.92 (d, J = 5.4 Hz, 1 H), 6.71 (s, 1 H), 4.13 (s, 3 H), 2.47 (s, 3 H); MS (ESI): m/z: 294 [M + H]$^+$. |
| 9 | 5-(5-ethyl-4-phenyl-1H-imidazol-2-yl)-4-methyl-thieno[3,2-b]pyrrole | 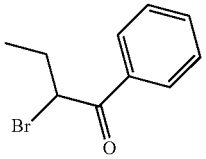<br>(Enamine, Cat. No. EN300-21953) | 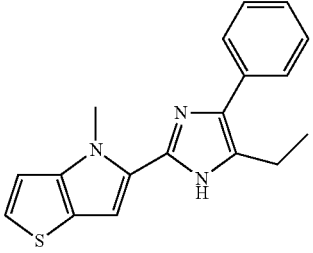 [SMILES: CCc1[nH]c(-c2cc3sccc3n2C)nc1-c1ccccc1] | $^1$H NMR (CDCl$_3$) δ (ppm): 7.69-7.58 (m, 2 H), 7.47-7.40 (m, 2 H), 7.33-7.28 (m, 1 H), 7.15 (d, J = 5.4 Hz, 1 H), 6.95 (d, J = 5.4 Hz, 1 H), 6.68 (s, 1 H), 4.15 (s, 3 H), 2.88 (q, J = 7.7 Hz, 2 H), 1.36 (t, J = 7.6 Hz, 3 H); MS (ESI): m/z: 308 [M + H]$^+$. |

TABLE 1-continued

| Ex. | Name | α-halogeno ketone | Structure | Analytical Data |
|---|---|---|---|---|
| 10 | 5-(5-isopropyl-4-phenyl-1H-imidazol-2-yl)-4-methyl-thieno[3,2-b]pyrrole | (Enamine, Cat. No. EN300-42834) | 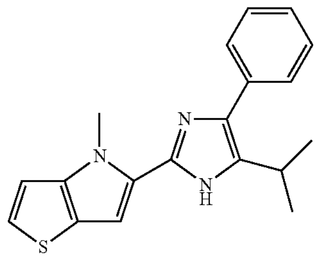 [SMILES: CC(C)c1[nH]c(-c2cc3sccc3n2C)nc1-c1ccccc1] | ¹H NMR (CDCl₃) δ (ppm): 7.68-7.52 (m, 2 H), 7.47-7.39 (m, 2 H), 7.35-7.29 (m, 1 H), 7.14 (d, J = 5.4 Hz, 2 H), 6.94 (d, J = 5.4 Hz, 2 H), 6.70 (s, 1 H), 4.13 (s, 3 H), 3.42-3.27 (m, 1 H), 1.38 (d, J = 6.8 Hz, 6 H)MS (ESI): m/z: 322 [M + H]⁺. |
| 11 | 4-ethyl-5-(4-ethyl-1H-imidazol-2-yl)thieno[3,2-b]pyrrole | (Sigma-Aldrich, Cat. No. 243299) | 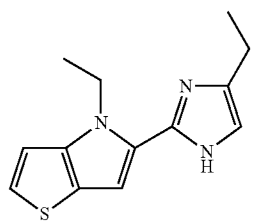 [SMILES: CCc1c[nH]c(-c2cc3sccc3n2CC)n1] | ¹H NMR (CDCl₃) δ (ppm): 7.15 (d, J = 5.4 Hz, 1 H), 6.97 (d, J = 5.4 Hz, 1 H), 6.82 (s, 1 H), 6.62 (s, 1 H), 4.63 (q, J = 7.2 Hz, 2 H), 2.69 (q, J = 7.3 Hz, 2 H), 1.38 (t, J = 7.2 Hz, 3 H), 1.29 (t, J = 7.3 Hz, 3 H); MS (ESI): m/z: 246 [M + H]⁺. |
| 12 | 5-(4-cyclobutyl-1H-imidazol-2-yl)-4-ethyl-thieno[3,2-b]pyrrole | (WO2014/86701) | 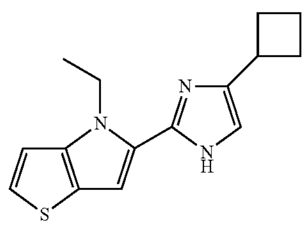 [SMILES: CCn1c(-c2nc(C3CCC3)c[nH]2)cc2sccc21] | ¹H NMR (CDCl₃) d (ppm): 7.14 (d, J = 5.4 Hz, 1 H), 6.96 (d, J = 5.4 Hz, 1 H), 6.86 (s, 1 H), 6.62 (s, 1 H), 4.63 (q, J = 7.2 Hz, 2 H), 3.60-3.50 (m, 1 H), 2.42-2.32 (m, 2 H), 2.25-2.11 (m, 2 H), 2.09-1.86 (m, 2 H), 1.38 (t, J = 1.2 Hz, 3 H); MS (ESI): m/z: 272 [M + H]⁺. |
| 13 | 4-methyl-5-(4-phenyl-5-propyl-1H-imidazol-2-yl)thieno[3,2-b]pyrrole | (Hyde, J. F. et al. J. Am. Chem. Soc, 1928, 50, 2287) | 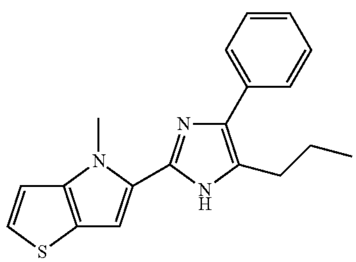 [SMILES: CCCc1[nH]c(-c2cc3sccc3n2C)nc1-c1ccccc1] | 1H NMR (CDCl₃) δ (ppm): = 7.70-7.58 (m, 2H), 7.46-7.40 (m, 2H), 7.34 7.28 (m, 1 H)7.15 (d, J = 5.4 Hz, 1 H), 6.95 (d, J = 5.4 Hz, 1 H), 6.66 (s, 1 H), 4.15 (s, 3 H), 2.82 (t, J = 7.3 Hz, 2 H), 1.78 (qd, J = 7.3, 15.0 Hz, 2 H), 1.03 (t, J = 7.3 Hz, 3 H); MS (ESI): m/z: 322 [M + H]⁺. |
| 14 | 5-(4-ethyl-1H-imidazol-2-yl)-6-methyl-thieno[2,3-b]pyrrole | (Sigma-Aldrich, Cat. No. 243299) | 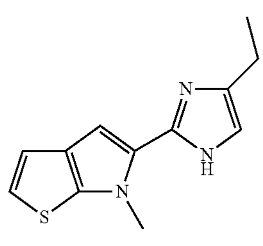 [SMILES: CCc1c[nH]c(-c2cc3ccsc3n2C)n1] | ¹H NMR (CDCl₃) δ (ppm): 6.97 (d, J = 5.4 Hz, 1 H), 6.87 (d, J = 5.4 Hz, 1 H), 6.80 (s, 1 H), 6.59 (s, 1 H), 4.05 (s, 3 H), 2.69 (q, J = 7.6 Hz, 2 H), 1.30 (t, J = 7.6 Hz, 3 H); MS (ESI): m/z: 232 [M + H]⁺. |
| 15 | 5-(5-ethyl-4-phenyl-1H-imidazol-2-yl)-6-methyl-thieno[2,3-b]pyrrole | (Enamine, Cat. No. EN300-21953) | 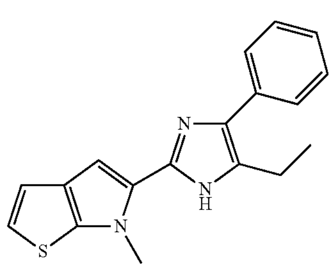 [SMILES: CCc1[nH]c(-c2cc3ccsc3n2C)nc1-c1ccccc1] | ¹H NMR (CDCl₃) δ (ppm): = 7.67-7.28 (m, 5 H), 6.97 (d, J = 4.9 Hz, 1 H), 6.87 (d, J = 4.9 Hz, 1 H), 6.66 (s, 1 H), 4.13 (s, 3 H), 2.87 (q, J = 13 Hz, 2 H), 1.36 (t, J = 7.3 Hz, 3 H); MS (ESI): m/z: 308 [M + H]⁺. |

TABLE 1-continued

| Ex. | Name | α-halogeno ketone | Structure | Analytical Data |
|---|---|---|---|---|
| 16 | 4-methyl-5-(4,5,6,7-tetrahydro-1H-benzimidazol-2-yl)thieno[3,2-b]pyrrole | (Sigma-Aldrich, Cat. No. 690422) | 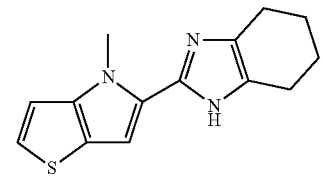 [SMILES: Cn1c(-c2nc3c([nH]2)CCCC3)cc2sccc21] | 1H NMR (CDCl₃) δ (ppm): = 7.14 (d, J = 5.4 Hz, 1 H), 6.93 (d, J = 5.4 Hz, 1H), 6.61 (s, 1 H), 4.08 (s, 3 H), 2.66-2.61 (m, 4 H), 1.86-1.81 (m, 4 H); MS (ESI): m/z: 258 [M + H]⁺. |
| 17 | 4-methyl-5-[4-(3,3,3-trifluoropropyl)-1H-imidazol-2-yl]thieno[3,2-b]pyrrole | (FCH group, Cat. No FCH2646621-1) | 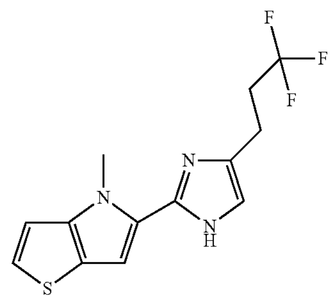 [SMILES: Cn1c(-c2nc(CCC(F)(F)F)c[nH]2)cc2sccc21] | 1H NMR (CDCl₃) δ (ppm): = 7.16 (d, J = 5.4 Hz, 1 H), 6.95 (d, J = 5.4 Hz, 1 H), 6.84 (s, 1 H), 6.64 (s, 1 H), 4.09 (s, 3 H), 2.95-2.86 (m, 2 H), 2.62-2.46 (m, 2 H) |

Intermediate 14: tert-Butyl 4-[3-(2-bromoethoxy) phenoxy]piperidine-1-carboxylate

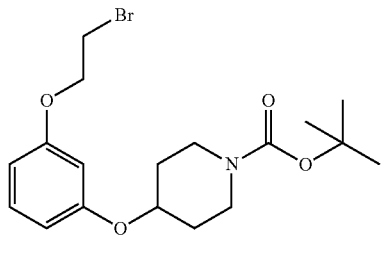 [SMILES: CC(C)(C)OC(=O)N1CCC(Oc2cccc(OCCBr)c2)CC1]

tert-Butyl 4-(3-hydroxyphenoxy)piperidine-1-carboxylate 0.64 g (3.0 mmol, 0.62 mL) of DIAD (Sigma-Aldrich, Cat. No. 225541) were added dropwise to a solution of 0.33 g (3.0 mmol) of resorcinol (Sigma-Aldrich, Cat. No. 398047), 0.42 g (2.0 mmol) of tert-butyl 4-hydroxypiperidine-1-carboxylate (Apollo, Cat. No. OR5404) and 0.80 g (3.0 mmol) of PPh₃ (Sigma-Aldrich, Cat. No. T84409) in 20 mL of dry THF at 0° C. The reaction mixture was allowed to reach RT and was stirred overnight. The solvent was then removed and the crude mixture was purified by flash chromatography on silica gel (hexane/acetone, 0% to 15% of acetone) to give 0.217 g of tert-butyl 4-(3-hydroxyphenoxy)piperidine-1-carboxylate (37%) as white solid. ¹H NMR (CDCl₃) δ (ppm): 7.16-7.11 (m, 1H), 6.52-6.48 (m, 1H), 6.46-6.41 (m, 2H), 4.96 (bs, 1H), 4.50-4.38 (m, 1H), 3.75-3.65 (m, 2H), 3.39-3.29 (m, 2H), 1.97-1.86 (m, 2H), 1.81-1.69 (m, 2H), 1.48 (s, 9H); MS (ESI): m/z: 238 [M−56+H]⁺.

tert-Butyl 4-[3-(2-bromoethoxy)phenoxy]piperidine-1-carboxylate 0.16 g (0.76 mmol, 0.158 mL) of DIAD (Sigma-Aldrich, Cat. No. 225541) were added dropwise to a solution comprising 0.150 g (0.51 mmol) of tert-butyl 4-(3-hydroxyphenoxy)piperidine-1-carboxylate, 0.100 g (0.76 mmol, 0.057 mL) of 2-bromoethanol (Sigma-Aldrich, Cat. No. B65586) and 0.203 g (0.76 mmol) of PPh₃ (Sigma-Aldrich, Cat. No. T84409) in 5 mL of dry THF at 0° C. The solution was allowed to reach RT and was stirred overnight. Then further 0.028 mL of 2-bromoethanol, 0.101 mg of PPh₃ and 0.079 mL of DIAD were added to the reaction mixture cooled down to 0° C. and the mixture was stirred at RT for further 24 h. The solvent was removed and the crude product was purified by flash chromatography on silica gel (hexane/acetone, 0% to 5% of acetone) to provide 0.105 g of tert-butyl 4-[3-(2-bromoethoxy)phenoxy]piperidine-1-carboxylate (51%) as colourless oil. ¹H NMR (CDCl₃) δ (ppm): 7.23-7.15 (m, 1H), 6.58-6.47 (m, 3H), 4.50-4.43 (m, 1H), 4.28 (t, J=6.4 Hz, 2H), 3.75-3.67 (m, 2H), 3.64 (t, J=6.4 Hz, 2H), 3.38-3.28 (m, 2H), 1.96-1.86 (m, 2H), 1.81-1.69 (m, 2H), 1.48 (s, 9H); MS (ESI): m/z: 344 [M−56+H]⁺.

Intermediate 15: tert-Butyl 3-[[4-(2-bromoethoxy) phenoxy]methyl]pyrrolidine-1-carboxylate

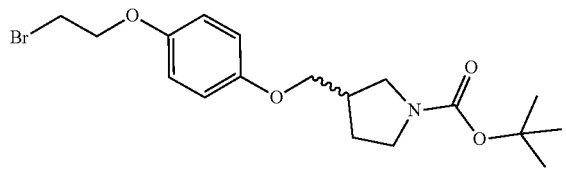 [SMILES: CC(C)(C)OC(=O)N1CCC(COc2ccc(OCCBr)cc2)C1]

tert-Butyl 3-[(4-hydroxyphenoxy)methyl]pyrrolidine-1-carboxylate 0.37 g of tert-butyl 3-[(4-hydroxyphenoxy)methyl]pyrrolidine-1-carboxylate was prepared according to the procedure for Intermediate 14, step 1, starting from 0.23 g (2.1 mmol) of hydroquinone (Sigma-Aldrich, Cat. No. H9003) and 0.22 g (1.0 mmol) of tert-butyl 3-(hydroxymethyl) pyrrolidine-1-carboxylate (Fluorochem, Cat. No. 048620) (yield: 24%). ¹H NMR (CDCl₃) δ (ppm): 6.82-6.73 (m, 4H), 4.59 (s, 1H), 3.94-3.80 (m, 2H), 3.63-3.55 (m, 1H), 3.53-

3.44 (m, 1H), 3.42-3.32 (m, 1H), 3.24-3.14 (m, 1H), 2.70-2.60 (m, 1H), 2.12-2.00 (m, 1H), 1.87-1.73 (m, 1H), 1.47 (s, 9H); MS (ESI): m/z: 238 [M−56+H]⁺.

tert-Butyl 3-[[4-(2-bromoethoxy)phenoxy]methyl]pyrrolidine-1-carboxylate 0.053 g of tert-butyl 3-[[4-(2-bromoethoxy)phenoxy]methyl]pyrrolidine-1-carboxylate was prepared according to the procedure for Intermediate 14, step 2, starting from 0.070 g (0.25 mmol) tert-butyl 3-[(4-hydroxyphenoxy)methyl]pyrrolidine-1-carboxylate and 2-bromoethanol (yield: 54%). ¹H NMR (CDCl₃) δ (ppm): 6.92-6.79 (m, 4H), 4.25 (t, J 6.4 Hz, 2H), 3.97-3.81 (m, 2H), 3.62 (t, J=6.1 Hz, 2H), 3.60-3.56 (m, 1H), 3.51-3.44 (m, 1H), 3.41-3.32 (m, 1H), 3.23-3.16 (m, 1H), 2.70-2.61 (m, 1H), 2.11-2.02 (m, 1H), 1.85-1.74 (m, 1H), 1.47 (s, 9H); MS (ESI): m/z: 344 [M−56+H]⁺.

Intermediate 16: tert-Butyl 4-[[4-(2-bromoethoxy)phenoxy]methyl]piperidine-1-carboxylate

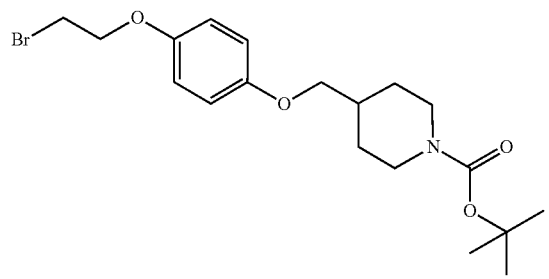 [SMILES: CC(C)(C)OC(=O)N1CCC(COc2ccc(OCCBr)cc2)CC1]

tert-Butyl 4-[(4-hydroxyphenoxy)methyl]piperidine-1-carboxylate 0.28 g of tert-butyl 4-[(4-hydroxyphenoxy)methyl]pyrrolidine-1-carboxylate was prepared according to the procedure for Intermediate 14, step 1, starting from 0.50 g (4.5 mmol) of hydroquinone (Sigma-Aldrich, Cat. No. H9003) and 0.65 g (3.0 mmol) of tert-butyl 4-(hydroxymethyl)piperidine-1-carboxylate (Sigma-Aldrich, Cat. No. 556017) (yield: 31%). ¹H NMR (CDCl₃) δ (ppm): 6.83-6.70 (m, 4H), 4.58 (bs, 1H), 4.22-4.10 (m, 2H), 3.75 (d, J=6.4 Hz, 2H), 2.81-2.69 (m, 2H), 2.00-1.88 (m, 1H), 1.86-1.77 (m, 2H), 1.48 (s, 9H), 1.31-1.23 (m, 2H); MS (ESI): m/z: 252 [M−56+H]⁺.

tert-Butyl 4-[[4-(2-bromoethoxy)phenoxy]methyl]piperidine-1-carboxylate 0.11 g of tert-butyl 4-[[4-(2-bromoethoxy)phenoxy]methyl]piperidine-1-carboxylate was prepared according to the procedure for Intermediate 14, step 2, starting from 0.28 g (0.90 mmol) of tert-butyl 4-[(4-hydroxyphenoxy)methyl]pyrrolidine-1-carboxylate and 2-bromoethanol (yield: 29%). ¹H NMR (CDCl₃) δ (ppm): 6.89-6.79 (m, 4H), 4.25 (t, J=6.4 Hz, 2H), 4.20-4.11 (m, 2H), 3.76 (d, J=6.4 Hz, 2H), 3.62 (t, J=6.4 Hz, 2H), 2.81-2.70 (m, 2H), 2.00-1.88 (m, 1H), 1.87-1.77 (m, 2H), 1.47 (s, 9H), 1.32-1.23 (m, 2H); MS (ESI): m/z: 358 [M−56+H]⁺.

Intermediate 17: tert-Butyl 4-[4-(2-bromoethoxy)phenoxy]piperidine-1-carboxylate

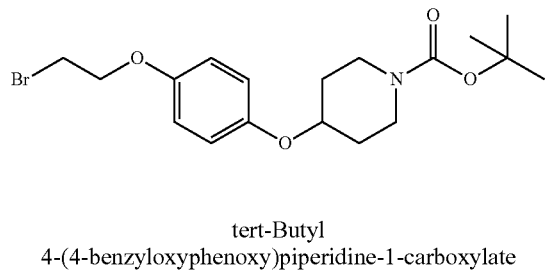

tert-Butyl 4-(4-benzyloxyphenoxy)piperidine-1-carboxylate 0.8 g of tert-butyl 4-(4-benzyloxyphenoxy)piperidine-1-carboxylate was prepared according to the procedure for Intermediate 14, step 1 starting from 0.60 g (3.0 mmol) of 4-benzyloxyphenol (Sigma-Aldrich, Cat. No. 158348) and 0.93 g (4.5 mmol) of tert-butyl 4-hydroxypiperidine-1-carboxylate (Apollo, Cat. No. OR5404) (Yield: 70%). ¹H NMR (CDCl₃) δ (ppm): 7.46-7.42 (m, 2H), 7.42-7.37 (m, 2H), 7.36-7.31 (m, 1H), 6.93-6.84 (m, 4H), 5.03 (s, 2H), 4.38-4.28 (m, 1H), 3.76-3.68 (m, 2H), 3.35-3.24 (m, 2H), 1.95-1.84 (m, 2H), 1.78-1.67 (m, 2H), 1.48 (s, 9H); MS (ESI): m/z: 328 [M−56+H]⁺.

tert-Butyl 4-(4-hydroxyphenoxy)piperidine-1-carboxylate 0.454 g (1.18 mmol) of tert-butyl 4-(4-benzyloxyphenoxy)piperidine-1-carboxylate dissolved in 47 mL of dry EtOH were hydrogenated in an H-cube apparatus using a 10% Pd/C cartridge at 25° C., at atmospheric pressure and with a flow of 0.5 mL/min for 5 h. The solution was then concentrated to provide 0.340 g of tert-butyl 4-(4-hydroxyphenoxy)piperidine-1-carboxylate (98%) as a white solid. ¹H NMR (CDCl₃) δ (ppm): 6.87-6.71 (m, 4H), 4.58 (bs, 1H), 4.36-4.27 (m, 1H), 3.76-3.67 (m, 2H), 3.37-3.24 (m, 2H), 1.95-1.82 (m, 2H), 1.78-1.66 (m, 2H), 1.48 (s, 9H); MS (ESI): m/z: 238 [M−56+H]⁺.

tert-Butyl 4-[4-(2-bromoethoxy)phenoxy]piperidine-1-carboxylate 0.31 g of tert-Butyl 4-[4-(2-bromoethoxy)phenoxy]piperidine-1-carboxylate was obtained according to the procedure for Intermediate 14, step 2, starting from 0.340 g (1.16) of tert-butyl 4-(4-hydroxyphenoxy)piperidine-1-carboxylate and 2-bromoethanol (yield: 66%). ¹H NMR (CDCl₃) δ (ppm): 6.92-6.80 (m, 4H), 4.37-4.31 (m, 1H), 4.25 (t, J=6.1 Hz, 2H), 3.76-3.67 (m, 2H), 3.63 (t, J=6.4 Hz, 2H), 3.35-3.26 (m, 2H), 1.95-1.85 (m, 2H), 1.77-1.67 (m, 2H), 1.48 (s, 9H); MS (ESI): m/z: 344 [M−56+H]⁺.

Intermediate 18: tert-Butyl 4-[4-(2-bromoethoxy)phenoxy]azepane-1-carboxylate

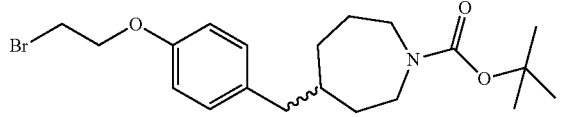 [SMILES: CC(C)(C)OC(=O)N1CCCC(Cc2ccc(OCCBr)cc2)CC1]

tert-Butyl 4-(4-benzyloxyphenoxy)azepane-1-carboxylate 0.74 g of tert-butyl 4-(4-benzyloxyphenoxy)azepane-1-carboxylate was prepared according to the procedure for Intermediate 14, step 1, starting from 0.60 g (3.0 mmol) of 4-benzyloxyphenol and 0.97 g (4.5 mmol) of tert-butyl 4-hydroxyazepane-1-carboxylate (Sigma-Aldrich, Cat. No. CDS009029) (yield: 62%). $^1$H NMR (CDCl$_3$) δ (ppm): 7.46-7.42 (m, 2H), 7.42-7.37 (m, 2H), 7.36-7.31 (m, 1H), 6.92-6.80 (m, 4H), 5.02 (s, 2H), 4.37-4.26 (m, 1H), 3.65-3.23 (m, 4H), 2.09-1.84 (m, 5H), 1.70-1.59 (m, 1H), 1.48 (s, 9H); MS (ESI): m/z: 342 [M−56+H]$^+$.

tert-Butyl 4-(4-hydroxyphenoxy)azepane-1-carboxylate 0.51 g of tert-butyl 4-(4-hydroxyphenoxy)azepane-1-carboxylate was prepared according to the procedure for Intermediate 17, step 2, starting from 0.71 g (1.8 mmol) of tert-butyl 4-(4-benzyloxyphenoxy)azepane-1-carboxylate (yield: 92%). $^1$H NMR (CDCl$_3$) δ (ppm): 6.82-6.72 (m, 4H), 4.58 (bs, 1H), 4.36-4.25 (m, 1H), 3.65-3.22 (m, 4H), 2.12-1.83 (m, 5H), 1.70-1.59 (m, 1H), 1.48 (s, 9H); MS (ESI): m/z: 252 [M−56+H]$^+$.

tert-Butyl 4-[4-(2-bromoethoxy)phenoxy]azepane-1-carboxylate 0.22 g of tert-butyl 4-[4-(2-bromoethoxy)phenoxy]azepane-1-carboxylate was prepared according to the procedure for Intermediate 14, step 2, starting from 0.36 g (1.2 mmol) of tert-butyl 4-(4-hydroxyphenoxy)azepane-1-carboxylate and 2-bromoethanol (yield: 47%). $^1$H NMR (CDCl$_3$) δ (ppm): 6.92-6.76 (m, 4H), 4.38-4.29 (m, 1H), 4.25 (t, J=6.4 Hz, 2H), 3.67-3.22 (m, 6H), 2.11-1.84 (m, 5H), 1.70-1.59 (m, 1H), 1.48 (s, 9H); MS (ESI): m/z: 358 [M−56+H]$^+$.

Intermediate 19: tert-Butyl 4-[4-(3-bromopropyl)phenoxy]piperidine-1-carboxylate

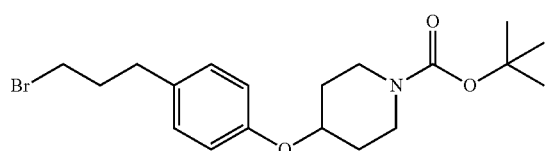

0.33 g of tert-butyl 4-[4-(3-bromopropyl)phenoxy]piperidine-1-carboxylate was prepared according to the procedure for Intermediate 14, step 1, starting from 0.22 g (1.0 mmol) of 4-(3-bromopropyl)phenol (U.S. Pat. No. 5,204,018) and 0.30 g (1.5 mmol) of tert-butyl 4-hydroxypiperidine-1-carboxylate (Apollo, Cat. No. OR5404) (yield: 82%). $^1$H NMR (CDCl$_3$) δ (ppm): 7.17-7.08 (m, 2H), 6.89-6.81 (m, 2H), 4.49-4.38 (m, 1H), 3.78-3.65 (m, 2H), 3.40 (t, J=6.6 Hz, 2H), 3.37-3.30 (m, 2H), 2.73 (t, J=7.3 Hz, 2H), 2.18-2.10 (m, 2H), 1.95-1.87 (m, 2H), 1.80-1.69 (m, 2H), 1.47 (s, 9H); MS (ESI): m/z: 342 [M−56+H]$^+$.

Intermediate 19A: tert-Butyl 4-[4-(3-bromopropyl)phenoxy]piperidine-1-carboxylate

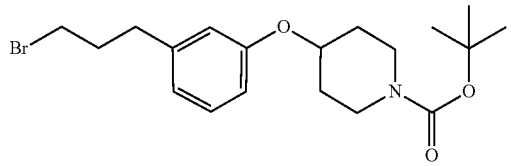 [SMILES: CC(C)(C)OC(=O)N1CCC(Oc2cccc(CCCBr)c2)CC1]

0.41 g of tert-butyl 4-[3-(3-bromopropyl)phenoxy]piperidine-1-carboxylate was prepared according to the procedure for Intermediate 14, step 1, starting from 0.28 g (1.3 mmol) of 3-(3-bromopropyl)phenol (Murphy, W. et al. J. Chem. Soc., Perkin Trans. 1: Org. Bio-Org. Chem. 1980, 7, 1567-1577) and 0.40 g (1.95 mmol) of tert-butyl 4-hydroxypiperidine-1-carboxylate (Apollo, Cat. No. OR5404) (yield: 79%). $^1$H NMR (CDCl$_3$) δ (ppm): 7.25-7.18 (m, 1H), 6.83-6.74 (m, 3H), 4.51-4.42 (m, 1H), 3.76-3.67 (m, 2H), 3.41 (t, J=6.4 Hz, 2H), 3.38-3.31 (m, 2H), 2.75 (t, J=7.3 Hz, 2H), 2.21-2.13 (m, 2H), 1.97-1.87 (m, 2H), 1.81-1.69 (m, 2H), 1.48 (s, 9H); MS (ESI): m/z: 342 [M−56+H]$^+$.

Intermediate 20: tert-Butyl 3-[[4-(3-bromopropyl)phenoxy]methyl]pyrrolidine-1-carboxylate

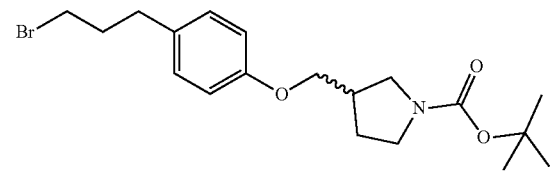 [SMILES: CC(C)(C)OC(=O)N1CCC(COc2ccc(CCCBr)cc2)C1]

0.37 g of tert-butyl 3-[[4-(3-bromopropyl)phenoxy]methyl]pyrrolidine-1-carboxylate was prepared according to the procedure for Intermediate 15, step 1, starting from 0.39 g (1.8 mmol) 4-(3-bromopropyl)phenol (U.S. Pat. No. 5,204,018) and 0.57 g (2.7 mmol) of tert-butyl 3-(hydroxymethyl)pyrrolidine-1-carboxylate (Fluorochem, Cat. No. 048620) (yield: 52%). $^1$H NMR (CDCl$_3$) δ (ppm): 7.16-7.07 (m, 2H), 6.87-6.78 (m, 2H), 3.95-3.85 (m, 2H), Part AB of ABX System: VA=3.6, VB=3.21, JAB=10.9 Hz, JAX=7.6 Hz, JBX=6.8 Hz, 3.52-3.44 (m, 1H), 3.42-3.33 (m, 3H), 2.76-2.62 (m, 3H), 2.17-2.03 (m, 3H), 1.85-1.75 (m, 1H), 1.47 (s, 9H); MS (ESI): m/z: 342 [M−56+H]$^+$.

Intermediate 21: tert-Butyl 4-[3-(2-bromoethoxy)phenoxy]azepane-1-carboxylate

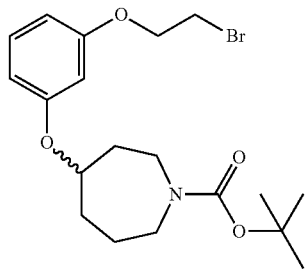 [SMILES: CC(C)(C)OC(=O)N1CCCC(Oc2cccc(OCCBr)c2)CC1]

tert-Butyl 4-(3-hydroxyphenoxy)azepane-1-carboxylate 0.43 g of tert-butyl 4-(3-hydroxyphenoxy)azepane-1-carboxylate was prepared according to the procedure for Intermediate 14, step 1, starting from 0.50 g (4.5 mmol) of resorcinol (Sigma-Aldrich, Cat. No. 398047) and 0.65 g (3.0 mmol) of tert-butyl 4-hydroxyazepane-1-carboxylate (Sigma-Aldrich, Cat. No. CDS009029) (yield: 46%). $^1$H NMR (CDCl$_3$+D$_2$O) δ (ppm): 7.19-7.05 (m, 1H), 6.52-6.33 (m, 3H), 4.48-4.32 (m, 1H), 3.68-3.15 (m, 4H), 2.16-1.81 (m, 5H), 1.72-1.61 (m, 1H), 1.48 (s, 9H); MS (ESI): m/z: 252 [M−56+H]$^+$.

tert-Butyl 4-[3-(2-bromoethoxy)phenoxy]azepane-1-carboxylate 0.13 g of tert-butyl 3-[[4-(2-bromoethoxy)phenoxy]methyl]pyrrolidine-1-carboxylate was prepared according to the procedure for Intermediate 14, step 2, starting from 0.19 g (0.61 mmol) of tert-butyl 4-(3-hydroxyphenoxy)azepane-1-carboxylate and 2-bromoethanol (yield: 51%). $^1$H NMR (CDCl$_3$) δ (ppm): 7.23-7.14 (m, 1H), 6.55-6.48 (m, 2H), 6.48-6.44 (m, 1H), 4.48-4.38 (m, 1H), 4.28 (t, J=6.4 Hz, 2H), 3.64 (t, J=6.1 Hz, 2H), 3.60-3.20 (m, 4H), 2.13-1.86 (m, 5H), 1.71-1.60 (m, 1H), 1.49 (s, 9H); MS (ESI): m/z: 358 [M−56+H]$^+$.

Intermediate 22: tert-butyl 4-[[4-(3-bromopropyl)phenoxy]methyl]piperidine-1-carboxylate

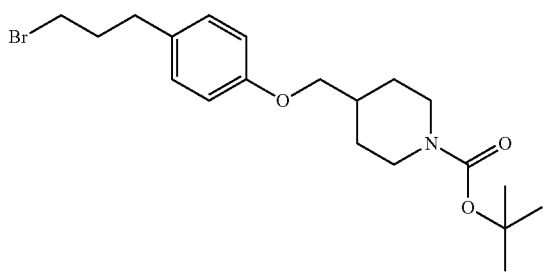 [SMILES: CC(C)(C)OC(=O)N1CCC(COc2ccc(CCCBr)cc2)CC1]

0.28 g of tert-butyl 4-[[4-(3-bromopropyl)phenoxy]methyl]piperidine-1-carboxylate was prepared according to the procedure for Intermediate 14, step 1, starting from 0.20 g (0.91 mmol) of 4-(3-bromopropyl)phenol (U.S. Pat. No. 5,204,018) and 0.29 g (1.4 mmol) of tert-butyl 4-(hydroxymethyl)piperidine-1-carboxylate (Sigma-Aldrich, Cat. No. 556017) (yield: 76%). $^1$H NMR (CDCl$_3$) δ (ppm): 7.17-7.07 (m, 2H), 6.87-6.76 (m, 2H), 4.21-4.11 (m, 2H), 3.79 (d, J=6.4 Hz, 2H), 3.39 (t, J=6.6 Hz, 2H), 2.83-2.69 (m, 4H), 2.19-2.09 (m, 2H), 2.01-1.90 (m, 1H), 1.88-1.76 (m, 2H), 1.47 (s, 9H), 1.34-1.19 (m, 2H); MS (ESI): m/z: 356 [M−56+H]$^+$.

Intermediate 23: tert-butyl 4-[4-(3-bromopropyl)phenoxy]azepane-1-carboxylate

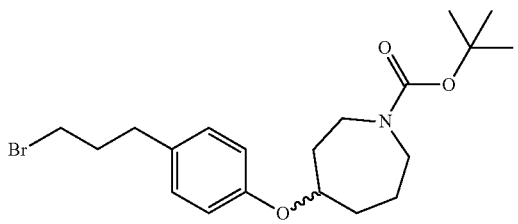 [SMILES: CC(C)(C)OC(=O)N1CCCC(Oc2ccc(CCCBr)cc2)CC1]

0.28 g of tert-butyl 4-[4-(3-bromopropyl)phenoxy]azepane-1-carboxylate was prepared according to the procedure for Intermediate 14, step 1, starting from 0.20 g (0.91 mmol) of 4-(3-bromopropyl)phenol (U.S. Pat. No. 5,204,018) and 0.29 g (1.4 mmol) of tert-butyl 4-hydroxyazepane-1-carboxylate (Intermediate 18, Step 2) (yield: 76%). $^1$H NMR (CDCl$_3$) δ (ppm): 7.14-7.07 (m, 2H), 6.85-6.77 (m, 2H), 4.45-4.38 (m, 1H), 3.65-3.24 (m, 6H), 2.72 (t, J=7.3 Hz, 2H), 2.18-2.10 (m, 2H), 2.10-2.02 (m, 1H), 1.99-1.85 (m, 4H), 1.70-1.59 (m, 1H), 1.48 (s, 9H); MS (ESI): m/z: 356 [M−56+H]$^+$.

Intermediate 24: tert-butyl 4-[[4-(3-bromopropyl)-2-[(1-tert-butoxycarbonyl-4-piperidyl)methoxy]phenoxy]methyl]piperidine-1-carboxylate

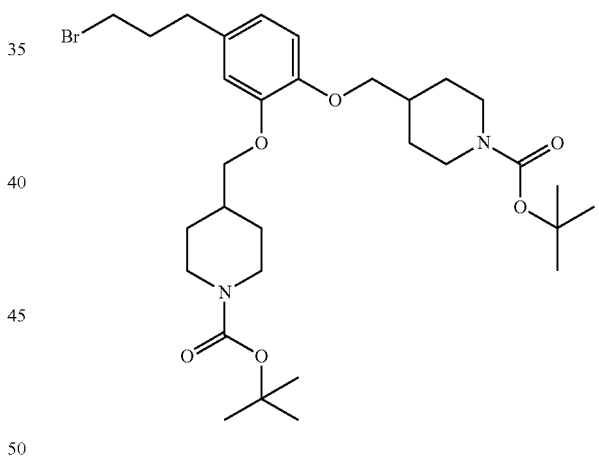

tert-butyl 4-[[2-[(1-tert-butoxycarbonyl-4-piperidyl)methoxy]-4-(3-hydroxypropyl)phenoxy]methyl]piperidine-1-carboxylate 0.079 g (0.47 mmol) of 4-(3-hydroxypropyl)benzene-1,2-diol (Yang, J. et al. Biorg. Med. Chem Lett. 2014, 24, 2680-2684), 0.03 g (0.2 mmol) of NaI and 0.61 g (1.9 mmol) of Cs$_2$CO$_3$ were suspended in 1.5 mL dry DMF under nitrogen atmosphere. 0.46 g (1.6 mmol) of tert-butyl 4-(bromomethyl)piperidine-1-carboxylate (Sigma-Aldrich, Cat. No. 796719) in 0.8 mL dry DMF was added and the suspension was stirred at 80° C. for 7 h.

The mixture was cooled down to RT and a further portion of NaI (0.014 g, 0.09 mmol), Cs$_2$CO$_3$ (0.23 g, 0.72 mmol) and tert-butyl 4-(bromomethyl)piperidine-1-carboxylate (0.2 g, 0.72 mmol) were added. The resulting mixture was heated at 80° C. overnight, then cooled down to RT and the product was extracted with EtOAc, dried over Na₂SO₄ and purified by column chromatography over silica gel (eluent: hexane/acetone, 0% to 18% of acetone) providing 148 mg (56%) of tert-butyl 4-[[2-[(1-tert-butoxycarbonyl-4-piperidyl)methoxy]-4-(3-hydroxypropyl)phenoxy]methyl]piperidine-1-carboxylate as a pale yellow oil. ¹H NMR (CDCl₃) δ (ppm): 6.85-6.69 (m, 3H), 4.22-4.08 (m, 4H), 3.86-3.78 (m, 4H), 3.69 (t, J 7.3 Hz, 2H), 2.82-2.71 (m, 4H), 2.65 (t, J=7.3 Hz, 2H), 2.06-1.94 (m, 2H), 1.92-1.78 (m, 6H), 1.48 (s, 9H), 1.47 (s, 9H), 1.33-1.19 (m, 4H); MS (ESI): m/z: 585 [M+Na]⁺.

tert-butyl 4-[[4-(3-bromopropyl)-2-[(1-tert-butoxycarbonyl-4-piperidyl)methoxy]phenoxy]methyl]piperidine-1-carboxylate A solution of 0.10 g (0.31 mmol) CBr₄ in 0.75 mL CH₂Cl₂ was added dropwise at −18° C. to a solution of 0.144 g (0.256 mmol) of tert-butyl 4-[[2-[(1-tert-butoxycarbonyl-4-piperidyl)methoxy]-4-(3-hydroxypropyl)phenoxy]methyl]piperidine-1-carboxylate and 0.081 g (0.31 mmol) of PPh₃ in 1.75 mL CH₂Cl₂. The reaction mixture was stirred at RT for 4 h. Then, the solution was concentrated and the residue was purified by column chromatography eluent: hexane/acetone, 0% to 7% of acetone) affording 118 mg (74%) of tert-butyl 4-[[4-(3-bromopropyl)-2-[(1-tert-butoxycarbonyl-4-piperidyl)methoxy]phenoxy]methyl]piperidine-1-carboxylate as a pale yellow oil. ¹H NMR (CDCl₃) δ (ppm): 6.85-6.67 (m, 3H), 4.24-4.05 (m, 4H), 3.87-3.75 (m, 4H), 3.39 (t, J=6.6 Hz, 2H), 2.83-2.63 (m, 6H), 2.19-2.10 (m, 2H), 2.05-1.93 (m, 2H), 1.88-1.79 (m, 4H), 1.48 (s, 9H), 1.47 (s, 9H), 1.32-1.18 (m, 4H); MS (ESI): m/z: 647 [M+Na]⁺.

Intermediate 25: tert-Butyl 4-[4-(2-bromoethyl)phenoxy]piperidine-1-carboxylate

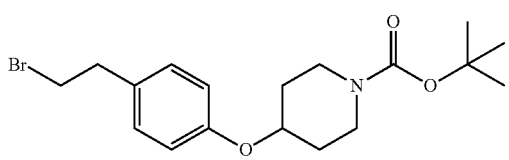 [SMILES: CC(C)(C)OC(=O)N1CCC(Oc2ccc(CCBr)cc2)CC1]

0.56 g of tert-butyl 4-[4-(2-bromoethyl)phenoxy]piperidine-1-carboxylate was prepared according to the procedure for Intermediate 14, step 1, starting from 0.40 g (2.0 mmol) of 4-(2-bromoethyl)phenol (Fluorochem, Cat. No. 233801) and 0.61 g (3.0 mmol) of tert-butyl 4-hydroxypiperidine-1-carboxylate (Apollo, Cat. No. OR5404) (yield: 73%). ¹H NMR (CDCl₃) δ (ppm): 7.18-7.08 (m, 2H), 6.91-6.81 (m, 2H), 4.50-4.37 (m, 1H), 3.76-3.65 (m, 2H), 3.54 (t, J=7.6 Hz, 2H), 3.39-3.28 (m, 2H), 3.11 (t, J=7.6 Hz, 2H), 1.99-1.85 (m, 2H), 1.80-1.68 (m, 2H), 1.48 (s, 9H); MS (ESI): m/z: 328 [M−56+H]⁺.

Intermediate 26: tert-Butyl 4-[3-[2-[4-ethyl-2-(4-methylthieno[3,2-b]pyrrol-5-yl)imidazol-1-yl]ethoxy]phenoxy]piperidine-1-carboxylate

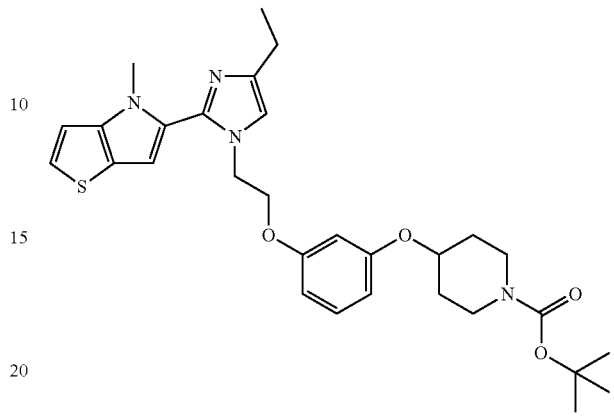

0.03 g (0.13 mmol) of 5-(4-ethyl-1H-imidazol-2-yl)-4-methyl-thieno[3,2-b]pyrrole (Example 2) were added to a suspension of 0.0060 g (0.16 mmol) of NaH (60% dispersion in mineral oil) in dry DMA (0.2 mL) cooled down to −15° C. The mixture was stirred at a temperature raging from −15° C. to 0° C. for 1 h, then a solution of 0.065 g of tert-butyl 4-[3-(2-bromoethoxy)phenoxy]piperidine-1-carboxylate (Intermediate 14) in 0.5 mL of dry DMA was added at 0° C. and the mixture was stirred overnight at RT. The reaction was stopped by adding water and the product was extracted with EtOAc. The combined organic layers were dried over Na₂SO₄, filtered and evaporated to dryness. The crude product was purified by flash chromatography on silica gel (hexane/acetone, 94:6%-60:40, v:v) to afford 0.043 g of tert-butyl 4-[3-[2-[4-ethyl-2-(4-methylthieno[3,2-b]pyrrol-5-yl)imidazol-1-yl]ethoxy]phenoxy]piperidine-1-carboxylate (Intermediate 26, yield: 60%) as white foam. ¹H NMR (DMSO-d₆) δ (ppm): 7.32 (d, J=5.4 Hz, 1H), 7.18 (d, J=5.4 Hz, 1H), 7.16-7.07 (m, 2H), 6.67 (s, 1H), 6.57-6.39 (m, 3H), 4.54-4.45 (m, 1H), 4.37-4.20 (m, 4H), 3.76 (s, 3H), 3.68-3.55 (m, 2H), 3.21-3.09 (m, 2H), 2.51 (q, J=7.3 Hz, 2H), 1.91-1.78 (m, 2H), 1.52-1.42 (m, 2H), 1.39 (s, 9H), 1.18 (t, J=7.3 Hz, 3H); MS (ESI): m/z: 551 [M+H]⁺.

Intermediate 27: tert-Butyl 4-[3-[2-[5-ethyl-2-(4-methylthieno[3,2-b]pyrrol-5-yl)imidazol-1-yl]ethoxy]phenoxy]piperidine-1-carboxylate

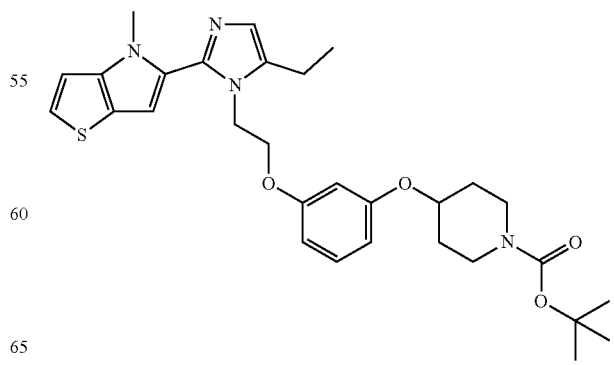

Purification of the crude Intermediate 26 by flash chromatography (hexane/acetone, from 94:6% to 60:40, v:v) provided also 0.0092 g of tert-butyl 4-[3-[2-[5-ethyl-2-(4-methylthieno[3,2-b]pyrrol-5-yl)imidazol-1-yl]ethoxy]phenoxy]piperidine-1-carboxylate (Intermediate 27, yield: 13%) as pale yellow foam. $^1$H NMR (DMSO-d$_6$) δ (ppm): 7.32 (d, J=5.4 Hz, 1H), 7.19 (d, J 5.4 Hz, 1H), 6.86 (s, 1H), 6.72 (s, 1H), 6.55-6.30 (m, 3H), 4.52-4.43 (m, 1H), 4.39-4.33 (m, 2H), 4.12-4.07 (m, 2H), 3.69 (s, 3H), 3.64-3.56 (m, 2H), 3.21-3.05 (m, 2H), 2.75-2.67 (m, 2H), 1.87-1.77 (m, 2H), 1.52-1.43 (m, 2H), 1.39 (s, 9H), 1.30-1.24 (m, 3H); MS (ESI): m/z: 551 [M+H]$^+$.

The following intermediates (see Table 2) were prepared starting from the appropriate mono or bi-substituted 5-(1H-imidazol-2-yl)-4-methyl-thieno[3,2-b]pyrroles (Examples 1, 2, 6, 7, 9, 10, 13 for Intermediates 28-46 and 48-85) or from 5-(4-ethyl-1H-imidazol-2-yl)-6-methyl-thieno[2,3-b]pyrrole (Example 14 for Intermediate 47) and the appropriate alkyl-bromides (Intermediates 14-24) according to the procedure for Intermediates 26 and 27.

TABLE 2

BOC Intermediates

| Int. | Name | Structure | Analytical Data |
|---|---|---|---|
| 28 | tert-butyl 4-[4-[2-[4-ethyl-2-(4-methylthieno[3,2-b]pyrrol-5-yl)imidazol-1-yl]ethoxy]phenoxy]piperidine-1-carboxylate | 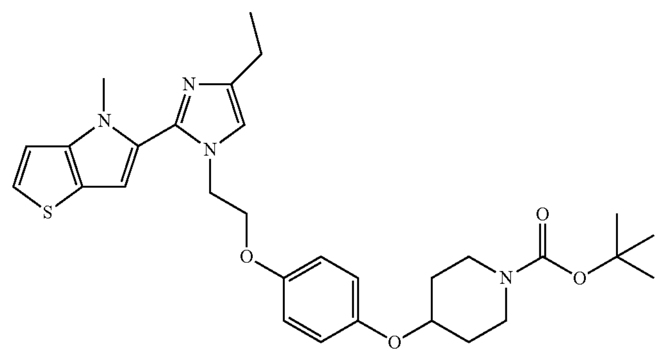 [SMILES: CCc1cn(CCOc2ccc(OC3CCN(C(=O)OC(C)(C)C)CC3)cc2)c(-c2cc3sccc3n2C)n1] | $^1$H NMR (CDCl$_3$) δ (ppm): 7.17 (d, J = 5.4 Hz, 1 H), 7.97 (d, J = 5.4 Hz, 1 H), 6.94 (s, 1H), 6.86-6.72 (m, 4 H), 6.59 (s, 1 H), 4.43-4.27 (m, 3 H), 4.20-4.13 (m, 2 H), 3.85 (s, 3 H), 3.76-3.25 (m, 4 H), 2.79-2.64 (m, 2 H), 1.94-1.65 (m, 4 H), 1.48 (s, 9 H), 1.34-1.22 (m, 3 H); MS (ESI): m/z: 551 [M + H]$^+$. |
| 29 | tert-butyl 4-[4-[2-[5-ethyl-2-(4-methylthieno[3,2-b]pyrrol-5-yl)imidazol-1-yl]ethoxy]phenoxy]piperidine-1-carboxylate | 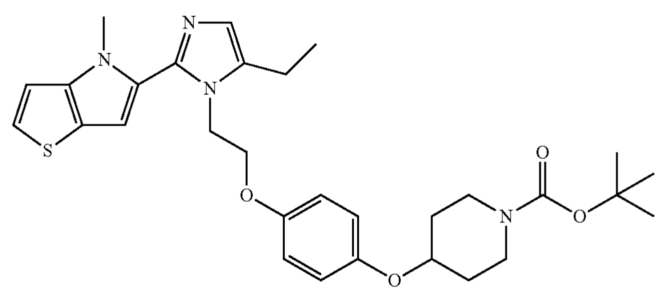 [SMILES: CCc1cnc(-c2cc3sccc3n2C)n1CCOc1ccc(OC2CCN(C(=O)OC(C)(C)C)CC2)cc1] | $^1$H NMR (CDCl$_3$) δ (ppm): 7.20 (d, J = 5.4 Hz, 1H), 7.05 (s, 1 H), 6.98 (d, J = 5.4 Hz, 1H), 6.81-6.58 (m, 5 H), 4.41 (t, J = 5.7, 2H), 4.35-4.27 (m, 1 H), 4.05 (t, J = 5.7, 2H), 3.80 (s, 3 H), 3.74-3.25 (m, 4 H), 2.76 (q, J = 7.6, 2 H), 1.92-1.65 (m, 4 H), 1.47 (s, 9 H), 1.40 (t, J = 7.6, 3 H); MS (ESI): m/z: 551 [M + H]$^+$. |
| 30 | tert-butyl 3-[[4-[2-[4-ethyl-2-(4-methylthieno[3,2-b]pyrrol-5-yl)imidazol-1-yl]ethoxy]phenoxy]methyl]pyrrolidine-1-carboxylate | 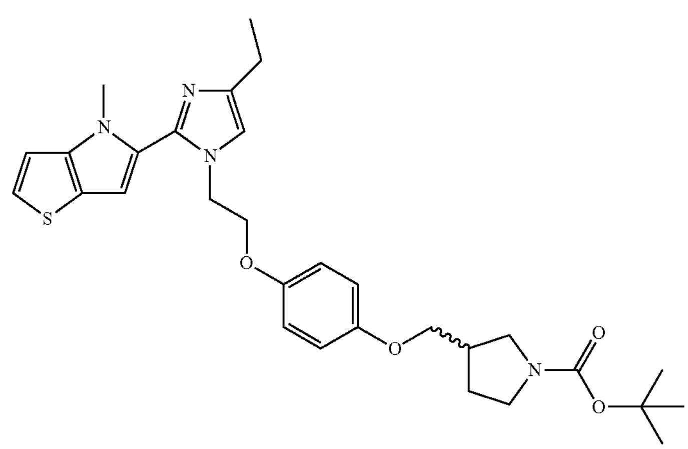 [SMILES: CCc1cn(CCOc2ccc(OCC3CCN(C(=O)OC(C)(C)C)C3)cc2)c(-c2cc3sccc3n2C)n1] | $^1$H NMR (CDCl$_3$) δ (ppm): 7.17 (d, J = 5.4 Hz, 1H), 6.97 (d, J = 5.4 Hz, 1H), 6.94 (s, 1 H), 6.84-6.69 (m, 4 H), 6.58 (s, 1 H), 4.37 (t, J = 5.4 Hz, 2H), 4.15 (t, J = 5.4 Hz, 2H), 3.83 (s, 3 H), 3.94-3.78 (m, 2 H), 3.66-3.09 (m, 4 H), 2.75-2.60 (m, 3 H), 2.12-1.69 (m, 2 H), 1.47 (s, 9 H), 1.29 (t, J = 7.6, 3H); MS (ESI): m/z: 551 [M + H]$^+$. |

TABLE 2-continued

BOC Intermediates

| Int. | Name | Structure | Analytical Data |
|---|---|---|---|
| 31 | tert-butyl 4-[[4-[2-[4-ethyl-2-(4-methylthieno[3,2-b]pyrrol-5-yl)imidazol-1-yl]ethoxy]phenoxy]methyl]piperidine-1-carboxylate | 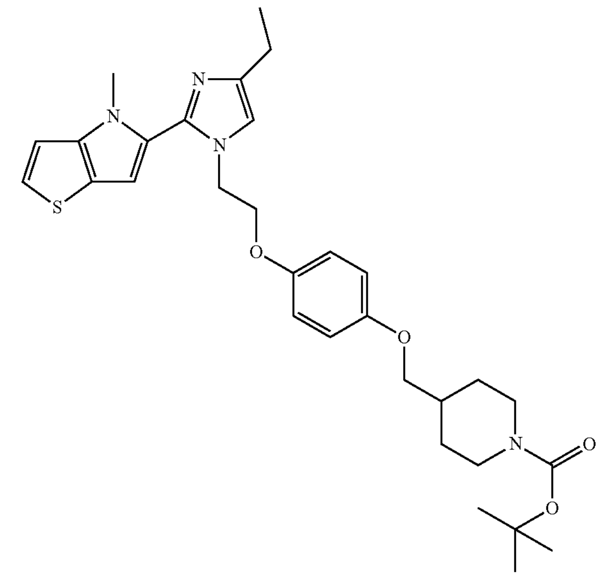 [SMILES: CCc1cn(CCOc2ccc(OCC3CCN(C(=O)OC(C)(C)C)CC3)cc2)c(-c2cc3sccc3n2C)n1] | $^1$H NMR (DMSO-d$_6$) δ (ppm): 7.32 (d, J = 4.9 Hz, 1 H), 7.18 (d, J = 5.4 Hz, 1 H), 7.14 (s, 1H), 6.82-6.73 (m, 4 H), 6.67 (s, 1 H), 4.31 (t, J = 5.4 Hz, 2 H), 4.18 (t, J = 5.4 Hz, 2 H), 4.03-3.88 (m, 2 H), 3.77 (s, 3 H), 3.73 (d, J = 6.4 Hz, 2 H), 2.71 (bs, 2 H), 2.52 (q, J = 7.6 Hz, 2 H), 1.93-1.80 (m, 1 H), 1.76-1.65 (m, 2 H), 1.39 (s, 9 H), 1.18 (t, J = 7.6 Hz, 3 H), 1.16-1.06 (m, 2 H); MS (ESI): m/z: 565 [M + H]$^+$. |
| 32 | tert-butyl 4-[[4-[2-[5-ethyl-2-(4-methylthieno[3,2-b]pyrrol-5-yl)imidazol-1-yl]ethoxy]phenoxy]methyl]piperidine-1-carboxylate | 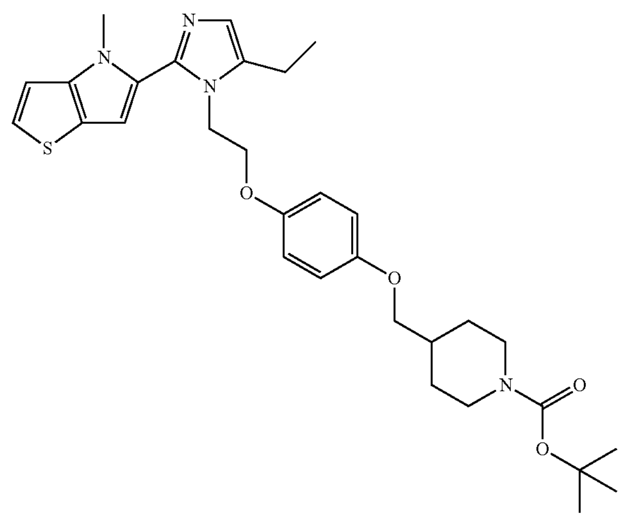 [SMILES: CCc1cnc(-c2cc3sccc3n2C)n1CCOc1ccc(OCC2CCN(C(=O)OC(C)(C)C)CC2)cc1] | $^1$H NMR (DMSO-d$_6$) δ (ppm): 7.37 (d, J = 5.4 Hz, 1 H), 7.21 (d, J = 5.4 Hz, 1 H), 7.03 (s, 1 H), 6.80 (s, 1 H), 6.76-6.62 (m, 4 H), 4.39 (t, J = 5.4 Hz, 2 H), 4.06 (t, J = 5.4 Hz, 2 H), 3.94 (bs, 2 H), 3.73-3.66 (m, 5 H), 2.77-2.64 (m, 4 H), 1.89-1.78 (m, 1 H), 1.74-1.66 (m, 2 H), 1.39 (s, 9 H), 1.28 (t, J = 7.3 Hz, 3 H), 1.16-1.04 (m, 2 H); MS (ESI): m/z: 565 [M + H]$^+$. |
| 33 | tert-butyl 4-[4-[2-[4-ethyl-2-(4-methylthieno[3,2-b]pyrrol-5-yl)imidazol-1-yl]ethoxy]phenoxy]azepane-1-carboxylate | 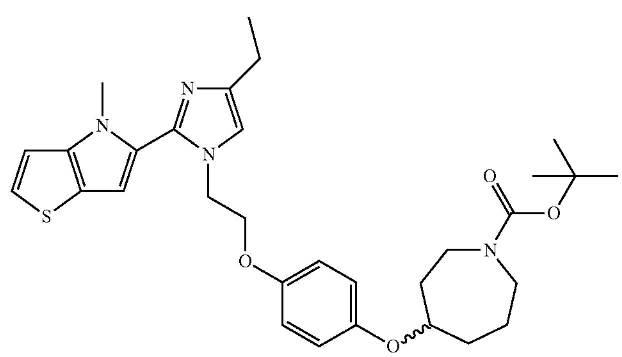 [SMILES: CCc1cn(CCOc2ccc(OC3CCCN(C(=O)OC(C)(C)C)CC3)cc2)c(-c2cc3sccc3n2C)n1] | $^1$H NMR (DMSO-d$_6$) δ (ppm): 7.32 (d, J = 5.4 Hz, 1 H), 7.18 (d, J = 5.4 Hz, 1 H), 7.14 (s, 1 H), 6.82-6.74 (m, 4 H), 6.67 (s, 1 H), 4.38-4.27 (m, 3 H), 4.18 (t, J = 5.4 Hz, 2 H), 3.77 (s, 3 H), 3.42-3.20 (m, 4 H), 2.53 (q, J = 7.4 Hz, 2 H), 1.99-1.87 (m, 1 H), 1.84-1.63 (m, 4 H), 1.60-1.50 (m, 1 H), 1.40 (s, 9 H), 1.18 (t, J = 7.6 Hz, 3 H); MS (ESI): m/z: 566 [M + H]$^+$. |

TABLE 2-continued

BOC Intermediates

| Int. | Name | Structure | Analytical Data |
|---|---|---|---|
| 34 | tert-butyl 4-[4-[2-[5-ethyl-2-(4-methylthieno[3,2-b]pyrrol-5-yl)imidazol-1-yl]ethoxy]phenoxy]azepane-1-carboxylate | 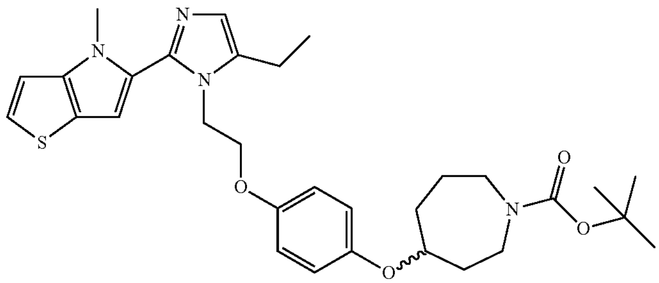 [SMILES: CCc1cnc(-c2cc3sccc3n2C)n1CCOc1ccc(OC2CCCN(C(=O)OC(C)(C)C)CC2)cc1] | ¹H NMR (DMSO-d₆) δ (ppm): 7.32 (d, J = 5.4 Hz, 1 H), 7.18 (d, J = 5.4 Hz, 1 H), 6.86 (s, 1 H), 6.77-6.63 (m, 5 H), 4.38-4.26 (m, 3 H), 4.05 (t, J = 5.4 Hz, 2 H), 3.69 (s, 3 H), 3.30-3.19 (m, 4 H), 2.71 (q, J = 7.4 Hz, 2 H), 1.98-1.84 (m, 1 H), 1.83-1.61 (m, 4 H), 1.60-1.48 (m, 1 H), 1.40 (s, 9 H), 1.27 (t, J = 7.4 Hz, 3 H); MS (ESI): m/z: 566 [M + H]⁺. |
| 35 | tert-butyl 4-[4-[3-[4-ethyl-2-(4-methylthieno[3,2-b]pyrrol-5-yl)imidazol-1-yl]propyl]phenoxy]piperidine-1-carboxylate | 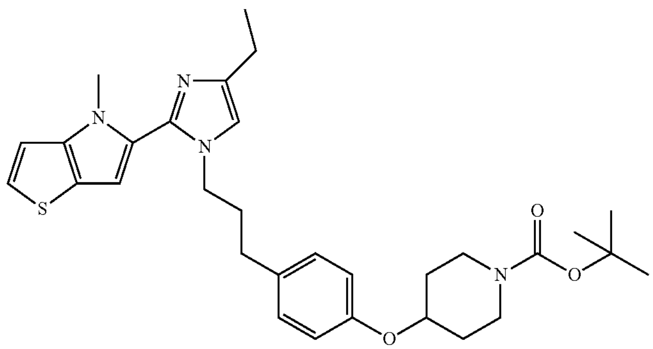 [SMILES: CCc1cn(CCCc2ccc(OC3CCN(C(=O)OC(C)(C)C)CC3)cc2)c(-c2cc3sccc3n2C)n1] | ¹H NMR (DMSO-d₆) δ (ppm): 7.32 (d, J = 5.4 Hz, 1 H), 7.17 (d, J = 5.4 Hz, 1 H), 7.07 (s, 1 H), 7.01-6.97 (m, 2 H), 6.81-6.75 (m, 2 H), 6.41 (s, 1 H), 4.48-4.39 (m, 1 H), 3.94 (t, J = 7.3 Hz, 2 H), 3.78 (s, 3 H), 3.69-3.59 (m, 2 H), 3.22-3.07 (m, 2 H), 2.53 (q, J = 7.3 Hz, 2 H), 2.44 (t, J = 7.3 Hz, 2 H), 2.00-1.92 (m, 2 H), 1.89-1.80 (m, 2 H), 1.51-1.42 (m, 2 H), 1.40 (s, 9 H), 1.18 (t, J = 7.6 Hz, 3 H); MS (ESI): m/z: 549 [M + H]⁺. |
| 36 | tert-butyl 4-[4-[3-[5-ethyl-2-(4-methylthieno[3,2-b]pyrrol-5-yl)imidazol-1-yl]propyl]phenoxy]piperidine-1-carboxylate | 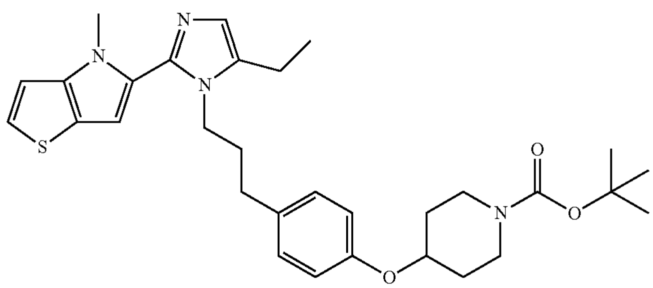 [SMILES: CCc1cnc(-c2cc3sccc3n2C)n1CCCc1ccc(OC2CCN(C(=O)OC(C)(C)C)CC2)cc1] | ¹H NMR (DMSO-d₆) δ (ppm): 7.32 (d, J = 5.4 Hz, 1 H), 7.17 (d, J = 5.4 Hz, 1 H), 7.02-6.95 (m, 2 H), 6.84 (s, 1 H), 6.81-6.75 (m, 2 H), 6.46 (s, 1 H), 4 49-4 40 (m, 1 H), 3.92 (t, J = 7.8 Hz, 2 H), 3.72 (s, 3 H), 3.68-3.59 (m, 2 H), 3.21-3.08 (m, 2 H), 2.57 (q, J = 7.3 Hz, 2 H), 2.43 (t, J = 7.3 Hz, 2 H), 1.90-1.78 (m, 4 H), 1.52-1.42 (m, 2 H), 1.40 (s, 9 H), 1.23 (t, J = 7.3 Hz, 3 H); MS (ESI): m/z: 549 [M + H]⁺. |
| 37 | tert-butyl 4-[4-[2-[4-cyclobutyl-2-(4-methylthieno[3,2-b]pyrrol-5-yl)imidazol-1-yl]ethoxy]phenoxy]piperidine-1-carboxylate | 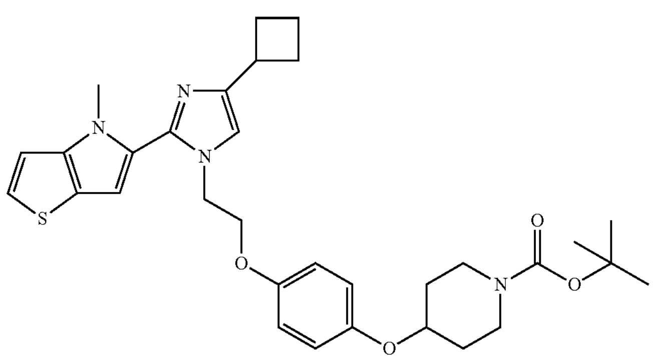 [SMILES: Cn1c(-c2nc(C3CCC3)cn2CCOc2ccc(OC3CCN(C(=O)OC(C)(C)C)CC3)cc2)cc2sccc21] | ¹H NMR (DMSO-d₆) δ (ppm): 7.33 (d, J = 5.4 Hz, 1 H), 7.21-7.16 (m, 2 H), 6.88-6.74 (m, 4 H), 6.68 (s, 1 H), 4.42-4.34 (m, 1 H), 4.31 (t, J = 5.3 Hz, 2 H), 4.19 (t, J = 5.3 Hz, 2 H), 3.78 (s, 3 H), 3.66-3.57 (m, 2 H), 3.47-3.37 (m, 1 H), 3.20-3.05 (m, 2 H), 2.25-2.09 (m, 4 H), 1.99-1.87 (m, 1 H), 1.86-1.76 (m, 3 H), 1.50-1.42 (m, 2 H), 1.39 (s, 9 H); MS (ESI): m/z: 577 [M + H]⁺. |

TABLE 2-continued

BOC Intermediates

| Int. | Name | Structure | Analytical Data |
|---|---|---|---|
| 38 | tert-butyl 4-[4-[2-[5-cyclobutyl-2-(4-methylthieno[3,2-b]pyrrol-5-yl)imidazol-1-yl]ethoxy]phenoxy]piperidine-1-carboxylate | 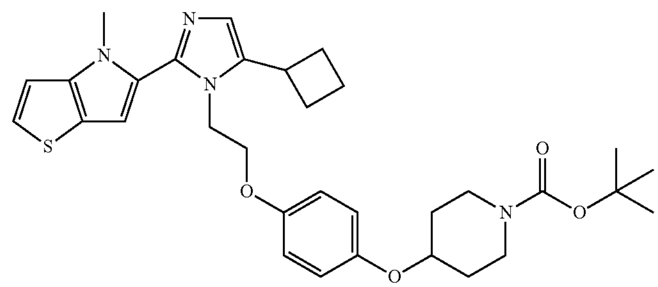 [SMILES: Cn1c(-c2ncc(C3CCC3)n2CCOc2ccc(OC3CCN(C(=O)OC(C)(C)C)CC3)cc2)cc2sccc21] | $^1$H NMR (DMSO-$d_6$) δ (ppm): 7.33 (d, J = 5.4 Hz, 1 H), 7.19 (d, J = 5.4 Hz, 1 H), 6.98 (s, 1 H), 6.82-6.76 (m, 2 H), 6.72 (s, 1 H), 6.68-6.61 (m, 2 H), 4.38-4.32 (m, 1 H), 4.28 (t, J = 5.4 Hz, 2 H), 3.99 (t, J = 5.8 Hz, 2 H), 3.71-3.57 (m, 6 H), 3.19-3.08 (m, 2 H), 2.39-2.30 (m, 2 H), 2.19-2.09 (m, 2 H), 2.05-1.94 (m, 1 H), 1.90-1.76 (m, 3 H), 1.50-1.36 (m, 11 H); MS (ESI): m/z: 577 [M + H]$^+$. |
| 39 | tert-butyl 4-[4-[2-[5-ethyl-2-(4-methylthieno[3,2-b]pyrrol-5-yl)-4-phenyl-imidazol-1-yl]ethoxy]phenoxy]piperidine-1-carboxylate | 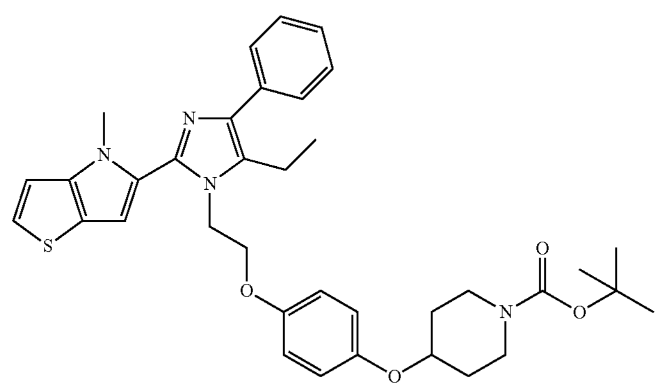 [SMILES: CCc1c(-c2ccccc2)nc(-c2cc3sccc3n2C)n1CCOc1ccc(OC2CCN(C(=O)OC(C)(C)C)CC2)cc1] | $^1$H NMR (DMSO-$d_6$) δ (ppm): 7.72-7.66 (m, 2 H), 7.46-7.38 (m, 2 H), 7.35 (d, J = 5.3 Hz, 1 H), 7.28-7.23 (m, 1 H), 7.21 (d, J = 4.9 Hz, 1 H), 6.82-6.76 (m, 3 H), 6.69-6.64 (m, 2 H), 4.46 (t, J = 5.4 Hz, 2 H), 4.37-4.29 (m, 1 H), 4.08 (t, J = 5.4 Hz, 2 H), 3.77 (s, 3 H), 3.66-3.56 (m, 2 H), 3.19-3.05 (m, 2 H), 2.97 (q, J = 7.3 Hz, 2 H), 1.85-1.74 (m, 2 H), 1.49-1.37 (m, 11 H), 1.26 (t, J = 7.3 Hz, 3 H); MS (ESI): m/z: 627 [M + H]$^+$. |
| 40 | tert-butyl 4-[3-[2-[5-ethyl-2-(4-methylthieno[3,2-b]pyrrol-5-yl)-4-phenyl-imidazol-1-yl]ethoxy]phenoxy]piperidine-1-carboxylate | 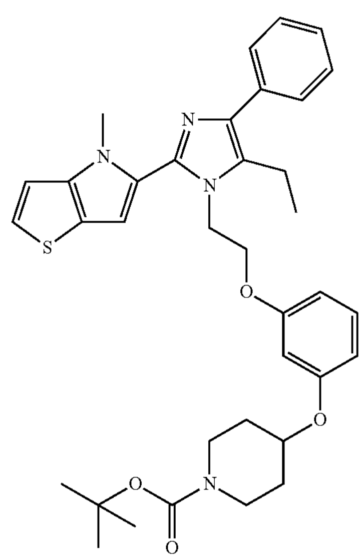 [SMILES: CCc1c(-c2ccccc2)nc(-c2cc3sccc3n2C)n1CCOc1cccc(OC2CCN(C(=O)OC(C)(C)C)CC2)c1] | $^1$H NMR (DMSO-$d_6$) δ (ppm): 7.73-7.65 (m, 2 H), 7.45-7.39 (m, 2 H), 7.35 (d, J = 5.4 Hz, 1 H), 7.29-7.23 (m, 1 H), 7.21 (d, J = 5.4 Hz, 1 H), 7.09-7.04 (m, 1 H), 6.81 (s, 1 H), 6.56-6.49 (m, 1 H), 6.35-6.30 (m, 2 H), 4.51-4.41 (m, 3 H), 4.13 (t, J = 5.4 Hz, 2 H), 3.77 (s, 3 H), 3.63-3.54 (m, 2 H), 3.20-3.08 (m, 2 H), 2.96 (q, J = 7.3 Hz, 2 H), 1.86-1.76 (m, 2 H), 1.51-1.36 (m, 11 H), 1.26 (t, J = 7.3 Hz, 3 H); MS (ESI): m/z: 627 [M + H]$^+$. |

TABLE 2-continued

BOC Intermediates

| Int. | Name | Structure | Analytical Data |
|---|---|---|---|
| 41 | tert-butyl 4-[3-[2-[4-ethyl-2-(4-methylthieno[3,2-b]pyrrol-5-yl)-5-phenyl-imidazol-1-yl]ethoxy]phenoxy]piperidine-1-carboxylate | 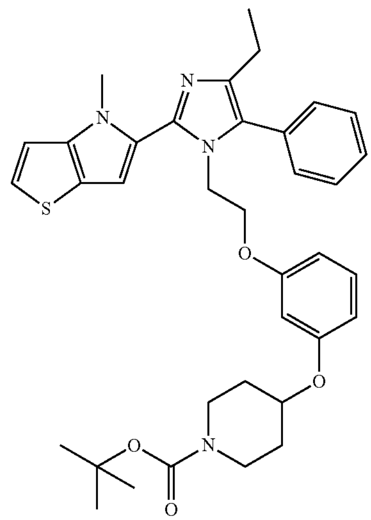 [SMILES: CCc1nc(-c2cc3sccc3n2C)n(CCOc2cccc(OC3CCN(C(=O)OC(C)(C)C)CC3)c2)c1-c1ccccc1] | $^1$H NMR (DMSO-d$_6$) δ (ppm): 7.55-7.41 (m, 5 H), 7.34 (d, J = 5.4 Hz, 1 H), 7.20 (d, J = 5.4 Hz, 1 H), 7.02-6.95 (m, 1 H), 6.77 (s, 1 H), 6.49-6.43 (m, 1 H), 6.15-6.12 (m, 1 H), 6.11-6.07 (m, 1 H), 4.47-4.35 (m, 3 H), 3.79 (s, 3 H), 3.74 (t, J = 5.8 Hz, 2 H), 3.64-3.54 (m, 2 H), 3.20-3.08 (m, 2 H), 2.46 (q, J = 7.3 Hz, 2 H), 1.86-1.76 (m, 2 H), 1.49-1.37 (m, 11 H), 1.13 (t, J = 7.3 Hz, 3 H); MS (ESI): m/z: 627 [M + H]$^+$. |
| 42 | tert-butyl 4-[3-[2-[4-ethyl-2-(4-methylthieno[3,2-b]pyrrol-5-yl)imidazol-1-yl]ethoxy]phenoxy]azepane-1-carboxylate | 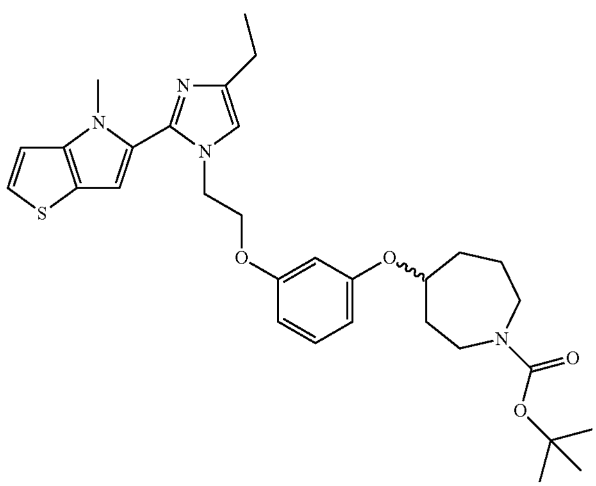 [SMILES: CCc1cn(CCOc2cccc(OC3CCCN(C(=O)OC(C)(C)C)CC3)c2)c(-c2cc3sccc3n2C)n1] | $^1$H NMR (DMSO-d$_6$) δ (ppm): 7.32 (d, J = 5.4 Hz, 1 H), 7.19 (d, J = 5.4 Hz, 1 H), 7.15-7.09 (m, 2 H), 6.67 (s, 1 H), 6.50-6.46 (m, 1 H), 6.45-6.41 (m, 1 H), 6.41-6.37 (m, 1 H), 4.50-4.40 (m, 1 H), 4.33 (t, J = 5.4 Hz, 2 H), 4.22 (t, J = 5.8 Hz, 2H), 3.77 (s, 3 H), 3.42-3.34 (m, 4 H), 2.53 (q, J = 7.3 Hz, 2 H), 2.00-1.90 (m, 1 H), 1.83-1.65 (m, 4 H), 1.63-1.50 (m, 1 H), 1.40 (s, 9 H), 1.18 (t, J = 7.6 Hz, 3 H); MS (ESI): m/z: 565 [M + H]$^+$. |
| 43 | tert-butyl 4-[3-[2-[5-ethyl-2-(4-methylthieno[3,2-b]pyrrol-5-yl)imidazol-1-yl]ethoxy]phenoxy]azepane-1-carboxylate | 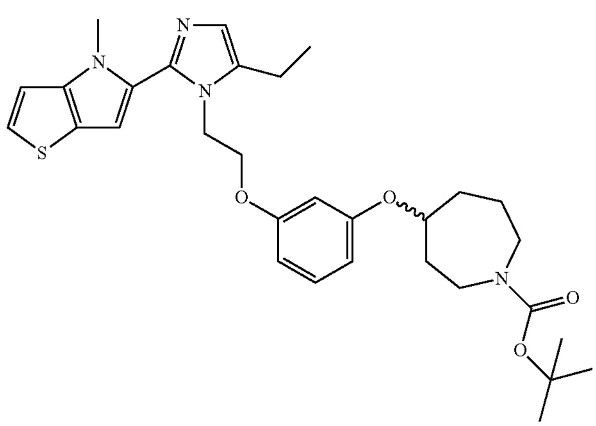 [SMILES: CCc1cnc(-c2cc3sccc3n2C)n1CCOc1cccc(OC2CCCN(C(=O)OC(C)(C)C)CC2)c1] | $^1$H NMR (DMSO-d$_6$) δ (ppm): 7.32 (d, J = 4.9 Hz, 1 H), 7.18 (d, J = 5.4 Hz, 1 H), 7.11-7.03 (m, 1 H), 6.86 (s, 1 H), 6.71 (s, 1 H), 6.49-6.42 (m, 1 H), 6.35-6.31 (m, 1 H), 6.31-6.29 (m, 1 H), 4.46-4.40 (m, 1 H), 4.37 (t, J = 5.4 Hz, 2 H), 4.08 (t, J = 5.3 Hz, 2 H), 3.69 (s, 3 H), 3.42-3.34 (m, 4 H), 2.71 (q, J = 7.3 Hz, 2 H), 2.02-1.88 (m, 1 H), 1.83-1.64 (m, 4 H), 1.61-1.50 (m, 1 H), 1.39 (s, 9 H), 1.27 (t, J = 7.3 Hz, 3 H); MS (ESI): m/z: 565 [M + H]$^+$. |

TABLE 2-continued

BOC Intermediates

| Int. | Name | Structure | Analytical Data |
|---|---|---|---|
| 44 | tert-butyl 4-[4-[2-[4-cyclobutyl-2-(4-methylthieno[3,2-b]pyrrol-5-yl)imidazol-1-yl]ethoxy]phenoxy]azepane-1-carboxylate | 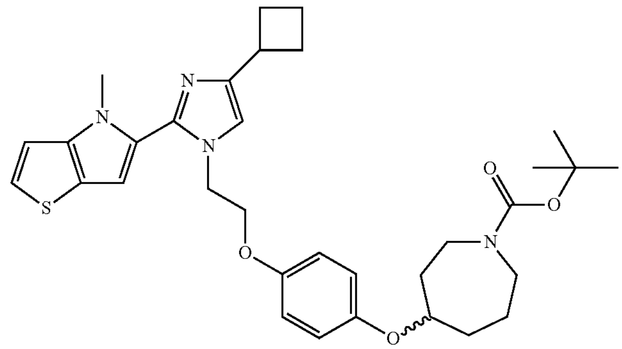 [SMILES: Cn1c(-c2nc(C3CCC3)cn2CCOc2ccc(OC3CCCN(C(=O)OC(C)(C)C)CC3)cc2)cc2sccc21] | $^1$H NMR (DMSO-d$_6$) δ (ppm): 7.33 (d, J = 4.9 Hz, 1 H), 7.22-7.12 (m, 2 H), 6.83-6.73 (m, 4 H), 6.68 (s, 1 H), 4.38-4.26 (m, 3 H), 4.19 (t, J = 5.4 Hz, 2 H), 3.78 (s, 3 H), 3.46-3.35 (m, 3 H), 2.27-2.09 (m, 4 H), 1.99-1.49 (m, 10 H), 1.40 (s, 9 H); MS (ESI): m/z: 591 [M + H]$^+$. |
| 45 | tert-butyl 4-[4-[2-[5-cyclobutyl-2-(4-methylthieno[3,2-b]pyrrol-5-yl)imidazol-1-yl]ethoxy]phenoxy]azepane-1-carboxylate | 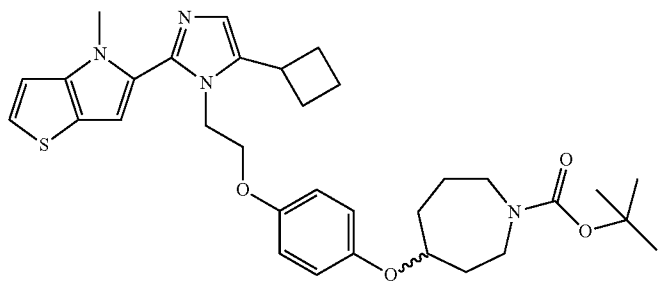 [SMILES: Cn1c(-c2ncc(C3CCC3)n2CCOc2ccc(OC3CCCN(C(=O)OC(C)(C)C)CC3)cc2)cc2sccc21] | $^1$H NMR (DMSO-d$_6$) δ (ppm): 7.32 (d, J = 5.4 Hz, 1 H), 7.18 (d, J = 5.4 Hz, 1 H), 6.98 (s, 1 H), 6.77-6.60 (m, 5 H), 4.37-4.23 (m, 3 H), 4.00 (t, J = 5.3 Hz, 2 H), 3.75-3.59 (m, 4 H), 3.42-3.36 (m, 2 H), 2.41-2.29 (m, 2 H), 2.20-1.49 (m, 12 H), 1.40 (s, 9 H); MS (ESI): m/z: 591 [M + H]$^+$. |
| 46 | tert-butyl 3-[[4-[3-[4-ethyl-2-(4-methylthieno[3,2-b]pyrrol-5-yl)imidazol-1-yl]propyl]phenoxy]methyl]pyrrolidine-1-carboxylate | 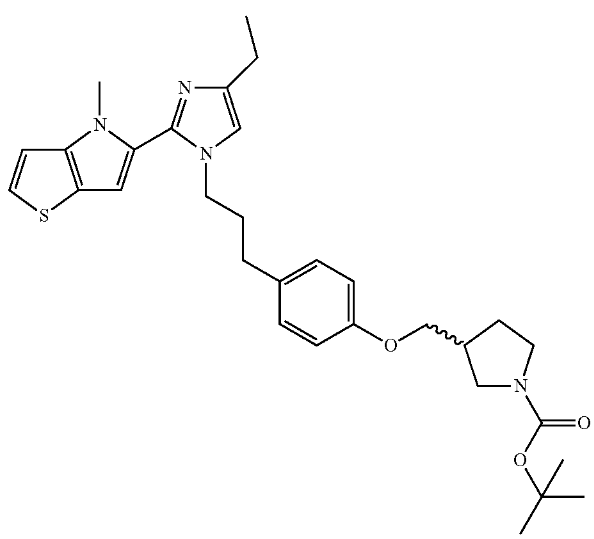 [SMILES: CCc1cn(CCCc2ccc(OCC3CCN(C(=O)OC(C)(C)C)C3)cc2)c(-c2cc3sccc3n2C)n1] | $^1$H NMR (DMSO-d$_6$) δ (ppm): 7.29 (d, J = 5.4 Hz, 1 H), 7.16 (d, J = 4.9 Hz, 1 H), 7.06 (s, 1 H), 7.03-6.98 (m, 2 H), 6.78-6.73 (m, 2 H), 6.34 (s, 1 H), 3.95-3.81 (m, 4 H), 3.78 (s, 3 H), 3.48-3.35 (m, 2 H), 3.29-3.18 (m, 1 H), 3.11-3.03 (m, 1 H), 2.62-2.52 (m, 3 H), 2.48-2.43 (m, 2 H), 2.03-1.91 (m, 3 H), 1.76-1.61 (m, 1 H), 1.39 (s, 9 H), 1.18 (t, J = 7.3 Hz, 3 H); MS (ESI): m/z: 549 [M + H]$^+$. |
| 47 | tert-butyl 4-[4-[2-[4-ethyl-2-(6-methylthieno[2,3-b]pyrrol-5-yl)imidazol-1-yl]ethoxy]phenoxy]piperidine-1-carboxylate | 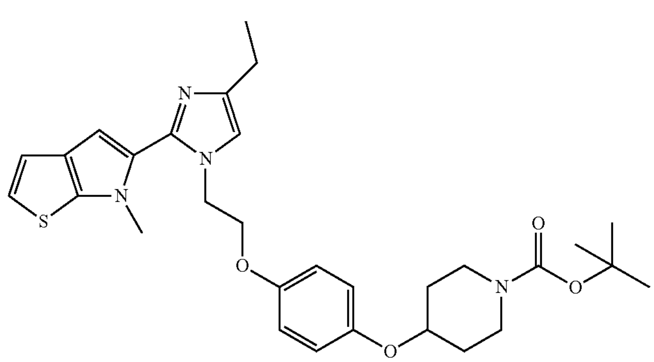 [SMILES: CCc1cn(CCOc2ccc(OC3CCN(C(=O)OC(C)(C)C)CC3)cc2)c(-c2cc3ccsc3n2C)n1] | $^1$H NMR (DMSO-d$_6$) δ (ppm): 7.14 (s, 1 H), 7.082 (d, J = 7.04 Hz, 1 H), 7.45 (d, J = 7.04 Hz, 1 H), 6.89-6.74 (m, 4 H), 6.63 (s, 1 H), 4.41-4.35 (m, 1 H), 4.31 (t, J = 5.4 Hz, 2 H), 4.19 (t, J = 5.4 Hz, 2 H), 3.72 (s, 3 H), 3.66-3.56 (m, 2 H), 3.21-3.05 (m, 2 H), 2.49 (q, J = 7.3 Hz, 2 H), 1.88-1.77 (m, 2 H), 1.51-1.42 (m, 2 H), 1.39 (s, 9 H), 1.18 (t, J = 7.3 Hz, 3 H); MS (ESI): m/z: 551 [M + H]$^+$. |

TABLE 2-continued

BOC Intermediates

| Int. | Name | Structure | Analytical Data |
|---|---|---|---|
| 48 | tert-butyl 4-[4-[2-[2-(4-methylthieno[3,2-b]pyrrol-5-yl)-5-phenyl-4-propyl-imidazol-1-yl]ethoxy]phenoxy]piperidine-1-carboxylate | 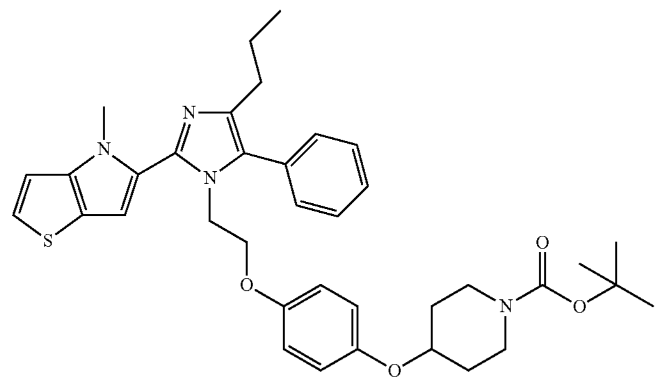 [SMILES: CCCc1nc(-c2cc3sccc3n2C)n(CCOc2ccc(OC3CCN(C(=O)OC(C)(C)C)CC3)cc2)c1-c1ccccc1] | $^1$H NMR (DMSO-d$_6$) δ (ppm): 7.55-7.41 (m, 5 H), 7.34 (d, J = 5.4 Hz, 1 H), 7.20 (d, J = 5.4 Hz, 1 H), 6.76 (s, 1 H), 6.71 (d, J = 9.3 Hz, 2 H), 6.43 (d, J = 9.3 Hz, 2 H), 4.35 (t, J = 5.9 Hz, 2 H), 4.33-4.27 (m, 1 H), 3.78 (s, 3 H), 3.69 (t, J = 5.9 Hz, 2 H), 3.64-3.55 (m, 2 H), 3.21-3.04 (m, 2 H), 2.42 (t, J = 7.6 Hz, 2 H), 1.85-1.74 (m, 2 H), 1.64-1.53 (m, 2 H), 1.47-1.35 (m, 11 H), 0.84 (t, J = 7.3 Hz, 3 H); MS (ESI): m/z: 641 [M + H]$^+$. |
| 49 | tert-butyl 4-[4-[2-[2-(4-methylthieno[3,2-b]pyrrol-5-yl)-4-phenyl-5-propyl-imidazol-1-yl]ethoxy]phenoxy]piperidine-1-carboxylate | 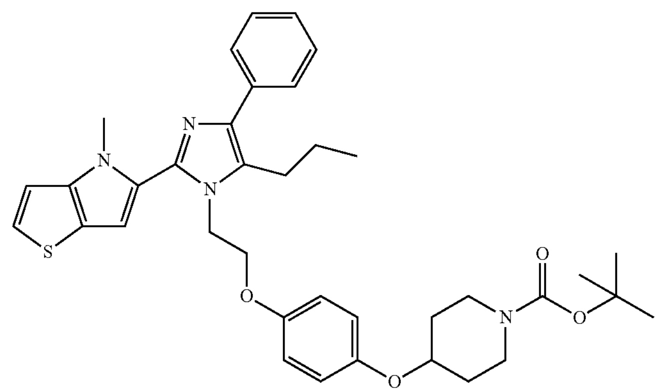 [SMILES: CCCc1c(-c2ccccc2)nc(-c2cc3sccc3n2C)n1CCOc1ccc(OC2CCN(C(=O)OC(C)(C)C)CC2)cc1] | $^1$H NMR (DMSO-d$_6$) δ (ppm): 7.71-7.63 (m, 2 H), 7.45-7.38 (m, 2 H), 7.35 (d, J = 5.4 Hz, 1 H), 7.27-7.23 (m, 1 H), 7.21 (d, J = 5.4 Hz, 1 H), 6.83-6.74 (m, 3 H), 6.70-6.63 (m, 2 H), 4.45 (t, J = 5.4 Hz, 2 H), 4.37-4.30 (m, 1 H), 4.07 (t, J = 5.4 Hz, 2 H), 3.77 (s, 3 H), 3.65-3.55 (m, 2 H), 3.19-3.05 (m, 2 H), 2.93-2.84 (m, 2 H), 1.84-1.75 (m, 2 H), 1.67-1.58 (m, 2 H), 1.48-1.40 (m, 2 H), 1.38 (s, 9 H), 0.98 (t, J = 7.1 Hz, 3 H); MS (ESI): m/z: 641 [M + H]$^+$. |
| 50 | tert-butyl 4-[[4-[3-[4-ethyl-2-(4-methylthieno[3,2-b]pyrrol-5-yl)imidazol-1-yl]propyl]phenoxy]methyl]piperidine-1-carboxylate | 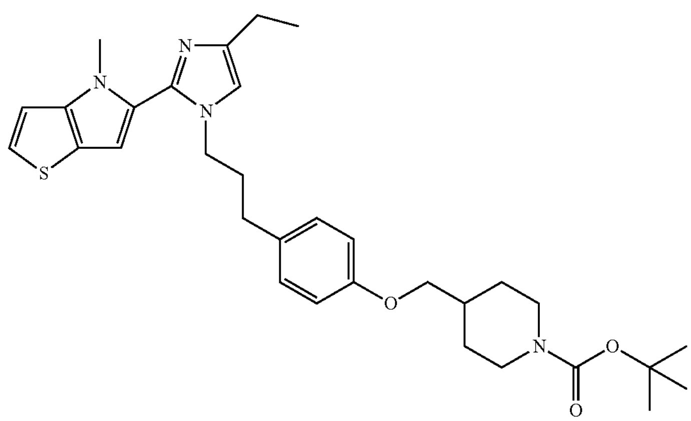 [SMILES: CCc1cn(CCCc2ccc(OCC3CCN(C(=O)OC(C)(C)C)CC3)cc2)c(-c2cc3sccc3n2C)n1] | $^1$H NMR (DMSO-d$_6$) δ (ppm): 7.31 (d, J = 5.4 Hz, 1 H), 7.17 (d, J = 5.4 Hz, 1 H), 7.07 (s, 1 H), 7.03-6.98 (m, 2 H), 6.79-6.71 (m, 2 H), 6.38 (s, 1 H), 4.02-3.89 (m, 4 H), 3.78 (s, 3 H), 3.75 (d, J = 6.4 Hz, 2 H), 2.84-2.64 (m, 2 H), 2.53 (q, J = 7.3 Hz, 2 H), 2.45 (t, J = 7.3 Hz, 2 H), 2.01-1.92 (m, 2 H), 1.92-1.81 (m, 1 H), 1.77-1.69 (m, 2 H), 1.40 (s, 9 H), 1.19 (t, J = 7.3 Hz, 3 H), 1.16-1.11 (m, 2 H); MS (ESI): m/z: 563 [M + H]$^+$. |
| 51 | tert-butyl 4-[[4-[3-[5-ethyl-2-(4-methylthieno[3,2-b]pyrrol-5-yl)imidazol-1-yl]propyl]phenoxy]methyl]piperidine-1-carboxylate | 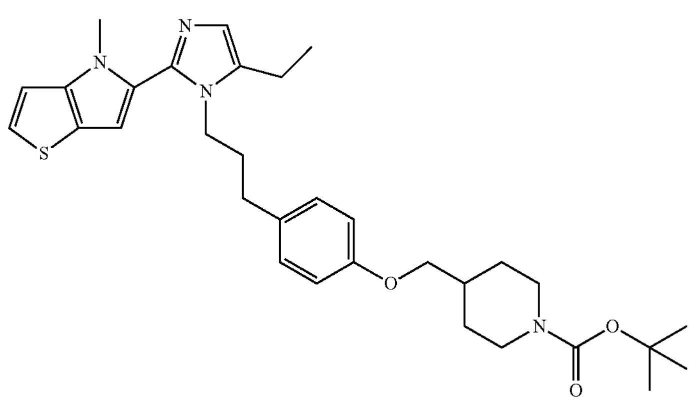 [SMILES: CCc1cnc(-c2cc3sccc3n2C)n1CCCc1ccc(OCC2CCN(C(=O)OC(C)(C)C)CC2)cc1] | $^1$H NMR (DMSO-d$_6$) δ (ppm): 7.31 (d, J = 5.4 Hz, 1 H), 7.16 (d, J = 5.4 Hz, 1 H), 7.03-6.97 (m, 2 H), 6.83 (s, 1 H), 6.77-6.71 (m, 2 H), 6.40 (s, 1 H), 4.03-3.89 (m, 4 H), 3.76 (d, J = 6.4 Hz, 2 H), 3.72 (s, 3 H), 2.83-2.65 (m, 2 H), 2.58 (q, J = 7.3 Hz, 2 H), 2.45 (t, J = 7.3 Hz, 2 H), 1.93-1.79 (m, 3 H), 1.77-1.70 (m, 2 H), 1.40 (s, 9 H), 1.27-1.07 (m, 5 H); MS (ESI): m/z: 563 [M + H]$^+$. |

TABLE 2-continued

BOC Intermediates

| Int. | Name | Structure | Analytical Data |
|---|---|---|---|
| 52 | tert-butyl 4-[4-[3-[4-ethyl-2-(4-methylthieno[3,2-b]pyrrol-5-yl)imidazol-1-yl]propyl]phenoxy]azepane-1-carboxylate | 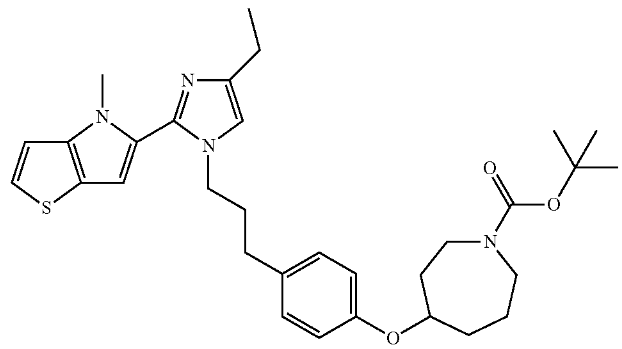 [SMILES: CCc1cn(CCCc2ccc(OC3CCCN(C(=O)OC(C)(C)C)CC3)cc2)c(-c2cc3sccc3n2C)n1] | ¹H NMR (DMSO-d₆) δ (ppm): 7.31 (d, J = 5.4 Hz, 1 H), 7.17 (d, J = 5.4 Hz, 1 H), 7.07 (s, 1 H), 7.01-6.96 (m, 2 H), 6.75-6.69 (m, 2 H), 6.41 (s, 1 H), 4.43-4.35 (m, 1 H), 3.94 (t, J = 7.3 Hz, 2 H), 3.78 (s, 3 H), 3.43-3.23 (m, 4 H), 2.51 (q, J = 7.3 Hz, 2 H), 2.44 (t, J = 7.3 Hz, 2H), 1.99-1.90 (m, 2 H), 1.83-1.50 (m, 6 H), 1.40 (s, 9 H), 1.18 (t, J = 7.3 Hz, 3 H); MS (ESI): m/z: 563 [M + H]⁺. |
| 53 | tert-butyl 4-[4-[3-[5-ethyl-2-(4-methylthieno[3,2-b]pyrrol-5-yl)imidazol-1-yl]propyl]phenoxy]azepane-1-carboxylate | 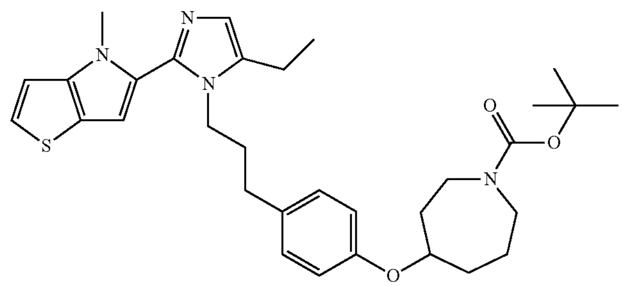 [SMILES: CCc1cnc(-c2cc3sccc3n2C)n1CCCc1ccc(OC2CCCN(C(=O)OC(C)(C)C)CC2)cc1] | ¹H NMR (DMSO-d₆) δ (ppm): 7.32 (d, J = 5.4 Hz, 1 H), 7.17 (d, J = 5.4 Hz, 1 H), 7.02-6.96 (m, 2 H), 6.84 (s, 1 H), 6.75-6.69 (m, 2 H), 6.45 (s, 1 H), 4.45-4.36 (m, 1 H), 3.92 (t, J = 7.3 Hz, 2 H), 3.73 (s, 3 H), 3.44-3.22 (m, 4 H), 2.57 (q, J = 7.3 Hz, 2 H), 2.44 (t, J = 7.3 Hz, 2 H), 2.03-1.48 (m, 8 H), 1.40 (s, 9 H), 1.23 (t, J = 7.3 Hz, 3 H); MS (ESI): m/z: 563 [M + H]⁺. |
| 54 | tert-butyl 4-[4-[3-[5-ethyl-2-(4-methylthieno[3,2-b]pyrrol-5-yl)-4-phenyl-imidazol-1-yl]propyl]phenoxy]piperidine-1-carboxylate | 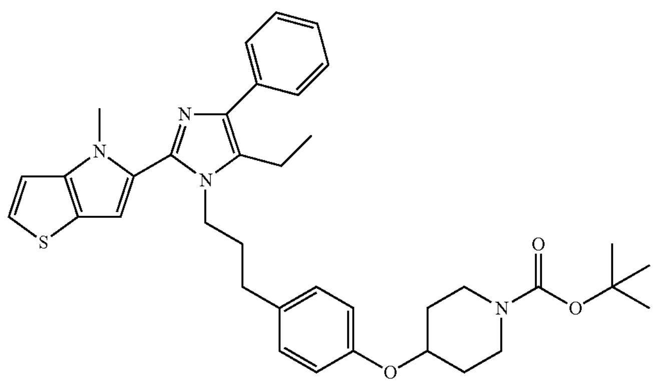 [SMILES: CCc1c(-c2ccccc2)nc(-c2cc3sccc3n2C)n1CCCc1ccc(OC2CCN(C(=O)OC(C)(C)C)CC2)cc1] | ¹H NMR (DMSO-d₆) δ (ppm): 7.74-7.63 (m, 2 H), 7.44-7.38 (m, 2 H), 7.35 (d, J = 5.2 Hz, 1 H), 7.28-7.22 (m, 1 H), 7.20 (d, J = 5.2 Hz, 1 H), 7.04-6.75 (m, 4 H), 6.56 (s, 1 H), 4.50-4.42 (m, 1 H), 4.05-3.98 (m, 2 H), 3.81 (s, 3 H), 3.68-3.59 (m, 2 H), 3.22-3.05 (m, 2 H), 2.81 (q, J = 7.5 Hz, 2 H), 2.54-2.44 (m, 2 H), 1.92-1.81 (m, 4 H), 1.53-1.43 (m, 2 H), 1.40 (s, 9 H), 1.18 (t, J = 7.5 Hz, 3 H); MS (ESI): m/z: 625 [M + H]⁺. |
| 55 | tert-butyl 4-[4-[3-[4-ethyl-2-(4-methylthieno[3,2-b]pyrrol-5-yl)-5-phenyl-imidazol-1-yl]propyl]phenoxy]piperidine-1-carboxylate | 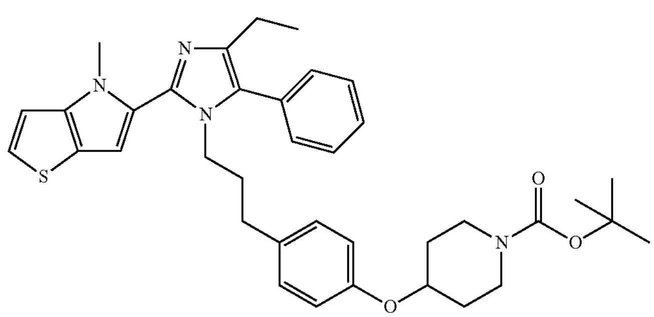 [SMILES: CCc1nc(-c2cc3sccc3n2C)n(CCCc2ccc(OC3CCN(C(=O)OC(C)(C)C)CC3)cc2)c1-c1ccccc1] | ¹H NMR (DMSO-d₆) δ (ppm): 7.51-7.46 (m, 2 H), 7.45-7.38 (m, 3 H), 7.34 (d, J = 5.4 Hz, 1 H), 7.20 (d, J = 5.4 Hz, 1 H), 6.76-6.65 (m, 4 H), 6.54 (s, 1 H), 4.46-4.33 (m, 1 H), 3.97 (t, J = 7.3 Hz, 2 H), 3.83 (s, 3 H), 3.68-3.57 (m, 2 H), 3.22-3.07 (m, 2 H), 2.45 (q, J = 7.6 Hz, 2 H), 2.14 (t, J = 7.3 Hz, 2 H), 1.88-1.78 (m, 2 H), 1.56-1.37 (m, 13 H), 1.13 (t, J = 7.6 Hz, 3 H); MS (ESI): m/z: 625 [M + H]⁺. |

TABLE 2-continued

BOC Intermediates

| Int. | Name | Structure | Analytical Data |
|---|---|---|---|
| 56 | tert-butyl 4-[4-[2-[4-isopropyl-2-(4-methylthieno[3,2-b]pyrrol-5-yl)-5-phenyl-imidazol-1-yl]ethoxy]phenoxy]piperidine-1-carboxylate | 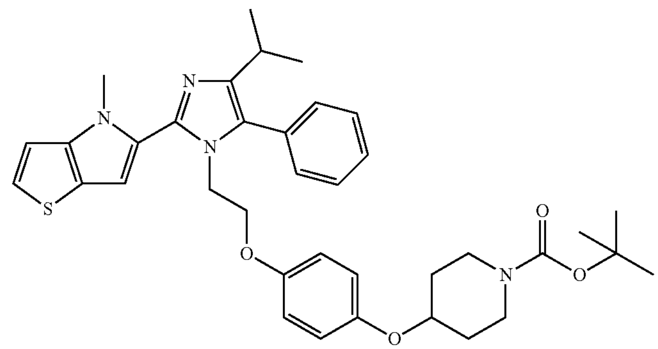 [SMILES: CC(C)c1nc(-c2cc3sccc3n2C)n(CCOc2ccc(OC3CCN(C(=O)OC(C)(C)C)CC3)cc2)c1-c1ccccc1] | $^1$H NMR (CDCl$_3$) δ (ppm): 7.52-7.37 (m, 5 H), 7.16 (d, J = 5.4 Hz, 1 H), 6.98 (d, J = 5.4 Hz, 1 H), 6.70-6.65 (m, 3 H), 6.44-6.39 (m, 2 H), 4.35 (t, J = 6.4 Hz, 2 H), 4.30-4.23 (m, 1 H), 3.83 (s, 3 H), 3.74 (t, J = 6.4 Hz, 2 H), 3.72-3.64 (m, 2 H), 3.34-3.23 (m, 2 H), 2.90 (sep, J = 6.7 Hz, 1 H), 1.90-1.62 (m, 4 H), 1.47 (s, 9 H), 1.27 (d, J = 6.7 Hz, 6 H); MS (ESI): m/z: 641 [M + H]$^+$. |
| 57 | tert-butyl 4-[4-[3-[4-cyclobutyl-2-(4-methylthieno[3,2-b]pyrrol-5-yl)imidazol-1-yl]propyl]phenoxy]piperidine-1-carboxylate | 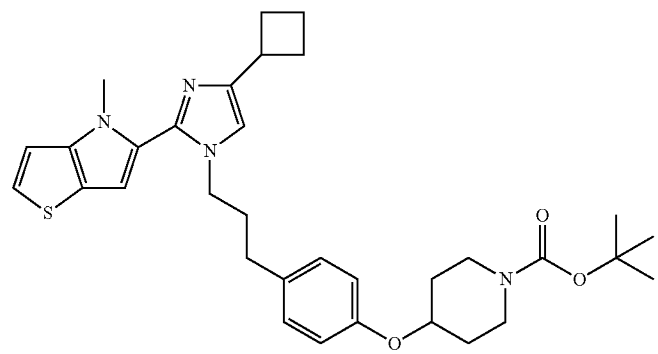 [SMILES: Cn1c(-c2nc(C3CCC3)cn2CCCc2ccc(OC3CCN(C(=O)OC(C)(C)C)CC3)cc2)cc2sccc21] | $^1$H NMR (CDCl$_3$) δ (ppm): 7.15 (d, J = 5.4 Hz, 1 H), 7.01-6.93 (m, 3 H), 6.81-6.75 (m, 3 H), 6.40 (s, 1 H), 4.44-4.36 (m, 1 H), 3.98 (t, J = 7.6 Hz, 2 H), 3.83 (s, 3 H), 3.75-3.66 (m, 2 H), 3.59-3.47 (m, 1 H), 3.37-3.28 (m, 2 H), 2.54 (t, J = 7.6 Hz, 2 H), 2.38-2.20 (m, 4 H), 2.09-1.85 (m, 6 H), 1.78-1.70 (m, 2 H), 1.48 (s, 9 H); MS (ESI): m/z: 575 [M + H]$^+$. |
| 58 | tert-butyl 4-[4-[3-[5-cyclobutyl-2-(4-methylthieno[3,2-b]pyrrol-5-yl)imidazol-1-yl]propyl]phenoxy]piperidine-1-carboxylate | 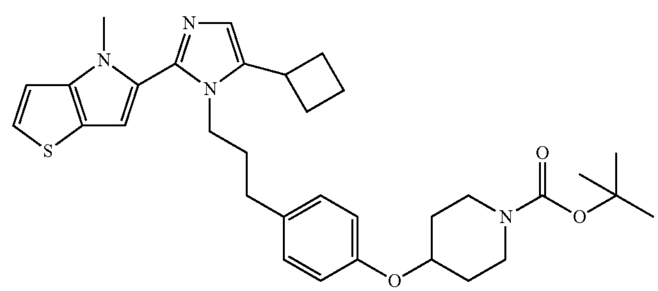 [SMILES: Cn1c(-c2ncc(C3CCC3)n2CCCc2ccc(OC3CCN(C(=O)OC(C)(C)C)CC3)cc2)cc2sccc21] | $^1$H NMR (CDCl$_3$) δ (ppm): 7.16 (d, J = 5.4 Hz, 1 H), 7.01 (s, 1 H), 7.00-6.95 (m, 3 H), 6.83-6.77 (m, 2 H), 6.42 (s, 1 H), 4.46-4.37 (m, 1 H), 3.91-3.83 (m, 2 H), 3.81 (s, 3 H), 3.76-3.63 (m, 2 H), 3.41-3.27 (m, 3 H), 2.51 (t, J = 7.3 Hz, 2 H), 2.34-2.13 (m, 4 H), 2.09-1.85 (m, 6 H), 1.80-1.67 (m, 2 H), 1.48 (s, 9 H); MS (ESI): m/z: 575 [M + H]$^+$. |
| 59 | tert-butyl 4-[4-[3-[2-(4-methylthieno[3,2-b]pyrrol-5-yl)-4-phenyl-imidazol-1-yl]propyl]phenoxy]piperidine-1-carboxylate | 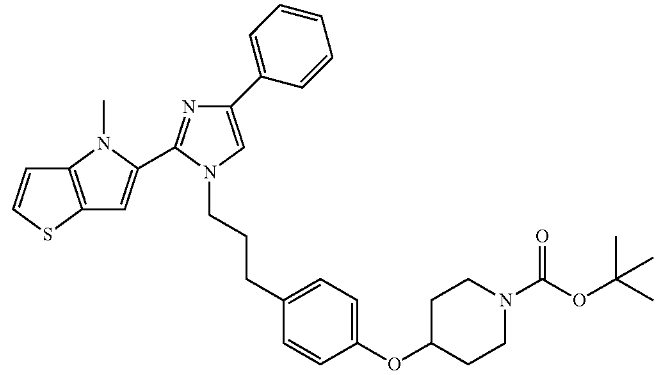 [SMILES: Cn1c(-c2nc(-c3ccccc3)cn2CCCc2ccc(OC3CCN(C(=O)OC(C)(C)C)CC3)cc2)cc2sccc21] | $^1$H NMR (DMSO-d$_6$) δ (ppm): 7.90 (s, 1 H), 7.85-7.79 (m, 2 H), 7.41-7.33 (m, 3 H), 7.25-7.18 (m, 2 H), 7.06-6.98 (m, 2 H), 6.82-6.76 (m, 2 H), 6.53 (s, 1 H), 4.49-4.38 (m, 1 H), 4.06 (t, J = 7.3 Hz, 2 H), 3.88 (s, 3 H), 3.68-3.59 (m, 2 H), 3.22-3.06 (m, 2 H), 2.52 (t, J = 7.3 Hz, 2 H), 2.10-2.01 (m, 2 H), 1.89-1.80 (m, 2 H), 1.51-1.42 (m, 2 H), 1.40 (s, 9 H); MS (ESI): m/z: 597 [M + H]$^+$. |

TABLE 2-continued

BOC Intermediates

| Int. | Name | Structure | Analytical Data |
|---|---|---|---|
| 60 | | 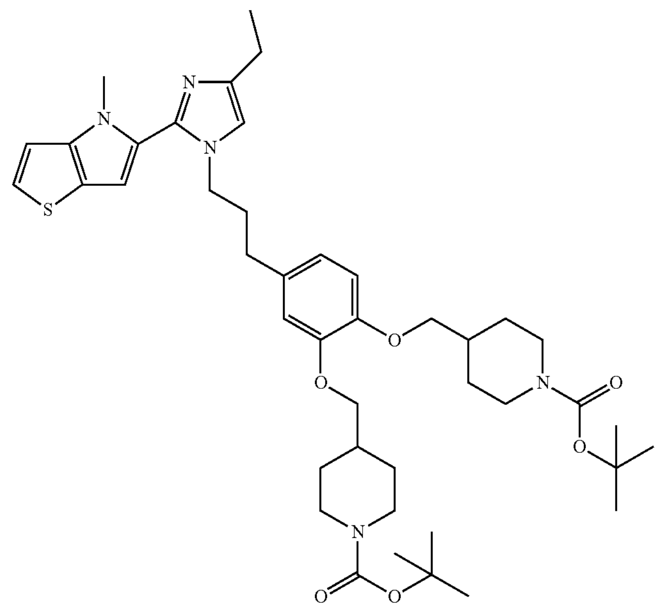 [SMILES: CCc1cn(CCCc2ccc(OCC3CCN(C(=O)OC(C)(C)C)CC3)c(OCC3CCN(C(=O)OC(C)(C)C)CC3)c2)c(-c2cc3sccc3n2C)n1] | ¹H NMR (DMSO-$d_6$) δ (ppm): 7.29 (d, J = 5.4 Hz, 1 H), 7.16 (d, J = 5.4 Hz, 1 H), 7.06 (s, 1 H), 6.78-6.71 (m, 2 H), 6.60-6.55 (m, 1 H), 6.39 (s, 1 H), 4.02-3.87 (m, 6 H), 3.78 (s, 3 H), 3.76-3.71 (m, 4 H), 2.83-2.58 (m, 4 H), 2.53 (q, J = 7.3 Hz, 2 H), 2.44 (t, J = 7.3 Hz, 2 H), 2.01-1.93 (m, 2 H), 1.91-1.80 (m, 2 H), 1.75-1.65 (m, 4 H), 1.39 (s, 9 H), 1.38 (s, 9 H), 1.21-1.08 (m, 7 H); MS (ESI): m/z: 777 [M + H]⁺. |
| 61 | tert-butyl 4-[4-[2-[2-(4-methylthieno[3,2-b]pyrrol-5-yl)-4-propyl-imidazol-1-yl]ethoxy]phenoxy]piperidine-1-carboxylate | 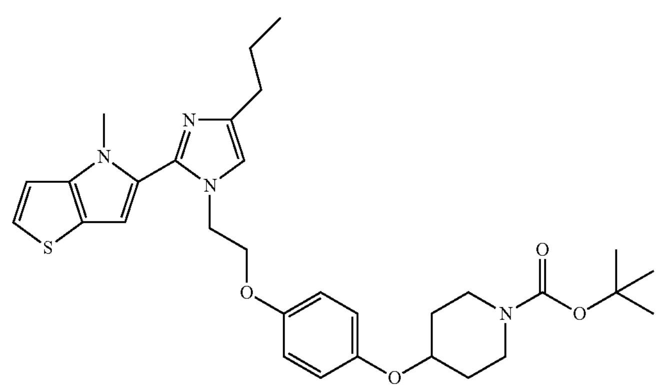 [SMILES: CCCc1cn(CCOc2ccc(OC3CCN(C(=O)OC(C)(C)C)CC3)cc2)c(-c2cc3sccc3n2C)n1] | ¹H NMR (CDCl₃) δ (ppm): 7.16 (d, J = 5.4 Hz, 1 H), 6.97 (d, J = 5.4 Hz, 1 H), 6.93 (s, 1 H), 6.85-6.71 (m, 4 H), 6.57 (bs, 1 H), 4.42-4.27 (m, 3 H), 4.15 (t, J = 5.1 Hz, 2H), 3.83 (bs, 3 H), 3.75-3.66 (m, 2 H), 3.35-3.25 (m, 2 H), 2.66-2.55 (m, 2 H), 1.94-1.80 (m, 2H), 1.77-1.65 (m, 4 H), 1.48 (s, 9 H), 1.00 (t, J = 7.3 Hz, 3 H); MS (ESI): m/z: 565 [M + H]⁺. |
| 62 | tert-butyl 4-[4-[2-[2-(4-methylthieno[3,2-b]pyrrol-5-yl)-5-propyl-imidazol-1-yl]ethoxy]phenoxy]piperidine-1-carboxylate | 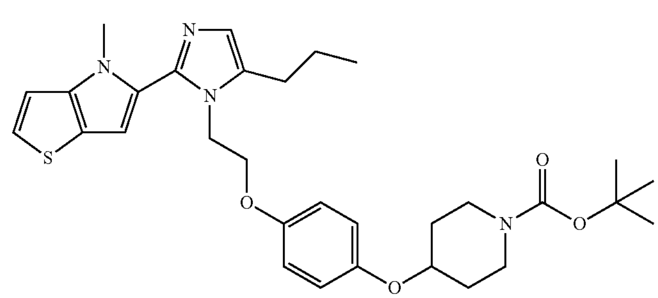 [SMILES: CCCc1cnc(-c2cc3sccc3n2C)n1CCOc1ccc(OC2CCN(C(=O)OC(C)(C)C)CC2)cc1] | ¹H NMR (CDCl₃) δ (ppm): 7.18 (d, J = 5.4 Hz, 1 H), 7.00 (s, 1 H), 6.98 (d, J = 5.4 Hz, 1 H), 6.79-6.73 (m, 2 H), 6.67-6.59 (m, 3 H), 4.39 (t, J = 5.9 Hz, 2 H), 4.33-4.24 (m, 1 H), 4.03 (t, J = 5.9 Hz, 2 H), 3.78 (s, 3 H), 3.73-3.66 (m, 2 H), 3.34-3.26 (m, 2 H), 2.68 (t, J = 7.3 Hz, 2 H), 1.92-1.65 (m, 6 H), 1.47 (s, 9 H), 1.09 (t, J = 7.3 Hz, 3 H); MS (ESI): m/z: 565 [M + H]⁺. |

TABLE 2-continued

BOC Intermediates

| Int. | Name | Structure | Analytical Data |
|---|---|---|---|
| 63 | tert-butyl 4-[4-[3-[2-(4-methylthieno[3,2-b]pyrrol-5-yl)-4-propyl-imidazol-1-yl]propyl]phenoxy]azepane-1-carboxylate | 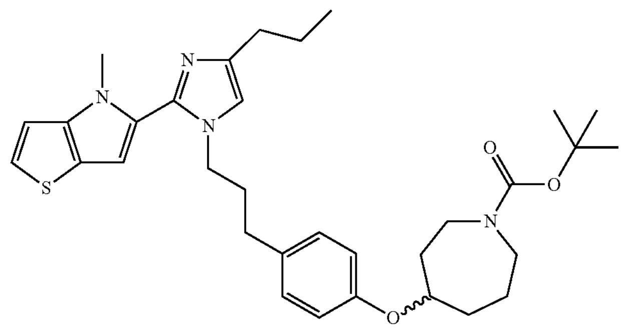 [SMILES: CCCc1cn(CCCc2ccc(OC3CCCN(C(=O)OC(C)(C)C)CC3)cc2)c(-c2cc3sccc3n2C)n1] | $^1$H NMR (DMSO-d$_6$) δ (ppm): 7.30 (d, J = 5.4 Hz, 1 H), 7.16 (d, J = 5.4 Hz, 1 H), 7.07 (s, 1 H), 7.01-6.94 (m, 2 H), 6.76-6.66 (m, 2 H), 6.40 (s, 1 H), 4.43-4.32 (m, 1 H), 3.94 (t, J = 7.3 Hz, 2 H), 3.78 (s, 3 H), 3.43-3.21 (m, 4 H), 2.51-2.38 (m, 4 H), 2.02-1.49 (m, 10 H), 1.40 (s, 9 H), 0.93 (t, J = 7.3 Hz, 3 H); MS (ESI): m/z: 577 [M + H]$^+$. |
| 64 | tert-butyl 4-[4-[3-[2-(4-methylthieno[3,2-b]pyrrol-5-yl)-5-propyl-imidazol-1-yl]propyl]phenoxy]azepane-1-carboxylate | 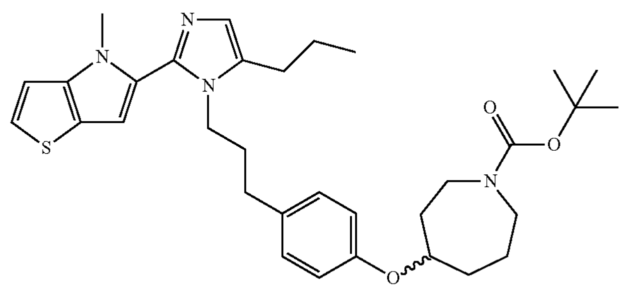 [SMILES: CCCc1cnc(-c2cc3sccc3n2C)n1CCCc1ccc(OC2CCCN(C(=O)OC(C)(C)C)CC2)cc1] | $^1$H NMR (DMSO-d$_6$) δ (ppm): 7.31 (d, J = 5.4 Hz, 1 H), 7.17 (d, J = 5.4 Hz, 1 H), 7.02-6.95 (m, 2 H), 6.82 (s, 1 H), 6.76-6.70 (m, 2 H), 6.46 (s, 1 H), 4.46-4.34 (m, 1 H), 3.91 (t, J = 8.3 Hz, 2 H), 3.72 (s, 3 H), 3.44-3.23 (m, 4 H), 2.50-2.40 (m, 4 H), 2.05-1.50 (m, 10 H), 1.40 (s, 9 H), 0.96 (t, J = 7.3 Hz, 3 H); MS (ESI): m/z: 577 [M + H]$^+$. |
| 65 | tert-butyl 4-[[2-[(1-tert-butoxycarbonyl-4-piperidyl)methoxy]-4-[3-[5-ethyl-2-(4-methylthieno[3,2-b]pyrrol-5-yl)imidazol-1-yl]propyl]phenoxy]methyl]piperidine-1-carboxylate | 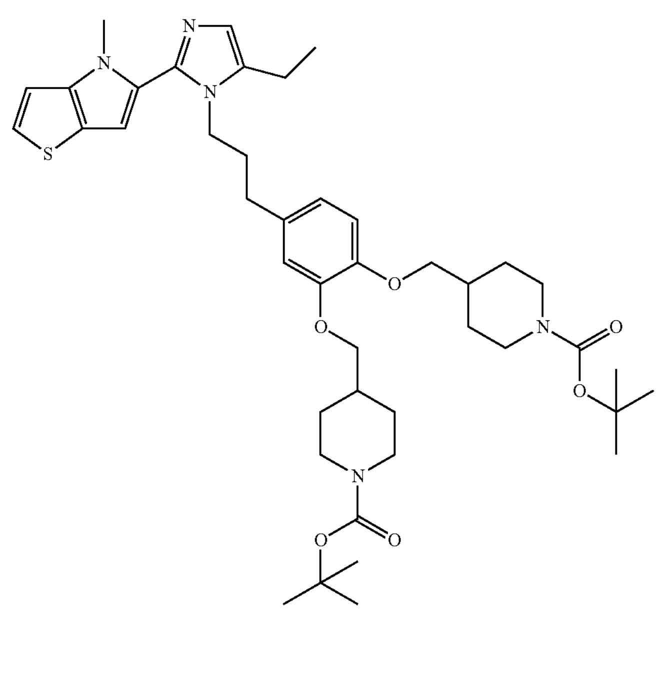 [SMILES: CCc1cnc(-c2cc3sccc3n2C)n1CCCc1ccc(OCC2CCN(C(=O)OC(C)(C)C)CC2)c(OCC2CCN(C(=O)OC(C)(C)C)CC2)c1] | $^1$H NMR (DMSO-d$_6$) δ (ppm): 7.29 (d, J = 5.4 Hz, 1 H), 7.15 (d, J = 5.4 Hz, 1 H), 6.82 (s, 1 H), 6.78-6.72 (m, 2 H), 6.61-6.55 (m, 1 H), 6.43 (s, 1 H), 4.03-3.86 (m, 6 H), 3.78-3.69 (m, 7 H), 2.83-2.63 (m, 4 H), 2.57 (q, J = 7.3 Hz, 2 H), 2.43 (t, J = 7.3 Hz, 2 H), 1.92-1.80 (m, 4 H), 1.77-1.65 (m, 4 H), 1.39 (s, 9 H), 1.38 (s, 9 H), 1.27-1.08 (m, 7 H) MS (ESI): m/z: 777 [M + H]$^+$. |

TABLE 2-continued

BOC Intermediates

| Int. | Name | Structure | Analytical Data |
|---|---|---|---|
| 66 | tert-butyl 4-[4-[2-[4-ethyl-2-(4-methylthieno[3,2-b]pyrrol-5-yl)imidazol-1-yl]ethyl]phenoxy]piperidine-1-carboxylate | 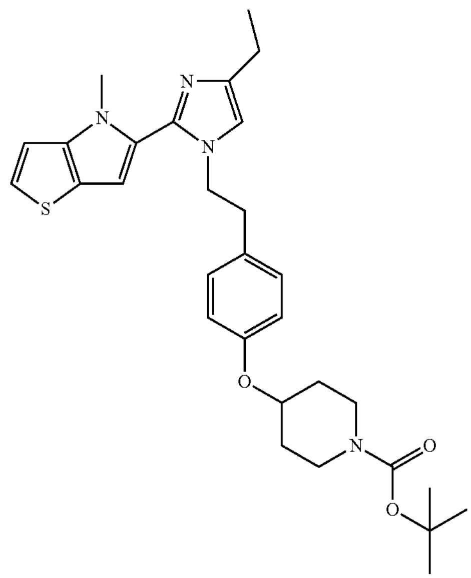 [SMILES: CCc1cn(CCc2ccc(OC3CCN(C(=O)OC(C)(C)C)CC3)cc2)c(-c2cc3sccc3n2C)n1] | $^1$H NMR (DMSO-d$_6$) δ (ppm): 7.30 (d, J = 5.4 Hz, 1 H), 7.14 (d, J = 5.4 Hz, 1 H), 7.06 (s, 1 H), 6.98-6.92 (m, 2 H), 6.84-6.79 (m, 2 H), 6.36 (s, 1 H), 4.51-4.42 (m, 1 H), 4.14 (t, J = 7.3 Hz, 2 H), 3.68-3.58 (m, 5 H), 3.21-3.08 (m, 2 H), 2.91 (t, J = 7.3 Hz, 2 H), 2.52 (q, J = 7.6 Hz, 2 H), 1.90-1.79 (m, 2 H), 1.51-1.42 (m, 2 H), 1.39 (s, 9 H), 1.17 (t, J = 7.6 Hz, 3 H) MS (ESI): m/z: 535 [M + H]$^+$. |
| 67 | tert-butyl 3-[[4-[3-[4-cyclobutyl-2-(4-methylthieno[3,2-b]pyrrol-5-yl)imidazol-1-yl]propyl]phenoxy]methyl]pyrrolidine-1-carboxylate | 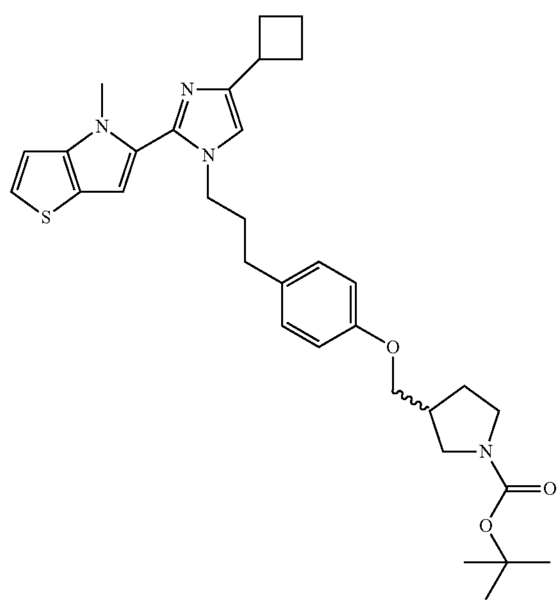 [SMILES: Cn1c(-c2nc(C3CCC3)cn2CCCc2ccc(OCC3CCN(C(=O)OC(C)(C)C)C3)cc2)cc2sccc21] | $^1$H NMR (DMSO-d$_6$) δ (ppm): 7.30 (d, J = 5.4 Hz, 1 H), 7.16 (d, J = 5.4 Hz, 1 H), 7.11 (s, 1 H), 7.04-6.97 (m, 2 H), 6.79-6.73 (m, 2 H), 6.35 (s, 1 H), 3.95-3.91 (m, 2 H), 3.90-3.81 (m, 2 H), 3.79 (s, 3 H), 3.48-3.33 (m, 3 H), 3.29-3.18 (m, 1 H), 3.11-3.04 (m, 1 H), 2.64-2.51 (m, 1 H), 2.48-2.42 (m, 2 H), 2.26-2.09 (m, 4 H), 2.06-1.58 (m, 6 H), 1.39 (s, 9 H); MS (ESI): m/z: 575 [M + H]$^+$. |

TABLE 2-continued

BOC Intermediates

| Int. | Name | Structure | Analytical Data |
|---|---|---|---|
| 68 | tert-butyl 3-[[4-[3-[5-cyclobutyl-2-(4-methylthieno[3,2-b]pyrrol-5-yl)imidazol-1-yl]propyl]phenoxy]methyl]pyrrolidine-1-carboxylate | 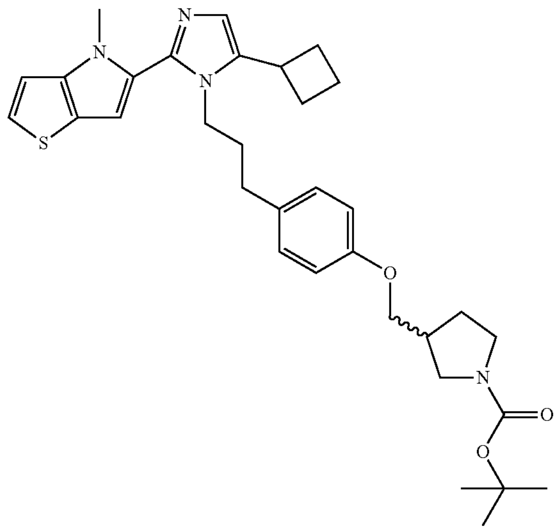 [SMILES: Cn1c(-c2ncc(C3CCC3)n2CCCc2ccc(OCC3CCN(C(=O)OC(C)(C)C)C3)cc2)cc2sccc21] | $^1$H NMR (DMSO-d$_6$) δ (ppm): 7.30 (d, J = 5.4 Hz, 1 H), 7.16 (d, J = 5.4 Hz, 1 H), 7.04-6.99 (m, 2 H), 6.93 (s, 1 H), 6.81-6.76 (m, 2 H), 6.39 (s, 1 H), 3.91-3.81 (m, 4 H), 3.72 (s, 3 H), 3.49-3.35 (m, 3 H), 3.28-3.17 (m, 1 H), 3.10-3.04 (m, 1 H), 2.61-2.53 (m, 1 H), 2.45 (t, J = 7.3 Hz, 2 H), 2.30-1.62 (m, 10 H), 1.39 (s, 9 H); MS (ESI): m/z: 575 [M + H]$^+$. |
| 69 | tert-butyl 4-[4-[3-[4-cyclobutyl-2-(4-methylthieno[3,2-b]pyrrol-5-yl)imidazol-1-yl]propyl]phenoxy]azepane-1-carboxylate | 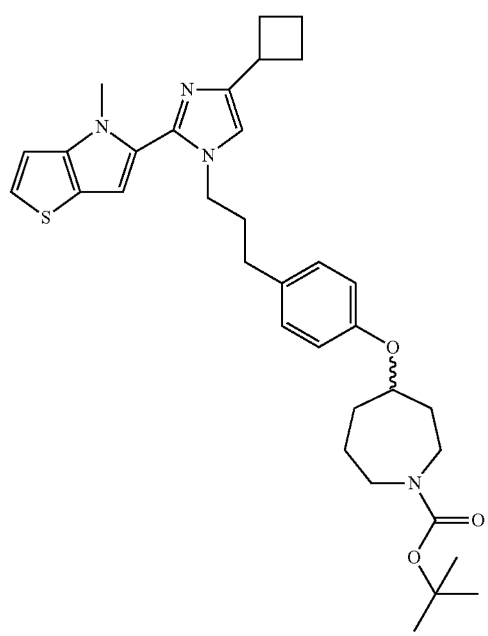 [SMILES: Cn1c(-c2nc(C3CCC3)cn2CCCc2ccc(OC3CCCN(C(=O)OC(C)(C)C)CC3)cc2)cc2sccc21] | $^1$H NMR (DMSO-d$_6$) δ (ppm): 7.31 (d, J = 5.4 Hz, 1 H), 7.17 (d, J = 5.4 Hz, 1 H), 7.12 (s, 1 H), 7.02-6.96 (m, 2 H), 6.76-6.68 (m, 2 H), 6.41 (s, 1 H), 4.45-4.31 (m, 1 H), 3.94 (t, J = 7.3 Hz, 2 H), 3.79 (s, 3 H), 3.45-3.35 (m, 3 H), 3.31-3.24 (m, 2 H), 2.44 (t, J = 7.3 Hz, 2 H), 2.26-2.08 (m, 4 H), 2.01-1.50 (m, 10 H), 1.40 (s, 9 H); MS (ESI): m/z: 589 [M + H]$^+$. |

TABLE 2-continued

| BOC Intermediates | | | |
|---|---|---|---|
| Int. | Name | Structure | Analytical Data |
| 70 | tert-butyl 4-[4-[3-[5-cyclobutyl-2-(4-methylthieno[3,2-b]pyrrol-5-yl)imidazol-1-yl]propyl]phenoxy]azepane-1-carboxylate | | $^1$H NMR (DMSO-d$_6$) δ (ppm): 7.31 (d, J = 5.4 Hz, 1 H), 7.16 (d, J = 5.4 Hz, 1 H), 7.03-6.97 (m, 2 H), 6.92 (s, 1 H), 6.78-6.70 (m, 2 H), 6.47 (s, 1 H), 4.47-4.36 (m, 2 H), 3.84 (t, J = 6.8 Hz, 1 H), 3.72 (s, 3 H), 3.46-3.35 (m, 5 H), 2.43 (t, J = 6.8 Hz, 2 H), 2.27-1.50 (m, 14 H), 1.40 (s, 9 H); MS (ESI): m/z: 589 [M + H]$^+$. |
| 71 | tert-butyl 4-[4-[3-[2-(4-methylthieno[3,2-b]pyrrol-5-yl)-4-propyl-imidazol-1-yl]propyl]phenoxy]piperidine-1-carboxylate | | $^1$H NMR (DMSO-d$_6$) δ (ppm): 7.31 (d, J = 5.4 Hz, 1 H), 7.16 (d, J = 5.4 Hz, 1 H), 7.07 (s, 1 H), 7.01-6.95 (m, 2 H), 6.80-6.74 (m, 2 H), 6.42 (s, 1 H), 4.48-4.39 (m, 1 H), 3.95 (t, J = 7.3 Hz, 2 H), 3.78 (s, 3 H), 3.68-3.58 (m, 2 H), 3.21-3.06 (m, 2 H), 2.48-2.39 (m, 4 H), 2.00-1.91 (m, 2 H), 1.89-1.80 (m, 2 H), 1.67-1.56 (m, 2 H), 1.51 1.42 (m, 2 H), 1.40 (s, 9 H), 0.93 (t, J = 7.3 Hz, 3 H); MS (ESI): m/z: 563 [M + H]$^+$. |
| 72 | tert-butyl 4-[4-[3-[2-(4-methylthieno[3,2-b]pyrrol-5-yl)-5-propyl-imidazol-1-yl]propyl]phenoxy]piperidine-1-carboxylate | | $^1$H NMR (DMSO-d$_6$) δ (ppm): 7.32 (d, J = 5.4 Hz, 1 H), 7.17 (d, J = 5.4 Hz, 1 H), 7.03-6.97 (m, 2 H), 6.82 (s, 1 H), 6.81-6.76 (m, 2 H), 6.47 (s, 1 H), 4.50-4.39 (m, 1 H), 3.92 (t, J = 7.8 Hz, 2 H), 3.72 (s, 3 H), 3.68-3.59 (m, 2 H), 3.21-3.05 (m, 2 H), 2.48-2.41 (m, 4 H), 1.90-1.76 (m, 4 H), 1.66-1.56 (m, 2 H), 1.52-1.43 (m, 2 H), 1.40 (s, 9 H), 0.96 (t, J = 7.3 Hz, 3 H); MS (ESI): m/z: 563 [M + H]$^+$. |

TABLE 2-continued

BOC Intermediates

| Int. | Name | Structure | Analytical Data |
|---|---|---|---|
| 73 | tert-butyl 4-[[4-[3-[4-cyclobutyl-2-(4-methylthieno[3,2-b]pyrrol-5-yl)imidazol-1-yl]propyl]phenoxy]methyl]piperidine-1-carboxylate | 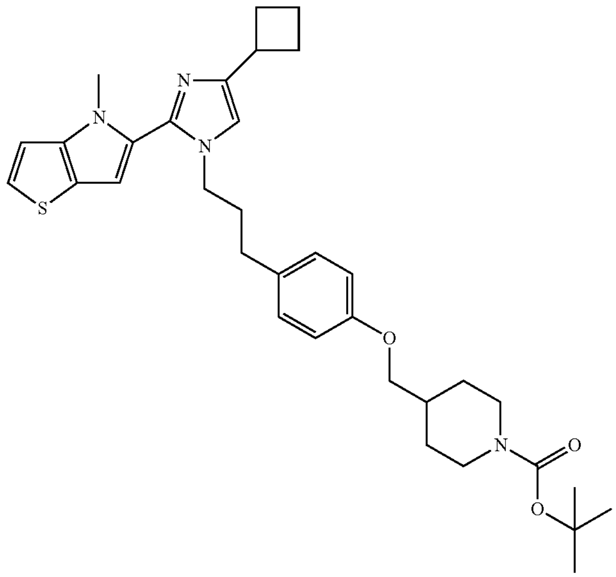 [SMILES: Cn1c(-c2nc(C3CCC3)cn2CCCc2ccc(OCC3CCN(C(=O)OC(C)(C)C)CC3)cc2)cc2sccc21] | $^1$H NMR (DMSO-d$_6$) δ (ppm): 7.31 (d, J = 5.4 Hz, 1 H), 7.16 (d, J = 5.4 Hz, 1 H), 7.11 (s, 1 H), 7.03-6.97 (m, 2 H), 6.77-6.71 (m, 2 H), 6.38 (s, 1 H), 4.02-3.89 (m, 4 H), 3.79 (s, 3 H), 3.75 (d, J = 6.4 Hz, 2 H), 3.46-3.36 (m, 1 H), 2.83-2.64 (m, 2 H), 2.45 (t, J = 7.3 Hz, 2 H), 2.26-2.09 (m, 4 H), 2.01-1.79 (m, 5 H), 1.77-1.68 (m, 2 H), 1.39 (s, 9 H), 1.19-1.06 (m, 2 H); MS (ESI): m/z: 589 [M + H]$^+$. |
| 74 | tert-butyl 4-[[4-[3-[5-cyclobutyl-2-(4-methylthieno[3,2-b]pyrrol-5-yl)imidazol-1-yl]propyl]phenoxy]methyl]piperidine-1-carboxylate | 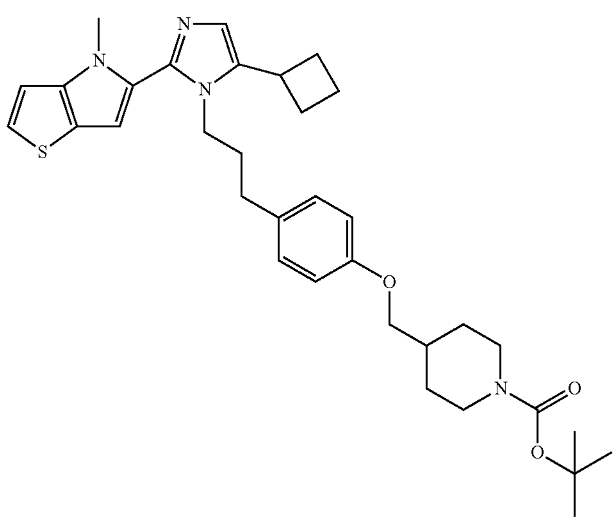 [SMILES: Cn1c(-c2ncc(C3CCC3)n2CCCc2ccc(OCC3CCN(C(=O)OC(C)(C)C)CC3)cc2)cc2sccc21] | $^1$H NMR (DMSO-d$_6$) δ (ppm): 7.31 (d, J = 5.4 Hz, 1 H), 7.16 (d, J = 5.4 Hz, 1 H), 7.03-6.97 (m, 2 H), 6.93 (s, 1 H), 6.79-6.73 (m, 2 H), 6.42 (s, 1 H), 4.02-3.90 (m, 2 H), 3.84 (t, J = 7.8 Hz, 2 H), 3.77 (d, J = 6.4 Hz, 2 H), 3.72 (s, 3 H), 3.48-3.39 (m, 1 H), 2.82-2.64 (m, 2 H), 2.44 (t, J = 7.3 Hz, 2 H), 2.30-2.21 (m, 2 H), 2.14-2.03 (m, 2 H), 2.02-1.68 (m, 7 H), 1.39 (s, 9 H), 1.20-1.07 (m, 2 H); MS (ESI): m/z: 589 [M + H]$^+$. |

TABLE 2-continued

BOC Intermediates

| Int. | Name | Structure | Analytical Data |
|---|---|---|---|
| 75 | tert-butyl 3-[[4-[3-[2-(4-methylthieno[3,2-b]pyrrol-5-yl)-4-propyl-imidazol-1-yl]propyl]phenoxy]methyl]pyrrolidine-1-carboxylate | 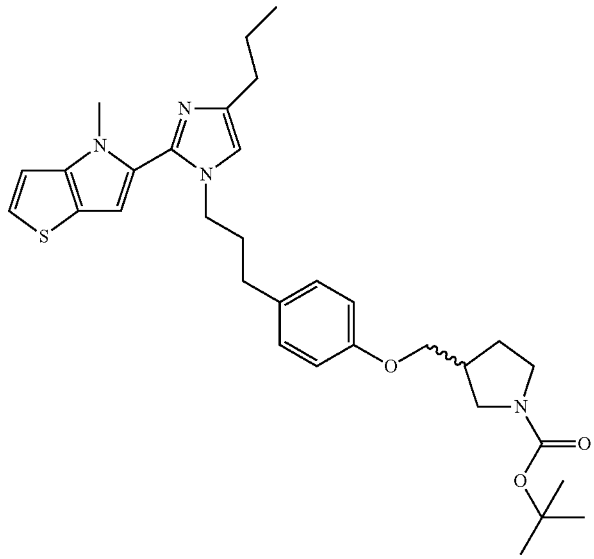 [SMILES: CCCc1cn(CCCc2ccc(OCC3CCN(C(=O)OC(C)(C)C)C3)cc2)c(-c2cc3sccc3n2C)n1] | ¹H NMR (DMSO-d₆) δ (ppm): 7.29 (d, J = 5.4 Hz, 1 H), 7.16 (d, J = 5.4 Hz, 1 H), 7.06 (s, 1 H), 7.03-6.96 (m, 2 H), 6.80-6.72 (m, 2 H), 6.35 (s, 1 H), 3.93 (t, J = 7.3 Hz, 2 H), 3.89-3.81 (m, 2 H), 3.78 (s, 3 H), 3.49-3.39 (m, 1 H), 3.38-3.34 (m, 1 H), 3.29-3.17 (m, 1 H), 3.11-3.04 (m, 1 H), 2.61-2.53 (m, 1 H), 2.48-2.39 (m, 4 H), 2.05-1.90 (m, 3 H), 1.76-1.56 (m, 3 H), 1.39 (s, 9 H), 0.93 (t, J = 7.3 Hz, 3 H); MS (ESI): m/z: 563 [M + H]⁺. |
| 76 | tert-butyl 3-[[4-[3-[2-(4-methylthieno[3,2-b]pyrrol-5-yl)-5-propyl-imidazol-1-yl]propyl]phenoxy]methyl]pyrrolidine-1-carboxylate | 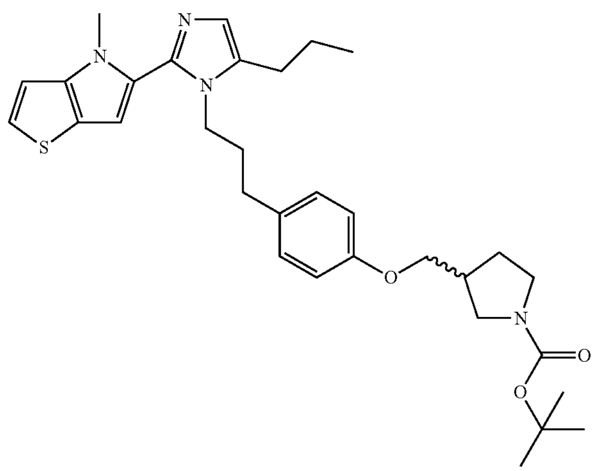 [SMILES: CCCc1cnc(-c2cc3sccc3n2C)n1CCCc1ccc(OCC2CCN(C(=O)OC(C)(C)C)C2)cc1] | ¹H NMR (DMSO-d₆) δ (ppm): 7.30 (d, J = 5.4 Hz, 1 H), 7.16 (d, J = 5.4 Hz, 1 H), 7.04-6.97 (m, 2 H), 6.82 (s, 1 H), 6.79-6.74 (m, 2 H), 6.39 (s, 1 H), 3.95-3.80 (m, 4 H), 3.71 (s, 3 H), 3.50-3.40 (m, 1 H), 3.38-3.34 (m, 1 H), 3.27-3.17 (m, 1 H), 3.11-3.04 (m, 1 H), 2.62-2.52 (m, 1 H), 2.48-2.42 (m, 4 H), 2.03-1.96 (m, 1 H), 1.86-1.78 (m, 2 H), 1.75-1.57 (m, 3 H), 1.39 (s, 9 H), 0.96 (t, J = 7.3 Hz, 3 H); MS (ESI): m/z: 563 [M + H]⁺. |
| 77 | tert-butyl 4-[4-[2-[4-cyclobutyl-2-(4-methylthieno[3,2-b]pyrrol-5-yl)imidazol-1-yl]ethyl]phenoxy]piperidine-1-carboxylate | 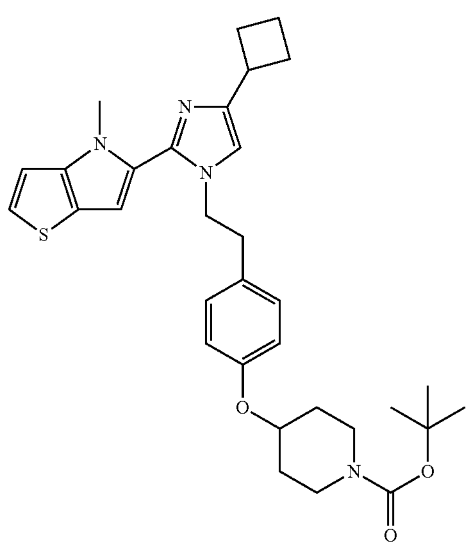 [SMILES: Cn1c(-c2nc(C3CCC3)cn2CCc2ccc(OC3CCN(C(=O)OC(C)(C)C)CC3)cc2)cc2sccc21] | ¹H NMR (DMSO-d₆) δ (ppm): 7.30 (d, J = 5.4 Hz, 1 H), 7.15 (d, J = 5.4 Hz, 1 H), 7.10 (s, 1 H), 6.98-6.93 (m, 2 H), 6.84-6.79 (m, 2 H), 6.38 (s, 1 H), 4.51-4.42 (m, 1 H), 4.14 (t, J = 7.3 Hz, 2 H), 3.68 (s, 3 H), 3.65-3.58 (m, 2 H), 3.44-3.35 (m, 1 H), 3.19-3.09 (m, 2 H), 2.91 (t, J = 7.3 Hz, 2 H), 2.27-2.07 (m, 4 H), 1.98-1.81 (m, 4 H), 1.51-1.42 (m, 2 H), 1.39 (s, 9 H); MS (ESI): m/z: 561 [M + H]⁺. |

TABLE 2-continued

BOC Intermediates

| Int. | Name | Structure | Analytical Data |
|---|---|---|---|
| 78 | tert-butyl 4-[3-[3-[4-ethyl-2-(4-methylthieno[3,2-b]pyrrol-5-yl)imidazol-1-yl]propyl]phenoxy]piperidine-1-carboxylate | 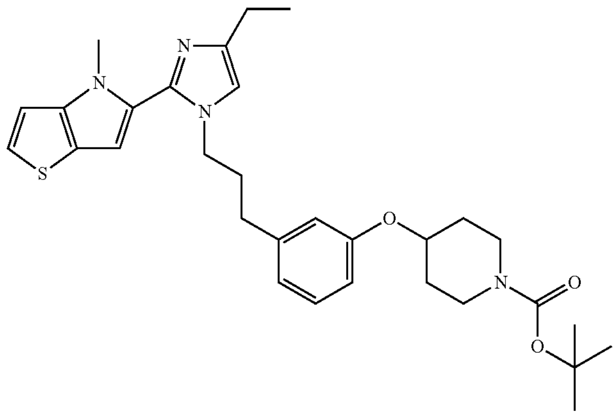 [SMILES: CCc1cn(CCCc2cccc(OC3CCN(C(=O)OC(C)(C)C)CC3)c2)c(-c2cc3sccc3n2C)n1] | $^1$H NMR (DMSO-d$_6$) δ (ppm): 7.30 (d, J = 5.4 Hz, 1 H), 7.15 (d, J = 5.4 Hz, 1 H), 7.14-7.09 (m, 1 H), 7.07 (s, 1 H), 6.79-6.74 (m, 2 H), 6.71-6.66 (m, 1 H), 6.37 (s, 1 H), 4.55-4.40 (m, 1 H), 3.96 (t, J = 7.3 Hz, 2 H), 3.78 (s, 3 H), 3.67-3.54 (m, 2 H), 3.21-3.07 (m, 2 H), 2.56-2.52 (m, 4 H), 2.04-1.94 (m, 2 H), 1.89-1.79 (m, 2 H), 1.50-1.42 (m, 2 H), 1.39 (s, 9 H), 1.18 (t, J = 1.6 Hz, 3 H); MS (ESI): m/z: 549 [M + H]$^+$. |
| 79 | tert-butyl 4-[3-[3-[5-ethyl-2-(4-methylthieno[3,2-b]pyrrol-5-yl)imidazol-1-yl]propyl]phenoxy]piperidine-1-carboxylate | 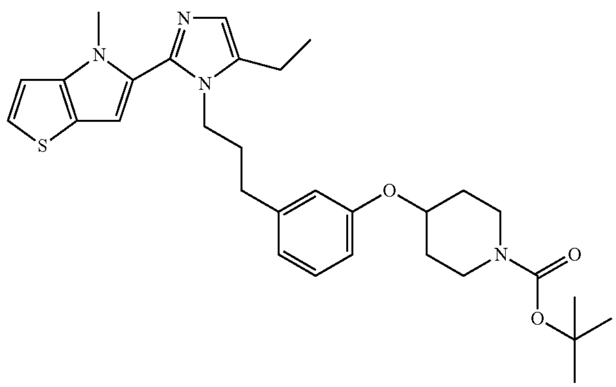 [SMILES: CCc1cnc(-c2cc3sccc3n2C)n1CCCc1cccc(OC2CCN(C(=O)OC(C)(C)C)CC2)c1] | $^1$H NMR (DMSO-d$_6$) δ (ppm): 7.31 (d, J = 5.4 Hz, 1 H), 7.16 (d, J = 5.4 Hz, 1 H), 7.14-7.08 (m, 1 H), 6.83 (s, 1 H), 6.79-6.74 (m, 2 H), 6.70-6.66 (m, 1 H), 6.41 (s, 1 H), 4.56-4.42 (m, 1 H), 3.94 (t, J = 7.8 Hz, 2 H), 3.73 (s, 3 H), 3.66-3.56 (m, 2 H), 3.20-3.05 (m, 2 H), 2.57 (q, J = 7.3 Hz, 2 H), 2.48-2.43 (m, 2 H), 1.92-1.78 (m, 4 H), 1.51-1.41 (m, 2 H), 1.39 (s, 9 H), 1.23 (t, J = 7.3 Hz, 3 H); MS (ESI): m/z: 549 [M + H]$^+$. |
| 80 | tert-butyl 4-[4-[2-[2-(4-methylthieno[3,2-b]pyrrol-5-yl)-4-propyl-imidazol-1-yl]ethyl]phenoxy]piperidine-1-carboxylate | 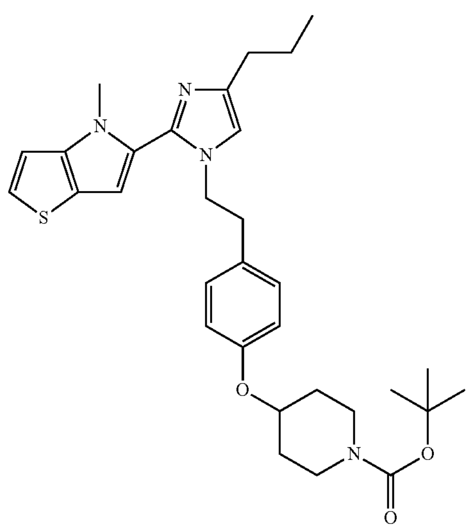 [SMILES: CCCc1cn(CCc2ccc(OC3CCN(C(=O)OC(C)(C)C)CC3)cc2)c(-c2cc3sccc3n2C)n1] | $^1$H NMR (DMSO-d$_6$) δ (ppm): 7.30 (d, J = 5.4 Hz, 1 H), 7.14 (d, J = 5.4 Hz, 1 H), 7.04 (s, 1 H), 6.96-6.90 (m, 2 H), 6.83-6.77 (m, 2 H), 6.35 (s, 1 H), 4.50-4.42 (m, 1 H), 4.15 (t, J = 7.3 Hz, 2 H), 3.68-3.57 (m, 5 H), 3.20-3.08 (m, 2 H), 2.90 (t, J = 7.1 Hz, 2 H), 2.45 (t, J = 7.3 Hz, 2 H), 1.89-1.78 (m, 2 H), 1.65-1.55 (m, 2 H), 1.50-1.42 (m, 2 H), 1.39 (s, 9 H), 0.92 (t, J = 7.6 Hz, 3 H); MS (ESI): m/z: 549 [M + H]$^+$. |

TABLE 2-continued

BOC Intermediates

| Int. | Name | Structure | Analytical Data |
|---|---|---|---|
| 81 | tert-butyl 4-[4-[2-[2-(4-methylthieno[3,2-b]pyrrol-5-yl)-5-propyl-imidazol-1-yl]ethyl]phenoxy]piperidine-1-carboxylate | 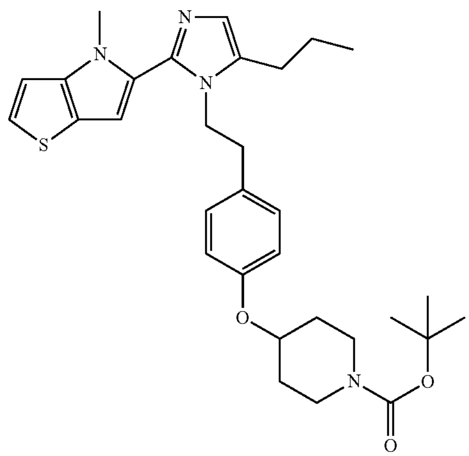 [SMILES: CCCc1cnc(-c2cc3sccc3n2C)n1CCc1ccc(OC2CCN(C(=O)OC(C)(C)C)CC2)cc1] | $^{1}$H NMR (DMSO-d$_6$) δ (ppm): 7.31 (d, J = 5.4 Hz, 1 H), 7.16 (d, J = 5.4 Hz, 1 H), 6.88-6.83 (m, 2 H), 6.81-6.74 (m, 3 H), 6.57 (s, 1 H), 4.51-4.40 (m, 1 H), 4.16 (t, J = 7.3 Hz, 2 H), 3.68-3.56 (m, 5 H), 3.22-3.07 (m, 2 H), 2.74 (t, J = 7.1 Hz, 2 H), 2.44 (t, J = 7.3 Hz, 2 H), 1.91-1.78 (m, 2 H), 1.68-1.55 (m, 2 H), 1.51-1.42 (m, 2 H), 1.39 (s, 9 H), 0.97 (t, J = 7.3 Hz, 3 H); MS (ESI): m/z: 549 [M + H]$^+$. |
| 82 | tert-butyl 4-[[4-[3-[2-(4-methylthieno[3,2-b]pyrrol-5-yl)-4-propyl-imidazol-1-yl]propyl]phenyl]methoxy]piperidine-1-carboxylate | 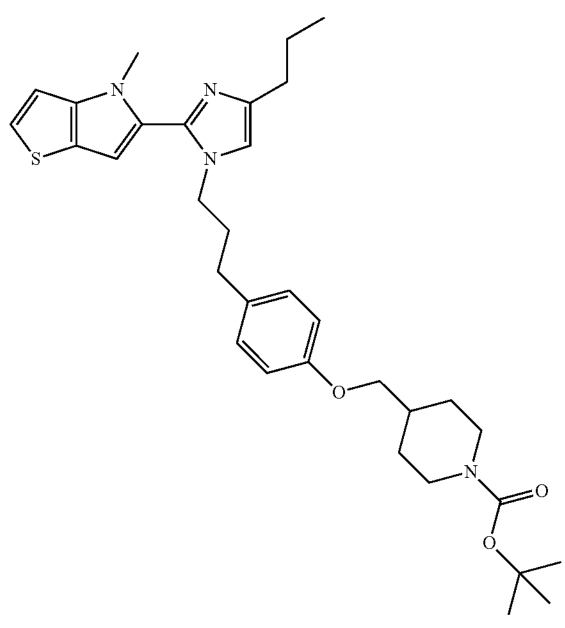 [SMILES: CCCc1cn(CCCc2ccc(OCC3CCN(C(=O)OC(C)(C)C)CC3)cc2)c(-c2cc3sccc3n2C)n1] | $^{1}$H NMR (CDCl$_3$) δ (ppm): 7.15 (d, J = 5.4 Hz, 1 H), 7.01-6.93 (m, 3 H), 6.79-6.71 (m, 3 H), 6.37 (s, 1 H), 4.30-4.05 (m, 2 H), 3.98 (t, J = 7.3 Hz, 2 H), 3.83 (s, 3 H), 3.79-3.74 (m, 2 H), 2.82-2.69 (m, 2 H), 2.61 (t, J = 7.3 Hz, 2 H), 2.53 (t, J = 7.3 Hz, 2 H), 2.01-1.99 (m, 2 H), 1.98-1.89 (m, 1 H), 1.87-1.79 (m, 2 H), 1.77-1.68 (m, 2 H), 1.48 (s, 9 H), 1.32-1.22 (m, 2 H), 1.00 (t, J = 7.3 Hz, 3 H); MS (ESI): m/z: 577 [M + H]$^+$. |

TABLE 2-continued

BOC Intermediates

| Int. | Name | Structure | Analytical Data |
|---|---|---|---|
| 83 | tert-butyl 4-[[4-[3-[2-(4-methylthieno[3,2-b]pyrrol-5-yl)-5-propyl-imidazol-1-yl]propyl]phenyl]methoxy]piperidine-1-carboxylate | 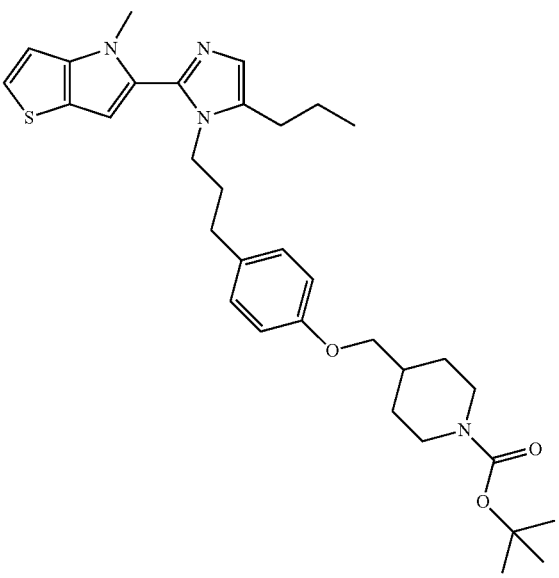 [SMILES: CCCc1cnc(-c2cc3sccc3n2C)n1CCCc1ccc(OCC2CCN(C(=O)OC(C)(C)C)CC2)cc1] | ¹H NMR (CDCl₃) δ (ppm): 7.16 (d, J = 5.4 Hz, 1 H), 7.01-6.91 (m, 4 H), 6.79-6.73 (m, 2 H), 6.39 (s, 1 H), 4.31-4.02 (m, 2 H), 3.94 (t, J = 7.3 Hz, 2 H), 3.83-3.74 (m, 5 H), 2.85-2.65 (m, 2 H), 2.57-2.45 (m, 4 H), 2.01-1.88 (m, 3 H), 1.87-1.80 (m, 2 H), 1.77-1.66 (m, 2 H), 1.48 (s, 9 H), 1.34-1.20 (m, 2 H), 1.04 (t, J = 7.3 Hz, 3 H); MS (ESI): m/z: 577 [M + H]⁺. |
| 84 | tert-butyl 4-[4-[2-[2-(4-methylthieno[3,2-b]pyrrol-5-yl)-4-propyl-imidazol-1-yl]ethoxy]phenoxy]azepane-1-carboxylate | 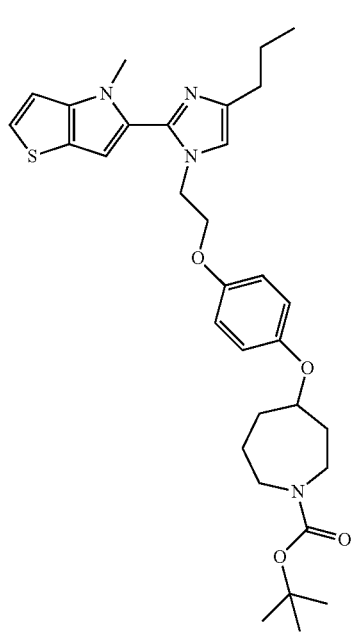 [SMILES: CCCc1cn(CCOc2ccc(OC3CCCN(C(=O)OC(C)(C)C)CC3)cc2)c(-c2cc3sccc3n2C)n1] | ¹H NMR (CDCl₃) δ (ppm): 7.16 (d, J = 5.4 Hz, 1 H), 6.97 (d, J = 5.4 Hz, 1 H), 6.93 (s, 1 H), 6.83-6.69 (m, 4 H), 6.57 (s, 1 H), 4.37 (t, J = 5.1 Hz, 2 H), 4.33-4.27 (m, 1 H), 4.15 (t, J = 5.1 Hz, 2 H), 3.82 (s, 3 H), 3.64-3.36 (m, 4 H), 2.61 (m, 2 H), 2.12-1.82 (m, 4 H), 1.79-1.68 (m, 2 H), 1.60 (m 2 H), 1.48 (s, 9 H), 1.00 (t, J = 7.3 Hz, 3 H); MS (ESI): m/z: 579 [M + H]⁺. |

TABLE 2-continued

BOC Intermediates

| Int. | Name | Structure | Analytical Data |
|---|---|---|---|
| 85 | tert-butyl 4-[4-[2-[2-(4-methylthieno[3,2-b]pyrrol-5-yl)-5-propyl-imidazol-1-yl]ethoxy]phenoxy]azepane-1-carboxylate | 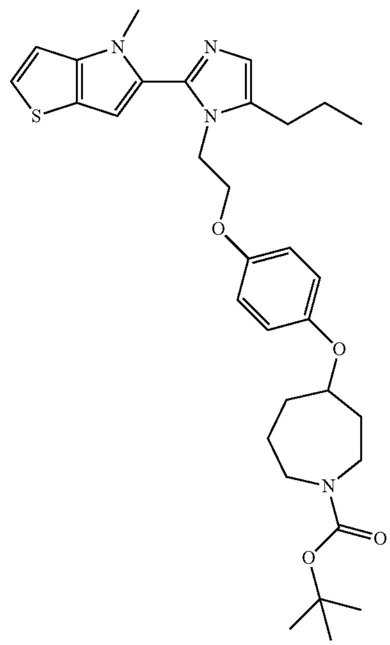 [SMILES: CCCc1cnc(-c2cc3sccc3n2C)n1CCOc1ccc(OC2CCCN(C(=O)OC(C)(C)C)CC2)cc1] | $^1$H NMR (CDCl$_3$) δ (ppm): 7.17 (d, J = 5.4 Hz, 1 H), 7.00-6.95 (m, 2 H), 6.77-6.59 (m, 5 H), 4.37 (t, J = 5.9 Hz, 2 H), 4.32-4.23 (m, 1 H), 4.02 (t, J = 5.9 Hz, 2 H), 3.76 (s, 3 H), 3.65-3.36 (m, 4 H), 2.68 (t, J = 7.3 Hz, 2 H), 2.09-1.82 (m, 4 H), 1.84-1.74 (m, 2 H), 1.68-1.56 (m, 2 H), 1.48 (s, 9 H), 1.09 (t, J = 7.3 Hz, 3 H); MS (ESI): m/z: 579 [M + H]$^+$. |
| 86 | tert-butyl 4-[4-[3-[4-cyclobutyl-2-(6-methylthieno[2,3-b]pyrrol-5-yl)imidazol-1-yl]propyl]phenoxy]piperidine-1-carboxylate | 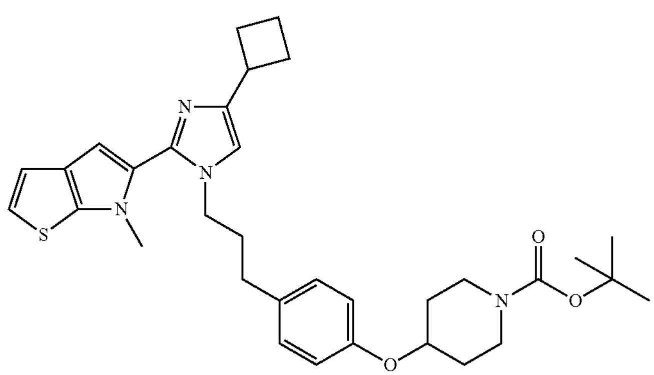 [SMILES: Cn1c(-c2nc(C3CCC3)cn2CCCc2ccc(OC3CCN(C(=O)OC(C)(C)C)CC3)cc2)cc2ccsc21] | $^1$H NMR (DMSO-d6) δ (ppm): 7.11 (s, 1 H), 7.07 (d, J = 5.4 Hz, 1 H), 7.03-6.98 (m, 3 H), 6.81-6.76 (m, 2 H), 6.34 (s, 1 H), 4.48-4.35 (m, 1 H), 3.93 (t, J = 7.3 Hz, 2 H), 3.75 (s, 3 H), 3.68-3.59 (m, 2 H), 3.46-3.36 (m, 1 H), 3.14 (bs, 2 H), 2.45 (t, J = 7.3 Hz, 2 H), 2.26-2.09 (m, 4 H), 2.02-1.79 (m, 6 H), 1.50-1.41 (m, 2 H), 1.40 (s, 9 H).; MS (ESI): m/z: 575 [M + H]$^+$. |
| 87 | tert-butyl 4-[4-[3-[5-cyclobutyl-2-(6-methylthieno[2,3-b]pyrrol-5-yl)imidazol-1-yl]propyl]phenoxy]piperidine-1-carboxylate | 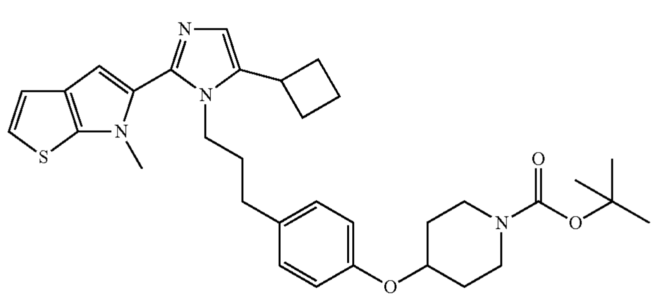 [SMILES: Cn1c(-c2ncc(C3CCC3)n2CCCc2ccc(OC3CCN(C(=O)OC(C)(C)C)CC3)cc2)cc2ccsc21] | $^1$H NMR (DMSO-d6) δ (ppm): 7.07 (d, J = 5.4 Hz, 1 H), 7.04-6.99 (m, 3 H), 6.92 (s, 1 H), 6.84-6.79 (m, 2 H), 6.39 (s, 1 H), 4.50-4.39 (m, 1 H), 3.83 (t, J = 7.3 Hz, 2 H), 3.71-3.58 (m, 5 H), 3.46-3.36 (m, 1 H), 3.14 (br. s, 2 H), 2.44 (t, J = 7.3 Hz, 2 H), 2.27-2.17 (m, 2 H), 2.14-2.03 (m, 2 H), 2.00-1.74 (m, 6 H), 1.54-1.43 (m, 2 H), 1.40 (s, 9 H); MS (ESI): m/z: 575 [M + H]$^+$. |

TABLE 2-continued

BOC Intermediates

| Int. | Name | Structure | Analytical Data |
|---|---|---|---|
| 88 | tert-butyl (3R)-3-[[4-[3-[4-cyclobutyl-2-(4-methylthieno[3,2-b]pyrrol-5-yl)imidazol-1-yl]propyl]phenoxy]methyl]pyrrolidine-1-carboxylate | 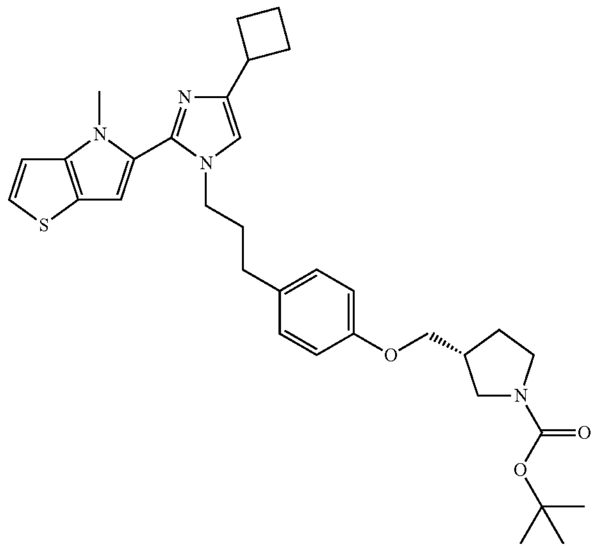 [SMILES: Cn1c(-c2nc(C3CCC3)cn2CCCc2ccc(OC[C@@H]3CCN(C(=O)OC(C)(C)C)C3)cc2)cc2sccc21] | $^1$H NMR (DMSO-d$_6$) δ (ppm): 7.30 (d, J = 5.4 Hz, 1 H), 7.16 (d, J = 5.4 Hz, 1 H), 7.11 (s, 1 H), 7.04-6.98 (m, 2 H), 6.79-6.73 (m, 2 H), 6.35 (s, 1 H), 3.97-3.81 (m, 4 H), 3.79 (s, 3 H), 3.47-3.33 (m, 3 H), 3.28-3.17 (m, 1 H), 3.11-3.01 (m, 1 H), 2.62-2.53 (m, 1 H), 2.46 (t, J = 7.3 Hz, 2 H), 2.26-2.10 (m, 4 H), 2.03-1.89 (m, 4 H), 1.88-1.77 (m, 1 H), 1.74-1.63 (m, 1H), 1.39 (s, 9 H).; MS (ESI): m/z: 575 [M + H]$^+$. |
| 89 | tert-butyl (3R)-3-[[4-[3-[5-cyclobutyl-2-(4-methylthieno[3,2-b]pyrrol-5-yl)imidazol-1-yl]propyl]phenoxy]methyl]pyrrolidine-1-carboxylate | 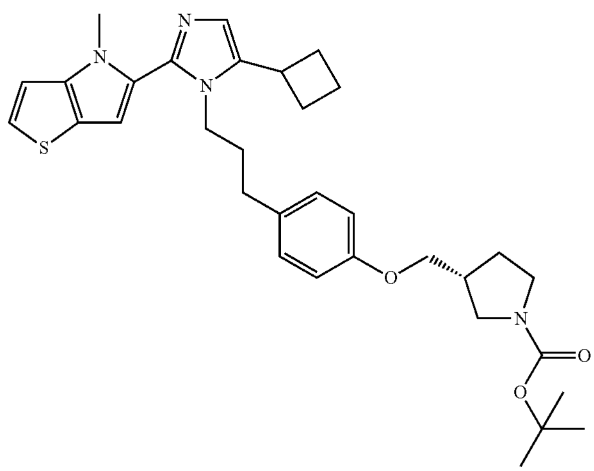 [SMILES: Cn1c(-c2ncc(C3CCC3)n2CCCc2ccc(OC[C@@H]3CCN(C(=O)OC(C)(C)C)C3)cc2)cc2sccc21] | $^1$H NMR (DMSO-d6) δ (ppm): 7.30 (d, J = 5.4 Hz, 1 H), 7.15 (d, J = 5.4 Hz, 1 H), 7.04-6.99 (m, 2 H), 6.93 (s, 1 H), 6.81-6.74 (m, 2 H), 6.39 (s, 1 H), 3.93-3.80 (m, 4 H), 3.72 (s, 3 H), 3.49-3.36 (m, 3 H), 3.26-3.15 (m, 1 H), 3.11-3.01 (m, 1 H), 2.62-2.53 (m, 1 H), 2.45 (t, J = 7.3 Hz, 2 H), 2.30-2.20 (m, 2 H), 2.14-2.03 (m, 2 H), 2.03-1.90 (m, 2 H), 1.88-1.63 (m, 4 H), 1.39 (s, 9 H); MS (ESI): m/z: 575 [M + H]$^+$. |
| 90 | tert-butyl (3S)-3-[[4-[3-[4-cyclobutyl-2-(4-methylthieno[3,2-b]pyrrol-5-yl)imidazol-1-yl]propyl]phenoxy]methyl]pyrrolidine-1-carboxylate | 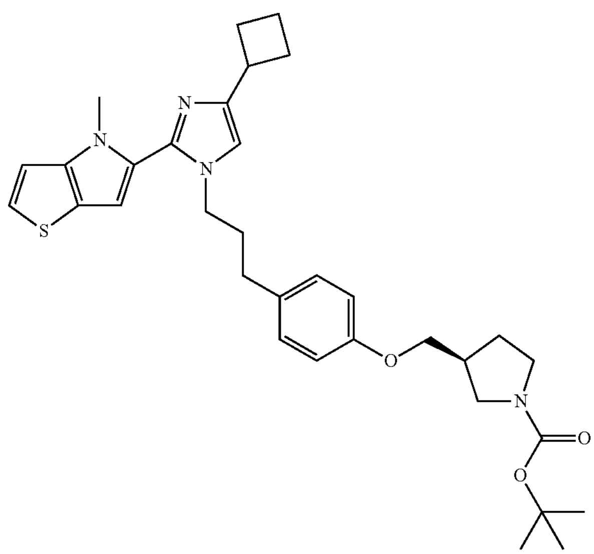 [SMILES: Cn1c(-c2nc(C3CCC3)cn2CCCc2ccc(OC[C@H]3CCN(C(=O)OC(C)(C)C)C3)cc2)cc2sccc21] | $^1$H NMR (DMSO-d6) δ (ppm): 7.30 (d, J = 5.4 Hz, 1 H), 7.16 (d, J = 5.4 Hz, 1 H), 7.11 (s, 1 H), 7.04-6.99 (m, 2 H), 6.79-6.73 (m, 2 H), 6.35 (s, 1 H), 3.93 (t, J = 7.3 Hz, 2 H), 3.89-3.81 (m, 2 H), 3.79 (s, 3 H), 3.47-3.35 (m, 3 H), 3.29-3.17 (m, 1 H), 3.11-3.03 (m, 1 H), 2.61-2.53 (m, 1 H), 2.45 (t, J = 7.3 Hz, 2 H), 2.26-2.09 (m, 4 H), 2.02-1.60 (m, 6 H), 1.39 (s, 9 H).; MS (ESI): m/z: 575 [M + H]$^+$. |

TABLE 2-continued

BOC Intermediates

| Int. | Name | Structure | Analytical Data |
|---|---|---|---|
| 91 | tert-butyl (3S)-3-[[4-[3-[5-cyclobutyl-2-(4-methylthieno[3,2-b]pyrrol-5-yl)imidazol-1-yl]propyl]phenoxy]methyl]pyrrolidine-1-carboxylate | 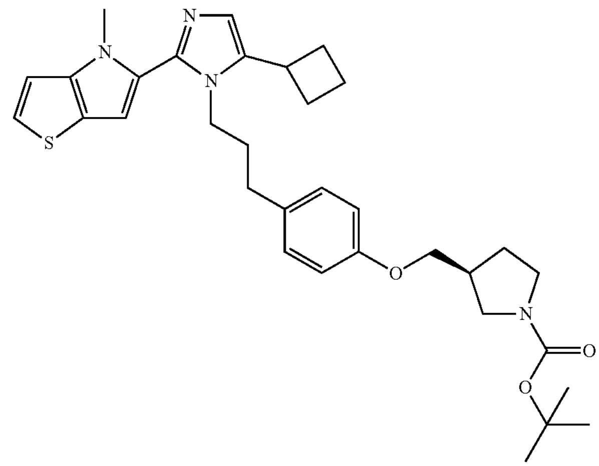 [SMILES: Cn1c(-c2ncc(C3CCC3)n2CCCc2ccc(OC[C@H]3CCN(C(=O)OC(C)(C)C)C3)cc2)cc2sccc21] | $^1$H NMR (DMSO-d6) δ (ppm): 7.29 (d, J = 5.4 Hz, 1 H), 7.15 (d, J = 5.4 Hz, 1 H), 7.04-6.97 (m, 2 H), 6.92 (s, 1 H), 6.80-6.75 (m, 2 H), 6.39 (s, 1 H), 3.93-3.80 (m, 4 H), 3.72 (s, 3 H), 3.48-3.36 (m, 3 H), 3.27-3.16 (m, 1 H), 3.13-3.04 (m, 1 H), 2.62-2.55 (m, 1 H), 2.44 (t, J = 7.3 Hz, 2 H), 2.31-2.20 (m, 2 H), 2.14-1.61 (m, 8 H), 1.39 (s, 9 H); MS (ESI): m/z: 575 [M + H]$^+$. |
| 92 | tert-butyl 4-[[4-[2-[4-cyclobutyl-2-(4-methylthieno[3,2-b]pyrrol-5-yl)imidazol-1-yl]ethoxy]phenoxy]methyl]piperidine-1-carboxylate | 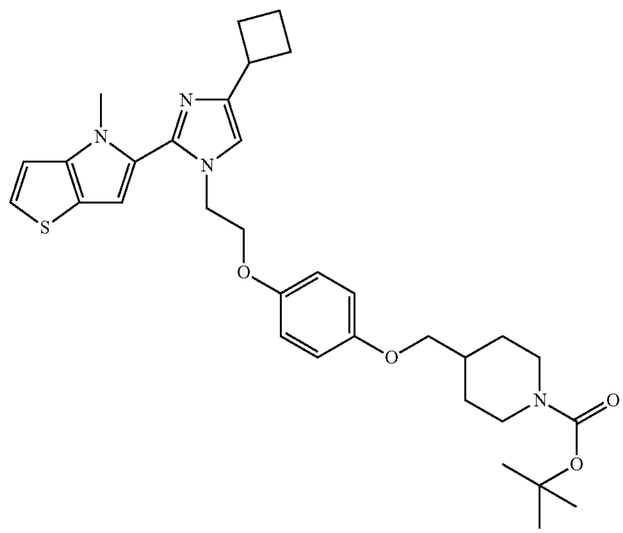 [SMILES: Cn1c(-c2nc(C3CCC3)cn2CCOc2ccc(OCC3CCN(C(=O)OC(C)(C)C)CC3)cc2)cc2sccc21] | $^1$H NMR (DMSO-d6) δ (ppm): 7.33 (d, J = 5.4 Hz, 1 H), 7.21-7.15 (m, 2 H), 6.83-6.73 (m, 4 H), 6.68 (s, 1 H), 4.31 (t, J = 5.3 Hz, 2 H), 4.18 (t, J = 5.3 Hz, 2 H), 3.95 (bs, 2 H), 3.78 (s, 3 H), 3.73 (d, J = 6.4 Hz, 2 H), 3.47-3.37 (m, 1 H), 2.73 (bs, 2 H), 2.25-2.09 (m, 4 H), 1.98-1.78 (m, 3 H), 1.75-1.67 (m, 2 H), 1.38 (s, 9H), 1.17-1.05 (m, 2 H); MS (ESI): m/z: 591 [M + H]$^+$. |
| 93 | tert-butyl 4-[3-[3-[4-cyclobutyl-2-(4-methylthieno[3,2-b]pyrrol-5-yl)imidazol-1-yl]propyl]phenoxy]piperidine-1-carboxylate | 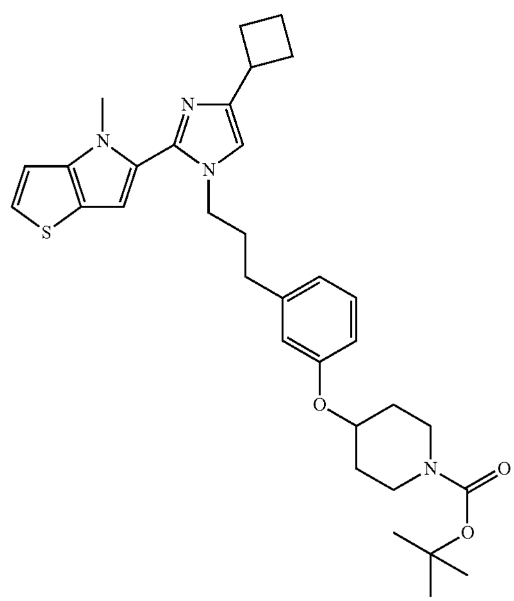 [SMILES: Cn1c(-c2nc(C3CCC3)cn2CCCc2cccc(OC3CCN(C(=O)OC(C)(C)C)CC3)c2)cc2sccc21] | $^1$H NMR (DMSO-d6) δ (ppm): 7.29 (d, J = 5.4 Hz, 1 H), 7.16-7.06 (m, 3 H), 6.78-6.71 (m, 2 H), 6.70-6.65 (m, 1 H), 6.33 (s, 1 H), 4.53-4.43 (m, 1 H), 3.92 (t, J = 7.3 Hz, 2 H), 3.75 (s, 3 H), 3.63-3.57 (m, 2 H), 3.45-3.36 (m, 1 H), 3.12 (bs, 2 H), 2.46 (t, J = 7.3 Hz, 2 H), 2.24-2.08 (m, 4 H), 2.02-1.76 (m, 6 H), 1.48-1.39 (m, 2 H), 1.37 (s, 9 H); MS (ESI): m/z: 575 [M + H]$^+$. |

TABLE 2-continued

BOC Intermediates

| Int. | Name | Structure | Analytical Data |
|------|------|-----------|-----------------|
| 94 | tert-butyl 4-[3-[3-[5-cyclobutyl-2-(4-methylthieno[3,2-b]pyrrol-5-yl)imidazol-1-yl]propyl]phenoxy]piperidine-1-carboxylate | 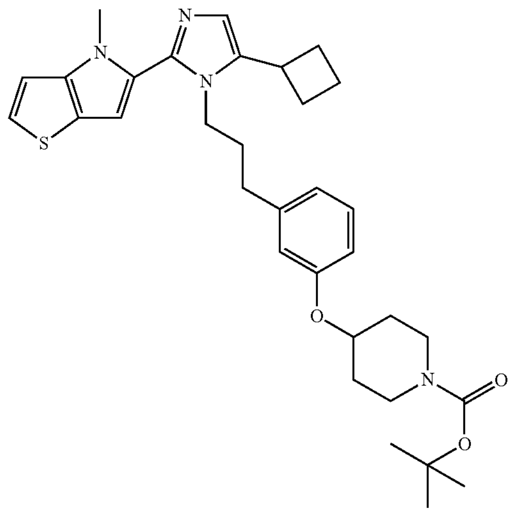 [SMILES: Cn1c(-c2ncc(C3CCC3)n2CCCc2cccc(OC3CCN(C(=O)OC(C)(C)C)CC3)c2)cc2sccc21] | $^1$H NMR (DMSO-d6) δ (ppm): 7.30 (d, J = 5.4 Hz, 1 H), 7.18-7.09 (m, 2 H), 6.93 (s, 1 H), 6.81-6.75 (m, 2 H), 6.72 - 6.65 (m, 1 H), 6.44 (s, 1 H), 4.55-4.46 (m, 1 H), 3.86 (t, J = 7.3 Hz, 2 H), 3.73 (s, 3 H), 3.66-3.56 (m, 2 H), 3.47-3.37 (m, 1 H), 3.14 (bs, 2 H), 2.46 (t, J = 7.3 Hz, 2 H), 2.27-2.18 (m, 2 H), 2.13-2.03 (m, 2 H), 2.00-1.78 (m, 6 H), 1.51-1.43 (m, 2 H), 1.39 (s, 9 H); MS (ESI): m/z: 575 [M + H]$^+$. |
| 95 | tert-butyl 4-[3-[2-[4-cyclobutyl-2-(4-methylthieno[3,2-b]pyrrol-5-yl)imidazol-1-yl]ethoxy]phenoxy]piperidine-1-carboxylate | 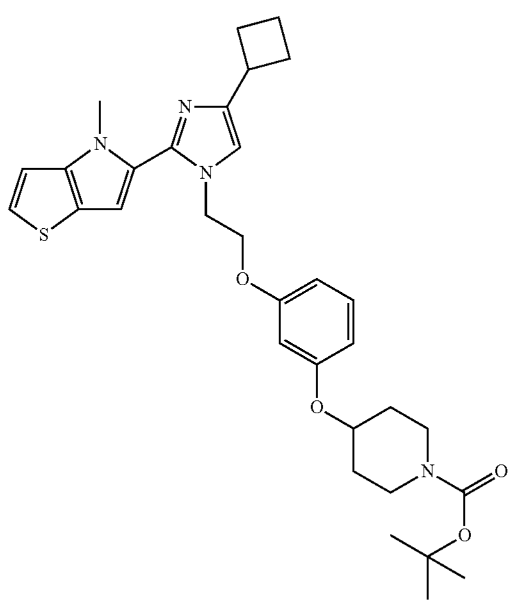 [SMILES: Cn1c(-c2nc(C3CCC3)cn2CCOc2cccc(OC3CCN(C(=O)OC(C)(C)C)CC3)c2)cc2sccc21] | $^1$H NMR (DMSO-d6) δ (ppm): 7.32 (d, J = 5.4 Hz, 1 H), 7.21-7.16 (m, 2 H), 7.15-7.08 (m, 1 H), 6.68 (s, 1 H), 6.57-6.52 (m, 1 H), 6.47-6.41 (m, 2 H), 4.55-4.47 (m, 1 H), 4.32 (t, J = 5.4 Hz, 2 H), 4.24 (t, J = 5.4 Hz, 2 H), 3.78 (s, 3 H), 3.66-3.57 (m, 2 H), 3.45-3.37 (m, 1 H), 3.15 (bs, 2 H), 2.26-2.10 (m, 4 H), 1.99-1.79 (m, 4 H), 1.53-1.43 (m, 2 H), 1.39 (s, 9 H); MS (ESI): m/z: 577 [M + H]$^+$. |

TABLE 2-continued

BOC Intermediates

| Int. | Name | Structure | Analytical Data |
|---|---|---|---|
| 96 | tert-butyl 4-[3-[2-[5-cyclobutyl-2-(4-methylthieno[3,2-b]pyrrol-5-yl)imidazol-1-yl]ethoxy]phenoxy]piperidine-1-carboxylate | 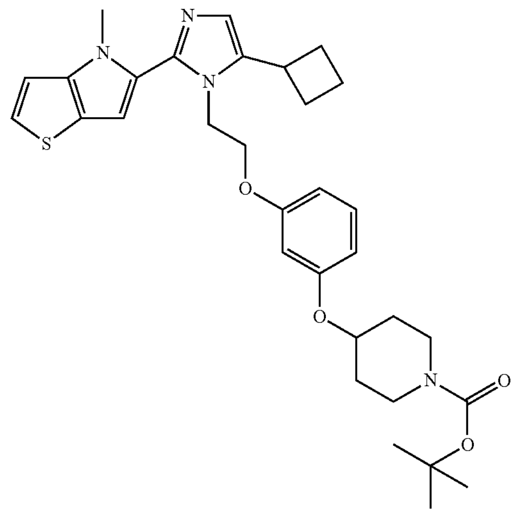 [SMILES: Cn1c(-c2ncc(C3CCC3)n2CCOc2cccc(OC3CCN(C(=O)OC(C)(C)C)CC3)c2)cc2sccc21] | $^1$H NMR (DMSO-d6) δ (ppm): 7.32 (d, J = 5.4 Hz, 1 H), 7.18 (d, J = 5.4 Hz, 1 H), 7.10-7.04 (m, 1 H), 6.98 (s, 1H), 6.71 (s, 1 H), 6.55-6.49 (m, 1H), 6.36-6.28 (m, 2 H), 4.52-4.44 (m, 1 H), 4.31 (t, J = 5.4 Hz, 2 H), 4.04 (t, J = 5.4 Hz, 2 H), 3.73-3.55 (m, 6 H), 3.17 (bs, 2 H), 2.41-2.32 (m, 2 H), 2.20-1.77 (m, 6 H), 1.51-1.42 (m, 2 H), 1.39 (s, 9 H); MS (ESI): m/z: 577 [M + H]$^+$. |
| 97 | tert-butyl 4-[4-[3-[4-methyl-2-(4-methylthieno[3,2-b]pyrrol-5-yl)imidazol-1-yl]propyl]phenoxy]piperidine-1-carboxylate | 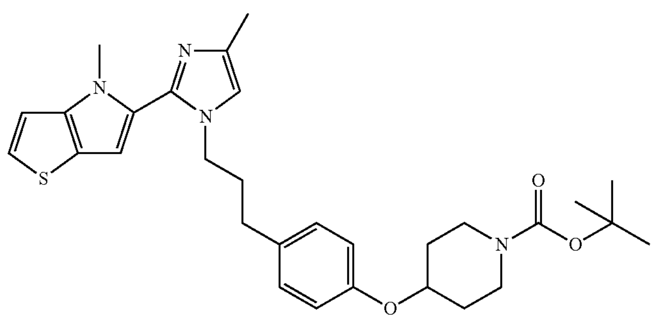 [SMILES: Cc1cn(CCCc2ccc(OC3CCN(C(=O)OC(C)(C)C)CC3)cc2)c(-c2cc3sccc3n2C)n1] | $^1$H NMR (DMSO-d6) δ (ppm): 7.31 (d, J = 5.4 Hz, 1 H), 7.17 (d, J = 5.4 Hz, 1 H), 7.07 (s, 1 H), 7.01-6.95 (m, 2 H), 6.81-6.73 (m, 2 H), 6.40 (s, 1 H), 4.47-4.38 (m, 1 H), 3.93 (t, J = 7.3 Hz, 2 H), 3.78 (s, 3 H), 3.68-3.59 (m, 2 H), 3.14 (bs, 2 H), 2.43 (t, J = 7.3 Hz, 2 H), 2.15 (s, 3 H), 1.98-1.89 (m, 2 H), 1.88-1.80 (m, 2 H), 1.50-1.42 (m, 2 H), 1.39 (s, 9 H); MS (ESI): m/z: 535 [M + H]$^+$. |
| 98 | tert-butyl 4-[4-[3-[5-methyl-2-(4-methylthieno[3,2-b]pyrrol-5-yl)imidazol-1-yl]propyl]phenoxy]piperidine-1-carboxylate | 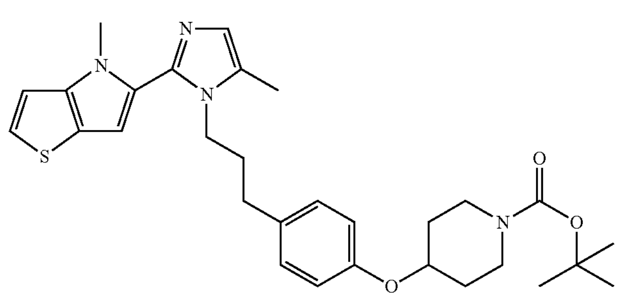 [SMILES: Cc1cnc(-c2cc3sccc3n2C)n1CCCc1ccc(OC2CCN(C(=O)OC(C)(C)C)CC2)cc1] | $^1$H NMR (DMSO-d6) δ (ppm): 7.32 (d, J = 5.4 Hz, 1 H), 7.17 (d, J = 5.4 Hz, 1 H), 7.04-6.95 (m, 2 H), 6.82 (s, 1 H), 6.80-6.76 (m, 2 H), 6.43 (s, 1 H), 4.49-4.40 (m, 1 H), 3.92 (t, J = 7.3 Hz, 2 H), 3.72 (s, 3 H), 3.68-3.59 (m, 2 H), 3.14 (bs, 2 H), 2.45 (t, J = 7.3 Hz, 2 H), 2.21 (s, 3 H), 1.89-1.80 (m, 4 H), 1.51-1.42 (m, 2 H), 1.39 (s, 9 H); MS (ESI): m/z: 535 [M + H]$^+$. |

TABLE 2-continued

BOC Intermediates

| Int. | Name | Structure | Analytical Data |
|---|---|---|---|
| 99 | tert-butyl 4-[[4-[2-[4-cyclobutyl-2-(4-methylthieno[3,2-b]pyrrol-5-yl)imidazol-1-yl]ethyl]phenoxy]methyl]piperidine-1-carboxylate | 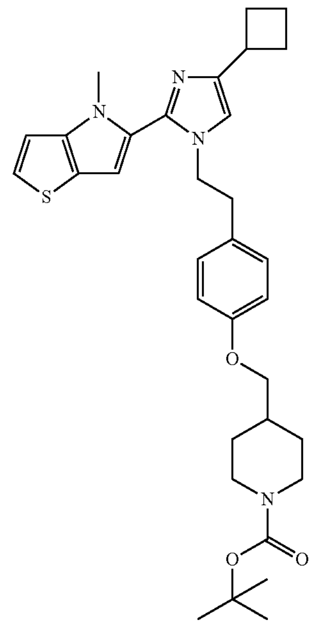 [SMILES: Cn1c(-c2nc(C3CCC3)cn2CCc2ccc(OCC3CCN(C(=O)OC(C)(C)C)CC3)cc2)cc2sccc21] | ¹H NMR (DMSO-d6) δ (ppm): 7.31 (d, J = 5.4 Hz, 1 H), 7.15 (d, J = 5.4 Hz, 1 H), 7.10 (s, 1 H), 7.00-6.93 (m, 2 H), 6.79-6.72 (m, 2 H), 6.46 (s, 1 H), 4.14 (t, J = 7.3 Hz, 2 H), 3.94 (bs, 2 H), 3.75 (d, J = 6.4 Hz, 2 H), 3.67 (s, 3 H), 3.45-3.35 (m, 1 H), 2.90 (t, J = 7.3 Hz, 2 H), 2.72 (bs, 2 H), 2.27-2.06 (m, 4 H), 2.00-1.78 (m, 3 H), 1.76-1.69 (m, 2 H), 1.38 (s, 9 H), 1.17-1.04 (m, 2 H); MS (ESI): m/z: 575 [M + H]⁺. |
| 100 | tert-butyl 4-[3-[3-[2-(4-methylthieno[3,2-b]pyrrol-5-yl)-4-propyl-imidazol-1-yl]propyl]phenoxy]piperidine-1-carboxylate | 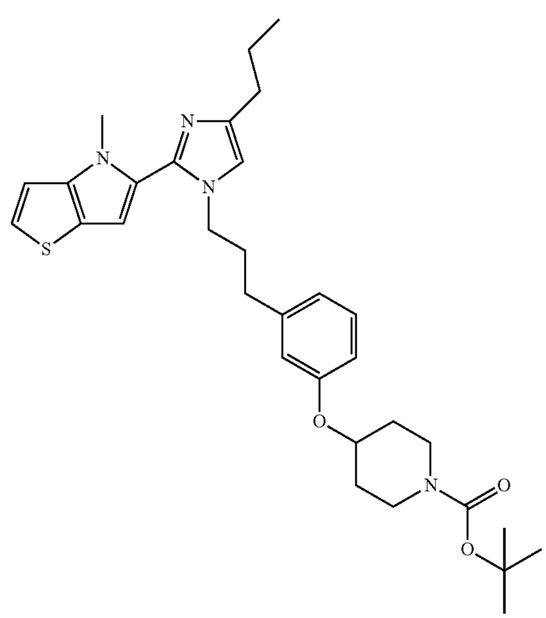 [SMILES: CCCc1cn(CCCc2cccc(OC3CCN(C(=O)OC(C)(C)C)CC3)c2)c(-c2cc3sccc3n2C)n1] | ¹H NMR (DMSO-d6) δ (ppm): 7.30 (d, J = 5.4 Hz, 1 H), 7.15 (d, J = 5.4 Hz, 1 H), 7.13-7.09 (m, 1 H), 7.07 (s, 1 H), 6.79-6.74 (m, 2 H), 6.70-6.66 (m, 1 H), 6.38 (s, 1 H), 4.54-4.45 (m, 1 H), 3.96 (t, J = 7.3 Hz, 2 H), 3.77 (s, 3 H), 3.66-3.57 (m, 2 H), 3.20-3.07 (m, 2 H), 2.49-2.43 (m, 4 H), 2.04-1.95 (m, 2 H), 1.88-1.80 (m, 2 H), 1.67-1.56 (m, 2 H), 1.50-1.42 (m, 2 H), 1.39 (s, 9 H), 0.93 (t, J = 7.6 Hz, 3 H); MS (ESI): m/z: 563 [M + H]⁺. |

TABLE 2-continued

BOC Intermediates

| Int. | Name | Structure | Analytical Data |
|---|---|---|---|
| 101 | tert-butyl 4-[3-[3-[2-(4-methylthieno[3,2-b]pyrrol-5-yl)-5-propyl-imidazol-1-yl]propyl]phenoxy]piperidine-1-carboxylate | 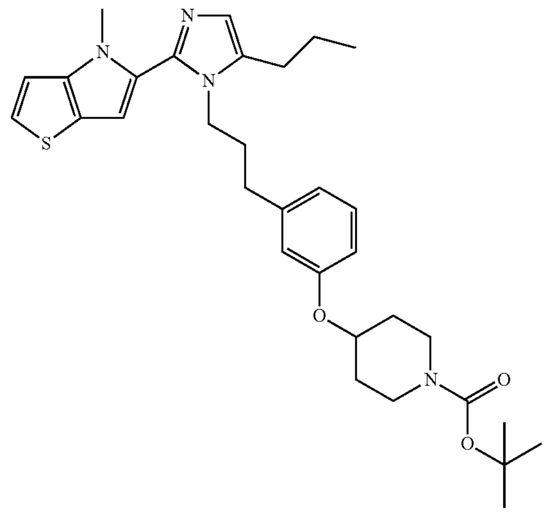 [SMILES: CCCc1cnc(-c2cc3sccc3n2C)n1CCCc1cccc(OC2CCN(C(=O)OC(C)(C)C)CC2)c1] | $^1$H NMR (DMSO-d6) δ (ppm): 7.30 (d, J = 5.4 Hz, 1 H), 7.16 (d, J = 5.4 Hz, 1 H), 7.14-7.09 (m, 1 H), 6.82 (s, 1 H), 6.79-6.75 (m, 2 H), 6.70-6.66 (m, 1 H), 6.43 (s, 1 H), 4.56-4.45 (m, 1 H), 3.98-3.89 (m, 2 H), 3.72 (s, 3 H), 3.66-3.56 (m, 2 H), 3.14 (bs, 2 H), 2.49-2.44 (m, 4 H), 1.91-1.80 (m, 4 H), 1.66-1.56 (m, 2 H), 1.51-1.42 (m, 2 H), 1.39 (s, 9 H), 0.96 (t, J = 13 Hz, 3 H); MS (ESI): m/z: 563 [M + H]$^+$. |
| 102 | tert-butyl 4-[3-[2-[2-(4-methylthieno[3,2-b]pyrrol-5-yl)-5-propyl-imidazol-1-yl]ethoxy]phenoxy]piperidine-1-carboxylate | 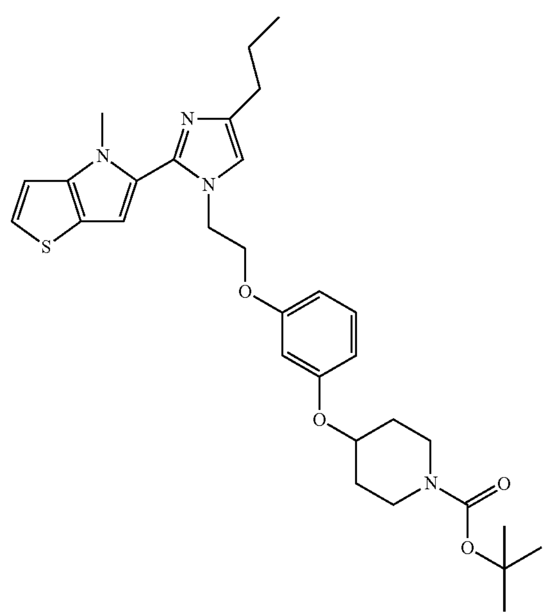 [SMILES: CCCc1cn(CCOc2cccc(OC3CCN(C(=O)OC(C)(C)C)CC3)c2)c(-c2cc3sccc3n2C)n1] | $^1$H NMR (DMSO-d6) δ (ppm): 7.32 (d, J = 5.4 Hz, 1 H), 7.18 (d, J = 5.4 Hz, 1 H), 7.15-7.09 (m, 2 H), 6.68 (s, 1 H), 6.57-6.53 (m, 1 H), 6.47-6.42 (m, 2 H), 4.54-4.46 (m, 1 H), 4.32 (t, J = 5.1 Hz, 2 H), 4.24 (t, J = 5.1 Hz, 2 H), 3.76 (s, 3 H), 3.66-3.58 (m, 2H), 3.15 (bs, 2 H), 2.46 (t, J = 7.3 Hz, 2 H), 1.89-1.81 (m, 2 H), 1.67-1.56 (m, 2 H), 1.52-1.42 (m, 2 H), 1.40 (s, 9 H), 0.93 (t, J = 7.6 Hz, 3 H); MS (ESI): m/z: 565 [M + H]$^+$. |

TABLE 2-continued

| BOC Intermediates | | | |
|---|---|---|---|
| Int. | Name | Structure | Analytical Data |
| 103 | tert-butyl 4-[3-[2-[2-(4-methylthieno[3,2-b]pyrrol-5-yl)-5-propyl-imidazol-1-yl]ethoxy]phenoxy]piperidine-1-carboxylate | | $^1$H NMR (CDCl3) δ (ppm): 7.17 (d, J = 4.9 Hz, 1 H), 7.14-7.07 (m, 1 H), 7.00-6.94 (m, 2 H), 6.61 (s, 1 H), 6.54-6.49 (m, 1 H), 6.35-6.29 (m, 2 H), 4.46-4.36 (m, 3 H), 4.05 (t, J = 5.9 Hz, 2 H), 3.76 (s, 3 H), 3.72-3.64 (m, 2 H), 3.37-3.29 (m, 2 H), 2.68 (t, J = 7.8 Hz, 2 H), 1.94-1.85 (m, 2 H), 1.84-1.68 (m, 4 H), 1.48 (s, 9 H), 1.10 (t, J = 7.3 Hz, 3 H); MS (ESI): m/z: 565 [M + H]$^+$. |
| 104 | tert-butyl 4-[[4-[3-[2-(4-methylthieno[3,2-b]pyrrol-5-yl)-4-propyl-imidazol-1-yl]propyl]phenoxy]methyl]piperidine-1-carboxylate | | $^1$H NMR (CDCl3) δ (ppm): 7.15 (d, J = 5.4 Hz, 1 H), 7.01-6.93 (m, 3 H), 6.79-6.71 (m, 3 H), 6.37 (s, 1 H), 4.30-4.05 (m, 2 H), 3.99 (t, J = 7.3 Hz, 2 H), 3.83 (s, 3 H), 3.77 (d, J = 6.4 Hz, 2 H), 2.82-2.69 (m, 2 H), 2.62 (t, J = 7.1 Hz, 2 H), 2.53 (t, J =7.3 Hz, 2 H), 2.04 (t, J = 7.3 Hz, 2 H), 1.98-1.89 (m, 1 H), 1.87-1.79 (m, 2 H), 1.77-1.68 (m, 2 H), 1.48 (s, 9H), 1.34-1.21 (m, 2 H), 1.00 (t, J = 7.3 Hz, 3 H); MS (ESI): m/z: 577 [M + H]$^+$. |
| 105 | tert-butyl 4-[[4-[3-[2-(4-methylthieno[3,2-b]pyrrol-5-yl)-5-propyl-imidazol-1-yl]propyl]phenoxy]methyl]piperidine-1-carboxylate | | $^1$H NMR (CDCl3) δ (ppm): 7.16 (d, J = 5.4 Hz, 1 H), 7.01-6.91 (m, 4 H), 6.82-6.72 (m, 2 H), 6.39 (s, 1 H), 4.31-4.02 (m, 2 H), 3.98-3.90 (m, 2 H), 3.83-3.74 (m, 5 H), 2.85-2.65 (m, 2 H), 2.56-2.44 (m, 4 H), 2.01-1.88 (m, 3 H), 1.87-1.78 (m, 2 H), 1.76-1.65 (m, 2 H), 1.48 (s, 9 H), 1.34-1.20 (m, 2 H), 1.04 (t, J = 7.3 Hz, 3 H); MS (ESI): m/z: 577 [M + H]$^+$. |

TABLE 2-continued

BOC Intermediates

| Int. | Name | Structure | Analytical Data |
|---|---|---|---|
| 106 | tert-butyl 4-[4-[2-[2-(4-methylthieno[3,2-b]pyrrol-5-yl)-4-propyl-imidazol-1-yl]ethoxy]phenoxy]azepane-1-carboxylate | 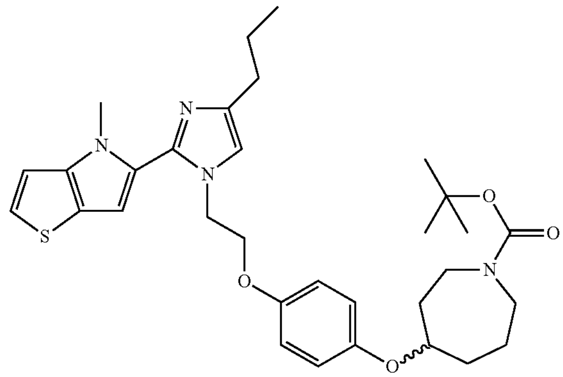 [SMILES: CCCc1cn(CCOc2ccc(OC3CCCN(C(=O)OC(C)(C)C)CC3)cc2)c(-c2cc3sccc3n2C)n1] | $^{1}$H NMR (CDCl3) δ (ppm): 7.16 (d, J = 5.4 Hz, 1 H), 6.97 (d, J = 5.4 Hz, 1 H), 6.93 (s, 1 H), 6.83-6.69 (m, 4 H), 6.57 (s, 1 H), 4.37 (t, J = 5.1 Hz, 2 H), 4.33-4.27 (m, 1 H), 4.15 (t, J = 5.1 Hz, 2 H), 3.82 (s, 3 H), 3.64-3.36 (m, 4H), 2.61 (bs, 2H), 2.10-1.81 (m, 4 H), 1.78-1.68 (m, 2 H), 1.60 (bs, 2 H), 1.48 (s, 9 H), 1.00 (t, J = 7.3 Hz, 3 H); MS (ESI): m/z: 579 [M + H]$^{+}$. |
| 107 | tert-butyl 4-[4-[2-[2-(4-methylthieno[3,2-b]pyrrol-5-yl)-5-propyl-imidazol-1-yl]ethoxy]phenoxy]azepane-1-carboxylate | 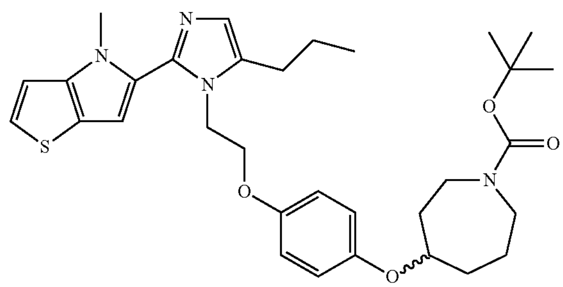 [SMILES: CCCc1cnc(-c2cc3sccc3n2C)n1CCOc1ccc(OC2CCCN(C(=O)OC(C)(C)C)CC2)cc1] | $^{1}$H NMR (CDCl3) δ (ppm): 7.17 (d, J = 5.4 Hz, 1 H), 7.01-6.94 (m, 2 H), 6.77-6.71 (m, 2 H), 6.66-6.56 (m, 3 H), 4.37 (t, J = 5.9 Hz, 2 H), 4.31-4.24 (m, 1 H), 4.02 (t, J = 5.9 Hz, 2 H), 3.76 (s, 3 H), 3.64-3.36 (m, 4 H), 2.68 (t, J = 7.8 Hz, 2 H), 2.08-1.57 (m, 8 H), 1.48 (s, 9 H), 1.09 (t, J = 7.3 Hz, 3 H); MS (ESI): m/z: 579 [M + H]$^{+}$. |
| 108 | tert-butyl 4-[4-[3-[2-(4-methylthieno[3,2-b]pyrrol-5-yl)-4-(3,3,3-trifluoropropyl)imidazol-1-yl]propyl]phenoxy]piperidine-1-carboxylate | 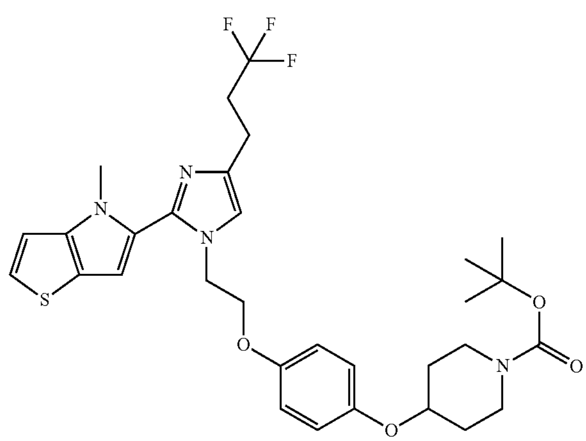 [SMILES: Cn1c(-c2nc(CCC(F)(F)F)cn2CCOc2ccc(OC3CCN(C(=O)OC(C)(C)C)CC3)cc2)cc2sccc21] | $^{1}$H NMR (DMSO-d6) δ (ppm): 7.17 (d, J = 5.4 Hz, 1 H), 7.01-6.93 (m, 3 H), 6.83-6.72 (m, 3 H), 6.40 (s, 1 H), 4.45-4.35 (m, 1 H), 3.99 (t, J = 7.3 Hz, 2 H), 3.81 (s, 3 H), 3.75-3.64 (m, 2 H), 3.37-3.27 (m, 2 H), 2.92-2.84 (m, 2 H), 2.62-2.47 (m, 4 H), 2.04 (t, J = 7.6 Hz, 2 H), 1.95-1.84 (m, 2 H), 1.78-1.67 (m, 2 H), 1.48 (s, 9 H); MS (ESI): m/z: 617 [M + H]$^{+}$. |

Example 18: 5-[4-ethyl-1-[2-[3-(4-piperidyloxy)phenoxy]ethyl]imidazol-2-yl]-4-methyl-thieno[3,2-b]pyrrole hydrochloride

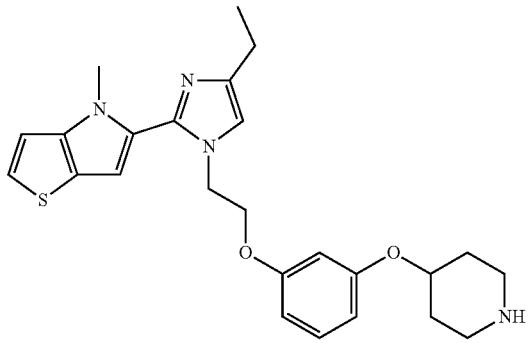 [SMILES: CCc1cn(CCOc2cccc(OC3CCNCC3)c2)c(-c2cc3sccc3n2C)n1]

0.042 g (0.076 mmol) of tert-butyl 4-[3-[2-[4-ethyl-2-(4-methylthieno[3,2-b]pyrrol-5-yl)imidazol-1-yl]ethoxy]phenoxy]piperidine-1-carboxylate (Intermediate 26) was dissolved at 0° C. in 0.5 mL of 4 M HCl in dioxane. The mixture was stirred at 0° C. for 30 min, then the solvent was removed, the residue was triturated with Et$_2$O and dried to afford 0.036 g of 5-[4-ethyl-1-[2-[3-(4-piperidyloxy)phenoxy]ethyl]imidazol-2-yl]-4-methyl-thieno[3,2-b]pyrrole hydrochloride (98%) as a white powder. $^1$H NMR (DMSO-d$_6$) δ (ppm): 8.87-8.71 (m, 2H), 7.76 (s, 1H), 7.55 (d, J 5.4 Hz, 1H), 7.28 (d, J=5.4 Hz, 1H), 7.20-7.11 (m, 1H), 7.04 (s, 1H), 6.63-6.45 (m, 3H), 4.65-4.56 (m, 1H), 4.52-4.44 (m, 2H), 4.39-4.28 (m, 2H), 3.77 (s, 3H), 3.25-3.14 (m, 2H), 3.15-2.99 (m, 2H), 2.71 (q, J=7.6 Hz, 2H), 2.14-1.70 (m, 4H), 1.26 (t, J=7.6 Hz, 3H); MS (ESI): m/z: 451 [M+H]$^+$.

The following compounds were obtained starting from the corresponding Boc-intermediates according to the procedure described Example 18.

In case of the examples 19, 21, 24, 26, 31-33, 37-39 the compounds were purified by preparative HPLC providing the products as trifluoroacetate salts (Examples 24 and 26) or as free bases after filtration on a bicarbonate SPE cartridge (200 mg) and eluting with MeOH (Examples 19, 21, 31, 32, 33, 39). In case of the examples 37 and 38 the compounds were filtered on a bicarbonate SPE cartridge (200 mg) and purified by flash chromatography on silica gel. Compounds 41, 43, 48, 49, 58 and 60 were purified by column chromatography on silica gel (CH$_2$Cl2/MeOH/NH$_3$).

TABLE 3

Final Products

| Ex. | Name | Structure | Analytical Data |
| --- | --- | --- | --- |
| 19 | 5-[5-ethyl-1-[2-[3-(4-piperidyloxy)phenoxy]ethyl]imidazol-2-yl]-4-methyl-thieno[3,2-b]pyrrole | 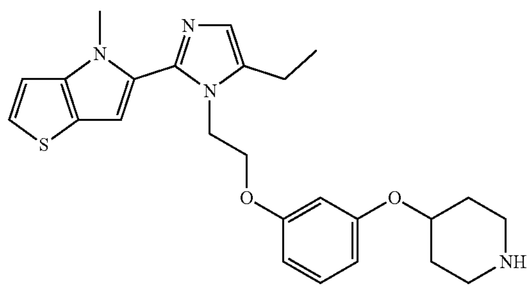 | $^1$H NMR (CDCl$_3$) δ (ppm): 7.19-7.15 (m, 1 H), 7.13-7.07 (m, 1 H), 7.01-6.95 (m, 2 H), 6.61 (s, 1 H), 6.54-6.27 (m, 3 H), 4.42-4.37 (m, 2 H), 4.36-4.30 (m, 1 H), 4.09-4.03 (m, 2 H), 3.78 (s, 3 H), 3.19-3.10 (m, 2 H), 2.81-2.71 (m, 4 H), 2.06-1.94 (m, 2 H), 1.73-1.59 (m, 2 H), 1.41-1.35 (m, 3 H); MS (ESI): m/z: 451 [M + H]$^+$. |
| 20 | 5-[4-ethyl-1-[2-[4-(4-piperidyloxy)phenoxy]ethyl]imidazol-2-yl]-4-methyl-thieno[3,2-b]pyrrole hydrochloride | 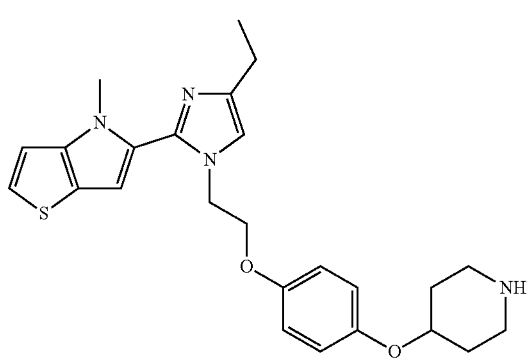 [SMILES: CCc1cn(CCOc2ccc(OC3CCNCC3)cc2)c(-c2cc3sccc3n2C)n1] | $^1$H NMR (DMSO-d$_6$) δ (ppm): 8.05-8.79 (m, 2 H), 7.79 (s, 1 H), 7.60-7.52 (m, 1 H), 7.32-7.27 (m, 1 H), 7.07 (s, 1 H), 6.94-6.72 (m, 4 H), 4.54-4.41 (m, 3 H), 4.35-4.24 (m, 2 H), 3.78 (s, 3 H), 3.24-2.95 (m, 4 H), 2.80-2.67 (m, 2 H), 2.07-1.69 (m, 4 H), 1.30-1.21 (m, 3 H); MS (ESI): m/z: 451 [M + H]$^+$. |

TABLE 3-continued

Final Products

| Ex. | Name | Structure | Analytical Data |
|---|---|---|---|
| 21 | 5-[5-ethyl-1-[2-[4-(4-piperidyloxy)phenoxy]ethyl]imidazol-2-yl]-4-methyl-thieno[3,2-b]pyrrole | 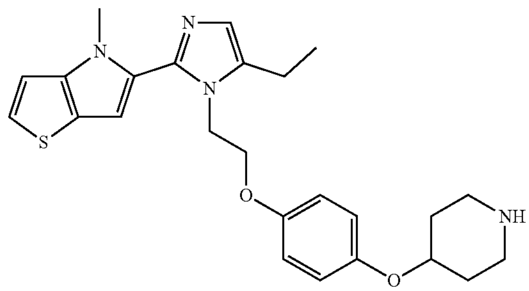 [SMILES: CCc1cnc(-c2cc3sccc3n2C)n1CCOc1ccc(OC2CCNCC2)cc1] | $^1$H NMR (CDCl$_3$) δ (ppm): 7.19-7.15 (m, 1 H), 7.00-6.95 (m, 2 H), 6.80-6.56 (m, 5 H), 4.40-4.34 (m, 2 H), 4.27-4.19 (m, 1 H), 4.05-4.00 (m, 2 H), 3.77 (s, 3 H), 3.21-3.09 (m, 2 H), 2.81-2.70 (m, 4 H), 2.02-1.60 (m, 4 H), 1.38 (m, 3 H); MS (ESI): m/z: 451 [M + H]$^+$. |
| 22 | 5-[4-ethyl-1-[2-[4-(pyrrolidin-3-ylmethoxy)phenoxy]ethyl]imidazol-2-yl]-4-methyl-thieno[3,2-b]pyrrole hydrochloride | 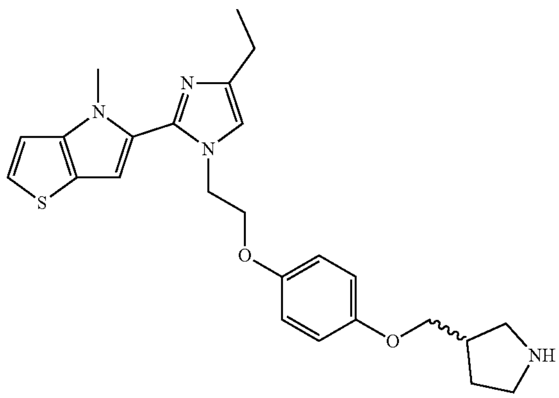 [SMILES: CCc1cn(CCOc2ccc(OCC3CCNC3)cc2)c(-c2cc3sccc3n2C)n1] | $^1$H NMR (DMSO-d$_6$) δ (ppm): 9.18-8.89 (m, 2 H), 7.78 (s, 1 H), 7.63-7.46 (m, 1 H), 7.32-7.27 (m, 1 H), 7.06 (s, 1 H), 6.90-6.72 (m, 4 H), 4.53-4.41 (m, 2 H), 4.54-4.41 (m, 2 H), 3.95-3.92 (m, 2 H), 3.77 (s, 3 H), 3.32-2.91 (m, 4 H), 2.80-2.56 (m, 3 H), 2.14-1.65 (m, 2 H), 1.31-1.23 (m, 3 H); MS (ESI): m/z: 451 [M + H]$^+$. |
| 23 | 5-[4-ethyl-1-[2-[4-(4-piperidylmethoxy)phenoxy]ethyl]imidazol-2-yl]-4-methyl-thieno[3,2-b]pyrrole hydrochloride | 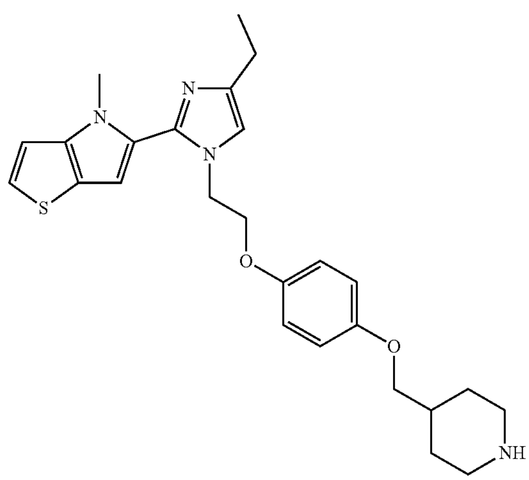 [SMILES: CCc1cn(CCOc2ccc(OCC3CCNCC3)cc2)c(-c2cc3sccc3n2C)n1] | $^1$H NMR (DMSO-d$_6$) δ (ppm): 8.84 (bs, 1 H), 8.57 (bs, 1 H), 7.78 (bs, 1 H), 7.56 (d, J = 5.4 Hz, 1 H), 7.29 (d, J = 5.4 Hz, 1 H), 7.06 (bs, 1 H), 6.85-6.71 (m, 4 H), 4.47 (t, J = 4.6 Hz, 2 H), 4.29 (t, J = 4.6 Hz, 2 H), 3.80-3.71 (m, 5 H), 3.32-3.21 (m, 2 H), 2.94-2.80 (m, 2 H), 2.73 (q, J = 7.5 Hz, 2 H), 2.06-1.94 (m, 1 H), 1.92-1.83 (m, 2 H), 1.53-1.39 (m, 2 H), 1.27 (t, J = 7.6 Hz, 3 H); MS (ESI): m/z: 465 [M + H]$^+$. |
| 24 | 5-[5-ethyl-1-[2-[4-(4-piperidylmethoxy)phenoxy]ethyl]imidazol-2-yl]-4-methyl-thieno[3,2-b]pyrrole trifluoroacetate | 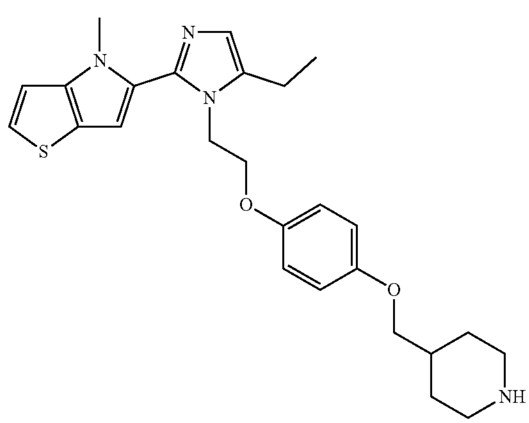 [SMILES: CCc1cnc(-c2cc3sccc3n2C)n1CCOc1ccc(OCC2CCNCC2)cc1] | $^1$H NMR (DMSO-d$_6$ + D$_2$O) δ (ppm): 7.74-7.70 (m, 1 H), 7.54 (d, J = 5.4 Hz, 1 H), 7.28 (d, J = 5.4 Hz, 1 H), 7.09 (s, 1 H), 6.79-6.64 (m, 4 H), 4.56 (t, J = 4.9 Hz, 2 H), 4.15 (t, J = 4.9 Hz, 2 H), 3.72 (d, J = 6.4 Hz, 2 H), 3.67 (s, 3 H), 3.32-3.24 (m, 2 H), 2.93-2.80 (m, 4 H), 2.03-1.92 (m, 1 H), 1.91-1.83 (m, 2 H), 1.47-1.35 (m, 2 H), 1.32 (t, J = 7.3 Hz, 3 H); MS (ESI): m/z: 465 [M + H]$^+$. |

TABLE 3-continued

Final Products

| Ex. | Name | Structure | Analytical Data |
|---|---|---|---|
| 25 | 5-[1-[2-[4-(azepan-4-yloxy)phenoxy]ethyl]-4-ethyl-imidazol-2-yl]-4-methyl-thieno[3,2-b]pyrrole hydrochloride | 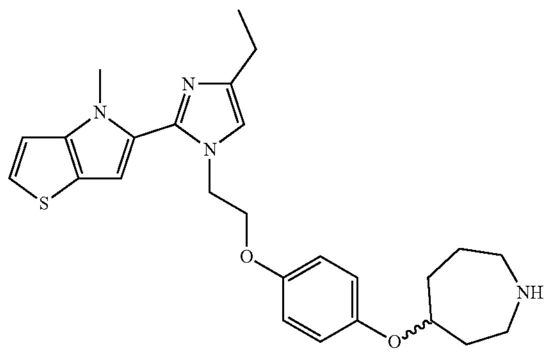 [SMILES: CCc1cn(CCOc2ccc(OC3CCCNCC3)cc2)c(-c2cc3sccc3n2C)n1] | $^1$H NMR (DMSO-d$_6$) δ (ppm): 8.91 (bs, 2 H), 7.79 (s, 1 H), 7.56 (d, J = 4.9 Hz, 1 H), 7.30 (d, J = 5.4 Hz, 1 H), 7.06 (bs, 1 H), 6.90-6.74 (m, 4 H), 4.60-4.41 (m, 3 H), 4.29 (t, J = 4.6 Hz, 2 H), 3.77 (s, 3 H), 3.25-3.01 (m, 4 H), 2.72 (q, J = 7.3 Hz, 2 H), 2.18-2.04 (m, 1 H), 2.03-1.75 (m, 4 H), 1.74-1.61 (m, 1 H), 1.26 (t, J = 7.6 Hz, 3 H); MS (ESI): m/z: 465 [M + H]$^+$. |
| 26 | 5-[1-[2-[4-(azepan-4-yloxy)phenoxy]ethyl]-5-ethyl-imidazol-2-yl]-4-methyl-thieno[3,2-b]pyrrole trifluoroacetate | 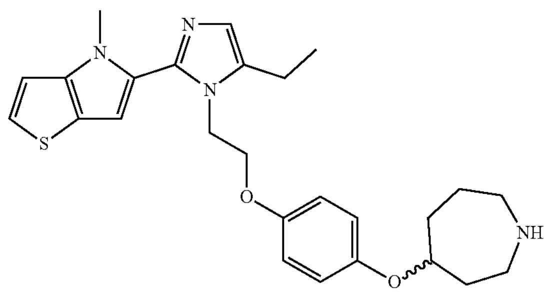 [SMILES: CCc1cnc(-c2cc3sccc3n2C)n1CCOc1ccc(OC2CCCNCC2)cc1] | $^1$H NMR (DMSO-d$_6$ + D$_2$O) δ (ppm): 7.67 (s, 1 H), 7.53 (d, J = 5.3 Hz, 1 H), 7.25 (d, J = 5.4 Hz, 1 H), 7.11-7.03 (m, 1 H), 6.84-6.64 (m, 4 H), 4.60-4.41 (m, 3 H), 4.14 (t, J = 4.9 Hz, 2 H), 3.67 (s, 3 H), 3.26-3.00 (m, 4 H), 2.83 (q, J = 7.3 Hz, 2 H), 2.13-2.01 (m, 1 H), 1.99-1.72 (m, 4 H), 1.72-1.61 (m, 1 H), 1.31 (t, J = 7.3 Hz, 3 H); MS (ESI): m/z: 465 [M + H]$^+$. |
| 27 | 5-[4-ethyl-1-[3-[4-(4-piperidyloxy)phenyl]propyl]imidazol-2-yl]-4-methyl-thieno[3,2-b]pyrrole hydrochloride | 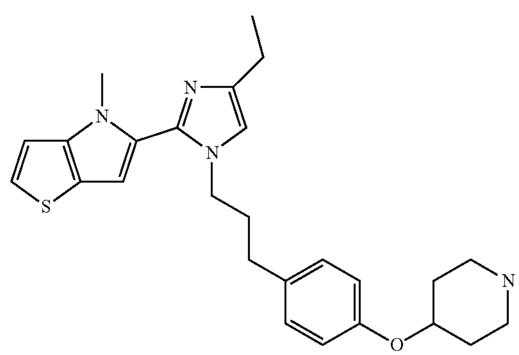 [SMILES: CCc1cn(CCCc2ccc(OC3CCNCC3)cc2)c(-c2cc3sccc3n2C)n1] | $^1$H NMR (DMSO-d$_6$ + D$_2$O): 7.66 (s, 1 H), 7.51 (d, J = 5.4 Hz, 1 H), 7.25 (d, J = 5.4 Hz, 1 H), 7.05-6.97 (m, 2 H), 6.83-6.75 (m, 3 H), 4.56-4.40 (m, 1 H), 4.03 (t, J = 7.5 Hz, 2 H), 3.71 (s, 3 H), 3.26-3.15 (m, 2 H), 3.09-2.99 (m, 2 H), 2.68 (q, J = 7.3 Hz, 2 H), 2.45 (t, J = 7.8 Hz, 2 H), 2.08-1.97 (m, 4 H), 1.82-1.67 (m, 2 H), 1.24 (t, J = 7.3 Hz, 3 H); MS (ESI): m/z: 449 [M + H]$^+$. |
| 28 | 5-[5-ethyl-1-[3-[4-(4-piperidyloxy)phenyl]propyl]imidazol-2-yl]-4-methyl-thieno[3,2-b]pyrrole hydrochloride | 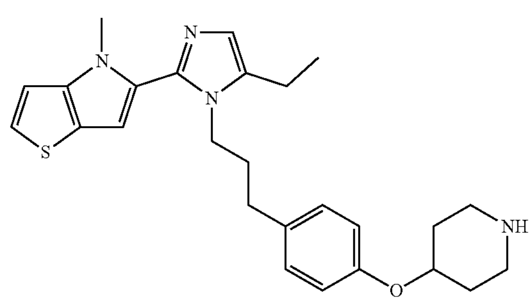 [SMILES: CCc1cnc(-c2cc3sccc3n2C)n1CCCc1ccc(OC2CCNCC2)cc1] | $^1$H NMR (DMSO-d$_6$ + D$_2$O) δ (ppm): 7.61 (s, 1 H), 7.53 (d, J = 5.4 Hz, 1 H), 7.25 (d, J = 5.4 Hz, 1 H), 7.02-6.95 (m, 2 H), 6.85 (s, 1 H), 6.81-6.73 (m, 2 H), 4.55-4.47 (m, 1 H), 4.03 (t, J = 7.8 Hz, 2 H), 3.67 (s, 3 H), 3.26-3.16 (m, 2 H), 3.09-3.00 (m, 2 H), 2.69 (q, J = 7.3 Hz, 2 H), 2.45 (t, J = 6.9 Hz, 2 H), 2.10-1.98 (m, 2 H), 1.96-1.85 (m, 2 H), 1.81-1.69 (m, 2 H), 1.27 (t, J = 7.3 Hz, 3 H); MS (ESI): m/z: 449 [M + H]$^+$. |

TABLE 3-continued

| | | Final Products | |
|---|---|---|---|
| Ex. | Name | Structure | Analytical Data |
| 29 | 5-[4-cyclobutyl-1-[2-[4-(4-piperidyloxy)phenoxy]ethyl]imidazol-2-yl]-4-methyl-thieno[3,2-b]pyrrole hydrochloride | | $^1$H NMR (DMSO-$d_6$ + $D_2O$) δ (ppm): 7.81 (s, 1 H), 7.54 (d, J = 5.4 Hz, 1 H), 7.27 (d, J = 4.9 Hz, 1 H), 7.04 (s, 1 H), 6.91-6.84 (m, 2 H), 6.81-6.73 (m, 2 H), 4.51-4.39 (m, 3 H), 4.32-4.25 (m, 2 H), 3.73 (s, 3 H), 3.67-3.58 (m, 1 H), 3.24-2.97 (m, 4 H), 2.39-1.68 (m, 10 H); MS (ESI): m/z: 477 [M + H]$^+$. |
| 30 | 5-[5-cyclobutyl-1-[2-[4-(4-piperidyloxy)phenoxy]ethyl]imidazol-2-yl]-4-methyl-thieno[3,2-b]pyrrole hydrochloride | | $^1$H NMR (DMSO-$d_6$ + $D_2O$) δ (ppm): 7.82 (s, 1 H), 7.52 (d, J = 5.4 Hz, 1 H), 7.25 (d, J = 5.4 Hz, 1 H), 7.06 (s, 1 H), 6.85-6.79 (m, 2 H), 6.68-6.61 (m, 2 H), 4.50-4.38 (m, 3 H), 4.11-4.05 (m, 2 H), 3.85-3.73 (m, 1 H), 3.66 (s, 3 H), 3.25-2.93 (m, 4 H), 2.46-1.63 (m, 10 H) MS (ESI): m/z: 477 [M + H]$^+$. |
| 31 | 5-[5-ethyl-4-phenyl-1-[2-[4-(4-piperidyloxy)phenoxy]ethyl]imidazol-2-yl]-4-methyl-thieno[3,2-b]pyrrole | | $^1$H NMR (CDCl$_3$) δ (ppm): 7.79-7.70 (m, 2 H), 7.47-7.40 (m, 2 H), 7.32-7.28 (m, 1 H), 7.19 (d, J = 5.4 Hz, 1 H), 6.99 (d, J = 5.4 Hz, 1 H), 6.75-6.69 (m, 2 H), 6.67-6.59 (m, 3 H), 4.53-4.39 (m, 3 H), 4.06 (t, J = 5.9 Hz, 2 H), 3.83 (s, 3 H), 3.39-3.19 (m, 4 H), 3.00 (q, J = 7.8 Hz, 2 H), 2.27-2.15 (m, 2 H), 2.13-2.02 (m, 2 H), 1.37 (t, J = 7.6 Hz, 3 H); MS (ESI): m/z: 527 [M + H]$^+$. |
| 32 | 5-[5-ethyl-4-phenyl-1-[2-[3-(4-piperidyloxy)phenoxy]ethyl]imidazol-2-yl]-4-methyl-thieno[3,2-b]pyrrole | | $^1$H NMR (CDCl$_3$) δ (ppm): 7.77-7.71 (m, 2 H), 7.46-7.39 (m, 2 H), 7.32-7.27 (m, 1 H), 7.18 (d, J = 5.4 Hz, 1 H), 7.13-7.07 (m, 1 H), 6.99 (d, J = 5.4 Hz, 1 H), 6.66 (s, 1 H), 6.50-6.44 (m, 1 H), 6.36-6.31 (m, 1 H), 6.30-6.26 (m, 1 H), 4.54-4.42 (m, 3 H), 4.09 (t, J = 5.9 Hz, 2 H), 3.82 (s, 3 H), 3.33-3.21 (m, 2 H), 3.17-3.07 (m, 2 H), 3.00 (q, J = 7.5 Hz, 2 H), 2.23-2.11 (m, 2 H), 2.05-1.91 (m, 2 H), 1.37 (t, J = 7.6 Hz, 3 H); MS (ESI): m/z: 527 [M + H]$^+$. |

TABLE 3-continued

| Ex. | Name | Structure | Analytical Data |
|---|---|---|---|
| 33 | 5-[4-ethyl-5-phenyl-1-[2-[3-(4-piperidyloxy)phenoxy]ethyl]imidazol-2-yl]-4-methyl-thieno[3,2-b]pyrrole | 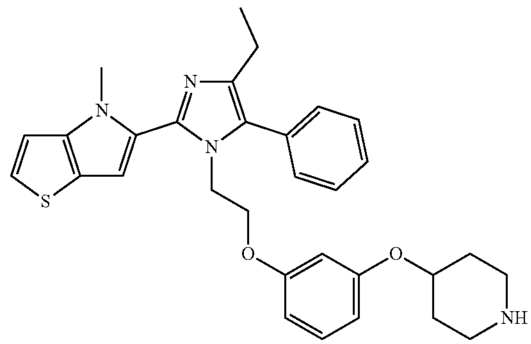 [SMILES: CCc1nc(-c2cc3sccc3n2C)n(CCOc2cccc(OC3CCNCC3)c2)c1-c1ccccc1] | $^1$H NMR (CDCl$_3$) δ (ppm): 7.53-7.48 (m, 2 H), 7.47-7.38 (m, 3 H), 7.18 (d, J = 4.9 Hz, 1 H), 7.05-6.96 (m, 2 H), 6.66 (s, 1 H), 6.47-6.39 (m, 1 H), 6.14-6.06 (m, 2 H), 4.52-4.35 (m, 3 H), 3.85 (s, 3 H), 3.75 (t, J = 6.1 Hz, 2 H), 3.31-3.20 (m, 2 H), 3.12 (bs, 2 H), 2.58 (q, J = 7.2 Hz, 2 H), 2.15 (bs, 2 H), 1.95 (bs, 2 H), 1.23 (t, J = 7.6 Hz, 3 H); MS (ESI): m/z: 527 [M + H]$^+$. |
| 34 | 5-[1-[2-[3-(azepan-4-yloxy)phenoxy]ethyl]-4-ethyl-imidazol-2-yl]-4-methyl-thieno[3,2-b]pyrrole hydrochloride | 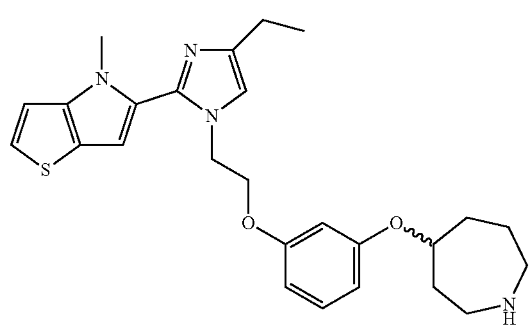 [SMILES: CCc1cn(CCOc2cccc(OC3CCCNCC3)c2)c(-c2cc3sccc3n2C)n1] | $^1$H NMR (DMSO-d$_6$ + D$_2$O) δ (ppm): 7.75 (s, 1 H), 7.54 (d, J = 5.4 Hz, 1 H), 7.28 (d, J = 4.9 Hz, 1 H), 7.17-7.11 (m, 1 H), 7.04 (s, 1 H), 6.56-6.51 (m, 1 H), 6.47-6.40 (m, 2 H), 4.67-4.59 (m, 1 H), 4.47 (t, J = 4.9 Hz, 2 H), 4.32 (t, J = 4.9 Hz, 2 H), 3.74 (s, 3 H), 3.26-3.04 (m, 4 H), 2.71 (q, J = 7.3 Hz, 2 H), 2.16-2.06 (m, 1 H), 2.02-1.91 (m, 2 H), 1.91-1.75 (m, 2 H), 1.74-1.64 (m, 1 H), 1.25 (t, J = 7.3 Hz, 3 H); MS (ESI): m/z: 465 [M + H]$^+$. |
| 35 | 5-[1-[2-[3-(azepan-4-yloxy)phenoxy]ethyl]-5-ethyl-imidazol-2-yl]-4-methyl-thieno[3,2-b]pyrrole hydrochloride | 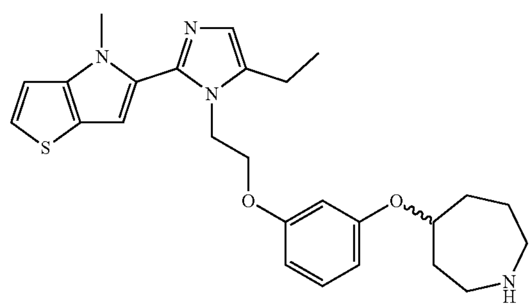 [SMILES: CCc1cnc(-c2cc3sccc3n2C)n1CCOc1cccc(OC2CCCNCC2)c1] | $^1$H NMR (DMSO-d$_6$ + D$_2$O) δ (ppm): 7.64 (bs, 1 H), 7.53 (d, J = 5.4 Hz, 1 H), 7.28 (d, J = 5.4 Hz, 1 H), 7.14-7.05 (m, 2 H), 6.53-6.47 (m, 1 H), 6.36-6.27 (m, 2 H), 4.64-4.51 (m, 3 H), 4.18 (t, J = 4.9 Hz, 2 H), 3.67 (s, 3 H), 3.24-3.02 (m, 4 H), 2.83 (q, J = 7.3 Hz, 2 H), 2.15-2.05 (m, 1 H), 2.01-1.73 (m, 4 H), 1.72-1.64 (m, 1 H), 1.31 (t, J = 7.3 Hz, 3 H); MS (ESI): m/z: 465 [M + H]$^+$. |
| 36 | 5-[1-[2-[4-(azepan-4-yloxy)phenoxy]ethyl]-4-cyclobutyl-imidazol-2-yl]-4-methyl-thieno[3,2-b]pyrrole hydrochloride | 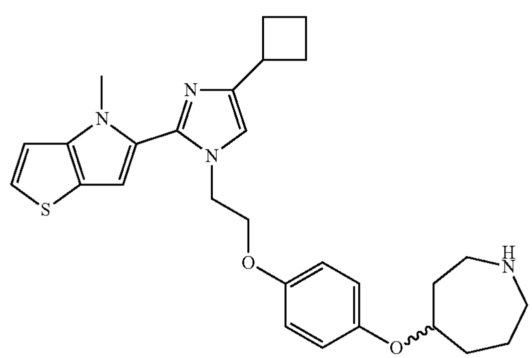 [SMILES: Cn1c(-c2nc(C3CCC3)cn2CCOc2ccc(OC3CCCNCC3)cc2)cc2sccc21] | $^1$H NMR (DMSO-d$_6$ + D$_2$O) δ (ppm): 7.83 (bs, 1 H), 7.53 (d, J = 5.4 Hz, 1 H), 7.28 (d, J = 5.4 Hz, 1 H), 7.05 (s, 1 H), 6.86-6.72 (m, 4 H), 4.55-4.40 (m, 3 H), 4.26 (t, J = 4.9 Hz, 2 H), 3.73 (s, 3 H), 3.67-3.58 (m, 1 H), 3.24-3.16 (m, 1 H), 3.13-3.01 (m, 3 H), 2.38-2.28 (m, 2 H), 2.25-2.14 (m, 2 H), 2.13-1.61 (m, 8 H); MS (ESI): m/z: 491 [M + H]$^+$. |

TABLE 3-continued

Final Products

| Ex. | Name | Structure | Analytical Data |
|---|---|---|---|
| 37 | 5-[1-[2-[4-(azepan-4-yloxy)phenoxy]ethyl]-5-cyclobutyl-imidazol-2-yl]-4-methyl-thieno[3,2-b]pyrrole | 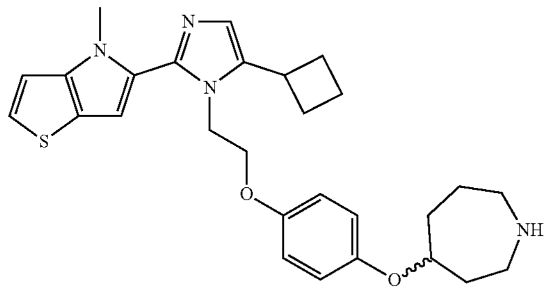 [SMILES: Cn1c(-c2ncc(C3CCC3)n2CCOc2ccc(OC3CCCNCC3)cc2)cc2sccc21] | $^1$H NMR (CDCl$_3$) δ (ppm): 7.17 (d, J = 5.4 Hz, 1 H), 7.04 (s, 1 H), 6.98 (d, J = 4.9 Hz, 1 H), 6.77-6.58 (m, 5 H), 4.57-4.49 (m, 1 H), 4.31 (t, J = 5.9 Hz, 2 H), 3.99 (t, J = 5.9 Hz, 2 H), 3.77 (s, 3 H), 3.64-3.56 (m, 1 H), 3.35-3.12 (m, 4 H), 2.49-2.38 (m, 2 H), 2.32-1.76 (m, 10 H); MS (ESI): m/z: 491 [M + H]$^+$. |
| 38 | 5-[4-ethyl-1-[3-[4-(pyrrolidin-3-ylmethoxy)phenyl]propyl]imidazol-2-yl]-4-methyl-thieno[3,2-b]pyrrole | 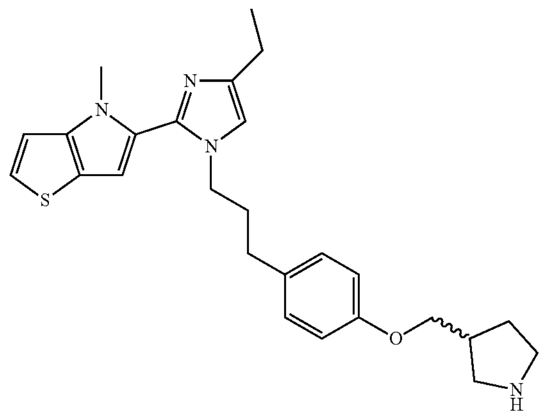 [SMILES: CCc1cn(CCCc2ccc(OCC3CCNC3)cc2)c(-c2cc3sccc3n2C)n1] | $^1$H NMR (CDCl$_3$) δ (ppm): 7.15 (d, J = 5.4 Hz, 1 H), 7.02-6.94 (m, 3 H), 6.81-6.73 (m, 3 H), 6.35 (s, 1 H), 3.97 (t, J = 7.4 Hz, 2 H), 3.94-3.81 (m, 5 H), Part AB of ABX System: VA = 3.28, VB = 2.98, JAB = 11.7 Hz, JAX = 7.8 Hz, JBX = 6.3 Hz, 3.22-3.15 (m, 1 H), 3.13-3.05 (m, 1 H), 2.72-2.63 (m, 3 H), 2.54 (t, J = 7.3 Hz, 2 H), 2.14-1.99 (m, 3 H), 1.77 1.66 (m, 1 H), 1.28 (t, J = 7.6 Hz, 3 H); MS (ESI): m/z: 449 [M + H]$^+$. |
| 39 | 5-[4-ethyl-1-[2-[4-(4-piperidyloxy)phenoxy]ethyl]imidazol-2-yl]-6-methyl-thieno[2,3-b]pyrrole | 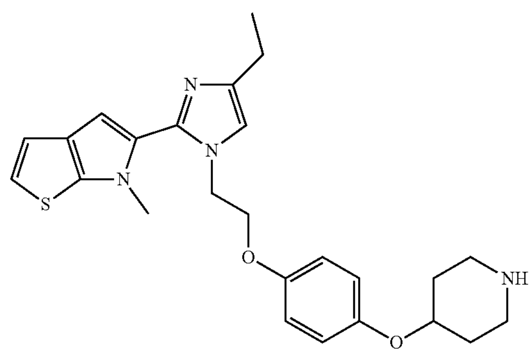 [SMILES: CCc1cn(CCOc2ccc(OC3CCNCC3)cc2)c(-c2cc3ccsc3n2C)n1] | $^1$H NMR (DMSO-d$_6$) δ (ppm): 7.13 (s, 1 H), 7.08 (d, J = 5.4 Hz, 1 H), 7.04 (d, J = 5.4 Hz, 1 H), 6.86-6.72 (m, 4 H), 6.63 (s, 1 H), 4.34-4.27 (m, 2 H), 4.25-4.12 (m, 3 H), 3.72 (s, 3 H), 2.98-2.89 (m, 2 H), 2.60-2.50 (m, 4 H), 1.89-1.76 (m, 2 H), 1.45-1.34 (m, 2 H), 1.18 (t, J = 7.6 Hz, 3 H); MS (ESI): m/z: 451 [M + H]$^+$. |
| 40 | 4-methyl-5-[5-phenyl-1-[2-[4-(4-piperidyloxy)phenoxy]ethyl]-4-propyl-imidazol-2-yl]thieno[3,2-b]pyrrole hydrochloride | 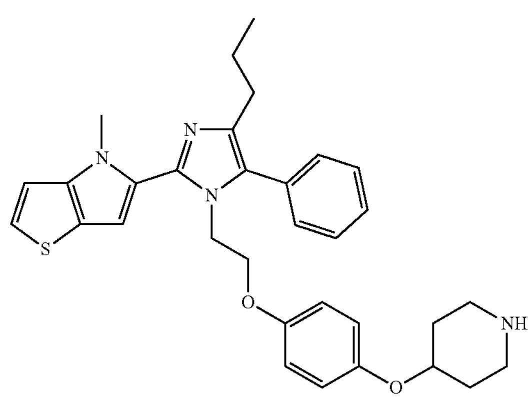 [SMILES: CCCc1nc(-c2cc3sccc3n2C)n(CCOc2ccc(OC3CCNCC3)cc2)c1-c1ccccc1] | $^1$H NMR (D$_2$O) δ (ppm): 7.51-7.36 (m, 5 H), 7.26 (d, J = 5.4 Hz, 1 H), 6.93 (d, J = 5.4 Hz, 1 H), 6.77 (s, 1 H), 6.62-6.55 (m, 2 H), 6.40-6.34 (m, 2 H), 4.47 (t, J = 4.9 Hz, 2 H), 4.36-4.27 (m, 1 H), 3.75 (t, J = 4.9 Hz, 2 H), 3.53 (s, 3 H), 3.29-3.20 (m, 2 H), 3.09-3.00 (m, 2 H), 2.49 (t, J = 7.3 Hz, 2 H), 2.01-1.89 (m, 2 H), 1.83-1.73 (m, 2 H), 1.54-1.43 (m, 2 H), 0.71 (t, J = 7.3 Hz, 3 H); MS (ESI): m/z: 541 [M + H]$^+$. |

TABLE 3-continued

Final Products

| Ex. | Name | Structure | Analytical Data |
|---|---|---|---|
| 41 | 4-methyl-5-[4-phenyl-1-[2-[4-(4-piperidyloxy)phenoxy]ethyl]-5-propyl-imidazol-2-yl]thieno[3,2-b]pyrrole | 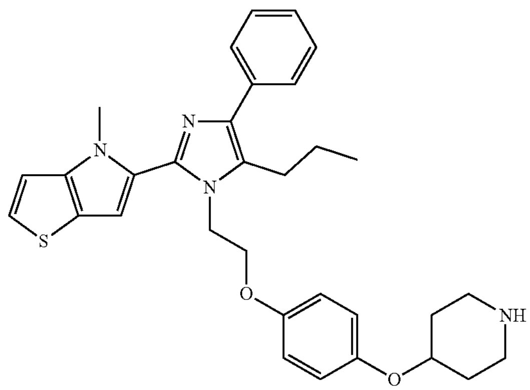 [SMILES: CCCc1c(-c2ccccc2)nc(-c2cc3sccc3n2C)n1CCOc1ccc(OC2CCNCC2)cc1] | $^1$H NMR (DMSO-d$_6$) δ (ppm): 7.71-7.66 (m, 2 H), 7.45-7.38 (m, 2 H), 7.35 (d, J = 5.4 Hz, 1 H), 7.28-7.23 (m, 1 H), 7.22 (d, J = 5.4 Hz, 1 H), 6.80 (s, 1 H), 6.78-6.73 (m, 2 H), 6.68-6.63 (m, 2 H), 4.45 (t, J = 5.6 Hz, 2 H), 4.25-4.16 (m, 1 H), 4.07 (t, J = 5.6 Hz, 2 H), 3.77 (s, 3 H), 2.98-2.83 (m, 4 H), 2.61-2.52 (m, 2 H), 1.88-1.78 (m, 2 H), 1.69-1.57 (m, 2 H), 1.47-1.34 (m, 2 H), 0.98 (t, J = 7.3 Hz, 3 H); MS (ESI): m/z: 541 [M + H]$^+$. |
| 42 | 5-[4-ethyl-1-[3-[4-(4-piperidyl-methoxy)phenyl]propyl]imidazol-2-yl]-4-methyl-thieno[3,2-b]pyrrole hydrochloride | 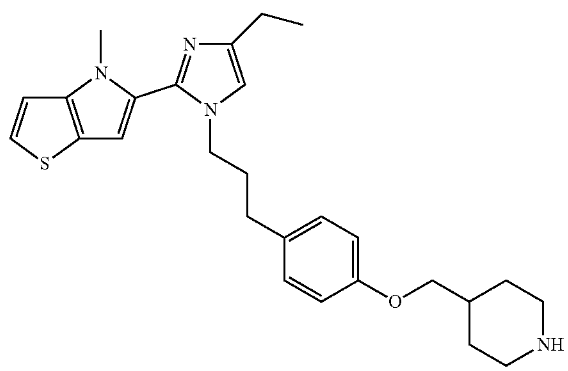 [SMILES: CCc1cn(CCCc2ccc(OCC3CCNCC3)cc2)c(-c2cc3sccc3n2C)n1] | $^1$H NMR (D$_2$O) δ (ppm): 7.33 (d, J = 5.4 Hz, 1 H), 7.24 (s, 1 H), 7.01 (d, J = 5.4 Hz, 1 H), 6.83-6.77 (m, 2 H), 6.58-6.52 (m, 3 H), 3.93 (t, J = 7.3 Hz, 2 H), 3.70 (d, J = 6.4 Hz, 2 H), 3.52 (s, 3 H), 3.40-3.33 (m, 2 H), 2.96-2.86 (m, 2 H), 2.59 (q, J = 7.8 Hz, 2 H), 2.40 (t, J = 7.3 Hz, 2 H), 2.05-1.89 (m, 5 H), 1.49-1.36 (m, 2 H), 1.14 (t, J = 7.8 Hz, 3 H); MS (ESI): m/z: 463 [M + H]$^+$. |
| 43 | 5-[5-ethyl-1-[3-[4-(4-piperidyl-methoxy)phenyl]propyl]imidazol-2-yl]-4-methyl-thieno[3,2-b]pyrrole | 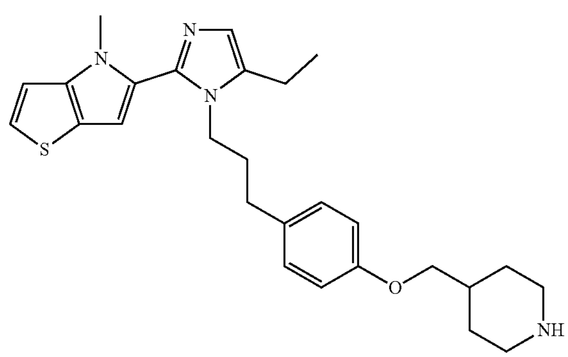 [SMILES: CCc1cnc(-c2cc3sccc3n2C)n1CCCc1ccc(OCC2CCNCC2)cc1] | $^1$H NMR (CDCl$_3$) δ (ppm): 7.15 (d, J = 5.4 Hz, 1 H), 7.00-6.95 (m, 3 H), 6.94 (s, 1 H), 6.79-6.73 (m, 2 H), 6.39 (s, 1 H), 3.94 (t, J = 7.3 Hz, 2 H), 3.80 (s, 3 H), 3.77 (d, J = 6.4 Hz, 2 H), 3.19-3.11 (m, 2 H), 2.72-2.64 (m, 2 H), 2.57 (q, J = 7.5 Hz, 2 H), 2.52 (t, J = 7.3 Hz, 2 H), 1.98-1.90 (m, 3 H), 1.88-1.82 (m, 2 H), 1.36-1.25 (m, 5 H); MS (ESI): m/z: 463 [M + H]$^+$. |
| 44 | 5-[1-[3-[4-(azepan-4-yloxy)phenyl]propyl]-4-ethyl-imidazol-2-yl]-4-methyl-thieno[3,2-b]pyrrole hydrochloride | 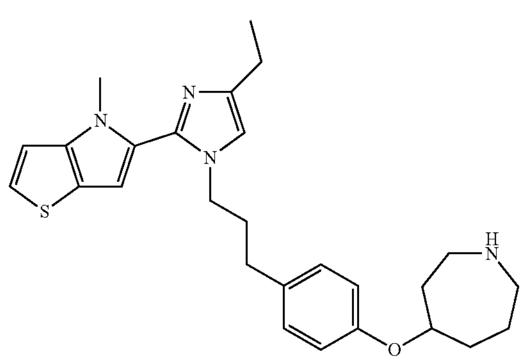 [SMILES: CCc1cn(CCCc2ccc(OC3CCCNCC3)cc2)c(-c2cc3sccc3n2C)n1] | $^1$H NMR (DMSO-d$_6$) δ (ppm): 9.11-8.86 (m, 2 H), 7.76 (s, 1 H), 7.56 (d, J = 5.4 Hz, 1 H), 7.29 (d, J = 5.4 Hz, 1 H), 7.05-6.99 (m, 2 H), 6.89 (bs, 1 H), 6.80-6.64 (m, 2 H), 4.61-4.53 (m, 1 H), 4.07 (t, J = 7.3 Hz, 2 H), 3.77 (s, 3 H), 3.24-3.02 (m, 4 H), 2.71 (q, J = 7.3 Hz, 2 H), 2.50-2.44 (m, 2 H), 2.19-1.63 (m, 8 H), 1.27 (t, J = 7.3 Hz, 3 H); MS (ESI): m/z: 463 [M + H]$^+$. |

TABLE 3-continued

Final Products

| Ex. | Name | Structure | Analytical Data |
|---|---|---|---|
| 45 | 5-[1-[3-[4-(azepan-4-yloxy)phenyl]propyl]-5-ethyl-imidazol-2-yl]-4-methyl-thieno[3,2-b]pyrrole hydrochloride | 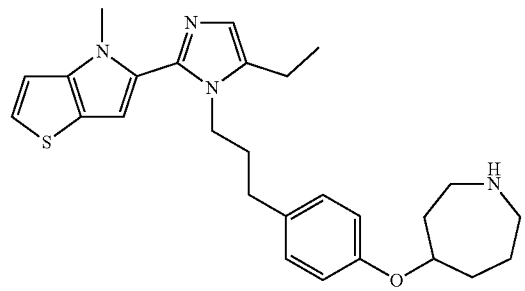 [SMILES: CCc1cnc(-c2cc3sccc3n2C)n1CCCc1ccc(OC2CCCNCC2)cc1] | $^1$H NMR (DMSO-d$_6$) δ (ppm): 8.99-8.78 (m, 2 H), 7.71-7.61 (bs, 1 H), 7.55 (d, J = 5.4 Hz, 1 H), 7.27 (d, J = 5.4 Hz, 1 H), 7.03-7.96 (m, 2 H), 6.90 (s, 1 H), 6.78-6.72 (m, 2 H), 4.64-4.53 (m, 1 H), 4.09-4.00 (m, 2 H), 3.71 (s, 3 H), 3.24-3.03 (m, 4 H), 2.76-2.65 (m, 2 H), 2.49-2.42 (m, 2 H), 2.18-1.63 (m, 8 H), 1.28 (t, J = 7.3 Hz, 3 H); MS (ESI): m/z: 463 [M + H]$^+$. |
| 46 | 5-[5-ethyl-4-phenyl-1-[3-[4-(4-piperidyloxy)phenyl]propyl]imidazol-2-yl]-4-methyl-thieno[3,2-b]pyrrole hydrochloride | 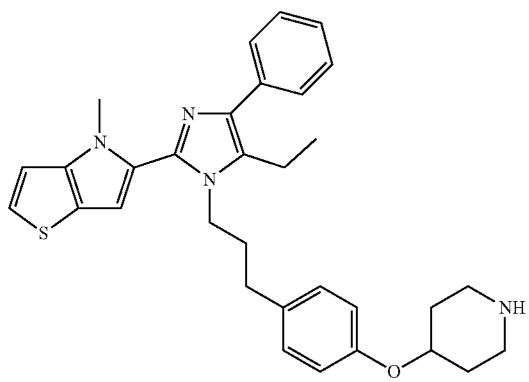 [SMILES: CCc1c(-c2ccccc2)nc(-c2cc3sccc3n2C)n1CCCc1ccc(OC2CCNCC2)cc1] | $^1$H NMR (DMSO-d$_6$ + D$_2$O) δ (ppm): 7.67-7.45 (m, 6 H), 7.28 (d, J = 4.9 Hz, 1 H), 7.03-6.98 (m, 2 H), 6.96 (bs, 1 H), 6.81-6.76 (m, 2 H), 4.57-4.49 (m, 1 H), 4.18-4.09 (m, 2 H), 3.77 (s, 3 H), 3.25-3.01 (m, 4 H), 2.86 (q, J = 7.7 Hz, 2 H), 2.54-2.46 (m, 2 H), 2.09-1.99 (m, 2 H), 1.97-1.88 (m, 2 H), 1.82-1.71 (m, 2 H), 1.18 (t, J = 7.6 Hz, 3 H); MS (ESI): m/z: 525 [M + H]$^+$. |
| 47 | 5-[4-ethyl-5-phenyl-1-[3-[4-(4-piperidyloxy)phenyl]propyl]imidazol-2-yl]-4-methyl-thieno[3,2-b]pyrrole hydrochloride | 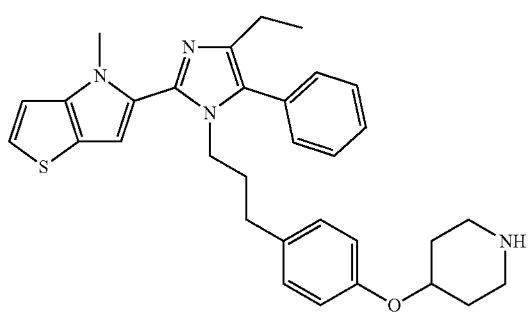 [SMILES: CCc1nc(-c2cc3sccc3n2C)n(CCCc2ccc(OC3CCNCC3)cc2)c1-c1ccccc1] | $^1$H NMR (DMSO-d$_6$ + D$_2$O) δ (ppm): 7.60-7.50 (m, 6 H), 7.29 (d, J = 5.4 Hz, 1 H), 6.95 (s, 1 H), 6.76-6.67 (m, 4 H), 4.53-4.46 (m, 1 H), 4.02 (t, J = 7.3 Hz, 2 H), 3.79 (s, 3 H), 3.23-3.01 (m, 4 H), 2.59 (q, J = 7.3 Hz, 2 H), 2.18 (t, J = 7.3 Hz, 2 H), 2.06-1.69 (m, 4 H), 1.60-1.52 (m, 2 H), 1.17 (t, J = 7.6 Hz, 3 H); MS (ESI): m/z: 525 [M + H]$^+$. |
| 48 | 5-[4-isopropyl-5-phenyl-1-[2-[4-(4-piperidyloxy)phenoxy]ethyl]imidazol-2-yl]-4-methyl-thieno[3,2-b]pyrrole | 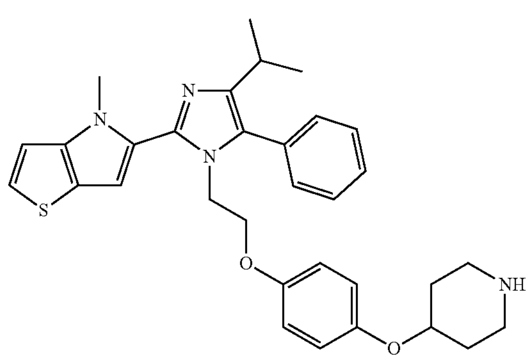 [SMILES: CC(C)c1nc(-c2cc3sccc3n2C)n(CCOc2ccc(OC3CCNCC3)cc2)c1-c1ccccc1] | $^1$H NMR (CDCl$_3$) δ (ppm): 7.53-7.36 (m, 5 H), 7.16 (d, J = 5.4 Hz, 1 H), 6.98 (d, J = 5.4 Hz, 1 H), 6.70-6.62 (m, 3 H), 6.45-6.36 (m, 2 H), 4.35 (t, J = 6.4 Hz, 2 H), 4.30-4.23 (m, 1 H), 3.83 (s, 3 H), 3.74 (t, J = 6.4, 2 H), 3.24-3.14 (m, 2 H), 2.95-2.85 (m, 3 H), 2.09-2.00 (m, 2 H), 1.82-1.72 (m, 2 H), 1.27 (d, J = 6.8 Hz, 6 H); MS (ESI): m/z: 541 [M + H]$^+$. |

TABLE 3-continued

Final Products

| Ex. | Name | Structure | Analytical Data |
|---|---|---|---|
| 49 | 5-[4-cyclobutyl-1-[3-[4-(4-piperidyloxy)phenyl]propyl]imidazol-2-yl]-4-methyl-thieno[3,2-b]pyrrole hydrochloride | 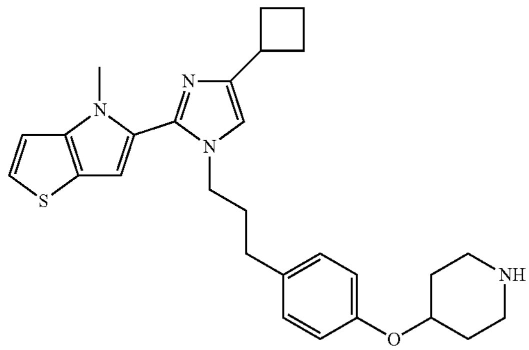 [SMILES: Cn1c(-c2nc(C3CCC3)cn2CCCc2ccc(OC3CCNCC3)cc2)cc2sccc21] | $^1$H NMR (DMSO-d$_6$) δ (ppm): 8.84-8.64 (m, 2 H), 7.87 (s, 1 H), 7.60-7.51 (m, 1 H), 7.27 (d, J = 4.9 Hz, 1 H), 7.07-7.01 (m, 2 H), 6.90 (s, 1 H), 6.85-6.79 (m, 2 H), 4.57-4.49 (m, 1 H), 4.11-4.01 (m, 2 H), 3.76 (s, 3 H), 3.66-3.57 (m, 1 H), 3.25-3.15 (m, 2 H), 3.09-2.96 (m, 2 H), 2.51-2.45 (m, 2 H), 2.40-2.29 (m, 2 H), 2.27-2.18 (m, 2 H), 2.13-1.70 (m, 8 H); MS (ESI): m/z: 475 [M + H]$^+$. |
| 50 | 5-[5-cyclobutyl-1-[3-[4-(4-piperidyloxy)phenyl]propyl]imidazol-2-yl]-4-methyl-thieno[3,2-b]pyrrole | 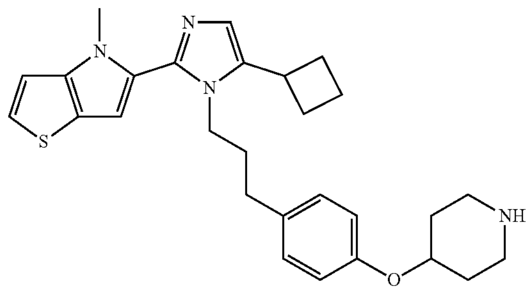 [SMILES: Cn1c(-c2ncc(C3CCC3)n2CCCc2ccc(OC3CCNCC3)cc2)cc2sccc21] | $^1$H NMR (CDCl$_3$) δ (ppm): 7.16 (d, J = 5.4 Hz, 1 H), 7.02-6.93 (m, 4 H), 6.83-6.77 (m, 2 H), 6.42 (s, 1 H), 4.39-4.30 (m, 1 H), 3.91-3.84 (m, 2 H), 3.80 (s, 3H), 3.42-3.31 (m, 1 H), 3.20-3.13 (m, 2 H), 2.82-2.73 (m, 2 H), 2.51 (t, J = 7.3 Hz, 2 H), 2.34-2.26 (m, 2 H), 2.25-2.13 (m, 2 H), 2.08-1.84 (m, 6 H), 1.70 (m, 2 H); MS (ESI): m/z: 475 [M + H]$^+$. |
| 51 | 4-methyl-5-[4-phenyl-1-[3-[4-(4-piperidyloxy)phenyl]propyl]imidazol-2-yl]thieno[3,2-b]pyrrole hydrochloride | 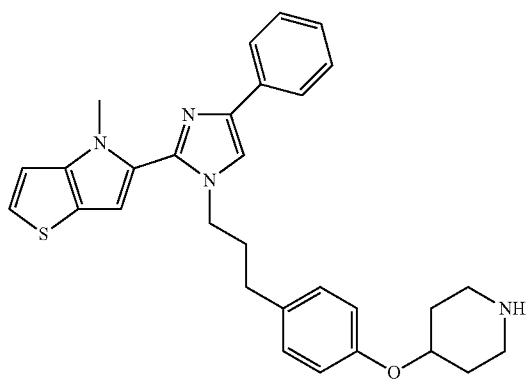 [SMILES: Cn1c(-c2nc(-c3ccccc3)cn2CCCc2ccc(OC3CCNCC3)cc2)cc2sccc21] | $^1$H NMR (DMSO-d$_6$ + D$_2$O) δ (ppm): 8.25 (s, 1 H), 7.90-7.72 (m, 2 H), 7.54-7.45 (m, 3 H), 7.43-7.36 (m, 1 H), 7.26 (d, J = 5.4 Hz, 1 H), 7.07-7.00 (m, 2 H), 6.85-6.76 (m, 3 H), 4.55-4.46 (m, 1 H), 4.12 (t, J = 7.3 Hz, 2 H), 3.81 (s, 3 H), 3.24-3.15 (m, 2 H), 3.07-2.99 (m, 2 H), 2.53 (t, J = 7.3 Hz, 2 H), 2.15-2.06 (m, 2 H), 2.05-1.96 (m, 2 H), 1.80-1.68 (m, 2 H); MS (ESI): m/z: 497 [M + H]$^+$. |
| 52 | 5-[1-[3-[3,4-bis(4-piperidylmethoxy)phenyl]propyl]-4-ethyl-imidazol-2-yl]-4-methyl-thieno[3,2-b]pyrrole dihydrochloride | 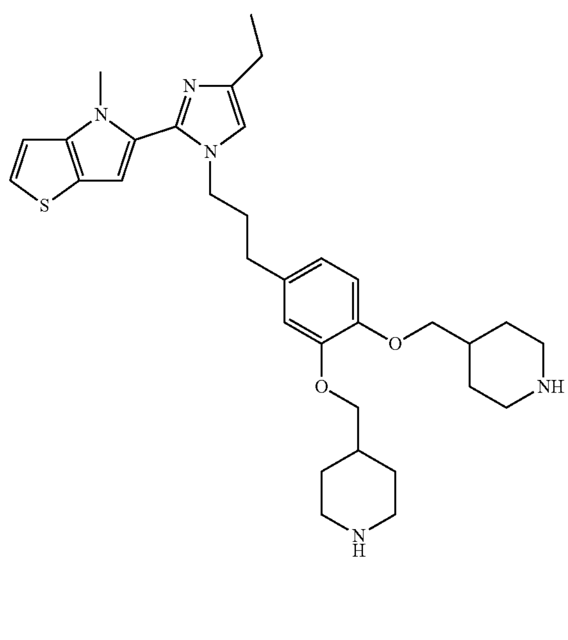 [SMILES: CCc1cn(CCCc2ccc(OCC3CCNCC3)c(OCC3CCNCC3)c2)c(-c2cc3sccc3n2C)n1] | $^1$H NMR (DMSO-d$_6$ + D$_2$O) δ (ppm): 7.66 (s, 1 H), 7.53 (d, J = 5.4 Hz, 1 H), 7.25 (d, J = 5.4 Hz, 1 H), 6.83-6.75 (m, 2 H), 6.75-6.70 (m, 1 H), 6.60-6.55 (m, 1 H), 4.04 (t, J = 7.3 Hz, 2 H), 3.77-3.69 (m, 7 H), 3.32-3.23 (m, 4 H), 2.93-2.81 (m, 4 H), 2.68 (q, J = 7.3 Hz, 2 H), 2.44 (t, J = 7.1 Hz, 2 H), 2.10-1.94 (m, 4 H), 1.93-1.82 (m, 4 H), 1.51-1.37 (m, 4 H), 1.24 (t, J = 7.3 Hz, 3 H); MS (ESI): m/z: 576 [M + H]$^+$. |

TABLE 3-continued

Final Products

| Ex. | Name | Structure | Analytical Data |
|---|---|---|---|
| 53 | 4-methyl-5-[1-[2-[4-(4-piperidyloxy)phenoxy]ethyl]-4-propyl-imidazol-2-yl]thieno[3,2-b]pyrrole | 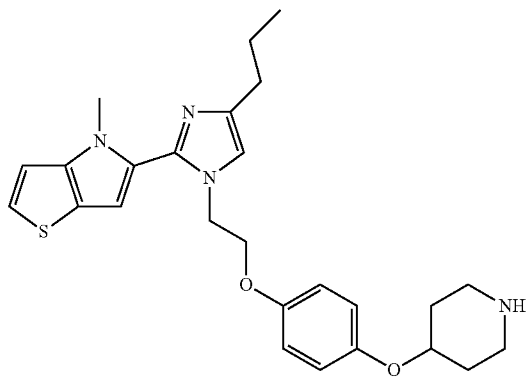 [SMILES: CCCc1cn(CCOc2ccc(OC3CCNCC3)cc2)c(-c2cc3sccc3n2C)n1] | ¹H NMR (DMSO-d₆) δ (ppm): 8.93-8.65 (m, 2 H), 7.78 (bs, 1 H), 7.55 (d, J = 5.4 Hz, 1 H), 7.29 (d, J = 5.4 Hz, 1 H), 7.06 (bs, 1 H), 6.94-6.73 (m, 4 H), 4.53-4.43 (m, 3 H), 4.29 (t, J = 4.6 Hz, 2 H), 3.77 (s, 3 H), 3.25-3.14 (m, 2 H), 3.12-2.94 (m, 2 H), 2.68 (t, J = 7.3 Hz, 2 H), 2.09-1.96 (m, 2 H), 1.83-1.60 (m, 4 H), 0.95 (t, J = 7.3 Hz, 3 H) MS (ESI): m/z: 465 [M + H]⁺. |
| 54 | 4-methyl-5-[1-[2-[4-(4-piperidyloxy)phenoxy]ethyl]-5-propyl-imidazol-2-yl]thieno[3,2-b]pyrrole | 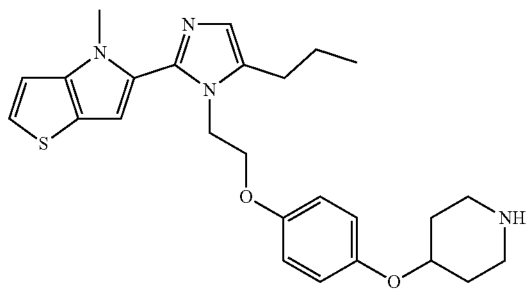 [SMILES: CCCc1cnc(-c2cc3sccc3n2C)n1CCOc1ccc(OC2CCNCC2)cc1] | ¹H NMR (DMSO-d₆) δ (ppm): 7.17 (d, J = 5.4 Hz, 1 H), 7.01-6.93 (m, 2 H), 6.79-6.73 (m, 2 H), 6.67-6.55 (m, 3 H), 4.37 (t, J = 5.9 Hz, 2 H), 4.27-4.17 (m, 1 H), 4.02 (t, J = 5.9 Hz, 2 H), 3.76 (s, 3 H), 3.22-3.10 (m, 2 H), 3.79-2.71 (m, 2 H), 2.68 (t, J = 7.3 Hz, 2 H), 2.05-1.94 (m, 2 H), 1.79 (sxt, J = 7.3 Hz, 2 H), 1.71-1.61 (m, 2 H), 1.09 (t, J = 7.3 Hz, 3 H); MS (ESI): m/z: 465 [M + H]⁺. |
| 55 | 5-[1-[3-[4-(azepan-4-yloxy)phenyl]propyl]-4-propyl-imidazol-2-yl]-4-methyl-thieno[3,2-b]pyrrole hydrochloride | 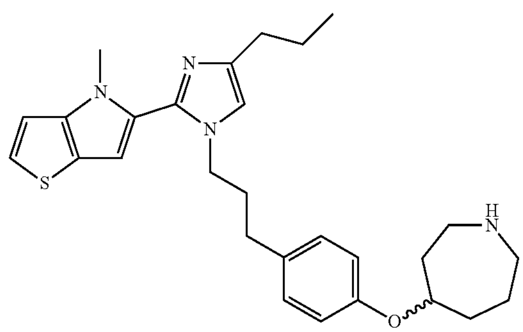 [SMILES: CCCc1cn(CCCc2ccc(OC3CCCNCC3)cc2)c(-c2cc3sccc3n2C)n1] | ¹H NMR (DMSO-d₆) δ (ppm): 8.99-8.76 (m, 2 H), 7.77 (s, 1 H), 7.56 (d, J = 5.4 Hz, 1 H), 7.29 (d, J = 5.4 Hz, 1 H), 7.06-6.98 (m, 2 H), 6.90 (s, 1 H), 6.81-6.73 (m, 2 H), 4.62-4.51 (m, 1 H), 4.07 (t, J = 7.1 Hz, 2 H), 3.76 (s, 3 H), 3.25-3.02 (m, 4 H), 2.66 (t, J = 7.1 Hz, 2 H)), 2.50-2.41 (m, 2 H), 2.17-1.59 (m, 10 H), 0.96 (t, J = 7.6 Hz, 3 H); MS (ESI): m/z: 477 [M + H]⁺. |
| 56 | 5-[1-[3-[4-(azepan-4-yloxy)phenyl]propyl]-5-propyl-imidazol-2-yl]-4-methyl-thieno[3,2-b]pyrrole hydrochloride | 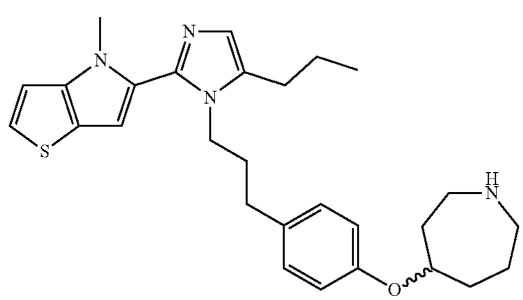 [SMILES: CCCc1cnc(-c2cc3sccc3n2C)n1CCCc1ccc(OC2CCCNCC2)cc1] | ¹H NMR (DMSO-d₆) δ (ppm): 8.94-8.71 (m, 2 H), 7.62 (s, 1 H), 7.54 (d, J = 5.4 Hz, 1 H), 7.27 (d, J = 5.4 Hz, 1 H), 7.04-6.97 (m, 2 H), 6.89 (s, 1 H), 6.79-6.71 (m, 2 H), 4.63-4.54 (m, 1 H), 4.10-4.00 (m, 2 H), 3.71 (s, 3 H), 3.25-3.03 (m, 4 H), 2.67-2.58 (m, 2 H), 2.50-2.44 (m, 2 H), 2.18-1.61 (m, 10 H), 1.00 (s, 3 H); MS (ESI): m/z: 477 [M + H]⁺. |

TABLE 3-continued

Final Products

| Ex. | Name | Structure | Analytical Data |
|---|---|---|---|
| 57 | 5-[1-[3-[3,4-bis(4-piperidylmethoxy)phenyl]propyl]-5-ethyl-imidazol-2-yl]-4-methyl-thieno[3,2-b]pyrrole dihydrochloride | 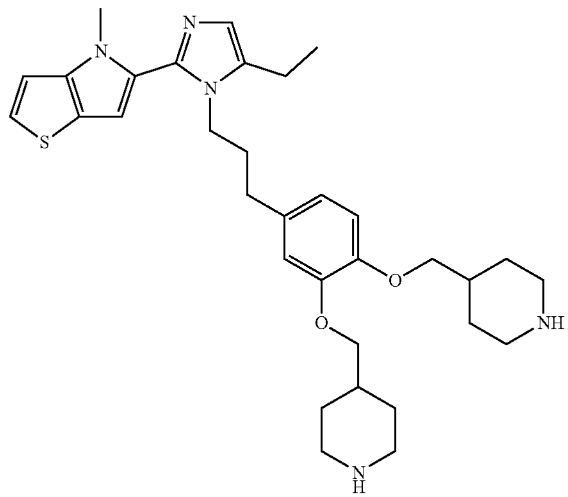 [SMILES: CCc1cnc(-c2cc3sccc3n2C)n1CCCc1ccc(OCC2CCNCC2)c(OCC2CCNCC2)c1] | $^1$H NMR (DMSO-d$_6$) δ (ppm): 7.59-7.43 (m, 2 H), 7.21 (d, J = 5.4 Hz, 1 H), 6.80-6.69 (m, 3 H), 6.60-6.52 (m, 1 H), 4.06-3.97 (m, 2 H), 3.76-3.65 (m, 7 H), 3.32-3.24 (m, 4 H), 2.93-2.83 (m, 4 H), 2.68 (q, J = 7.3 Hz, 2 H), 2.44 (t, J = 1.0 Hz, 2 H), 2.05-1.84 (m, 8 H), 1.51-1.37 (m, 4 H), 1.26 (t, J = 7.3 Hz, 3 H); MS (ESI): m/z: 576 [M + H]$^+$. |
| 58 | 5-[4-ethyl-1-[2-[4-(4-piperidyloxy)phenyl]ethyl]imidazol-2-yl]-4-methyl-thieno[3,2-b]pyrrole | 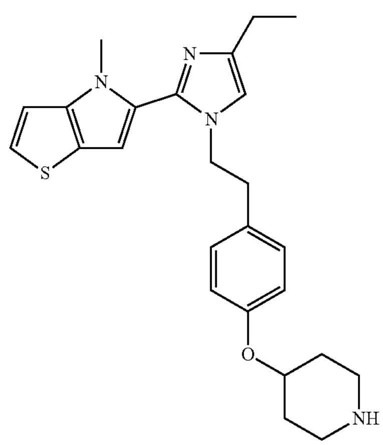 [SMILES: CCc1cn(CCc2ccc(OC3CCNCC3)cc2)c(-c2cc3sccc3n2C)n1] | $^1$H NMR (CDCl$_3$) δ (ppm): 7.13 (d, J = 5.4 Hz, 1 H), 6.98-6.88 (m, 3 H), 6.82-6.74 (m, 2 H), 6.71 (s, 1 H), 6.27 (s, 1 H), 4.36-4.28 (m, 1 H), 4.18 (t, J = 7.3 Hz, 2 H), 3.71 (s, 3 H), 3.19-3.09 (m, 2 H), 2.95 (t, J = 7.3 Hz, 2 H), 2.79-2.70 (m, 2 H), 2.65 (q, J = 7.6 Hz, 2 H), 2.07-2.00 (m, 2 H), 1.72-1.59 (m, 2 H), 1.27 (t, J = 7.6 Hz, 3 H); MS (ESI): m/z: 435 [M + H]$^+$. |
| 59 | 5-[4-cyclobutyl-1-[3-[4-(pyrrolidin-3-ylmethoxy)phenyl]propyl]imidazol-2-yl]-4-methyl-thieno[3,2-b]pyrrole hydrochloride | 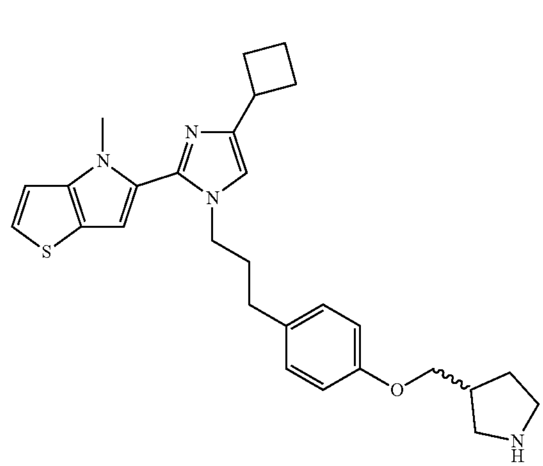 [SMILES: Cn1c(-c2nc(C3CCC3)cn2CCCc2ccc(OCC3CCNC3)cc2)cc2sccc21] | $^1$H NMR (DMSO-d$_6$ + D$_2$O) δ (ppm): 7.75 (s, 1 H), 7.52 (d, J = 5.4 Hz, 1 H), 7.25 (d, J = 5.4 Hz, 1 H), 7.06-6.97 (m, 2 H), 6.81 (s, 1 H), 6.77-6.71 (m, 2 H), 4.03 (t, J = 7.3 Hz, 2 H), 3.93-3.81 (m, 2 H), 3.71 (s, 3 H), 3.58-3.54 (m, 1 H), Part AB of ABX System: VA = 3.34, VB = 2.97, JAB = 11 Hz, JAX = 6.8 Hz, JBX = 7.4 Hz, 3.29-3.21 (m, 1 H), 3.20-3.12 (m, 1 H), 2.73-2.64 (m, 1 H), 2.46 (t, J = 7.3 Hz, 2 H), 2.37-2.28 (m, 2 H), 2.24-2.14 (m, 2 H), 2.13-1.95 (m, 4 H), 1.92-1.82 (m, 1 H), 1.78-1.67 (m, 1 H); MS (ESI): m/z: 475 [M + H]$^+$. |

TABLE 3-continued

Final Products

| Ex. | Name | Structure | Analytical Data |
|-----|------|-----------|-----------------|
| 60 | 5-[5-cyclobutyl-1-[3-[4-(pyrrolidin-3-ylmethoxy)phenyl]propyl]imidazol-2-yl]-4-methyl-thieno[3,2-b]pyrrole | 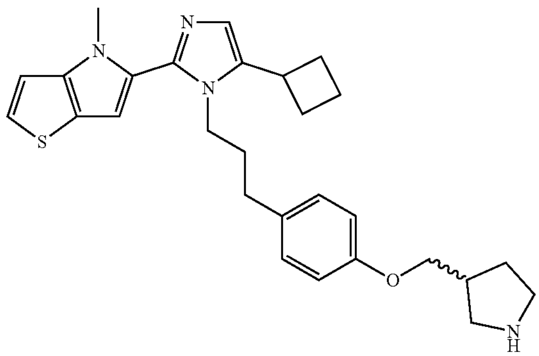 [SMILES: Cn1c(-c2ncc(C3CCC3)n2CCCc2ccc(OCC3CCNC3)cc2)cc2sccc21] | $^1$H NMR (CDCl$_3$) δ (ppm): 7.15 (d, J = 5.4 Hz, 1 H), 7.02-6.91 (m, 4 H), 6.82-6.74 (m, 2 H), 6.38 (s, 1 H), 3.93-3.76 (m, 7 H), 3.42-3.33 (m, 1 H), Part AB of ABX System: VA = 3.15, VB = 2.84, JAB = 11.2 Hz, JAX = 7.9 Hz, JBX = 5.8 Hz, 3.08-3.01 (m, 1 H), 2.99-2.91 (m, 1 H), 2.63-2.55 (m, 1 H), 2.51 (t, J = 7.3 Hz, 2 H), 2.36-1.84 (m, 9 H), 1.65-1.53 (m, 1 H); MS (ESI): m/z: 475 [M + H]$^+$. |
| 61 | 5-[1-[3-[4-(azepan-4-yloxy)phenyl]propyl]-4-cyclobutyl-imidazol-2-yl]-4-methyl-thieno[3,2-b]pyrrole hydrochloride | 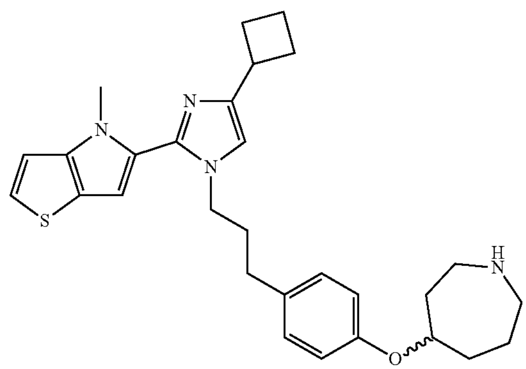 [SMILES: Cn1c(-c2nc(C3CCC3)cn2CCCc2ccc(OC3CCCNCC3)cc2)cc2sccc21] | $^1$H NMR (DMSO-d$_6$ + D$_2$O) δ (ppm): 7.82 (bs, 1 H), 7.54 (d, J = 5.4 Hz, 1 H), 7.27 (d, J = 5.4 Hz, 1 H), 7.05-6.98 (m, 2 H), 6.87 (s, 1 H), 6.79-6.69 (m, 2 H), 4.62-4.50 (m, 1 H), 4.05 (t, J = 7.3 Hz, 2 H), 3.73 (s, 3 H), 3.64-3.54 (m, 1 H), 3.25-3.03 (m, 4 H), 2.46 (t, J = 7.3 Hz, 2 H), 2.39-2.29 (m, 2 H), 2.26-2.16 (m, 2 H), 2.15-1.64 (m, 10 H); MS (ESI): m/z: 489 [M + H]$^+$. |
| 62 | 5-[1-[3-[4-(azepan-4-yloxy)phenyl]propyl]-5-cyclobutyl-imidazol-2-yl]-4-methyl-thieno[3,2-b]pyrrole hydrochloride | 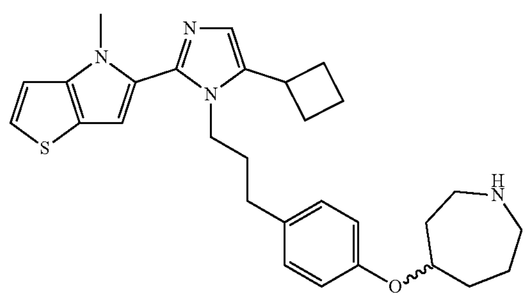 [SMILES: Cn1c(-c2ncc(C3CCC3)n2CCCc2ccc(OC3CCCNCC3)cc2)cc2sccc21] | $^1$H NMR (DMSO-d$_6$ + D$_2$O) δ (ppm): 7.68 (bs, 1 H), 7.50 (d, J = 5.4 Hz, 1 H), 7.24 (d, J = 5.4 Hz, 1 H), 7.03-6.95 (m, 2 H), 6.84 (s, 1 H), 6.78-6.72 (m, 2 H), 4.62-4.53 (m, 1 H), 3.93 (t, J = 7.3 Hz, 2 H), 3.68 (s, 3 H), 3.26-3.04 (m, 5 H), 2.44 (t, J = 7.3 Hz, 2 H), 2.32-1.62 (m, 14 H); MS (ESI): m/z: 489 [M + H]$^+$. |
| 63 | 4-methyl-5-[1-[3-[4-(4-piperidyloxy)phenyl]propyl]-4-propyl-imidazol-2-yl]thieno[3,2-b]pyrrole hydrochloride | 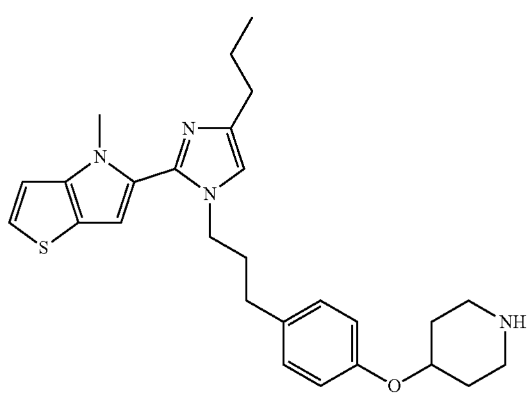 [SMILES: CCCc1cn(CCCc2ccc(OC3CCNCC3)cc2)c(-c2cc3sccc3n2C)n1] | $^1$H NMR (DMSO-d$_6$ + D$_2$O) δ (ppm): 7.73 (s, 1 H), 7.55 (d, J = 5.4 Hz, 1 H), 7.26 (d, J = 5.4 Hz, 1 H), 7.05-6.98 (m, 2 H), 6.88 (s, 1 H), 6.84-6.73 (m, 2 H), 4.59-4.48 (m, 1 H), 4.07 (t, J = 7.3 Hz, 2 H), 3.73 (s, 3 H), 3.26-3.16 (m, 2 H), 3.11-3.00 (m, 2 H), 2.65 (t, J = 7.3 Hz, 2 H), 2.45 (t, J = 7.3 Hz, 2 H), 2.10-1.99 (m, 4 H), 1.80-1.63 (m, 4 H), 0.95 (t, J = 7.3 Hz, 3 H); MS (ESI): m/z: 463 [M + H]$^+$. |

TABLE 3-continued

Final Products

| Ex. | Name | Structure | Analytical Data |
|---|---|---|---|
| 64 | 4-methyl-5-[1-[3-[4-(4-piperidyloxy)phenyl]propyl]-5-propyl-imidazol-2-yl]thieno[3,2-b]pyrrole hydrochloride | 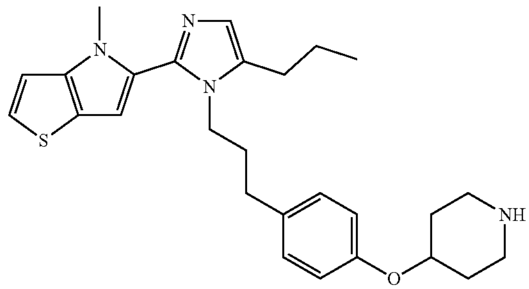 [SMILES: CCCc1cnc(-c2cc3sccc3n2C)n1CCCc1ccc(OC2CCNCC2)cc1] | $^1$H NMR (DMSO-d$_6$ + D$_2$O) δ (ppm): 7.61-7.46 (m, 2 H), 7.25 (d, J = 5.4 Hz, 1 H), 7.04-6.95 (m, 2 H), 6.85 (s, 1 H), 6.81-6.75 (m, 2 H), 4.57-4.46 (m, 1 H), 4.00 (t, J = 7.3 Hz, 2 H), 3.67 (s, 3 H), 3.26-3.14 (m, 2 H), 3.10-2.97 (m, 2 H), 2.59 (t, J = 7.3 Hz, 2 H), 2.45 (t, J = 7.3 Hz, 2 H), 2.09-1.97 (m, 2 H), 1.94-1.83 (m, 2 H), 1.80-1.71 (m, 2 H), 1.69-1.58 (m, 2 H), 0.98 (t, J = 7.3 Hz, 3 H); MS (ESI): m/z: 463 [M + H]$^+$. |
| 65 | 5-[4-cyclobutyl-1-[3-[4-(4-piperidylmethoxy)phenyl]propyl]imidazol-2-yl]-4-methyl-thieno[3,2-b]pyrrole hydrochloride | 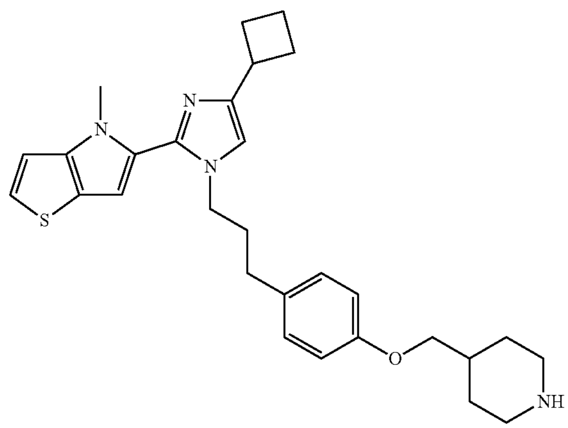 [SMILES: Cn1c(-c2nc(C3CCC3)cn2CCCc2ccc(OCC3CCNCC3)cc2)cc2sccc21] | $^1$H NMR (DMSO-d$_6$ + D$_2$O) δ (ppm): 7.77 (s, 1 H), 7.54 (d, J = 5.4 Hz, 1 H), 7.25 (d, J = 5.4 Hz, 1 H), 7.04-6.95 (m, 2 H), 6.81 (s, 1 H), 6.75-6.69 (m, 2 H), 4.03 (t, J = 7.3 Hz, 2 H), 3.76-3.68 (m, 5 H), 3.57-3.54 (m, 1 H), 3.32-3.25 (m, 2 H), 2.93-2.83 (m, 2 H), 2.45 (t, J = 7.3 Hz, 2 H), 2.37-2.28 (m, 2 H), 2.25-2.14 (m, 2 H), 2.10-1.95 (m, 4 H), 1.92-1.84 (m, 3 H), 1.50-1.38 (m, 2 H); MS (ESI): m/z: 489 [M + H]$^+$. |
| 66 | 5-[5-cyclobutyl-1-[3-[4-(4-piperidylmethoxy)phenyl]propyl]imidazol-2-yl]-4-methyl-thieno[3,2-b]pyrrole hydrochloride | 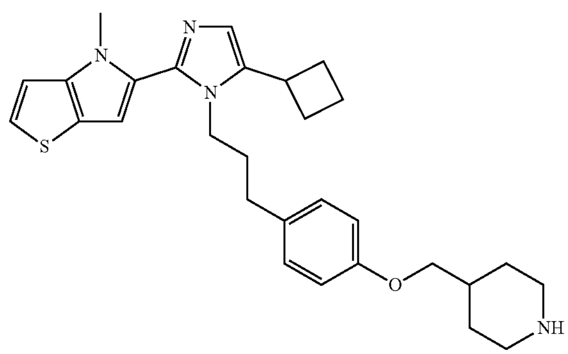 [SMILES: Cn1c(-c2ncc(C3CCC3)n2CCCc2ccc(OCC3CCNCC3)cc2)cc2sccc21] | $^1$H NMR (DMSO-d$_6$ + D$_2$O) δ (ppm): 7.63 (bs, 1 H), 7.48 (d, J = 5.4 Hz, 1 H), 7.23 (d, J = 5.4 Hz, 1 H), 7.01-6.93 (m, 2 H), 6.79-6.68 (m, 3 H), 3.92 (t, J = 7.8 Hz, 2 H), 3.76 (d, J = 6.4 Hz, 2 H), 3.67 (s, 3 H), 3.57-3.51 (m, 1 H), 3.33-3.23 (m, 2 H), 2.93-2.82 (m, 2 H), 2.44 (t, J = 7.3 Hz, 2 H), 2.34-2.25 (m, 2 H), 2.21-2.11 (m, 2 H), 2.07-1.96 (m, 2 H), 1.94-1.80 (m, 5 H), 1.50-1.36 (m, 2 H); MS (ESI): m/z: 489 [M + H]$^+$. |
| 67 | 4-methyl-5-[4-propyl-1-[3-[4-(pyrrolidin-3-ylmethoxy)phenyl]propyl]imidazol-2-yl]thieno[3,2-b]pyrrole hydrochloride | 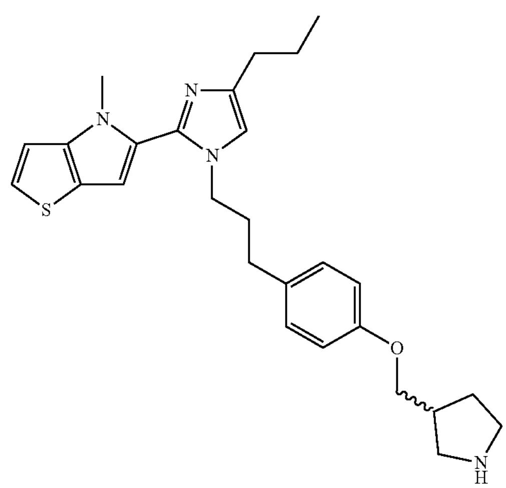 [SMILES: CCCc1cn(CCCc2ccc(OCC3CCNC3)cc2)c(-c2cc3sccc3n2C)n1] | $^1$H NMR (DMSO-d$_6$ + D$_2$O) δ (ppm): 7.69 (bs, 1 H), 7.53 (d, J = 5.4 Hz, 1 H), 7.26 (d, J = 5.4 Hz, 1 H), 7.04-6.97 (m, 2 H), 6.81 (bs, 1 H), 6.78-6.72 (m, 2 H), 4.05 (t, J = 7.3 Hz, 2 H), 3.94-3.81 (m, 2 H), 3.72 (s, 3 H), Part AB of ABX System: VA = 3.34, VB = 2.97, JAB = 11.6 Hz, JAX = 8.1 Hz, JBX = 7.3 Hz, 3.29-3.21 (m, 1 H), 3.20-3.12 (m, 1 H), 2.73-2.61 (m, 3 H), 2.46 (t, J = 7.3 Hz, 2 H), 2.14-1.99 (m, 3 H), 1.77-1.62 (m, 3 H), 0.94 (t, J = 7.3 Hz, 3 H); MS (ESI): m/z: 463 [M + H]$^+$. |

TABLE 3-continued

Final Products

| Ex. | Name | Structure | Analytical Data |
|---|---|---|---|
| 68 | 4-methyl-5-[5-propyl-1-[3-[4-(pyrrolidin-3-ylmethoxy)phenyl]propyl]imidazol-2-yl]thieno[3,2-b]pyrrole | 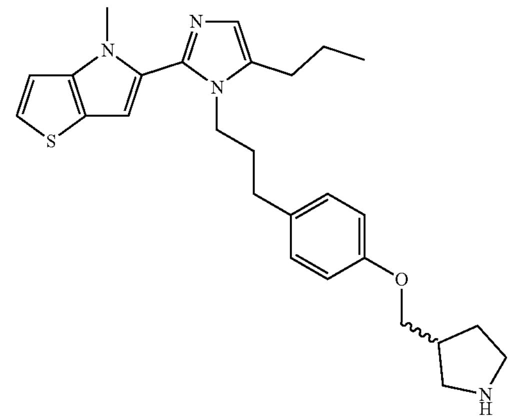 [SMILES: CCCc1cnc(-c2cc3sccc3n2C)n1CCCc1ccc(OCC2CCNC2)cc1] | $^1$H NMR (CDCl$_3$) δ (ppm): 7.16 (d, J = 4.9 Hz, 1 H), 7.00-6.95 (m, 3 H), 6.93 (s, 1 H), 6.81-6.73 (m, 2 H), 6.38 (s, 1 H), 3.97-3.81 (m, 4 H), 3.79 (s, 3 H), Part AB of ABX System: VA = 3.17, VB = 2.86, JAB = 11.3 Hz, JAX = 7.9 Hz, JBX = 5.9 Hz, 3.10-3.02 (m, 1 H), 3.01-2.94 (m, 1 H), 2.64-2.57 (m, 1 H), 2.56-2.45 (m, 4 H), 2.06-1.98 (m, 1 H), 1.97-1.89 (m, 2 H), 1.76-1.67 (m, 2 H), 1.65-1.55 (m, 1 H), 1.04 (t, J = 7.3 Hz, 3 H); MS (ESI): m/z: 463 [M + H]$^+$. |
| 69 | 5-[4-cyclobutyl-1-[2-[4-(4-piperidyloxy)phenyl]ethyl]imidazol-2-yl]-4-methyl-thieno[3,2-b]pyrrole | 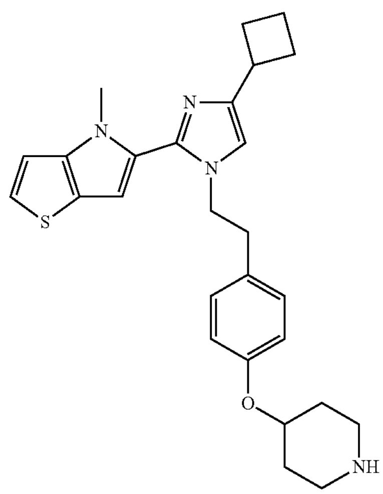 [SMILES: Cn1c(-c2nc(C3CCC3)cn2CCc2ccc(OC3CCNCC3)cc2)cc2sccc21] | $^1$H NMR (CDCl$_3$) δ (ppm): 7.13 (d, J = 5.4 Hz, 1 H), 6.96-6.90 (m, 3 H), 6.82-6.76 (m, 2 H), 6.73 (s, 1 H), 6.27 (s, 1 H), 4.42-4.33 (m, 1 H), 4.18 (t, J = 7.3 Hz, 2 H), 3.73 (s, 3 H), 3.56-3.46 (m, 1 H), 3.24-3.13 (m, 2H), 2.96 (t, = 7.3 Hz, 2 H), 2.90-2.79 (m, 2 H), 2.38-2.17 (m, 4 H), 2.11-1.71 (m, 6 H); MS (ESI): m/z: 461 [M + H]$^+$. |
| 70 | 5-[4-ethyl-1-[3-[3-(4-piperidyloxy)phenyl]propyl]imidazol-2-yl]-4-methyl-thieno[3,2-b]pyrrole hydrochloride | 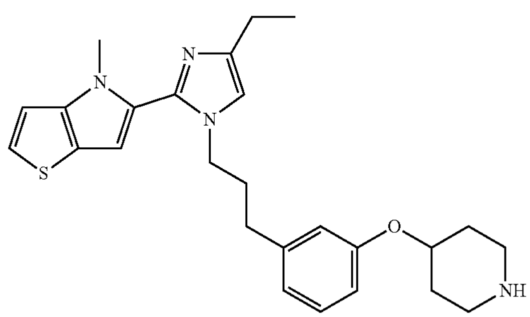 [SMILES: CCc1cn(CCCc2cccc(OC3CCNCC3)c2)c(-c2cc3sccc3n2C)n1] | $^1$H NMR (DMSO-d$_6$) δ (ppm): 8.80 (bs, 2 H), 7.79 (bs, 1 H), 7.56 (d, J = 5.4 Hz, 1 H), 7.28 (d, J = 5.4 Hz, 1 H), 7.16-7.06 (m, 1 H), 6.88 (bs, 1 H), 6.82-6.77 (m, 2 H), 6.74-6.67 (m, 1 H), 4.63-4.52 (m, 1 H), 4.09 (t, J = 7.3 Hz, 2 H), 3.77 (s, 3 H), 3.23-3.15 (m, 2 H), 3.08-2.99 (m, 2 H), 2.72 (q, J = 7.3 Hz, 2 H), 2.54 (t, J = 7.3 Hz, 2 H), 2.16-1.99 (m, 4 H), 1.82-1.71 (m, 2 H), 1.27 (t, J = 7.3 Hz, 3 H); MS (ESI): m/z: 449 [M + H]$^+$. |
| 71 | 5-[5-ethyl-1-[3-[3-(4-piperidyloxy)phenyl]propyl]imidazol-2-yl]-4-methyl-thieno[3,2-b]pyrrole hydrochloride | 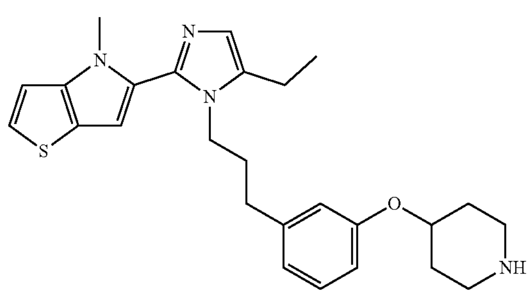 | $^1$H NMR (DMSO-d$_6$ + D$_2$O) δ (ppm): 7.54-7.41 (m, 2 H), 7.22 (d, J = 5.4 Hz, 1 H), 7.13-7.03 (m, 1 H), 6.82-6.63 (m, 4 H), 4.61-4.51 (m, 1 H), 4.03 (t, J = 7.3 Hz, 2 H), 3.67 (s, 3 H), 3.26-3.14 (m, 2 H), 3.09-2.98 (m, 2 H), 2.65 (q, J = 7.3 Hz, 2 H), 2.48-2.45 (m, 2 H), 2.08-1.98 (m, 2 H), 1.97-1.88 (m, 2 H), 1.80-1.68 (m, 2 H), 1.25 (t, J = 7.3 Hz, 3 H); MS (ESI): m/z: 449 [M + H]$^+$. |

TABLE 3-continued

Final Products

| Ex. | Name | Structure | Analytical Data |
| --- | --- | --- | --- |
| 72 | 4-methyl-5-[1-[2-[4-(4-piperidyloxy)phenyl]ethyl]-4-propyl-imidazol-2-yl]thieno[3,2-b]pyrrole hydrochloride | 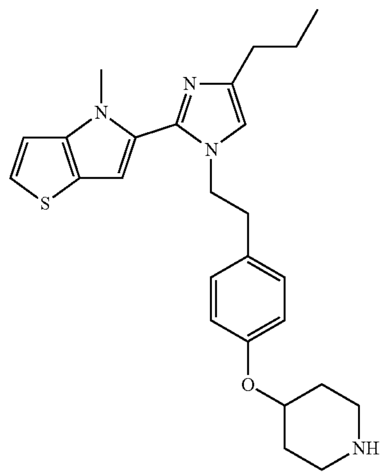 [SMILES: CCCc1cn(CCc2ccc(OC3CCNCC3)cc2)c(-c2cc3sccc3n2C)n1] | $^1$H NMR (DMSO-$d_6$ + $D_2O$) δ (ppm): 7.72 (s, 1 H), 7.53 (d, J = 5.4 Hz, 1 H), 7.23 (d, J = 5.4 Hz, 1 H), 6.97-6.90 (m, 2 H), 6.86-6.78 (m, 2 H), 6.66 (s, 1 H), 4.59-4.50 (m, 1 H), 4.31 (t, J = 6.8 Hz, 2 H), 3.50 (s, 3 H), 3.24-3.16 (m, 2 H), 3.08-2.97 (m, 4 H), 2.63 (t, J = 7.3 Hz, 2 H), 2.08-1.98 (m, 2 H), 1.80-1.71 (m, 2 H), 1.69-1.60 (m, 2 H), 0.93 (t, J = 7.3 Hz, 3 H); MS (ESI): m/z: 449 [M + H]$^+$. |
| 73 | 4-methyl-5-[1-[2-[4-(4-piperidyloxy)phenyl]ethyl]-5-propyl-imidazol-2-yl]thieno[3,2-b]pyrrole | 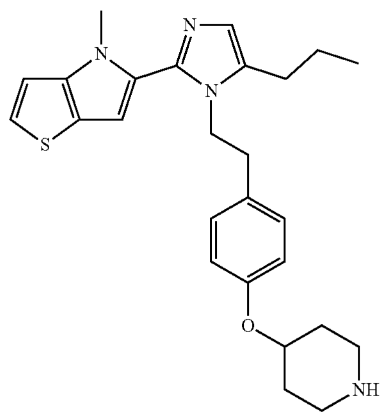 [SMILES: CCCc1cnc(-c2cc3sccc3n2C)n1CCc1ccc(OC2CCNCC2)cc1] | $^1$H NMR (CDCl$_3$ + $D_2O$) δ (ppm): 7.16 (d, J = 5.4 Hz, 1 H), 6.96 (d, J = 5.4 Hz, 1 H), 6.93 (s, 1 H), 6.88-6.83 (m, 2 H), 6.77-6.72 (m, 2 H), 6.46 (s, 1 H), 4.36-4.26 (m, 1 H), 4.18 (t, J = 7.3 Hz, 2 H), 3.70 (s, 3 H), 3.19-3.07 (m, 2 H), 2.81 (t, J = 7.3 Hz, 2 H), 2.77-2.67 (m, 2 H), 2.48 (t, J = 7.3 Hz, 2 H), 2.04-1.96 (m, 2 H), 1.78-1.62 (m, 4 H), 1.05 (t, J = 7.3 Hz, 3 H); MS (ESI): m/z: 449 [M + H]$^+$. |
| 74 | 4-methyl-5-[1-[3-[4-(4-piperidyloxymethyl)phenyl]propyl]-4-propyl-imidazol-2-yl]thieno[3,2-b]pyrrole hydrochloride | 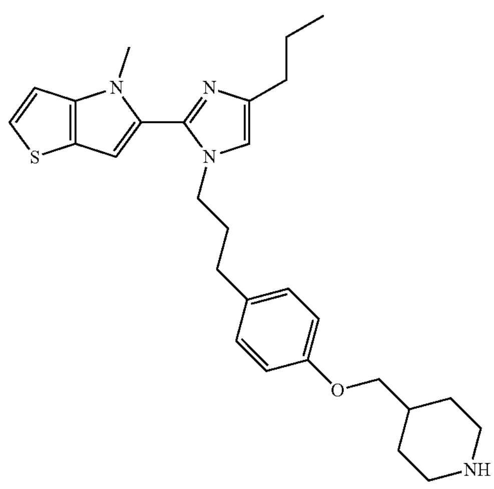 [SMILES: CCCc1cn(CCCc2ccc(OCC3CCNCC3)cc2)c(-c2cc3sccc3n2C)n1] | $^1$H NMR (DMSO-$d_6$) δ (ppm): 8.87-8.72 (m, 1 H), 8.62-8.42 (m, 1 H), 7.84-7.64 (bs, 1 H), 7.56 (d, J = 5.4 Hz, 1 H), 7.28 (d, J = 5.4 Hz, 1 H), 7.30-7.24 (m, 2 H), 6.91-6.81 (bs, 1 H), 6.78-6.72 (m, 2 H), 4.06 (t, J = 7.3 Hz, 2 H), 3.80-3.71 (m, 5 H), 3.34-3.23 (m, 2 H), 2.97-2.82 (m, 2 H), 2.66 (t, J = 7.3 Hz, 2 H), 2.49-2.41 (m, 2 H), 2.13-1.96 (m, 3 H), 1.93-1.83 (m, 2 H), 1.75-1.63 (m, 2 H), 1.52-1.39 (m, 2 H), 0.96 (t, J = 7.3 Hz, 3 H); MS (ESI): m/z: 477 [M + H]$^+$. |

TABLE 3-continued

Final Products

| Ex. | Name | Structure | Analytical Data |
|---|---|---|---|
| 75 | 4-methyl-5-[1-[3-[4-(4-piperidyloxymethyl)phenyl]propyl]-5-propyl-imidazol-2-yl]thieno[3,2-b]pyrrole hydrochloride | 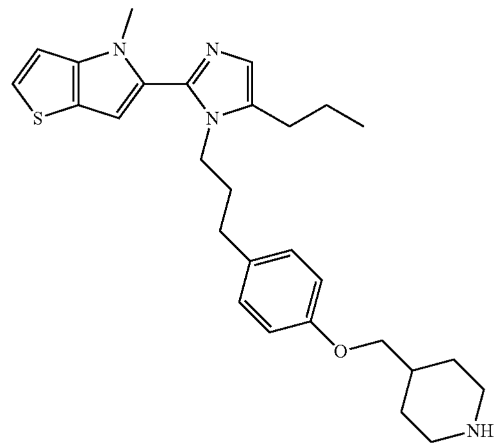 [SMILES: CCCc1cnc(-c2cc3sccc3n2C)n1CCCc1ccc(OCC2CCNCC2)cc1] | $^1$H NMR (DMSO-d$_6$) δ (ppm): 8.85-8.68 (m, 1 H), 8.58-8.40 (m, 1 H), 7.71-7.62 (bs, 1 H), 7.56 (d, J = 5.4 Hz, 1 H), 7.27 (d, J = 5.4 Hz, 1 H), 7.03-6.97 (m, 2 H), 6.86 (bs, 1 H), 6.76-6.70 (m, 2 H), 4.04 (t, J = 7.3 Hz, 2 H), 3.80-3.74 (m, 2 H), 3.71 (s, 3 H), 3.34-3.25 (m, 2 H), 2.96-2.80 (m, 2 H), 2.63 (t, J = 7.3 Hz, 2 H), 2.49-2.43 (m, 2 H), 2.06-1.98 (m, 1 H), 1.95-1.84 (m, 4 H), 1.76-1.62 (m, 2 H), 1.54-1.39 (m, 2 H), 1.01 (t, J = 7.3 Hz, 3 H); MS (ESI): m/z: 477 [M + H]$^+$. |
| 76 | 5-[1-[2-[4-(azepan-4-yloxy)phenoxy]ethyl]-4-propyl-imidazol-2-yl]-4-methyl-thieno[3,2-b]pyrrole | 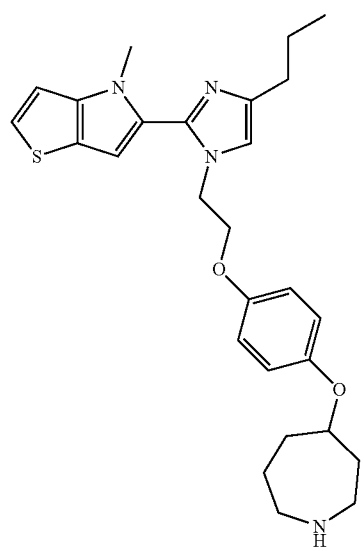 [SMILES: CCCc1cn(CCOc2ccc(OC3CCCNCC3)cc2)c(-c2cc3sccc3n2C)n1] | $^1$H NMR (CDCl$_3$) δ (ppm): 7.15 (d, J = 4.9 Hz, 1 H), 6.97 (d, J = 4.9 Hz, 1 H), 6.92 (s, 1 H), 6.83-6.70 (m, 4 H), 6.56 (s, 1 H), 4.53-4.46 (m, 1 H), 4.36 (t, J = 5.1 Hz, 2H), 4.14 (t, J = 5.1 Hz, 2 H), 3.82 (s, 3 H), 3.21-2.98 (m, 2 H), 2.90-2.65 (m, 2 H), 2.60 (t, J = 7.3 Hz, 2 H), 2.23-1.81 (m, 6 H), 1.78-1.66 (m, 2 H), 1.00 (t, J = 7.3 Hz, 3 H); MS (ESI): m/z: 479 [M + H]$^+$. |
| 77 | 5-[1-[2-[4-(azepan-4-yloxy)phenoxy]ethyl]-5-propyl-imidazol-2-yl]-4-methyl-thieno[3,2-b]pyrrole | 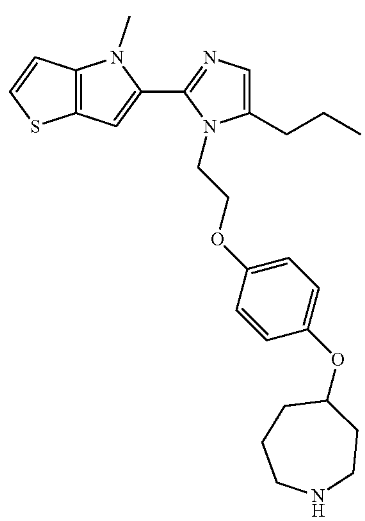 [SMILES: CCCc1cnc(-c2cc3sccc3n2C)n1CCOc1ccc(OC2CCCNCC2)cc1] | $^1$H NMR (DMSO-d$_6$) δ (ppm): 7.32 (d, J = 5.4 Hz, 1 H), 7.19 (d, J = 5.4 Hz, 1 H), 6.86 (s, 1 H), 6.78-6.61 (m, 5 H), 4.46-4.39 (m, 1 H), 4.35 (t, J = 5.4 Hz, 2 H), 4.03 (t, J = 5.4 Hz, 2 H), 3.68 (s, 3 H), 3.07-2.79 (m, 4 H), 2.66 (t, J = 7.3 Hz, 2 H), 2.10-1.45 (m, 8 H), 1.01 (t, J = 7.3 Hz, 3 H); MS (ESI): m/z: 479 [M + H]$^+$. |

TABLE 3-continued

Final Products

| Ex. | Name | Structure | Analytical Data |
|---|---|---|---|
| 78 | 5-[4-cyclobutyl-1-[3-[4-(4-piperidyloxy)phenyl]propyl]imidazol-2-yl]-6-methyl-thieno[2,3-b]pyrrole hydrochloride | 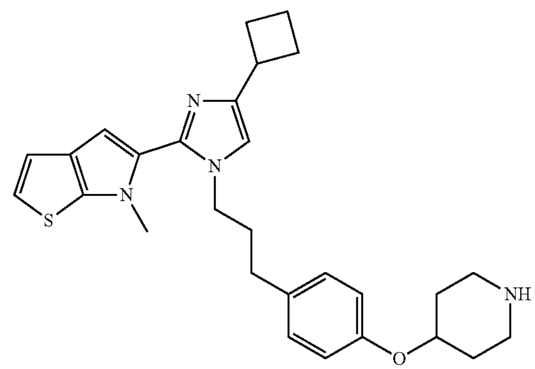 [SMILES: Cn1c(-c2nc(C3CCC3)cn2CCCc2ccc(OC3CCNCC3)cc2)cc2ccsc21] | $^1$H NMR (DMSO-d$_6$ + D$_2$O) δ (ppm): 7.74 (bs, 1 H), 7.20 (d, J = 5.4 Hz, 1 H), 7.07 (d, J = 5.4 Hz, 1 H), 7.04-6.99 (m, 2 H), 6.83-6.73 (m, 3 H), 4.57-4.46 (m, 1 H), 4.02 (t, J = 7.3 Hz, 2 H), 3.67 (s, 3 H), 3.65-3.56 (m, 1 H), 3.25-3.16 (m, 2 H), 3.08-3.00 (m, 2 H), 2.45 (t, J = 7.3 Hz, 2 H), 2.38-2.27 (m, 2 H), 2.24-2.13 (m, 2 H), 2.10-1.96 (m, 5 H), 1.91-1.82 (m, 1 H), 1.80-1.70 (m, 2 H); MS (ESI): m/z: 475 [M + H]$^+$. |
| 79 | 5-[5-cyclobutyl-1-[3-[4-(4-piperidyloxy)phenyl]propyl]imidazol-2-yl]-6-methyl-thieno[2,3-b]pyrrole | 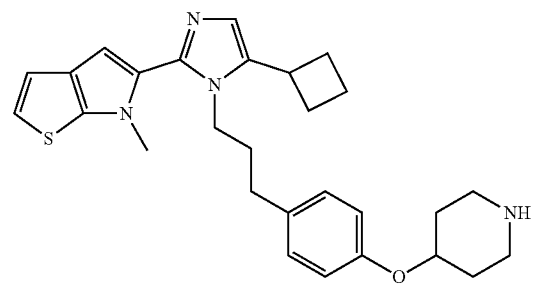 [SMILES: Cn1c(-c2ncc(C3CCC3)n2CCCc2ccc(OC3CCNCC3)cc2)cc2ccsc21] | $^1$H NMR (CDCl$_3$ + D$_2$O) δ (ppm): 7.04-6.94 (m, 4 H), 6.89 (d, J = 5.4 Hz, 1 H), 6.83-6.76 (m, 2 H), 6.40 (s, 1 H), 4.39-4.27 (m, 1 H), 3.87 (t, J = 7.8 Hz, 2 H), 3.75 (s, 3 H), 3.42-3.31 (m, 1 H), 3.19-3.09 (m, 2 H), 2.79-2.68 (m, 2 H), 2.51 (t, J = 7.3 Hz, 2 H), 2.34-2.24 (m, 2 H), 2.23-2.12 (m, 2 H), 2.06-1.85 (m, 6 H), 1.73-1.62 (m, 2 H).; MS (ESI): m/z: 475 [M + H]$^+$. |
| 80 | 5-[4-cyclobutyl-1-[3-[4-[[(3R)-pyrrolidin-3-yl]methoxy]phenyl]propyl]imidazol-2-yl]-4-methyl-thieno[3,2-b]pyrrole hydrochloride | 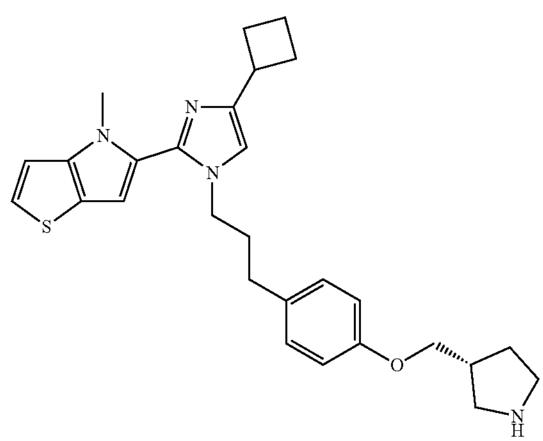 [SMILES: Cn1c(-c2nc(C3CCC3)cn2CCCc2ccc(OC[C@@H]3CCNC3)cc2)cc2sccc21] | $^1$H NMR (DMSO-d$_6$ + D$_2$O) δ (ppm): 7.75 (s, 1 H), 7.53 (d, J = 5.4 Hz, 1 H), 7.25 (d, J = 5.4 Hz, 1 H), 7.04-6.98 (m, 2 H), 6.81 (s, 1 H), 6.76-6.70 (m, 2 H), 4.03 (t, J = 7.3 Hz, 2 H), Part AB of ABX System: VA = 3.9, VB = 3.85, JAB = 9.5 Hz, JAX = 6.1 Hz, JBX = 7.1 Hz, 3.71 (s, 3 H), 3.58-3.53 (m, 1 H), Part AB of ABX System: VA = 3.34, VB = 2.97, JAB = 11.6 Hz, JAX = 8.1 Hz, JBX = 7.3 Hz), 3.28-3.21 (m, 1 H), 3.20-3.12 (m, 1 H), 2.72-2.64 (m, 1 H), 2.45 (t, J = 7.3 Hz, 2 H), 2.37-2.28 (m, 2 H), 2.24-1.96 (m, 6 H), 1.93-1.83 (m, 1 H), 1.76-1.67 (m, 1 H); MS (ESI): m/z: 475 [M + H]$^+$. |
| 81 | 5-[5-cyclobutyl-1-[3-[4-[[(3R)-pyrrolidin-3-yl]methoxy]phenyl]propyl]imidazol-2-yl]-4-methyl-thieno[3,2-b]pyrrole hydrochloride | 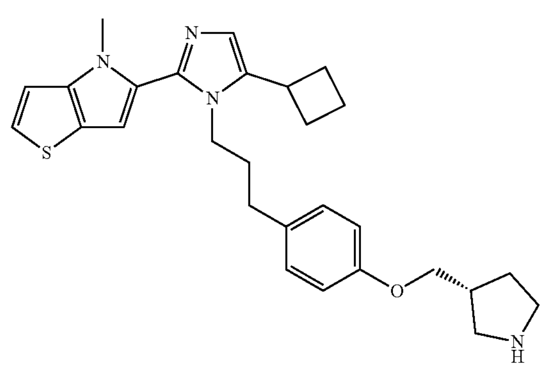 [SMILES: Cn1c(-c2ncc(C3CCC3)n2CCCc2ccc(OC[C@@H]3CCNC3)cc2)cc2sccc21] | $^1$H NMR (DMSO-d$_6$ + D$_2$O) δ (ppm): 7.72 (s, 1 H), 7.50 (d, J = 5.4 Hz, 1 H), 7.23 (d, J = 5.4 Hz, 1 H), 7.02-6.96 (m, 2 H), 6.81 (s, 1 H), 6.77-6.71 (m, 2 H), 3.98-3.82 (m, 4H), 3.67 (s, 3 H), 3.58-3.52 (m, 1 H), Part AB of ABX System: VA = 3.34, VB = 2.97, JAB = 11.6 Hz, JAX = 8.1 Hz, JBX = 7.8 Hz, 3.29-3.21 (m, 1 H), 3.19-3.12 (m, 1 H), 2.73-2.65 (m, 1 H), 2.44 (t, J = 7.3 Hz, 2 H), 2.34-2.25 (m, 2 H), 2.22-1.96 (m, 4 H), 1.91-1.80 (m, 3 H), 1.78-1.67 (m, 1 H); MS (ESI): m/z: 475 [M + H]$^+$. |

TABLE 3-continued

Final Products

| Ex. | Name | Structure | Analytical Data |
| --- | --- | --- | --- |
| 82 | 5-[4-cyclobutyl-1-[3-[4-[[(3S)-pyrrolidin-3-yl]methoxy]phenyl]propyl]imidazol-2-yl]-4-methyl-thieno[3,2-b]pyrrole hydrochloride | 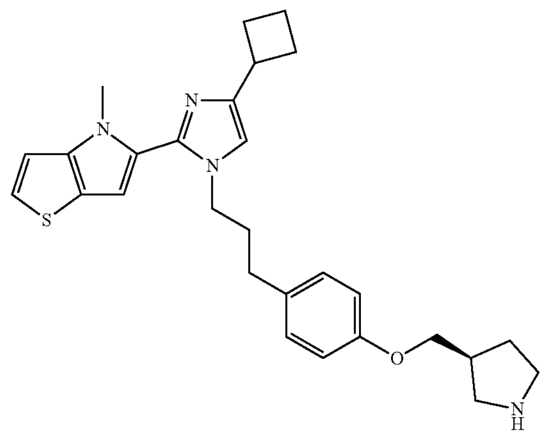 [SMILES: Cn1c(-c2nc(C3CCC3)cn2CCCc2ccc(OC[C@H]3CCNC3)cc2)cc2sccc21] | $^1$H NMR (DMSO-d$_6$ + D$_2$O) δ (ppm): 7.77 (bs, 1 H), 7.54 (d, J = 5.4 Hz, 1 H), 7.25 (d, J = 5.4 Hz, 1 H), 7.05-6.99 (m, 2 H), 6.84 (bs, 1 H), 6.79-6.72 (m, 2 H), 4.03 (t, J = 7.3 Hz, 2 H), Part AB of ABX System: VA = 3.91, VB = 3.86, JAB = 9.4 Hz, JAX = 6.1 Hz, JBX = 7.4 Hz, 3.72 (s, 3 H), 3.65-3.55 (m, 1 H), Part AB of ABX System: VA = 3.34, VB = 2.97, JAB = 11.5 Hz, JAX = 7.9 Hz, JBX = 7.3 Hz, 3.28-3.21 (m, 1 H), 3.20-3.12 (m, 1 H), 2.72-2.65 (m, 1 H), 2.46 (t, J = 7.3 Hz, 2 H), 2.38-2.28 (m, 2 H), 2.25-2.15 (m, 2 H), 2.14-1.96 (m, 4 H), 1.92-1.84 (m, 1 H), 1.78-1.68 (m, 1 H); MS (ESI): m/z: 475 [M + H]$^+$. |
| 83 | 5-[5-cyclobutyl-1-[3-[4-[[(3S)-pyrrolidin-3-yl]methoxy]phenyl]propyl]imidazol-2-yl]-4-methyl-thieno[3,2-b]pyrrole | 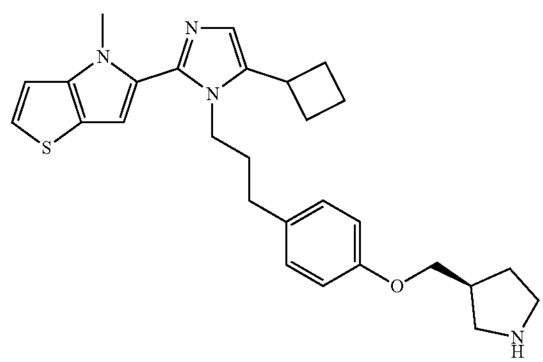 [SMILES: Cn1c(-c2ncc(C3CCC3)n2CCCc2ccc(OC[C@H]3CCNC3)cc2)cc2sccc21] | $^1$H NMR (CDCl$_3$ + D$_2$O) δ (ppm): 7.15 (d, J = 5.4 Hz, 1 H), 7.02-6.92 (m, 4 H), 6.81-6.73 (m, 2 H), 6.36 (s, 1 H), 3.94-3.81 (m, 4 H), 3.78 (s, 3 H), 3.42-3.32 (m, 1 H), Part AB of ABX System: VA = 3.14, VB = 2.84, JAB = 11.4 Hz, JAX = 7.4 Hz, JBX = 5.6 Hz, 3.08-3.01 (m, 1 H), 2.98-2.91 (m, 1 H), 2.64-2.55 (m, 1 H), 2.50 (t, J = 7.3 Hz, 2 H), 2.37-2.27 (m, 2 H), 2.24-2.14 (m, 2 H), 2.09-1.84 (m, 5 H), 1.66-1.55 (m, 1 H); MS (ESI): m/z: 475 [M + H]$^+$. |
| 84 | 5-[4-cyclobutyl-1-[2-[4-(4-piperidyl-methoxy)phenoxy]ethyl]imidazol-2-yl]-4-methyl-thieno[3,2-b]pyrrole hydrochloride | 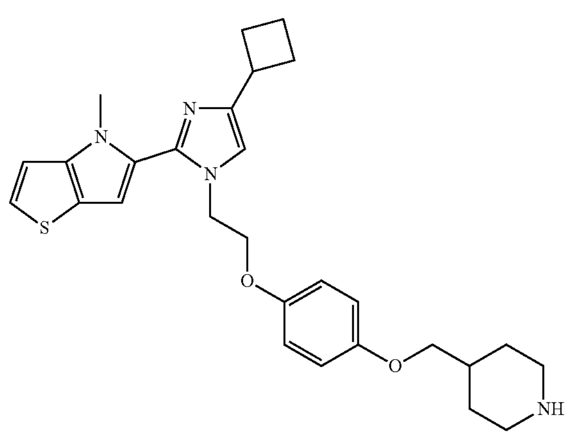 [SMILES: Cn1c(-c2nc(C3CCC3)cn2CCOc2ccc(OCC3CCNCC3)cc2)cc2sccc21] | $^1$H NMR (DMSO-d$_6$ + D$_2$O) δ (ppm): 7.76 (s, 1 H), 7.51 (d, J = 5.4 Hz, 1 H), 7.25 (d, J = 5.4 Hz, 1 H), 7.01 (s, 1 H), 6.83-6.70 (m, 4 H), 4.44 (t, J = 4.9 Hz, 2 H), 4.25 (t, J = 4.9 Hz, 2 H), 3.75-3.69 (m, 5 H), 3.62-3.54 (m, 1 H), 3.31-3.22 (m, 2 H), 2.91-2.81 (m, 2 H), 2.35-2.27 (m, 2 H), 2.22-2.12 (m, 2 H), 2.05-1.93 (m, 2 H), 1.91-1.82 (m, 3 H), 1.47-1.35 (m, 2 H); MS (ESI): m/z: 491 [M + H]$^+$. |

TABLE 3-continued

Final Products

| Ex. | Name | Structure | Analytical Data |
| --- | --- | --- | --- |
| 85 | 5-[4-cyclobutyl-1-[3-[3-(4-piperidyloxy)phenyl]propyl]imidazol-2-yl]-4-methyl-thieno[3,2-b]pyrrole hydrochloride | 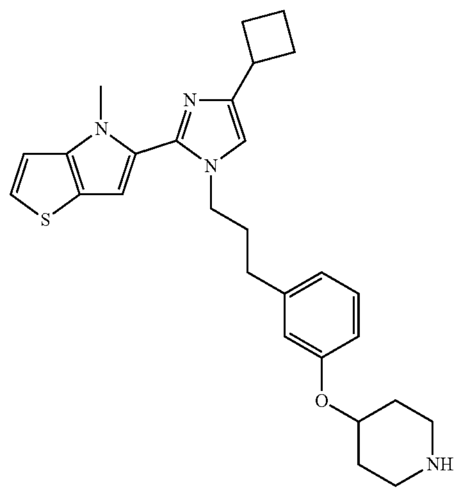 [SMILES: Cn1c(-c2nc(C3CCC3)cn2CCCc2cccc(OC3CCNCC3)c2)cc2sccc21] | $^1$H NMR (DMSO-$d_6$) δ (ppm): 8.86 (bs, 2 H), 7.87 (bs, 1 H), 7.56 (d, J = 5.4 Hz, 1 H), 7.28 (d, J = 5.4 Hz, 1 H), 7.17-7.08 (m, 1 H), 6.87 (bs, 1 H), 6.82-6.77 (m, 2 H), 6.74-6.68 (m, 1 H), 4.63-4.55 (m, 1 H), 4.08 (t, J = 7.3 Hz, 2 H), 3.76 (s, 3 H), 3.65-3.57 (m, 1 H), 3.23-3.14 (m, 2 H), 3.08-2.98 (m, 2 H), 2.53 (t, J = 7.6 Hz, 2 H), 2.39-2.30 (m, 2 H), 2.29-2.18 (m, 2 H), 2.16-1.98 (m, 5 H), 1.93-1.84 (m, 1 H), 1.82-1.72 (m, 2 H); MS (ESI): m/z: 475 [M + H]$^+$. |
| 86 | 5-[5-cyclobutyl-1-[3-[3-(4-piperidyloxy)phenyl]propyl]imidazol-2-yl]-4-methyl-thieno[3,2-b]pyrrole hydrochloride | 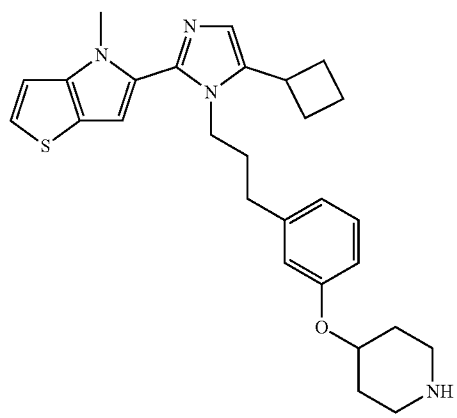 [SMILES: Cn1c(-c2ncc(C3CCC3)n2CCCc2cccc(OC3CCNCC3)c2)cc2sccc21] | $^1$H NMR (DMSO-$d_6$ + $D_2O$) δ (ppm): 7.66 (bs, 1 H), 7.49 (d, J = 5.4 Hz, 1 H), 7.22 (d, J = 5.4 Hz, 1 H), 7.15-7.06 (m, 1 H), 6.83-6.74 (m, 3 H), 6.71-6.63 (m, 1 H), 4.62-4.52 (m, 1 H), 3.94 (t, J = 7.6 Hz, 2 H), 3.67 (s, 3 H), 3.58-3.51 (m, 1 H), 3.24-3.16 (m, 2 H), 3.09-2.98 (m, 2 H), 2.47 (t, J = 7.3 Hz, 2 H), 2.31-2.23 (m, 2 H), 2.20-2.11 (m, 2 H), 2.08-1.93 (m, 3 H), 1.92-1.82 (m, 3 H), 1.80-1.69 (m, 2 H); MS (ESI): m/z: 475 [M + H]$^+$. |
| 87 | 5-[4-cyclobutyl-1-[2-[3-(4-piperidyloxy)phenoxy]ethyl]imidazol-2-yl]-4-methyl-thieno[3,2-b]pyrrole hydrochloride | 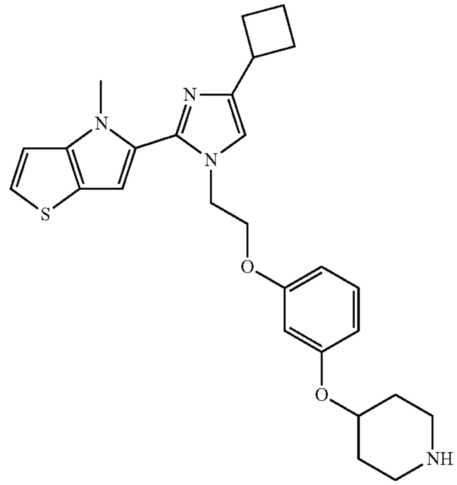 [SMILES: Cn1c(-c2nc(C3CCC3)cn2CCOc2cccc(OC3CCNCC3)c2)cc2sccc21] | $^1$H NMR (DMSO-$d_6$ + $D_2O$) δ (ppm): 7.78 (bs, 1 H), 7.53 (d, J = 5.4 Hz, 1 H), 7.27 (d, J = 5.4 Hz, 1 H), 7.18-7.11 (m, 1 H), 7.02 (s, 1 H), 6.62-6.55 (m, 1 H), 6.48-6.40 (m, 2 H), 4.62-4.54 (m, 1 H), 4.46 (t, J = 4.9 Hz, 2 H), 4.32 (t, J = 4.9 Hz, 2 H), 3.72 (s, 3 H), 3.60-3.55 (m, 1H), 3.24-3.15 (m, 2 H), 3.09-2.99 (m, 2 H), 2.37-2.28 (m, 2 H), 2.24-2.13 (m, 2 H), 2.08-1.69 (m, 6 H); MS (ESI): m/z: 477 [M + H]$^+$. |

TABLE 3-continued

Final Products

| Ex. | Name | Structure | Analytical Data |
|---|---|---|---|
| 88 | 5-[5-cyclobutyl-1-[2-[3-(4-piperidyloxy)phenoxy]ethyl]imidazol-2-yl]-4-methyl-thieno[3,2-b]pyrrole hydrochloride | 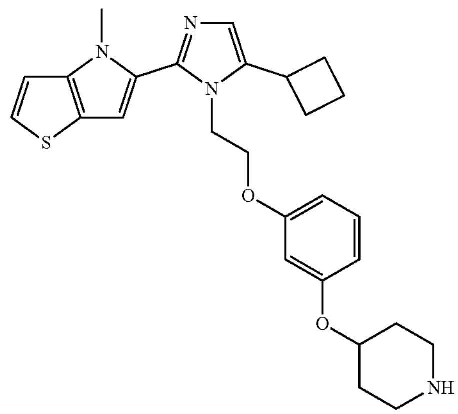 [SMILES: Cn1c(-c2ncc(C3CCC3)n2CCOc2cccc(OC3CCNCC3)c2)cc2sccc21] | $^1$H NMR (DMSO-$d_6$ + $D_2O$) δ (ppm): 7.76 (bs, 1 H), 7.50 (d, J = 5.4 Hz, 1 H), 7.25 (d, J = 5.4 Hz, 1 H), 7.13-7.07 (m, 1 H), 7.03 (s, 1 H), 6.57-6.51 (m, 1 H), 6.35-6.27 (m, 2 H), 4.58-4.50 (m, 1 H), 4.45 (t, J = 4.9 Hz, 2 H), 4.12 (t, J = 4.9 Hz, 2 H), 3.81-3.72 (m, 1H), 3.66 (s, 3H), 3.24-3.13 (m, 2 H), 3.09-2.98 (m, 2 H), 2.45-2.37 (m, 2 H), 2.27-2.16 (m, 2 H), 2.09-1.68 (m, 6 H); MS (ESI): m/z: 477 [M + H]$^+$. |
| 89 | 4-methyl-5-[4-methyl-1-[3-[4-(4-piperidyloxy)phenyl]propyl]imidazol-2-yl]thieno[3,2-b]pyrrole hydrochloride | 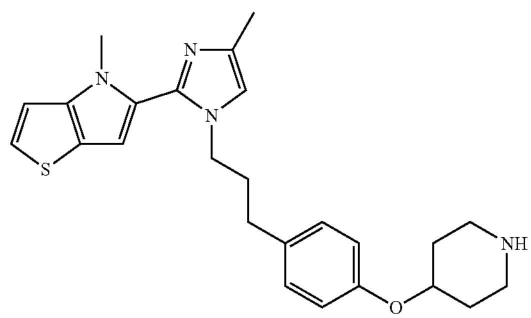 [SMILES: Cc1cn(CCCc2ccc(OC3CCNCC3)cc2)c(-c2cc3sccc3n2C)n1] | $^1$H NMR (DMSO-$d_6$ + $D_2O$) δ (ppm): 7.66 (s, 1 H), 7.53 (d, J = 5.4 Hz, 1 H), 7.26 (d, J = 5.4 Hz, 1 H), 7.04-6.97 (m, 2 H), 6.85 (s, 1 H), 6.81-6.76 (m, 2 H), 4.55-4.45 (m, 1 H), 4.05 (t, J = 7.3 Hz, 2 H), 3.72 (s, 3 H), 3.25-3.16 (m, 2 H), 3.09-2.98 (m, 2 H), 2.44 (t, J = 7.3 Hz, 2 H), 2.33 (s, 3 H), 2.10-1.97 (m, 4 H), 1.79-1.66 (m, 2 H); MS (ESI): m/z: 435 [M + H]$^+$. |
| 90 | 4-methyl-5-[5-methyl-1-[3-[4-(4-piperidyloxy)phenyl]propyl]imidazol-2-yl]thieno[3,2-b]pyrrole hydrochloride | 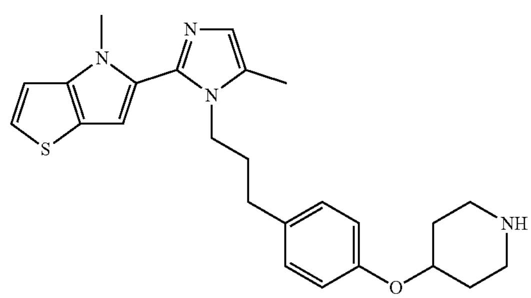 [SMILES: Cc1cnc(-c2cc3sccc3n2C)n1CCCc1ccc(OC2CCNCC2)cc1] | $^1$H NMR (DMSO-$d_6$ + $D_2O$) δ (ppm): 7.60-7.47 (m, 2 H), 7.24 (d, J = 5.4 Hz, 1 H), 7.04-6.95 (m, 2 H), 6.84 (s, 1 H), 6.80-6.72 (m, 2 H), 4.56-4.45 (m, 1 H), 4.03 (t, J = 7.3 Hz, 2 H), 3.67 (s, 3 H), 3.26-3.15 (m, 2 H), 3.10-2.98 (m, 2 H), 2.46 (t, J = 7.3 Hz, 2 H), 2.34 (s, 3 H), 2.06-1.98 (m, 2 H), 1.96-1.87 (m, 2 H), 1.80-1.69 (m, 2 H); MS (ESI): m/z: 435 [M + H]$^+$. |
| 91 | 5-[4-cyclobutyl-1-[2-[4-(4-piperidylmethoxy)phenyl]ethyl]imidazol-2-yl]-4-methyl-thieno[3,2-b]pyrrole | 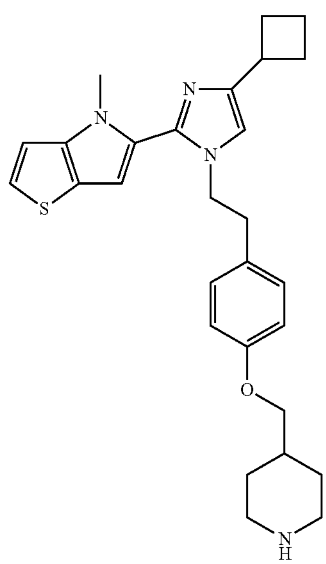 [SMILES: Cn1c(-c2nc(C3CCC3)cn2CCc2ccc(OCC3CCNCC3)cc2)cc2sccc21] | $^1$H NMR (CDCl$_3$ + $D_2O$) δ (ppm): 7.14 (d, J = 5.4 Hz, 1 H), 6.98-6.88 (m, 3 H), 6.79-6.69 (m, 3 H), 6.35 (s, 1 H), 4.18 (t, J = 7.3 Hz, 2 H), 3.75 (d, J = 6.4 Hz, 2 H), 3.70 (s, 3 H), 3.55-3.46 (m, 1 H), 3.19-3.10 (m, 2 H), 2.94 (t, J = 7.3 Hz, 2 H), 2.70-2.60 (m, 2 H), 2.37-2.17 (m, 4 H), 2.06-1.80 (m, 5 H), 1.35-1.26 (m, 2 H); MS (ESI): m/z: 475 [M + H]$^+$. |

TABLE 3-continued

Final Products

| Ex. | Name | Structure | Analytical Data |
| --- | --- | --- | --- |
| 92 | 4-methyl-5-[1-[3-[3-(4-piperidyloxy)phenyl]propyl]-4-propyl-imidazol-2-yl]thieno[3,2-b]pyrrole hydrochloride | 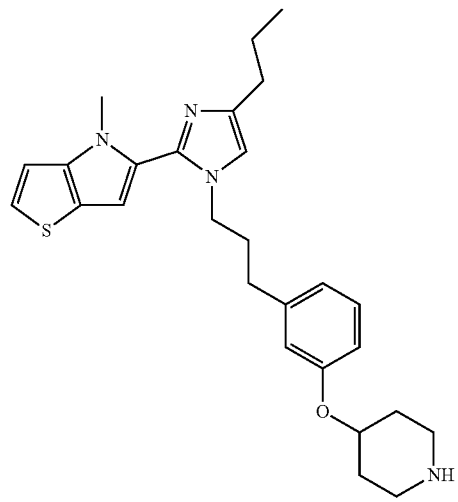 [SMILES: CCCc1cn(CCCc2cccc(OC3CCNCC3)c2)c(-c2cc3sccc3n2C)n1] | $^1$H NMR (DMSO-d$_6$) δ (ppm): 8.84 (bs, 2 H), 7.78 (bs, 1 H), 7.56 (d, J = 5.4 Hz, 1 H), 7.29 (d, J = 5.4 Hz, 1 H), 7.16-7.09 (m, 1 H), 6.88 (bs, 1 H), 6.83-6.78 (m, 2 H), 6.74-6.68 (m, 1 H), 4.65-4.54 (m, 1 H), 4.09 (t, J = 7.3 Hz, 2 H), 3.76 (s, 3 H), 3.24-3.14 (m, 2 H), 3.08-2.94 (m, 2 H), 2.67 (t, J = 7.3 Hz, 2 H), 2.53 (t, J = 7.3 Hz, 2 H), 2.15-1.99 (m, 4 H), 1.83-1.64 (m, 4 H), 0.96 (t, J = 7.3 Hz, 3 H); MS (ESI): m/z: 463 [M + H]$^+$. |
| 93 | 4-methyl-5-[1-[3-[3-(4-piperidyloxy)phenyl]propyl]-5-propyl-imidazol-2-yl]thieno[3,2-b]pyrrole | 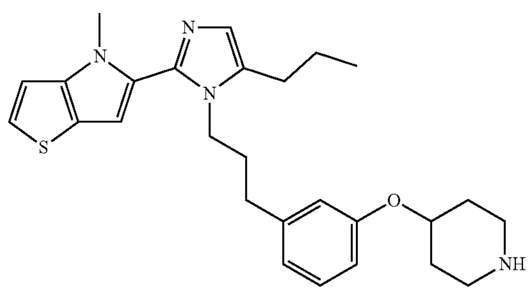 [SMILES: CCCc1cnc(-c2cc3sccc3n2C)n1CCCc1cccc(OC2CCNCC2)c1] | $^1$H NMR (CDCl$_3$ + D$_2$O) δ (ppm): 7.19-7.13 (m, 2 H), 6.97 (d, J = 5.4 Hz, 1 H), 6.92 (s, 1 H), 6.78-6.73 (m, 1 H), 6.70-6.63 (m, 2 H), 6.40 (s, 1 H), 4.41-4.34 (m, 1 H), 3.96 (t, J = 7.8 Hz, 2 H), 3.79 (s, 3 H), 3.19-3.10 (m, 2 H), 2.80-2.71 (m, 2 H), 2.58-2.42 (m, 4 H), 2.06-1.91 (m, 4 H), 1.75-1.62 (m, 4 H), 1.03 (t, J = 7.3 Hz, 3 H); MS (ESI): m/z: 463 [M + H]$^+$. |
| 94 | 4-methyl-5-[1-[2-[3-(4-piperidyloxy)phenoxy]ethyl]-4-propyl-imidazol-2-yl]thieno[3,2-b]pyrrole hydrochloride | 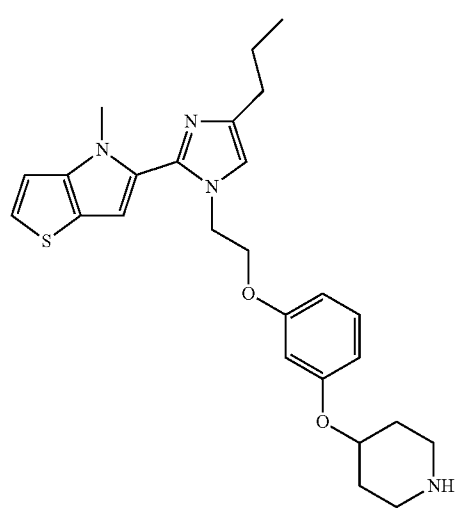 [SMILES: CCCc1cn(CCOc2cccc(OC3CCNCC3)c2)c(-c2cc3sccc3n2C)n1] | $^1$H NMR (DMSO-d$_6$) δ (ppm): 7.68 (bs, 1 H), 7.50 (d, J = 5.4 Hz, 1 H), 7.25 (d, J = 5.4 Hz, 1 H), 7.17-7.10 (m, 1 H), 7.01 (s, 1 H), 6.61-6.55 (m, 1 H), 6.46-6.42 (m, 2 H), 4.62-4.53 (m, 1 H), 4.46 (t, J = 4.9 Hz, 2 H), 4.30 (t, J = 4.9 Hz, 2 H), 3.71 (s, 3 H), 3.26-3.13 (m, 2 H), 3.11-2.97 (m, 2 H), 2.64 (t, J = 7.3 Hz, 2 H), 2.11-1.96 (m, 2 H), 1.81-1.71 (m, 2 H), 1.70-1.57 (m, 2 H), 0.91 (t, J = 7.3 Hz, 3 H); MS (ESI): m/z: 465 [M + H]$^+$. |

TABLE 3-continued

Final Products

| Ex. | Name | Structure | Analytical Data |
|---|---|---|---|
| 95 | 4-methyl-5-[1-[2-[3-(4-piperidyloxy)phenoxy]ethyl]-5-propyl-imidazol-2-yl]thieno[3,2-b]pyrrole | 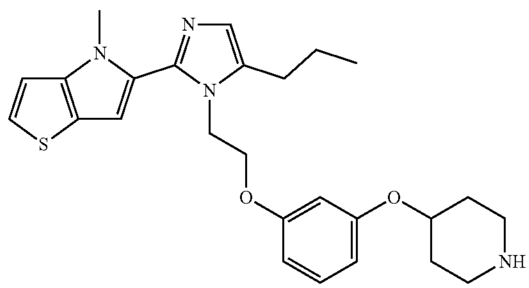 [SMILES: CCCc1cnc(-c2cc3sccc3n2C)n1CCOc1cccc(OC2CCNCC2)c1] | $^1$H NMR (CDCl$_3$ + D$_2$O) δ (ppm): 7.17 (d, J = 5.4 Hz, 1 H), 7.13-7.05 (m, 1 H), 7.02-6.90 (m, 2 H), 6.60 (s, 1 H), 6.55-6.46 (m, 1 H), 6.38-6.26 (m, 2 H), 4.39 (t, J = 5.9 Hz, 2 H), 4.35-4.28 (m, 1 H), 4.05 (t, J = 5.9 Hz, 2 H), 3.76 (s, 3 H), 3.18-3.05 (m, 2 H), 2.76-2.63 (m, 4 H), 2.04-1.93 (m, 2 H), 1.84-1.73 (m, 2 H), 1.70-1.56 (m, 2 H), 1.09 (t, J = 7.3 Hz, 3 H); MS (ESI): m/z: 465 [M + H]$^+$. |
| 96 | 4-methyl-5-[1-[3-[4-(4-piperidylmethoxy)phenyl]propyl]-4-propyl-imidazol-2-yl]thieno[3,2-b]pyrrole hydrochloride | 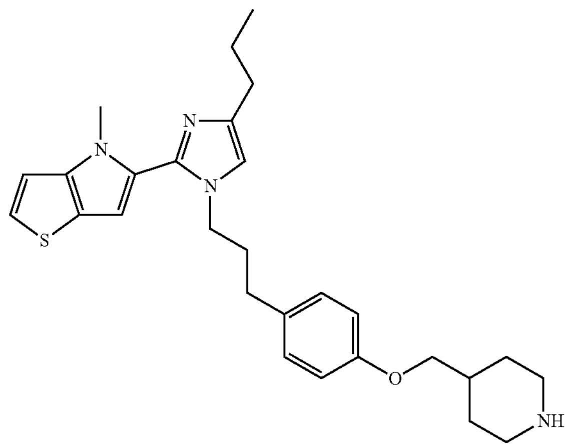 [SMILES: CCCc1cn(CCCc2ccc(OCC3CCNCC3)cc2)c(-c2cc3sccc3n2C)n1] | $^1$H NMR (DMSO-d$_6$) δ (ppm): 8.79 (bs, 1 H), 8.52 (bs, 1 H), 7.74 (bs, 1 H), 7.54 (d, J = 5.4 Hz, 1 H), 7.28 (d, J = 5.4 Hz, 1 H), 7.05-6.98 (m, 2 H), 6.86 (s, 1 H), 6.78-6.69 (m, 2 H), 4.06 (t, J = 7.3 Hz, 2 H), 3.80-3.71 (m, 5 H), 3.33-3.21 (m, 2 H), 2.96-2.81 (m, 2 H), 2.66 (t, J = 7.1 Hz, 2 H), 2.48 (t, J = 7.3 Hz, 2 H), 2.13-1.96 (m, 3 H), 1.93-1.82 (m, 2 H), 1.75-1.61 (m, 2 H), 1.52-1.39 (m, 2 H), 0.96 (t, J = 7.3 Hz, 3 H); MS (ESI): m/z: 477 [M + H]$^+$. |
| 97 | 4-methyl-5-[1-[3-[4-(4-piperidylmethoxy)phenyl]propyl]-5-propyl-imidazol-2-yl]thieno[3,2-b]pyrrole hydrochloride | 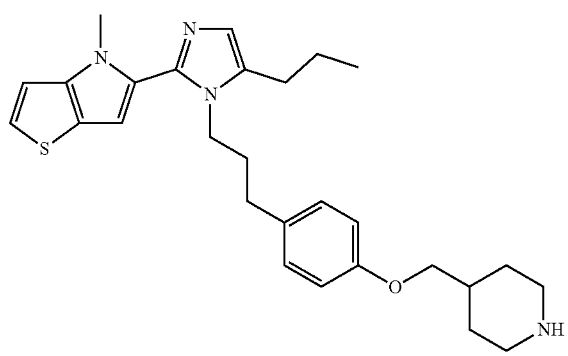 [SMILES: CCCc1cnc(-c2cc3sccc3n2C)n1CCCc1ccc(OCC2CCNCC2)cc1] | $^1$H NMR (DMSO-d$_6$) δ (ppm): 8.77 (bs, 1 H), 8.49 (bs, 1 H), 7.66 (bs, 1 H), 7.56 (d, J = 5.4 Hz, 1 H), 7.27 (d, J = 5.4 Hz, 1 H), 7.03-6.95 (m, 2 H), 6.86 (bs, 1 H), 6.76-6.70 (m, 2 H), 4.04 (d, J = 7.3 Hz, 2 H), 3.76 (d, J = 6.4 Hz, 2 H), 3.71 (s, 3 H), 3.34-3.21 (m, 2 H), 2.96-2.80 (m, 2 H), 2.63 (t, J = 7.6 Hz, 2 H), 2.49-2.43 (m, 2 H), 2.06-1.97 (m, 1 H), 1.95-1.84 (m, 4 H), 1.75-1.62 (m, 2 H), 1.54-1.39 (m, 2H), 1.01 (t, J = 7.3 Hz, 3 H); MS (ESI): m/z: 477 [M + H]$^+$. |
| 98 | 5-[1-[2-[4-(azepan-4-yloxy)phenoxy]ethyl]-4-propyl-imidazol-2-yl]-4-methyl-thieno[3,2-b]pyrrole | 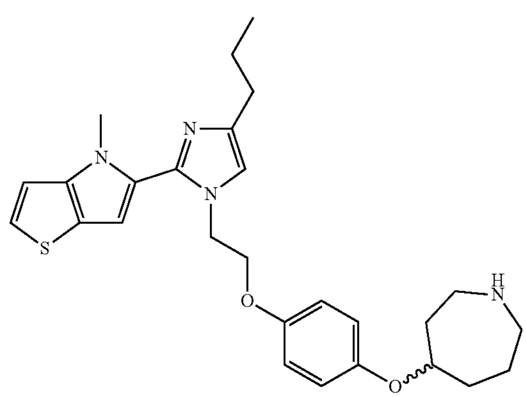 [SMILES: CCCc1cn(CCOc2ccc(OC3CCCNCC3)cc2)c(-c2cc3sccc3n2C)n1] | $^1$H NMR (CDCl$_3$) δ (ppm): 7.16 (d, J = 5.4 Hz, 1 H), 6.97 (d, J = 5.4 Hz, 1 H), 6.92 (s, 1 H), 6.83-6.70 (m, 4 H), 6.56 (s, 1 H), 4.53-4.46 (m, 1 H), 4.36 (t, J = 5.4 Hz, 2 H), 4.14 (t, J = 5.4 Hz, 2 H), 3.82 (s, 3 H), 3.21-2.98 (m, 4 H), 2.60 (t, J = 7.6 Hz, 2 H), 2.23-1.81 (m, 6 H), 1.77-1.65 (m, 2 H), 1.00 (t, J = 7.3 Hz, 3 H); MS (ESI): m/z: 479 [M + H]$^+$. |

TABLE 3-continued

Final Products

| Ex. | Name | Structure | Analytical Data |
|---|---|---|---|
| 99 | 5-[1-[2-[4-(azepan-4-yloxy)phenoxy]ethyl]-5-propyl-imidazol-2-yl]-4-methyl-thieno[3,2-b]pyrrole | 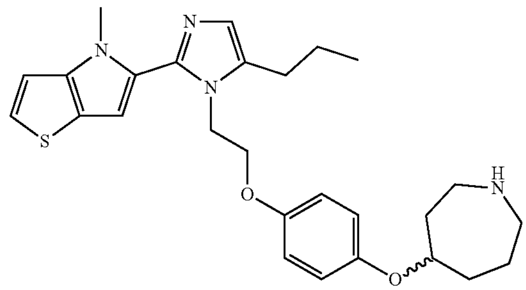 [SMILES: CCCc1cnc(-c2cc3sccc3n2C)n1CCOc1ccc(OC2CCCNCC2)cc1] | $^1$H NMR (DMSO-d$_6$) δ (ppm): 7.32 (d, J = 5.4 Hz, 1 H), 7.19 (d, J = 5.4 Hz, 1 H), 6.86 (s, 1 H), 6.78-6.61 (m, 5 H), 4.46-4.39 (m, 1 H), 4.35 (t, J = 5.4 Hz, 2 H), 4.03 (t, J = 5.4 Hz, 2 H), 3.68 (s, 3 H), 3.06-2.78 (m, 4 H), 2.66 (t, J = 7.8 Hz, 2 H), 2.05-1.48 (m, 8 H), 1.01 (t, J = 7.3 Hz, 3 H); MS (ESI): m/z: 479 [M + H]$^+$. |
| 100 | 4-methyl-5-[1-[3-[4-(4-piperidyloxy)phenyl]propyl]-4-(3,3,3-trifluoropropyl)imidazol-2-yl]thieno[3,2-b]pyrrole | 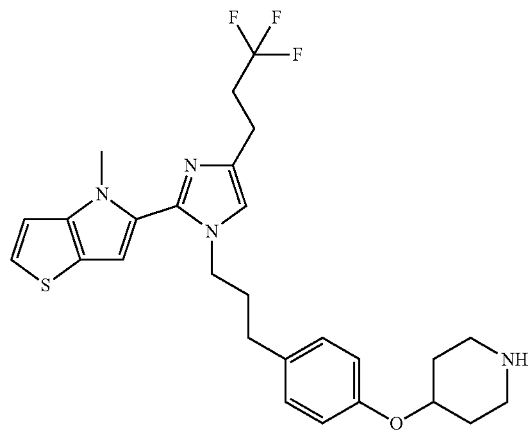 [SMILES: Cn1c(-c2nc(CCC(F)(F)F)cn2CCCc2ccc(OC3CCNCC3)cc2)cc2sccc21] | $^1$H NMR (DMSO-d$_6$) δ (ppm): 7.32 (d, J = 5.4 Hz, 1 H), 7.21 (s, 1 H), 7.17 (d, J = 5.4 Hz, 1 H), 7.00-6.95 (m, 2 H), 6.79-6.72 (m, 2 H), 6.44 (s, 1 H), 4.35-4.24 (m, 1 H), 3.95 (t, J = 7.3 Hz, 2 H), 3.78 (s, 3 H), 3.01-2.90 (m, 2 H), 2.79-2.71 (m, 2 H), 2.67-2.54 (m, 4 H), 2.43 (t, J = 7.3 Hz, 2H), 2.01-1.82 (m, 4 H), 1.50-1.38 (m, 2 H); MS (ESI): m/z: 517 [M + H]$^+$. |

Compounds 101 and 102 were obtained starting from compound 2 and 1-bromo-2-methoxy-ethane (Sigma-Aldrich, Cat. No. 238155) according to the procedure described for Intermediate 26 and separated by column chromatography on silica gel (hexane/acetone, 95:5→60:40, v:v). Compounds 103 and 104 were obtained starting from compound 2 and 2-bromoethoxybenzene (Sigma-Aldrich, Cat. No. B75506-25G) and compound 105 from compound 2 and benzylbromide (Sigma-Aldrich, Cat. No. B17905) according to the procedure described for Intermediate 26.

| | | | |
|---|---|---|---|
| 101 | 5-[5-ethyl-1-(2-methoxyethyl)imidazol-2-yl]-4-methyl-thieno[3,2-b]pyrrole | | $^1$H NMR (CDCl$_3$) δ (ppm): 7.18-7.15 (m, 1 H), 7.00-6.93 (m, 2 H), 6.60 (s, 1 H), 4.21-4.15 (m, 2 H), 3.81 (s, 3 H), 3.56-3.50 (m, 2 H), 3.25 (s, 3 H), 2.74-2.60 (m, 2 H), 1.39-1.33 (m, 3 H); MS (ESI): m/z: 290 [M + H]$^+$. |
| 102 | 5-[4-ethyl-1-(2-methoxyethyl)imidazol-2-yl]-4-methyl-thieno[3,2-b]pyrrole | | $^1$H NMR (CDCl$_3$) δ (ppm): 7.18-7.14 (m, 1 H), 6.98-6.95 (m, 1 H), 6.88 (s, 1 H), 6.55 (s, 1 H), 4.19-4.14 (m, 2 H), 3.85 (s, 3 H), 3.66-3.61 (m, 2 H), 3.34 (s, 3 H), 2.80-2.62 (m, 2 H), 1.34-1.27 (m, 3 H); MS (ESI): m/z: 290 [M + H]$^+$. |

-continued

| | | | |
|---|---|---|---|
| 103 | 5-[5-ethyl-1-(2-phenoxyethyl)imidazol-2-yl]-4-methyl-thieno[3,2-b]pyrrole | 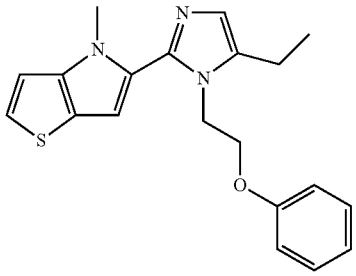 [SMILES: CCc1cnc(-c2cc3sccc3n2C)n1CCOc1ccccc1] | ¹H NMR (CDCl₃) δ (ppm): 7.32-7.25 (m, 2 H), 7.20-7.15 (m, 1 H), 7.02-6.93 (m, 3 H), 6.88-6.80 (m, 2 H), 4.23-4.18 (m, 2 H), 3.84 (s, 3 H), 2.76-2.62 (m, 2 H), 1.34-1.24 (m, 3 H); MS (ESI): m/z: 352 [M + H]⁺. |
| 104 | 5-[4-ethyl-1-(2-phenoxyethyl)imidazol-2-yl]-4-methyl-thieno[3,2-b]pyrrole | 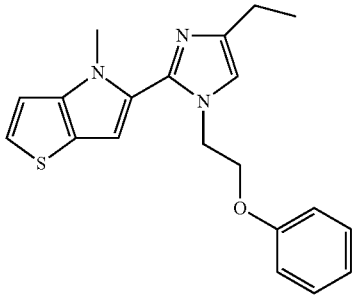 [SMILES: CCc1cn(CCOc2ccccc2)c(-c2cc3sccc3n2C)n1] | ¹H NMR (CDCl₃) δ (ppm): 7.32-7.25 (m, 2 H), 7.20-7.15 (m, 1 H), 7.02-6.93 (m, 3 H), 6.88-6.80 (m, 2 H), 6.60 (s, 1 H), 4.44-4.37 (m, 2 H), 4.23-4.18 (m, 2 H), 3.84 (s, 3 H), 2.76-2.62 (m, 2 H), 1.34-1.24 (m, 3 H); MS (ESI): m/z: 352 [M + H]⁺. |
| 105 | 5-(1-benzyl-5-ethyl-imidazol-2-yl)-4-methyl-thieno[3,2-b]pyrrole | 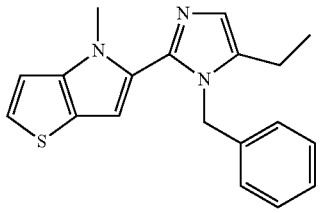 [SMILES: CCc1cnc(-c2cc3sccc3n2C)n1Cc1ccccc1] | ¹H NMR (CDCl₃) δ (ppm): 7.40-7.29 (m, 3 H), 7.17-7.12 (m, 1 H), 7.10-7.04 (m, 2 H), 6.98-6.93 (m, 1 H), 6.73 (s, 1 H), 6.41 (s, 1 H), 5.22 (s, 2 H), 3.85 (s, 3 H), 2.78-2.61 (m, 2 H), 1.33-1.26 (m, 3 H); MS (ESI): m/z: 322 [M + H]⁺. |

Example 106: 4-Methyl-5-[4-(4-pyridyl)-1H-imidazol-2-yl]thieno[3,2-b]pyrrole

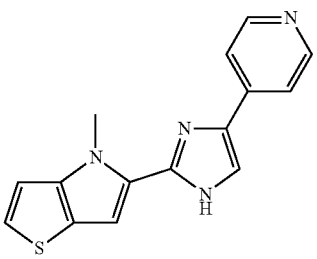 [SMILES: Cn1c(-c2nc(-c3ccncc3)c[nH]2)cc2sccc21]

4-Methyl-5-[4-(4-pyridyl)-1H-imidazol-2-yl]thieno[3,2-b]pyrrole was prepared staring from 4-methylthieno[3,2-b]pyrrole-5-carboxamidine acetate (Intermediate 11) and 2-bromo-1-(4-pyridyl)ethanone (Fluorochem, Cat No. 017122) according to the procedure described for Example 1 and purified by flash chromatography on silica gel (CH₂Cl₂/MeOH/NH₃, 97:3:0.5, v:v:v). ¹H NMR (MeOH-d₄) δ (ppm): 8.53-8.46 (m, 2H), 7.88-7.79 (m, 3H), 7.25 (d, J 5.4 Hz, 1H), 7.09 (d, J=5.4 Hz, 1H), 6.83 (s, 1H), 4.14 (s, 3H); MS (ESI): m/z: 281 [M+H]⁺.

Example 107: 5-(1H-Benzimidazol-2-yl)-4-methyl-thieno[3,2-b]pyrrole

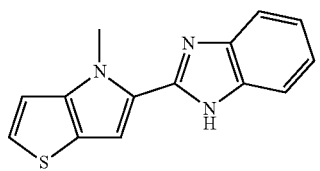 [SMILES: Cn1c(-c2nc3ccccc3[nH]2)cc2sccc21]

0.050 g (0.30 mmol) of 4-methylthieno[3,2-b]pyrrole-5-carbaldehyde (Aldrich, Cat. N. CDS015804), 0.033 g (0.30 mmol) of o-phenylendiamine (Aldrich, Cat. N. P23938-5G) and iodobenzene diacetate (Aldrich, Cat. N. 178721-25G) were stirred at −15° C. in solvent free conditions. The mixture was then warmed to RT becoming a sticky brown oil. After stirring at RT for 1.5 h a further portion of 0.018 g (0.18 mmol) of o-phenylendiamine was added. The obtained dark oil was purified by column chromatography on silica gel (EtOAc/hexane 3:97, v:v to 30:70 v:v) to provide 0.025 g of 5-(1H-benzimidazol-2-yl)-4-methyl-thieno[3,2-b]pyrrole (33%). ¹H NMR (DMSO-d₆) δ (ppm): 12.74-12.57 (bs, 1H), 7.68-7.46 (m, 2H), 7.44-7.39 (m, 1H), 7.28-7.22 (m, 1H), 7.21-7.14 (m, 3H), 4.26 (s, 3H); MS (ESI): m/z: 254 [M+H]⁺.

Example 108: 4-Methyl-5-[1-[3-[4-(4-piperidyloxy)phenyl]propyl]benzimidazol-2-yl]thieno[3,2-b]pyrrole hydrochloride

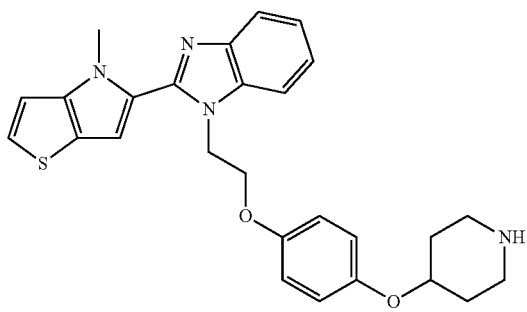 [SMILES: Cn1c(-c2nc3ccccc3n2CCOc2ccc(OC3CCNCC3)cc2)cc2sccc21]

tert-Butyl 4-[4-[3-[2-(4-methylthieno[3,2-b]pyrrol-5-yl)benzimidazol-1-yl]propyl]phenoxy]piperidine-1-carboxylate tert-Butyl 4-[4-[3-[2-(4-methylthieno[3,2-b]pyrrol-5-yl)benzimidazol-1-yl]propyl]phenoxy]piperidine-1-carboxylate was prepared starting from 5-(1H-benzimidazol-2-yl)-4-methyl-thieno[3,2-b]pyrrole (Example 107) and tert-butyl 4-[4-(3-bromopropyl)phenoxy]piperidine-1-carboxylate (Intermediate 19) according to the procedure for Intermediate 26. $^1$H NMR (CDCl$_3$) δ (ppm): 7.95-7.74 (m, 1H), 7.39-7.29 (m, 3H), 7.26 (d, J 5.4 Hz, 1H), 7.06-6.99 (m, 3H), 6.85-6.80 (m, 2H), 6.59 (s, 1H), 4.48-4.39 (m, 1H), 4.38-4.31 (t, J=7.1 Hz, 2H), 4.02 (s, 3H), 3.76-3.66 (m, 2H), 3.38-3.26 (m, 2H), 2.64 (t, J=7.1 Hz, 2H), 2.25-2.15 (m, 2H), 1.97-1.85 (m, 2H), 1.80-1.69 (m, 2H), 1.48 (s, 9H); MS (ESI): m/z: 571 [M+H]$^+$.

4-Methyl-5-[1-[3-[4-(4-piperidyloxy)phenyl]propyl]benzimidazol-2-yl]thieno[3,2-b]pyrrole hydrochloride 4-Methyl-5-[1-[3-[4-(4-piperidyloxy)phenyl]propyl]benzimidazol-2-yl]thieno[3,2-b]pyrrole hydrochloride was obtained starting from tert-butyl 4-[4-[3-[2-(4-methylthieno[3,2-b]pyrrol-5-yl)benzimidazol-1-yl]propyl]phenoxy]piperidine-1-carboxylate according to the procedure described Example 18. $^1$H NMR (DMSO-d$_6$) δ (ppm): 8.80-8.57 (m, 2H), 7.86-7.75 (m, 2H), 7.54 (d, J=5.4 Hz, 1H), 7.49-7.38 (m, 2H), 7.29 (d, J=5.4 Hz, 1H), 7.12-7.05 (m, 2H), 6.89-6.81 (m, 3H), 4.59-4.52 (m, 1H), 4.40 (t, J=7.3 Hz, 2H), 3.94 (s, 3H), 3.27-3.14 (m, 2H), 3.10-3.00 (m, 2H), 2.58 (t, J=7.3 Hz, 2H), 2.16-1.99 (m, 4H), 1.83-1.71 (m, 2H); MS (ESI): m/z: 471 [M+H]$^+$.

2. Biological Testing

2.1 Assay of Enzyme Inhibition of KDM1A (LSD1)

The KDM1A inhibiting activity was determined using a TR-FRET assay (time resolved fluorescence resonance energy transfer, Lance® Ultra Demethylase technology (Perkin Elmer, Waltham, Mass., USA)), which comprises a Europium chelate donor dye (TRF0404, Perkin Elmer, Waltham, Mass., USA) together with ULight™ (TR0102, Perkin Elmer, Waltham, Mass., USA), a small molecular weight acceptor dye with a red-shifted fluorescent emission, and a biotinylated 21 aminoacids histone H3-derived monomethylated peptide (H3K4me) [Lys(Me1)4]-Histone H3 (1-21)-GGK(biotin), (64355, Anaspec, Fremont, Calif., USA) as substrate. The intensity of the light emission is proportional to the level of biotinylated reaction product. The complex of human recombinant KDM1A/CoREST protein was produced in E. coli as separate proteins and co-purified as previously described. (Forneris, F. et al. Trends Biochem, Sci, 2008, 33, 181-189) (Forneris, F. et al. J. Biol. Chem. 2007, 282, 20070-20074).

Demethylase Assay Conditions:

0.25 nM KDM1A/CoREST protein and compound in 100% DMSO were added in a final volume of 48 μL assay buffer (Tris HCl 50 mM pH 8.8, NaCl 50 mM, DTT 1 mM, Tween-20 0.01%) to each well of a 96 well half area flat bottom white plate (3693 Costar, Sigma-Aldrich, St. Louis, M, USA).

Demethylase reaction was started by the addition of 50 nM histone H3K4 monomethylated. After 20 min at RT, 300 μM tranylcypromine (P8511-1G, Sigma-Aldrich, St. Louis, Mo. 63103) was added to stop the reaction.

Detection Step Conditions:

10 μL of the assay mixture was transferred from the original plate into a 384 well white plate (6007290 OptiPlate™, Perkin Elmer, Waltham, Mass., USA) and 10 μL of the detection Mix containing 2 nM Eu-antibody and 10 nM U-Light-Streptavidin in 1× Lance Detection Buffer (TRF0404, TR0102, CR97100, Perkin Elmer, Waltham, Mass., USA). The resulting mixture was incubated in the dark for 1 h at RT. Then, TR-FRET signal was read by a fluorimeter (Infinite® F200, Tecan, Mannedorf, Switzerland) (Excitation 320 nm, Emission 665 nm and 620 nm, delay time 50 s, window time 100 s).

IC$_{50}$ Determination:

The inhibitor concentrations ranged from 0.025 to 500 μM (serial 1:3 dilutions). The IC$_{50}$ was calculated using GraphPad Software.

Compounds 2, 4-8, 11, 13, 15, 16 and 70 exhibit IC$_{50}$ values of less than 10 M, examples 9, 10 and 12 exhibit IC$_{50}$ values of less than 1 μM, examples 18-54 and 57-62 exhibit an IC$_{50}$ value of less than 0.1 μM.

2.2 Cell Growth

CellTiter-Flor® (Promega) is as a nonlytic, single-reagent-addition fluorescence assay that measures the relative number of living cells in a culture population after experimental manipulation. The CellTiter-Fluor™ Cell Viability Assay measures the conserved and constitutive protease activity within live cells and therefore acts as a marker for cell viability.

Human leukemia MV4-11 cells, (obtained from the Deutsche Sammlung von Mikroorganismen und Zellkulturen, ACC 102) or NB4 cells, (obtained from the Deutsche Sammlung von Mikroorganismen und Zellkulturen) in exponential growth, were incubated for 48 h with different concentrations of the inhibitors. After 48 h a volume of CellTiter-Fluor® Reagent equal to one fifth of volume of cell culture medium was added. The content was mixed and incubates for at least 90 min at 37° C. degree to obtain a stable signal. The fluorescence was recorded using an excitation wavelength of 360 nm and an emission at 535 nm. The IC$_{50}$ was calculated using GraphPad Software.

Compounds 18-33 exhibit IC$_{50}$ values of less than 10 μM against human leukemia MV4-11 cells and IC$_{50}$ values of less than 20 μM against human leukemia NB4 cells, compounds 39-50 and 57 IC$_{50}$ values of less than 10 μM against human leukemia NB4 cells.

2.3 Bioluminescent-Coupled Assay for Monoamine Oxidases (MAO-Glo Assay)

The MAO Glo Assay from Promega (cat. V1402, Promega, Madison, Wis.) was used to measure the effect of inhibitors on MAO A and MAO B activity. Human recombinant MAO A and MAO B were expressed in *Pichia pastoris* and purified as published (Binda C. et al. Proc. Natl. Acad. Sci. USA, 2003, 9750-9755). The assay was performed at RT in 50 μL (25 μL reaction solution+25 μL detection reagent) in 96 well half area white plates (cat. 3693, Corning, Corning, N.Y.). Luminescence was measured after 20 min incubation in the dark using a microplate reader (Infinite F200, Tecan Group, Switzerland) with an integration time of 0.25 s per well. 50 nM MAO A or 125 nM MAO B were incubated with five different inhibitor concentrations (from 0.004 μM to 100 μM) for 15 min at RT in Promega MAO Buffer or Promega MAO B Buffer (MAO Glo Assay kit, catalogue number V1402, Promega, Madison, Wis.). After 30 min of incubation the reaction was stopped with the Promega detection reagent. All compounds were tested twice and $IC_{50}$ values were calculated using GraphPad Prism version 4.0 (GraphPad Software, San Diego, Calif.).

Compounds 7, 10, 19-20, and 23-26 were at least 10 times more active against KDM1A (LSD1) compared to both MAO A and MAO B.

The invention claimed is:

1. A compound of formula (I)

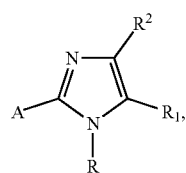

(I)

or a stereoisomer or a pharmaceutically acceptable salt thereof,
wherein
A is

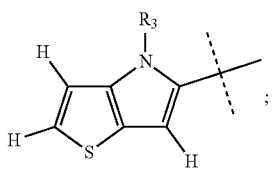

R is hydrogen or $L^1$-$R^5$;
$R^1$, $R^2$ are independently, hydrogen, $C_1$-$C_4$-alkyl, $C_3$-$C_7$ cycloalkyl, aryl, heteroaryl, —$(CH_2)_zCF_3$, or $R^1$ and $R^2$, taken together with the carbon atoms they are bound to, form a heterocycle or heteroaryl that is fused to the imidazole moiety in formula (I);
z is an integer from zero to 6;
$R^3$ is hydrogen or $C_1$-$C_4$-alkyl;
$L^1$ is —$(CH_2)_j$—Y— or —$CH_2$—;
j is an integer from 2 to 6;
Y is a bond, oxygen, or $CH_2$;
$R^5$ is $C_1$-$C_4$-alkyl or aryl, wherein the aryl is optionally substituted by halogen, $C_1$-$C_6$-alkyl or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6; and
W is oxygen, sulphur, NH, or $CH_2$.

2. The compound of claim 1, wherein $R^1$ is hydrogen.
3. The compound of claim 1, wherein $R^2$ is cyclobutyl.
4. The compound of claim 1, wherein $R^3$ is methyl or ethyl.
5. The compound of claim 1, wherein
R is hydrogen or $L^1$-$R^5$;
$L^1$ is —$(CH_2)_2$—Y—;
Y is $CH_2$;
$R^5$ is phenyl optionally substituted by $L^2$-$R^6$;
$L^2$ is —W—$(CH_2)_p$—;
$R^6$ is heterocyclyl, wherein the heterocyclyl is optionally substituted by $C_1$-$C_6$-alkyl;
p is zero; and
W is oxygen.
6. The compound of claim 5, wherein $R^6$ is piperidinyl.
7. A compound of formula (I)

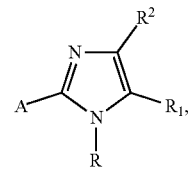

(I)

or a stereoisomer or a pharmaceutically acceptable salt thereof,
wherein
A is

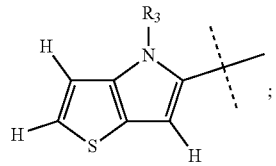

R is hydrogen or $L^1$-$R^5$;
$R^1$ is hydrogen;
$R^2$ is hydrogen, $C_1$-$C_4$-alkyl, $C_3$-$C_7$ cycloalkyl, aryl, heteroaryl, or —$(CH_2)_zCF_3$;
z is an integer from zero to 6;
$R^3$ is hydrogen or $C_1$-$C_4$-alkyl;
$L^1$ is —$(CH_2)_j$—Y— or —$CH_2$—;
j is an integer from 2 to 6;
Y is a bond, oxygen, or $CH_2$;
$R^5$ is $C_1$-$C_4$-alkyl or aryl, wherein the aryl is optionally substituted by halogen, $C_1$-$C_6$-alkyl or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6; and
W is oxygen, sulphur, NH, or $CH_2$.

8. The compound of claim 7, wherein $R^2$ is cyclobutyl.
9. The compound of claim 7, wherein $R^3$ is methyl or ethyl.
10. The compound of claim 7, wherein
R is hydrogen or $L^1$-$R^5$;
$L^1$ is —$(CH_2)_2$—Y—;
Y is $CH_2$;

$R^5$ is phenyl optionally substituted by $L^2$-$R^6$;
$L^2$ is —W—$(CH_2)_p$—;
$R^6$ is heterocyclyl, wherein the heterocyclyl is optionally substituted by $C_1$-$C_6$-alkyl;
p is zero; and
W is oxygen.

11. The compound of claim 10, wherein $R^6$ is piperidinyl.

12. A compound of formula (I)

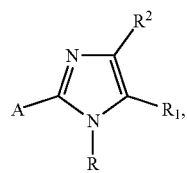

(I)

or a stereoisomer or a pharmaceutically acceptable salt thereof,
wherein
A is

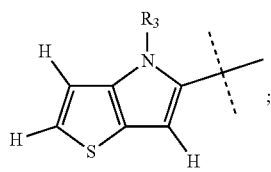

R is hydrogen or $L^1$-$R^5$;
$R^1$ is hydrogen, $C_1$-$C_4$-alkyl, $C_3$-$C_7$ cycloalkyl, aryl, heteroaryl, or —$(CH_2)_z$$CF_3$;
$R^2$ is $C_3$-$C_7$ cycloalkyl;
z is an integer from zero to 6;
$R^3$ is hydrogen or $C_1$-$C_4$-alkyl;
$L^1$ is —$(CH_2)_j$—Y— or —$CH_2$—;
j is an integer from 2 to 6;
Y is a bond, oxygen, or $CH_2$;
$R^5$ is aryl, wherein the aryl is optionally substituted by halogen, $C_1$-$C_6$-alkyl or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6; and
W is oxygen, sulphur, NH, or $CH_2$.

13. The compound of claim 12, wherein $R^2$ is cyclobutyl.

14. The compound of claim 12, wherein $R^3$ is methyl or ethyl.

15. The compound of claim 12, wherein
R is $(CH_2)_3$—$R^5$; and
$R^5$ is phenyl optionally substituted by halogen, $C_1$-$C_6$-alkyl or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6; and
W is oxygen, sulphur, NH, or $CH_2$.

16. The compound of claim 12, wherein $R^6$ is piperidinyl.

17. The compound of claim 12, wherein
$R^2$ is cyclobutyl;
$R^3$ is methyl or ethyl; and
R is $(CH_2)_3$—$R^5$;

$R^5$ is aryl that is optionally substituted by halogen, $C_1$-$C_6$-alkyl, or $L^2$-$R^6$;
$L^2$ is —$(CH_2)_m$— or —$(CH_2)_n$—W—$(CH_2)_p$—;
$R^6$ is heterocyclyl, wherein the heterocyclyl is optionally substituted by $C_1$-$C_6$-alkyl;
m, n, p are, independently, zero or an integer from 1 to 6; and
W is oxygen, sulphur, NH, or $CH_2$.

18. A method of treating cancer in a subject wherein the method comprises the step of administering a compound of claim 1 to a subject in need thereof in an effective amount.

19. The method of claim 18, wherein the cancer is acute myeloid leukemia, chronic myeloid leukemia, acute chronic lymphoblastic leukemia, chronic lymphoblastic leukemia, myelodysplastic syndrome, multiple myeloma, Hodgkin's disease, non-Hodgkin's lymphoma, cutaneous T-cell lymphoma, peripheral T-cell lymphoma, adult T-cell leukemia, large B-cell lymphoma, a mammary tumor, a pulmonary tumor, pleural mesothelioma, adenocarcinoma, non-small lung cancer, small-cell lung cancer a skin tumor, melanoma, squamous cell carcinoma, Kaposi's sarcoma, keratocanthoma, osteosarcoma, fibrosarcoma, rhabdomyosarcoma, neuroblastoma, glioblastoma, cerebral tumor, head and neck cancer, a testicular tumor, an ovarian tumor, cervical carcinoma, an endometrial tumor, a prostate tumor, thyroid carcinoma, colon cancer, a gastric tumor, a gastrointestinal adenocarcinoma, hepatocellular carcinoma, pancreatic carcinoma, a renal tumor, teratocarcinoma, or embryonic carcinoma.

20. The method of claim 18, wherein the cancer is leukemia, non-small cell lung cancer, hepatocellular carcinoma, or glioblastoma.

21. A method of treating cancer in a subject wherein the method comprises the step of administering a compound of claim 7 to a subject in need thereof in an effective amount.

22. The method of claim 21, wherein the cancer is acute myeloid leukemia, chronic myeloid leukemia, acute chronic lymphoblastic leukemia, chronic lymphoblastic leukemia, myelodysplastic syndrome, multiple myeloma, Hodgkin's disease, non-Hodgkin's lymphoma, cutaneous T-cell lymphoma, peripheral T-cell lymphoma, adult T-cell leukemia, large B-cell lymphoma, a mammary tumor, a pulmonary tumor, pleural mesothelioma, adenocarcinoma, non-small lung cancer, small-cell lung cancer a skin tumor, melanoma, squamous cell carcinoma, Kaposi's sarcoma, keratocanthoma, osteosarcoma, fibrosarcoma, rhabdomyosarcoma, neuroblastoma, glioblastoma, cerebral tumor, head and neck cancer, a testicular tumor, an ovarian tumor, cervical carcinoma, an endometrial tumor, a prostate tumor, thyroid carcinoma, colon cancer, a gastric tumor, a gastrointestinal adenocarcinoma, hepatocellular carcinoma, pancreatic carcinoma, a renal tumor, teratocarcinoma, or embryonic carcinoma.

23. The method of claim 21, wherein the cancer is leukemia, non-small cell lung cancer, hepatocellular carcinoma, or glioblastoma.

24. A method of treating cancer in a subject wherein the method comprises the step of administering a compound of claim 12 to a subject in need thereof in an effective amount.

25. The method of claim 24, wherein the cancer is acute myeloid leukemia, chronic myeloid leukemia, acute chronic lymphoblastic leukemia, chronic lymphoblastic leukemia, myelodysplastic syndrome, multiple myeloma, Hodgkin's disease, non-Hodgkin's lymphoma, cutaneous T-cell lymphoma, peripheral T-cell lymphoma, adult T-cell leukemia, large B-cell lymphoma, a mammary tumor, a pulmonary tumor, pleural mesothelioma, adenocarcinoma, non-small lung cancer, small-cell lung cancer a skin tumor, melanoma, squamous cell carcinoma, Kaposi's sarcoma, keratocanthoma, osteosarcoma, fibrosarcoma, rhabdomyosarcoma, neuroblastoma, glioblastoma, cerebral tumor, head and neck cancer, a testicular tumor, an ovarian tumor, cervical carcinoma, an endometrial tumor, a prostate tumor, thyroid carcinoma, colon cancer, a gastric tumor, a gastrointestinal adenocarcinoma, hepatocellular carcinoma, pancreatic carcinoma, a renal tumor, teratocarcinoma, or embryonic carcinoma.

26. The method of claim 24, wherein the cancer is leukemia, non-small cell lung cancer, hepatocellular carcinoma, or glioblastoma.

* * * * *

UNITED STATES PATENT AND TRADEMARK OFFICE
CERTIFICATE OF CORRECTION

Page 1 of 1

PATENT NO. : 10,961,255 B2
APPLICATION NO. : 16/722554
DATED : March 30, 2021
INVENTOR(S) : Paola Vianello et al.

It is certified that error appears in the above-identified patent and that said Letters Patent is hereby corrected as shown below:

In the Claims

At Column 147, Claim number 15, Line number 54:
"R is $(CH_2)_3$-$R^5$; and"
Should read:
-- R is -$(CH_2)_3$-$R^5$; and --

At Column 147, Claim number 17, Line number 67:
"R is $(CH_2)_3$-$R^5$;"
Should read:
-- R is -$(CH_2)_3$-$R^5$; --

At Column 148, Claim number 19, Line number 20:
"lung cancer, small-cell lung cancer a skin tumor, melanoma;"
Should read:
-- lung cancer, small-cell lung cancer, a skin tumor, melanoma --

At Column 148, Claim number 22, Line number 44:
"lung cancer, small-cell lung cancer a skin tumor, melanoma;"
Should read:
-- lung cancer, small-cell lung cancer, a skin tumor, melanoma --

At Column 149, Claim number 25, Line number 1:
"lung cancer, small-cell lung cancer a skin tumor, melanoma;"
Should read:
-- lung cancer, small-cell lung cancer, a skin tumor, melanoma --

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*